US010858316B2

(12) United States Patent
Fletcher et al.

(10) Patent No.: US 10,858,316 B2
(45) Date of Patent: Dec. 8, 2020

(54) SMALL MOLECULE INHIBITORS OF THE MCL-1 ONCOPROTEIN AND USES THEREOF

(71) Applicant: University of Maryland, Baltimore, Baltimore, MD (US)

(72) Inventors: Steven Fletcher, Baltimore, MD (US); Maryanna Lanning, Baltimore, MD (US); Lijia Chen, Columbia, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/743,546

(22) PCT Filed: Jul. 8, 2016

(86) PCT No.: PCT/US2016/041577
§ 371 (c)(1),
(2) Date: Jan. 10, 2018

(87) PCT Pub. No.: WO2017/011323
PCT Pub. Date: Jan. 19, 2017

(65) Prior Publication Data
US 2018/0208554 A1 Jul. 26, 2018

Related U.S. Application Data

(60) Provisional application No. 62/191,045, filed on Jul. 10, 2015, provisional application No. 62/191,673, filed on Jul. 13, 2015.

(51) Int. Cl.
| | | |
|---|---|---|
| *C07C 311/21* | (2006.01) | |
| *C07D 215/58* | (2006.01) | |
| *C07C 311/29* | (2006.01) | |
| *C07C 311/51* | (2006.01) | |
| *C07C 229/64* | (2006.01) | |
| *C07D 257/02* | (2006.01) | |
| *C07D 261/12* | (2006.01) | |
| *C07D 309/04* | (2006.01) | |
| *A61P 35/02* | (2006.01) | |

(52) U.S. Cl.
CPC ............ *C07C 311/21* (2013.01); *A61P 35/02* (2018.01); *C07C 229/64* (2013.01); *C07C 311/29* (2013.01); *C07C 311/51* (2013.01); *C07D 215/58* (2013.01); *C07D 257/02* (2013.01); *C07D 261/12* (2013.01); *C07D 309/04* (2013.01); *C07C 2601/08* (2017.05)

(58) Field of Classification Search
CPC ..... C07D 311/21; A61K 31/55; C07C 311/21; C07C 311/29; A61P 31/55
See application file for complete search history.

(56) References Cited

U.S. PATENT DOCUMENTS 6,541,491 B1 4/2003 Davies et al.
2011/0053915 A1 3/2011 Ivaschenko et al.

FOREIGN PATENT DOCUMENTS

| DE | 19502179 A1 | 8/1996 |
|---|---|---|
| WO | 2001021596 A1 | 3/2001 |
| WO | 2010114919 A2 | 10/2010 |
| WO | 2013052943 A2 | 4/2013 |
| WO | 2017011323 A1 | 1/2017 |

OTHER PUBLICATIONS

Roman, Tetrahedron Letters, 55, 1229-1233, 2014. (Year: 2014).*
Jiang, Organic Letters, vol. 15(18), 4884-4887, 2013. (Year: 2013).*
Kuduk, Bloorg & Med Chem Lett, vol. 24, 1417-1420, 2014. (Year: 2014).*
Kou, E J Med Chem, vol. 75, 282-288, 2014. (Year: 2014).*
Nandan, Proteins: Structure, Function and Bioinformatics, vol. 67, 53-64, 2007. (Year: 2007).*
Lee, Letters in Peptide Science, vol. 2, 1995, 253-258. (Year: 1995).*
Li, J BIoinformatics and COmputational Biology, vol. 4(2), 2006, 403-414. (Year: 2006).*
Extended European Search Report for Application No. 16824947; dated Mar. 5, 2019; 4 pages.
European Examination Report EP Application No. 16 824 947.2 dated Apr. 6, 2020 (10 pages).
Abulwerdi Fardokht, et al. "A Novel Small-Molecule Inhibitor of Mcl-1 Blocks Pancreatic Cancer Growth In vitro and In vivo" Mol Cancer Ther. 2014, 13(3):565-575.
Abulwerdi Fardokht A, et al., "3-Substituted-N-(4-Hydroxynaphthalen-1-yl)arylsulfonamides as a Novel Class of Selective Mcl-1 Inhibitors: Structure-Based Design, Synthesis, SAR, and Biological Evaluation", J. Med. Chem., 2014, 57:4111-4133.
Adams JM, et al., "The Bcl-2 Apoptotic Switch in Cancer Development and Therapy", Oncogene, 2007, 26 (9)1324-1337.
Backus HHJ, et al., Rb, mcl-1 and p53 Expression Correlate with Clinical Outcome in Patients with Liver Metastases from Colorectal Cancer, Ann. Oncol. 2001, 12:779-785.
Belmar Johannes, et al., "Small molecule Mcl-1 inhibitors for the treatment of cancer", Pharmacol. Ther., 2015, 145:76-84.
Brotin Emilie, et al., "Bcl-xL and MCL-1 constitute pertinent targets in ovarian carcinoma and their concomitant inhibition is sufficient to induce apoptosis", Int. J. Cancer, 2010, 126:885-895.
Bruncko Milan, et al., "Structure-Guided Design of a Series of MCL-1 Inhibitors with High Affinity and Selectivity", J. Med. Chem., 2015, 58:2180-2194.
Burke Jason P, et al., "Discovery of Tricyclic Indoles that Potently Inhibit Mcl-1 Using Fragment-Based Methods and Structure-Based Design", J. Med. Chem., 2015, 58(9):3794-3805.

(Continued)

*Primary Examiner* — D Margaret M Seaman
(74) *Attorney, Agent, or Firm* — Morgan, Lewis & Bockius LLP

(57) ABSTRACT

Compounds that inhibit Myeloid Cell Leukemia-1 (Mcl-1) oncoprotein, and methods of using the same, are provided for treating disease.

20 Claims, 23 Drawing Sheets

(56) References Cited

OTHER PUBLICATIONS

Chen Lijia, et al., "Small-Molecule Inhibitors of the Mcl-1 Oncoprotein", Austin J. Anal. Pharm. Chem., 2014, 1(3):1015 (6 pages).
Chetoui Nizar, et al., "Down-Regulation of Mcl-1 by Small Interfering RNA Sensitizes Resistant Melanoma Cells to Fas-Mediated Apoptosis", Mol. Cancer Res., 2008, 6(1):42-52.
Cohen Nicole A, et al., "A Competitive Stapled Peptide Screen Identifies a Selective Small Molecule that Overcomes MCL-1-dependent Leukemia Cell Survival", Chem. Biol., 2012, 19(9):1175-1186.
Ding Qingqing, et al., "Myeloid Cell Leukemia-1 Inversely Correlates with Glycogen Synthase Kinase-3beta Activity and Associates with Poor Prognosis in Human Breast Cancer", Cancer Res., 2007, 67(10):4564-4571.
Ding Xiao, et al., "De Novo Design, Synthesis and Evaluation of Benzylpiperazine Derivatives as Highly Selective Binders of Mcl-1", Chem. Med. Chem., 2013, 8:1986-2014.
Friberg Anders, et al., "Discovery of Potent Myeloid Cell Leukemia 1 (Mcl-1) Inhibitors Using Fragment-Based Methods and Structure-Based Design", J. Med. Chem., 2013, 56(1)15-30.
Glaser Stefan P, et al., "Anti-Apoptotic Mcl-1 is Essential for the Development and Sustained Growth of Acute Myeloid Leukemia", Genes Dev., 2012, 26:120-125.
Gloaguen Celine, et al., "First Evidence That Oligopyridines, alpha-Helix Foldamers, Inhibit Mcl-1 and Sensitize Ovarian Carcinoma Cells to Bcl-xL-Targeting Strategies", J. Med. Chem., 2015, 58:1644-1668.
Leverson JD, et al., "Potent and Selective Small-Molecule Mcl-1 Inhibitors Demonstrate on-Target Cancer Cell Killing Activity as Single Agents and in Combination with ABT-263 (Navitoclax)", Cell. Death Dis., 2015, 6: e1590; doi:10.1038/cddis.2014.561, (11 pages).
Petros Andrew M. et al., "Fragment-Based Discovery of Potent Inhibitors of the Anti-Apoptotic MCL-1 Protein", Bioorg. Med. Chem. Lett., 2014, 24:1484-1488.

Richard David J. et al., "Hydroxyquinoline-Derived Compounds and Analoguing of Selective MCL-1 Inhibitors Using a Functional Biomarker", Bioorg. Med. Chem., 2013, 21(21), (17 pages).
Song Lanxi, et al., "Mcl-1 Regulates Survival and Sensitivity to Diverse Apoptotic Stimuli in Human Non-Small Cell Lung Cancer Cells", Cancer Biology & Therapy, 2005, 4(3):267-276.
Stewart Michelle L, et al., "The MCL-1 BH3 Helix is an Exclusive MCL-1 inhibitior and Apoptosis Sensitizer", Nat. Chem. Biol., 2010, 6(8):595-601.
Tanaka Yuta, et al., "Discovery of Potent Mcl-1/Bcl-xL Dual Inhibitors by Using a Hybridization Strategy Based on Structural Analysis of Target Proteins", J. Med. Chem., 2013, 56:9635-9645.
Van Delft Mark F, et al. "The BH3 Mimetic ABT-737 Targets Selective Bcl-2 Proteins and Efficiently Induces Apoptosis via Bak/Bax if Mcl-1 is Neutralized", Cancer Cell, 2006, 10(5):389-399.
Warr Matthew R, et al., "Unique Biology of Mcl-1: Therapeutic Opportunities in Cancer", Curr. Mol. Med., 2008, 8: 138-147.
Wei San-Hua, et al., "Inducing Apoptosis and Enhancing Chemosensitivity to Gemcitabine via RNA Interference Targeting Mcl-1 Gene in Pancreatic Carcinoma Cell", Cancer Chemother. Pharmacol., 2008, 62:1055-1064.
Wenzel S-S, et al., "MCL1 Is Deregulated in Subgroups of Diffuse Large B-Cell Lymphoma", Leukemia, 2013, 27: 1381-1390.
Yang Chao-Yie, et al., "Analysis of Flexibility and Hotspots in Bcl-xL and Mcl-1 Proteins for the Design of Selective Small-Molecule Inhibitors", ACS Med. Chem. Lett., 2012, 3:308-312.
Zhang Zhichao, et al., "Novel Soluble Myeloid Cell Leukemia Sequence 1 (Mcl-1) Inhibitor (E,E)-2-(Benzylaminocarbonyl)-3-Styrylacrylonitrile (4g) Developed Using a Fragment-Based Approach", Eur. J. Med. Chem., 2013, 59:141-149.
Zhang Zhichao, et al., "Fragment-Based Design, Synthesis, and Biological Evaluation of N-Substituted-5-(4-Isopropytthiophenol)-2-Hydroxynicotinamide Derivatives as Novel Mcl-1 Inhibitors", Eur. J. Med. Chem., 2013, 60:410-420.

* cited by examiner

SMALL MOLECULE INHIBITORS OF THE MCL-1 ONCOPROTEIN AND USES THEREOF

CROSS-REFERENCE TO RELATED APPLICATIONS

This application is a U.S. National Phase Application under 35 U.S.C. 371 of International Application No. PCT/US2016/41577, filed Jul. 8, 2016, which claims the benefit of U.S. Provisional Patent Application No. 62/191,045, filed Jul. 10, 2015, and U.S. Provisional Patent Application No. 62/191,673, filed Jul. 13, 2015, each of which is incorporated herein by reference in its entirety.

FIELD OF THE INVENTION

The invention relates generally to compounds and methods of using the same for treating conditions characterized by the overexpression or unregulated activity of anti-apoptotic B-Cell Lymphoma (Bcl-2) family proteins and more particularly, but not exclusively, to compounds that bind to the protein Myeloid Cell Leukemia-1 (Mcl-1).

BACKGROUND OF THE INVENTION

The B-Cell Lymphoma-2 (Bcl-2) family of proteins regulates the intrinsic apoptosis pathway that is responsible for programmed cell death. The pathway involves protein-protein interactions (PPIs) between pro-apoptotic members of the Bcl-2 family, such as Bim, Bak and Bad, and anti-apoptotic members, such as Bcl-xL and myeloid cell leukemia-1 (Mcl-1). Through conserved hydrophobic crevices, the anti-apoptotic Bcl-2 proteins capture the BH3 α-helical domains of their pro-apoptotic counterparts, effectively "neutralizing" their cell killing functions. Evasion of apoptosis is a hallmark of cancer, and is also one culprit for the development of resistance to current chemo- and radio-therapies.

Mcl-1 overexpression and/or amplification of the Mcl-1 gene immortalizes cells, and has been observed in many human solid tumors, including pancreatic, prostate, cervical, lung and breast cancers, as well as B-cell lymphomas and hematological cancers, including acute myeloid leukemia (AML). While certain Bcl-$_{xL}$/Bcl-2 inhibitors perform well in clinical trials, their low affinity for Mcl-1 is a contributing factor to the observed resistance of several tumor cell lines. Moreover, the upregulation of Mcl-1 has been directly linked to the reduced efficacy of several FDA-approved anti-cancer chemotherapies. Accordingly, the pharmacologic inhibition of Mcl-1 is an attractive, complementary, and/or adjuvant strategy towards the execution of cancer cells by re-activating apoptosis.

In a similar vein to the inhibition of Bcl-$_{xL}$, the development of synthetic agents capable of disrupting the interaction between Mcl-1 and the BH3 α-helical "death" domains of pro-apoptotic Bcl-2 proteins could "neutralize" Mcl-1's cell survival role.

Provided herein are small molecules that selectively bind Mcl-1 with high affinity and methods for using such compounds to treat diseases characterized by overexpression or unregulated anti-apoptotic B-cell lymphoma-2 (Bcl-2) family proteins.

SUMMARY OF THE INVENTION

In an embodiment, the invention includes compounds of formula (I):

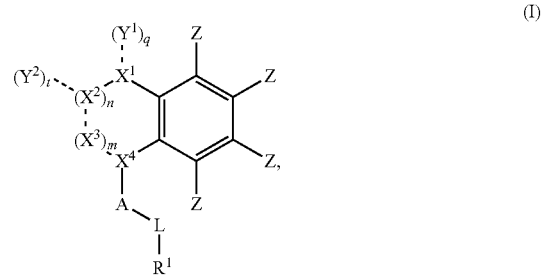

wherein $X^1$ may be a substituent selected from the group consisting of H, C, CH, $CH_2$, and $CH_3$;

$X^2$ may be a substituent selected from the group consisting of C, CH, and $CH_2$, and n=0 or 1;

$X^3$ may be a substituent selected from the group consisting of N, CH, and $CH_2$, and m=0 or 1;

$X^4$ may be a substituent selected from the group consisting of C, CH, N, and $NR^2$, wherein the dashed lines can independently represent a single bond, a double bond, or no bond;

A may be a substituent selected from the group consisting of S(=O), S(=O)$_2$, C(=O), C(=O)O, and $CH_2$;

L may be a bond or an $NR^3$ substituent;

each Z may independently represent a substituent selected from the group consisting of H, halo, cyano, hydroxy, nitro, and optionally substituted acylsulfonamide, alkyl, alkylaryl, alkylhetaryl, alkylheterocycloalkyl, alkenyl, alkynyl, alkenyl-cycloalkyl, alkynyl-cycloalkyl, carbonyl, carboxaldehyde, carboxyl, cycloalkyl, cycloalkyl-alkenyl, cycloalkyl-heterocycloalkyl, cycloalkyl-heteroaryl, alkoxy, alkoxycarbonyl, acyl, acyloxy, amino, amido, aryl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroaryl, heteroarylalkyl, heterocycloalkyl, hydroxamate, and heterocycloalkyl;

$Y^1$ and $Y^2$ each may independently represent a substituent selected from the group consisting of H, OR$^4$, CONR$^4$OR$^4$, CONR$^4$R$^4$, CONR$^4$—SO$_2$R$^4$, COOR$^4$, and optionally substituted alkyl, aryl, and heteroaryl, and q=0 or 1, and t=0 or 1;

each $R^1$, $R^2$, $R^3$, and $R^4$ may independently represent a substituent selected from the group consisting of H and optionally substituted alkyl, cycloalkyl, sulfinyl, sulfonyl, and aryl; and $R^1$ and $R^3$ may, taken together, comprise an optionally substituted cycloalkyl or heterocycloalkyl ring; and pharmaceutically acceptable salts, solvates, hydrates, cocrystals, or prodrugs thereof.

In some embodiments, the compounds of formula (I) may include the proviso that if (1) $X^1$, $X^2$, $X^3$, and $X^4$ together form part of a benzene ring, (2) $Y^1$ is OH or O-alkyl and q=1, (3) A is S(=O)$_2$ or C(=O), and (4) L is NR$^3$, then $Y^2$ is COOR$^4$ and t=1.

In some embodiments of formula (I), the dashed line between $X^1$ and $X^2$ may represent a double bond and the dashed line between $X^3$ and $X^4$ may represent a double bond. Accordingly, in some embodiments, $X^1$, $X^2$, $X^3$, and $X^4$ may represent a portion of an aromatic ring.

In some embodiments of formula (I) $Y^1$ and $Y^2$ may collectively represent a carboxylic acid bioisostere which may, for example, be an optionally substituted alkyl ester, an acylsulfonamide, a hydroxamic acid, a hydroxamate, a tetrazole, a hydroxyisoxazole, an isoxazol-3-one, or a sulfonamide.

In some embodiments, the compounds of formula (I) may include one or more of:

4-(N-(4-(4-chloro-3,5-dimethyl phenoxy)phenyl)sulfamoyl)-1-hydroxy-2-naphthoic acid, 4-(N-(4-(4-chloro-3,5-dimethylphenoxy)phenyl)-N-isobutylsulfamoyl)-1-hydroxy-2-naphthoic acid, 4-(N-(4-(4-chloro-3,5-dimethylphenoxy)phenyl)-N-cyclopentylsulfamoyl)-1-hydroxy-2-naphthoic acid, 4-(N-benzyl-N-(4-(4-chloro-3,5-dimethylphenoxy)phenyl)sulfamoyl)-1-hydroxy-2-naphthoic acid, 4-(N-benzylsulfamoyl)-1-hydroxy-2-naphthoic acid, 4-(N-(4-chlorophenyl)sulfamoyl)-1-hydroxy-2-naphthoic acid, 4-(N-(3-chlorobenzyl)sulfamoyl)-1-hydroxy-2-naphthoic acid, 1-hydroxy-4-(N-(4-(trifluoromethyl)phenyl)sulfamoyl)-2-naphthoic acid, 4-(N-(2-chlorobenzyl)sulfamoyl)-1-hydroxy-2-naphthoic acid, 1-hydroxy-4-(N-(p-tolyl)sulfamoyl)-2-naphthoic acid, 1-hydroxy-4-(N-(4-isopropylphenyl)sulfamoyl)-2-naphthoic acid, 4-(N-(3-cyanophenyl)sulfamoyl)-1-hydroxy-2-naphthoic acid, 4-(N-([1,1'-biphenyl]-2-yl)sulfamoyl)-1-hydroxy-2-naphthoic acid, 4-(N-([1,1'-biphenyl]-4-yl)sulfamoyl)-1-hydroxy-2-naphthoic acid, 4-(N-([1,1'-biphenyl]-3-yl)sulfamoyl)-1-hydroxy-2-naphthoic acid, 1-hydroxy-4-((4-phenylpiperazin-1-yl)sulfonyl)-2-naphthoic acid, 1-hydroxy-4-(N-(naphthalen-1-yl)sulfamoyl)-2-naphthoic acid, 1-hydroxy-4-(N-(naphthalen-2-yl)sulfamoyl)-2-naphthoic acid, 4-(N-(4-cyanophenyl)sulfamoyl)-1-hydroxy-2-naphthoic acid, 1-hydroxy-4-(N-(4-methoxyphenyl)sulfamoyl)-2-naphthoic acid, 1-hydroxy-4-(N-(2-(trifluoromethyl)phenyl)sulfamoyl)-2-naphthoic acid, 1-hydroxy-4-(N-(4-nitrophenyl)sulfamoyl)-2-naphthoic acid, 4-(N-(2-bromophenyl)sulfamoyl)-1-hydroxy-2-naphthoic acid, 4-(N-(3-bromophenyl)sulfamoyl)-1-hydroxy-2-naphthoic acid, 4-(N-(cyclohexylmethyl)sulfamoyl)-1-hydroxy-2-naphthoic acid, methyl 4-(N-(4-bromophenyl)-N-isobutylsulfamoyl)-1-methoxy-2-naphthoate, methyl 4-(N-(4-bromophenyl)-N-isobutylsulfamoyl)-1-hydroxy-2-naphthoate, 4-(N-(4-bromophenyl)-N-isobutylsulfamoyl)-1-methoxy-2-naphthoic acid, 1-hydroxy-4-(piperidin-1-ylsulfonyl)-2-naphthoic acid, 4-(N-(4-chlorobenzyl)sulfamoyl)-1-hydroxy-2-naphthoic acid, 4-(N-(2,4-dibromophenyl)sulfamoyl)-1-hydroxy-2-naphthoic acid, 1-hydroxy-4-(N-(4-isopropoxyphenyl)sulfamoyl)-2-naphthoic acid, 1-hydroxy-4-(N-(4-(naphthalen-1-yloxy)phenyl)sulfamoyl)-2-naphthoic acid, 4-(N,N-dimethylsulfamoyl)-1-hydroxy-2-naphthoic acid, 1-hydroxy-4-(N-(4-phenoxyphenyl)sulfamoyl)-2-naphthoic acid, 4-(N-(4-(3-bromophenoxy)phenyl)sulfamoyl)-1-hydroxy-2-naphthoic acid, 1-hydroxy-4-(N-(4-(p-tolyloxy)phenyl)sulfamoyl)-2-naphthoic acid, 4-(N-(4-(2,4-dichlorophenoxy)phenyl)sulfamoyl)-1-hydroxy-2-naphthoic acid, 4-((4-benzylpiperazin-1-yl)sulfonyl)-1-hydroxy-2-naphthoic acid, 4-(N-(4-(4-chlorophenoxy)phenyl)sulfamoyl)-1-hydroxy-2-naphthoic acid, 4-(N-(4-(3,5-dimethylphenoxy)phenyl)sulfamoyl)-1-hydroxy-2-naphthoic acid, 1-hydroxy-4-(N-phenylsulfamoyl)-2-naphthoic acid, 4-(N-(4-bromophenyl)-N-isobutylsulfamoyl)-1-hydroxy-2-naphthoic acid, 1-hydroxy-4-sulfamoyl-2-naphthoic acid, 1-hydroxy-4-(N-isobutyl-N-(4-isopropoxyphenyl)sulfamoyl)-2-naphthoic acid, 4-(N-(4-bromophenyl)sulfamoyl)-1-hydroxy-2-naphthoic acid, methyl 1-hydroxy-4-(N-isobutyl-N-(4-isopropoxyphenyl)sulfamoyl)-2-naphthoate, acetoxymethyl 1-hydroxy-4-(N-isobutyl-N-(4-isopropoxyphenyl)sulfamoyl)-2-naphthoate, 1-(phenylsulfonyl)-1,2,3,4-tetrahydroquinoline-6-carboxylic acid, 1-((4-bromophenyl)sulfonyl)-1,2,3,4-tetrahydroquinoline-6-carboxylic acid, 1-((4-phenoxyphenyl)sulfonyl)-1,2,3,4-tetrahydroquinoline-6-carboxylic acid, 1-(naphthalen-2-ylsulfonyl)-1,2,3,4-tetrahydroquinoline-6-carboxylic acid, 1-((4-(3,5-dimethylphenoxy)phenyl)sulfonyl)-1,2,3,4-tetrahydroquinoline-6-carboxylic acid, 1-((4-(p-tolylthio)phenyl)sulfonyl)-1,2,3,4-tetrahydroquinoline-6-carboxylic acid, 1-((benzyloxy)carbonyl)-1,2,3,4-tetrahydroquinoline-6-carboxylic acid, 1-(isobutoxycarbonyl)-1,2,3,4-tetrahydroquinoline-6-carboxylic acid, 1-(tert-butoxycarbonyl)-1,2,3,4-tetrahydroquinoline-6-carboxylic acid, 1-(4-phenoxybenzyl)-1,2,3,4-tetrahydroquinoline-6-carboxylic acid, 1-(3-(4-chloro-3,5-dimethylphenoxy)propyl)-1,2,3,4-tetrahydroquinoline-6-carboxylic acid, phenyl 1-((4-(4-chloro-3,5-dimethylphenoxy)phenyl)sulfonyl)-1,2,3,4-tetrahydroquinoline-6-carboxylate, 1-((4-(4-chloro-3,5-dimethylphenoxy)phenyl)sulfonyl)-1,2,3,4-tetrahydroquinoline-6-carboxamide, methyl 1-((4-(4-chloro-3,5-dimethylphenoxy)phenyl)sulfonyl)-1,2,3,4-tetrahydroquinoline-6-carboxylate, acetoxymethyl 1-((4-(4-chloro-3,5-dimethylphenoxy)phenyl)sulfonyl)-1,2,3,4-tetrahydroquinoline-6-carboxylate, 1-((4-fluorophenyl)sulfonyl)-1,2,3,4-tetrahydroquinoline-6-carboxylic acid, 1-([1,1'-biphenyl]-4-ylsulfonyl)-1,2,3,4-tetrahydroquinoline-6-carboxylic acid, 1-((4-(p-tolyloxy)phenyl)sulfonyl)-1,2,3,4-tetrahydroquinoline-6-carboxylic acid, 1-(quinolin-8-ylsulfonyl)-1,2,3,4-tetrahydroquinoline-6-carboxylic acid, 1-((5-(dimethylamino)naphthalen-1-yl)sulfonyl)-1,2,3,4-tetrahydroquinoline-6-carboxylic acid, 1-((4-(4-chloro-3,5-dimethylphenoxy)phenyl)sulfonyl)-1,2,3,4-tetrahydroquinoline-6-carboxylic acid, (±)-1-(phenylsulfonyl)-1,2,3,4-tetrahydroquinoline-3-carboxylic acid, (±)-1-((4-bromophenyl)sulfonyl)-1,2,3,4-tetrahydroquinoline-3-carboxylic acid, (±)-1-((4-fluorophenyl)sulfonyl)-1,2,3,4-tetrahydroquinoline-3-carboxylic acid, (±)-1-([1,1'-biphenyl]-4-ylsulfonyl)-1,2,3,4-tetrahydroquinoline-3-carboxylic acid, (±)-1-(naphthalen-2-ylsulfonyl)-1,2,3,4-tetrahydroquinoline-3-carboxylic acid, (±)-1-((4-(4-chloro-3,5-dimethylphenoxy)phenyl)sulfonyl)-1,2,3,4-tetrahydroquinoline-3-carboxylic acid, (±)-1-(3-(4-chloro-3,5-dimethylphenoxy)propyl)-1,2,3,4-tetrahydroquinoline-3-carboxylic acid, 4-(N-isobutylphenylsulfonamido)benzoic acid, 4-(N-isobutyl-[1,1'-biphenyl]-4-ylsulfonamido)benzoic acid, 4-(N-isobutylnaphthalene-2-sulfonamido)benzoic acid, 2-hydroxy-4-(N-isobutylphenylsulfonamido)benzoic acid, 2-hydroxy-4-(N-isobutyl-4-methylphenylsulfonamido)benzoic acid, 4-(4-bromo-N-isobutylphenylsulfonamido)-2-hydroxybenzoic acid, 2-hydroxy-4-(N-isobutyl-4-(p-tolyloxy)phenylsulfonamido)benzoic acid, 4-(4-(3,5-dimethylphenoxy)-N-isobutylphenylsulfonamido)-2-hydroxybenzoic acid, 4-(4-(2,4-dichlorophenoxy)-N-isobutylphenylsulfonamido)-2-hydroxybenzoic acid, 2-hydroxy-4-(4-phenoxyphenylsulfonamido)benzoic acid, 3-(N-isobutylphenylsulfonamido)benzoic acid, 3-(N-isobutyl-4-methylphenylsulfonamido)benzoic acid, 2-hydroxy-5-(N-isobutylnaphthalene-2-sulfonamido)benzoic acid, 5-(4-(4-chloro-3,5-dimethylphenoxy)-N-isobutylphenylsulfonamido)-2-hydroxybenzoic acid, methyl 2-hydroxy-4-(N-isobutyl-4-phenoxyphenylsulfonamido)benzoate, 4-(N-benzyl-4-phenoxyphenylsulfonamido)-2-hydroxy-N-(phenylsulfonyl)benzamide, 4-(N-benzyl-4-phenoxyphenylsulfonamido)-2-hydroxy-N-(methylsulfonyl)benzamide, 4-(N-isobutyl-4-phenoxyphenylsulfonamido)-2-((4-(((3-nitro-4-(((tetrahydro-2H-pyran-4-yl)methyl)amino)phenyl)sulfonyl)carbamoyl)benzyl)oxy)benzoic acid, 4-(4-fluoro-N-isobutylphenylsulfonamido)benzoic acid, 4-(4-(4-chloro-3,5-dimethylphenoxy)-N-isobutylphenylsulfonamido)benzoic acid, 2-hydroxy-4-(N-isobutylnaphthalene-2-sulfonamido)benzoic acid, 2-hydroxy-4-(N-isobutyl-[1,1'-biphenyl]-4-ylsulfonamido)benzoic acid, 4-(N-cyclopentyl-[1,1'-biphenyl]-4-ylsulfonamido)-2-hydroxybenzoic acid, 4-(N-cyclopentylnaphthalene-2-sulfonamido)-2-hydroxybenzoic acid, 4-(4-(4-chloro-3,5-dimethylphenoxy)-N-cyclopentylphenylsulfonamido)-2-hydroxybenzoic acid, 3-(N-isobutylnaphthalene-2-sulfonamido)benzoic acid, 3-(N-isobutyl-[1,1'-biphenyl]-4-ylsulfonamido)benzoic acid, 3-(4-(4-chloro-3,5-dimethylphenoxy)-N-isobutylphenylsulfonamido)benzoic acid, phenyl 2-hydroxy-4-(N-isobutyl-4-phenoxyphenylsulfonamido)benzoate, acetoxymethyl 2-hydroxy-4-(N-isobutyl-4-phenoxyphenylsulfonamido)benzoate, N-(4-cyano-3-hydroxyphenyl)-N-isobutyl-4-phenoxybenzenesulfonamide, 4-(N-benzyl-4-phenoxyphenylsulfonamido)-2-hydroxy-N-((3-nitro-4-(((tetrahydro-2H-pyran-4-yl)methyl)amino)phenyl)sulfonyl)benzamide, 4-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide, 3-(4-(4-chloro-3,5-dimethylphenoxy)-N-isobutylphenylsulfonamido)-2-hydroxybenzoic acid, 4-(4-fluoro-N-isobutylphenylsulfonamido)-2-hydroxybenzoic acid, 2-hydroxy-4-(N-isobutyl-4-phenoxyphenylsulfonamido)benzoic acid, 4-(N-benzyl-[1,1'-biphenyl]-4-ylsulfonamido)-2-hydroxybenzoic acid, 4-(N-benzylnaphthalene-2-sulfonamido)-2-hydroxybenzoic acid, 4-(N-benzyl-4-(4-chloro-3,5-dimethylphenoxy)phenylsulfonamido)-2-hydroxybenzoic acid, 3-(4-fluoro-N-isobutylphenylsulfonamido)benzoic acid, 2-hydroxy-5-(N-isobutylphenylsulfonamido)benzoic acid, 2-hydroxy-5-(N-isobutyl-[1,1'-biphenyl]-4-ylsulfonamido)benzoic acid, N-(4-(2H-tetrazol-5-yl)phenyl)-N-isobutyl-4-phenoxybenzenesulfonamide, N,2-dihydroxy-4-(N-isobutyl-4-phenoxyphenylsulfonamido)benzamide, N-isobutyl-N-(4-(3-oxo-2,3-dihydroisoxazol-5-yl)phenyl)-4-phenoxybenzenesulfonamide, 5-(N-benzyl-4-(4-chloro-3,5-dimethylphenoxy)phenylsulfonamido)-2-hydroxybenzoic acid, 5-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide, and the pharmaceutically acceptable salts, solvates, hydrates, cocrystals, or prodrugs thereof.

In some embodiments, the compounds of formula (I) may include those compounds wherein $R^1$ and $R^3$ each independently represent a substituent selected from the group consisting of optionally substituted alkyl and aryl; and $R^1$ and $R^3$ may, taken together, comprise an optionally substituted cycloalkyl or heterocycloalkyl ring.

In an embodiment, the invention includes compounds of formula (II):

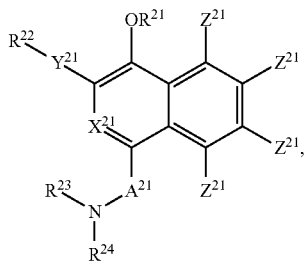

wherein each $R^{21}$ and $R^{22}$ may independently represent a substituent selected from the group consisting of H and optionally substituted alkyl and aryl;

$A^{21}$ may be a substituent selected from the group consisting of $S(=O)$, $S(=O)_2$, $C(=O)$, and $CH_2$;

$X^{21}$ may be CH or N;

each $Z^{21}$ may independently represent a substituent selected from the group consisting of H, halo, cyano, hydroxy, nitro, and optionally substituted acylsulfonamide, alkyl, alkylaryl, alkylhetaryl, alkylheterocycloalkyl, alkenyl, alkynyl, alkenyl-cycloalkyl, alkynyl-cycloalkyl, carbonyl, carboxaldehyde, carboxyl, cycloalkyl, cycloalkyl-alkenyl, cycloalkyl-heterocycloalkyl, cycloalkyl-heteroaryl, alkoxy, alkoxycarbonyl, acyl, acyloxy, amino, amido, aryl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroaryl, heteroarylalkyl, heterocycloalkyl, hydroxamate, sulfanyl, sulfinyl, sulfonyl, sulfonamidyl, sulfoxyl, and sulfonate;

$Y^{21}$ may be a substituent selected from the group consisting of —C(O)O—, —CONR$^{22}$—, —CONR$^{22}$—SO$_2$—, —CONR$^{22}$O—,

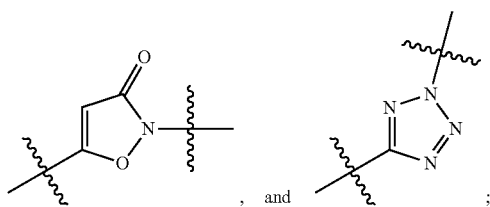 [SMILES: *c1cc(=O)n(*)o1 ; *c1nnn(*)n1]

, and ;

$R^{23}$ and $R^{24}$ each may independently represent a substituent selected from the group consisting of H and optionally substituted alkyl and aryl; and $R^{23}$ and $R^{24}$ may, taken together, comprise an optionally substituted cycloalkyl or heterocycloalkyl ring;

$R^{25}$ may be a substituent selected from the group consisting of H and optionally substituted alkyl, aryl, sulfinyl, and sulfonyl; and pharmaceutically acceptable salts, solvates, hydrates, cocrystals, or prodrugs thereof.

In some embodiments, $Y^{21}$ and $R^{22}$ may collectively represent an optionally substituted acylsulfonamide.

In some embodiments of formula (II) $Y^{21}$ and $R^{22}$ may collectively represent a carboxylic acid bioisostere which may, for example, be an optionally substituted alkyl ester, an acylsulfonamide, a hydroxamic acid, a hydroxamate, a tetrazole, a hydroxyisoxazole, an isoxazol-3-one, or a sulfonamide.

In some embodiments, the compounds of formula (II) may include one or more of:

4-(N-(4-(4-chloro-3,5-dimethyl phenoxy)phenyl)sulfamoyl)-1-hydroxy-2-naphthoic acid,
4-(N-(4-(4-chloro-3,5-dimethylphenoxy)phenyl)-N-isobutylsulfamoyl)-1-hydroxy-2-naphthoic acid,
4-(N-(4-(4-chloro-3,5-dimethylphenoxy)phenyl)-N-cyclopentylsulfamoyl)-1-hydroxy-2-naphthoic acid,
4-(N-benzyl-N-(4-(4-chloro-3,5-dimethylphenoxy)phenyl)sulfamoyl)-1-hydroxy-2-naphthoic acid,
4-(N-benzylsulfamoyl)-1-hydroxy-2-naphthoic acid,
4-(N-(4-chlorophenyl)sulfamoyl)-1-hydroxy-2-naphthoic acid,
4-(N-(3-chlorobenzyl)sulfamoyl)-1-hydroxy-2-naphthoic acid,
1-hydroxy-4-(N-(4-(trifluoromethyl)phenyl)sulfamoyl)-2-naphthoic acid,
4-(N-(2-chlorobenzyl)sulfamoyl)-1-hydroxy-2-naphthoic acid,
1-hydroxy-4-(N-(p-tolyl)sulfamoyl)-2-naphthoic acid,
1-hydroxy-4-(N-(4-isopropylphenyl)sulfamoyl)-2-naphthoic acid,
4-(N-(3-cyanophenyl)sulfamoyl)-1-hydroxy-2-naphthoic acid,
4-(N-([1,1'-biphenyl]-2-yl)sulfamoyl)-1-hydroxy-2-naphthoic acid,
4-(N-([1,1'-biphenyl]-4-yl)sulfamoyl)-1-hydroxy-2-naphthoic acid,
4-(N-([1,1'-biphenyl]-3-yl)sulfamoyl)-1-hydroxy-2-naphthoic acid,
1-hydroxy-4-((4-phenylpiperazin-1-yl)sulfonyl)-2-naphthoic acid,
1-hydroxy-4-(N-(naphthalen-1-yl)sulfamoyl)-2-naphthoic acid,
1-hydroxy-4-(N-(naphthalen-2-yl)sulfamoyl)-2-naphthoic acid,
4-(N-(4-cyanophenyl)sulfamoyl)-1-hydroxy-2-naphthoic acid,
1-hydroxy-4-(N-(4-methoxyphenyl)sulfamoyl)-2-naphthoic acid,
1-hydroxy-4-(N-(2-(trifluoromethyl)phenyl)sulfamoyl)-2-naphthoic acid,
1-hydroxy-4-(N-(4-nitrophenyl)sulfamoyl)-2-naphthoic acid,
4-(N-(2-bromophenyl)sulfamoyl)-1-hydroxy-2-naphthoic acid,
4-(N-(3-bromophenyl)sulfamoyl)-1-hydroxy-2-naphthoic acid,
4-(N-(cyclohexylmethyl)sulfamoyl)-1-hydroxy-2-naphthoic acid,
methyl 4-(N-(4-bromophenyl)-N-isobutylsulfamoyl)-1-methoxy-2-naphthoate,
methyl 4-(N-(4-bromophenyl)-N-isobutylsulfamoyl)-1-hydroxy-2-naphthoate,
4-(N-(4-bromophenyl)-N-isobutylsulfamoyl)-1-methoxy-2-naphthoic acid,
1-hydroxy-4-(piperidin-1-ylsulfonyl)-2-naphthoic acid,
4-(N-(4-chlorobenzyl)sulfamoyl)-1-hydroxy-2-naphthoic acid,
4-(N-(2,4-dibromophenyl)sulfamoyl)-1-hydroxy-2-naphthoic acid,
1-hydroxy-4-(N-(4-isopropoxyphenyl)sulfamoyl)-2-naphthoic acid,
1-hydroxy-4-(N-(4-(naphthalen-1-yloxy)phenyl)sulfamoyl)-2-naphthoic acid,
4-(N,N-dimethylsulfamoyl)-1-hydroxy-2-naphthoic acid, 1-hydroxy-4-(N-(4-phenoxyphenyl)sulfamoyl)-2-naphthoic acid,
4-(N-(4-(3-bromophenoxy)phenyl)sulfamoyl)-1-hydroxy-2-naphthoic acid,
1-hydroxy-4-(N-(4-(p-tolyloxy)phenyl)sulfamoyl)-2-naphthoic acid,
4-(N-(4-(2,4-dichlorophenoxy)phenyl)sulfamoyl)-1-hydroxy-2-naphthoic acid,
4-((4-benzylpiperazin-1-yl)sulfonyl)-1-hydroxy-2-naphthoic acid,
4-(N-(4-(4-chlorophenoxy)phenyl)sulfamoyl)-1-hydroxy-2-naphthoic acid,
4-(N-(4-(3,5-dimethylphenoxy)phenyl)sulfamoyl)-1-hydroxy-2-naphthoic acid,
1-hydroxy-4-(N-phenylsulfamoyl)-2-naphthoic acid,
4-(N-(4-bromophenyl)-N-isobutylsulfamoyl)-1-hydroxy-2-naphthoic acid,
1-hydroxy-4-sulfamoyl-2-naphthoic acid,
1-hydroxy-4-(N-isobutyl-N-(4-isopropoxyphenyl)sulfamoyl)-2-naphthoic acid,
4-(N-(4-bromophenyl)sulfamoyl)-1-hydroxy-2-naphthoic acid,
methyl 1-hydroxy-4-(N-isobutyl-N-(4-isopropoxyphenyl)sulfamoyl)-2-naphthoate,
acetoxymethyl 1-hydroxy-4-(N-isobutyl-N-(4-isopropoxyphenyl)sulfamoyl)-2-naphthoate, and the pharmaceutically acceptable salts, solvates, hydrates, cocrystals, or prodrugs thereof.

In some embodiments, the compounds of formula (II) may include those compounds wherein $R^{23}$ and $R^{24}$ each independently represent a substituent selected from the group consisting of optionally substituted alkyl and aryl; and $R^{23}$ and $R^{24}$ may, taken together, comprise an optionally substituted cycloalkyl or heterocycloalkyl ring.

In an embodiment, the invention includes one or more compounds of formula (IIIa) or formula (IIIb):

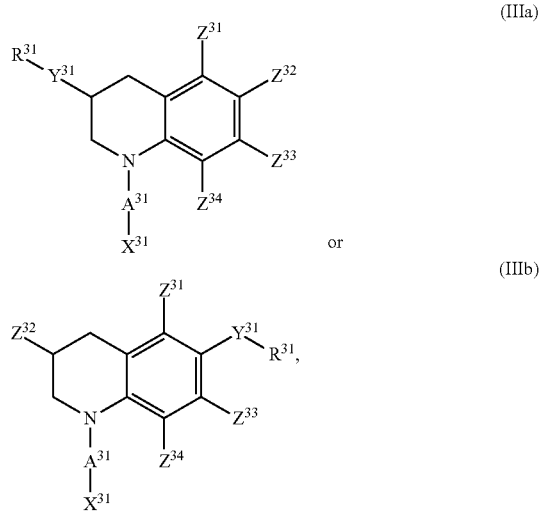

wherein each $R^{31}$ may independently represent a substituent selected from the group consisting of H and an optionally substituted alkyl and aryl;
$A^{31}$ may be a bond or a substituent selected from the group consisting of S(=O), S(=O)$_2$, C(=O), C(=O)O, and CH$_2$;
$X^{31}$ may be a substituent selected from the group consisting of optionally substituted alkyl and aryl;

$Y^{31}$ may be a substituent selected from the group consisting of —C(O)O—, —CONR$^{31}$—, —CONR$^{31}$—SO$_2$—, —CONR$^{31}$O—,

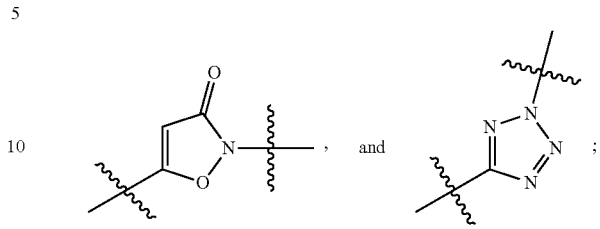

$Z^{31}$, $Z^{32}$, $Z^{33}$, and $Z^{34}$ each may independently represent a substituent selected from the group consisting of H, halo, cyano, hydroxy, nitro, and optionally substituted acylsulfonamide, alkyl, alkylaryl, alkylhetaryl, alkylheterocycloalkyl, alkenyl, alkynyl, alkenyl-cycloalkyl, alkynyl-cycloalkyl, carboxaldehyde, carbonyl, carboxyl, cycloalkyl, cycloalkyl-alkenyl, cycloalkyl-heterocycloalkyl, cycloalkyl-heteroaryl, alkoxy, alkoxycarbonyl, acyl, acyloxy, amino, amido, aryl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroaryl, heteroarylalkyl, heterocycloalkyl, hydroxamate, sulfanyl, sulfinyl, sulfonyl, sulfonamidyl, sulfoxyl, and sulfonate; and
pharmaceutically acceptable salts, solvates, hydrates, cocrystals, or prodrugs thereof.

In some embodiments, $Y^{31}$ and $R^{31}$ may collectively represent an optionally substituted acylsulfonamide.

In some embodiments of formula (IIIa) and formula (IIIb) $Y^{31}$ and $R^{31}$ may collectively represent a carboxylic acid bioisostere which may, for example, be an optionally substituted alkyl ester, an acylsulfonamide, a hydroxamic acid, a hydroxamate, a tetrazole, a hydroxyisoxazole, an isoxazol-3-one, or a sulfonamide.

In some embodiments, the compound of formula (IIIa) or formula (IIIb) may include one or more of:
1-(phenylsulfonyl)-1,2,3,4-tetrahydroquinoline-6-carboxylic acid,
1-((4-bromophenyl)sulfonyl)-1,2,3,4-tetrahydroquinoline-6-carboxylic acid,
1-((4-phenoxyphenyl)sulfonyl)-1,2,3,4-tetrahydroquinoline-6-carboxylic acid,
1-(naphthalen-2-ylsulfonyl)-1,2,3,4-tetrahydroquinoline-6-carboxylic acid,
1-((4-(3,5-dimethylphenoxy)phenyl)sulfonyl)-1,2,3,4-tetrahydroquinoline-6-carboxylic acid,
1-((4-(p-tolylthio)phenyl)sulfonyl)-1,2,3,4-tetrahydroquinoline-6-carboxylic acid,
1-((benzyloxy)carbonyl)-1,2,3,4-tetrahydroquinoline-6-carboxylic acid,
1-(isobutoxycarbonyl)-1,2,3,4-tetrahydroquinoline-6-carboxylic acid,
1-(tert-butoxycarbonyl)-1,2,3,4-tetrahydroquinoline-6-carboxylic acid,
1-(4-phenoxybenzyl)-1,2,3,4-tetrahydroquinoline-6-carboxylic acid,
1-(3-(4-chloro-3,5-dimethylphenoxy)propyl)-1,2,3,4-tetrahydroquinoline-6-carboxylic acid,
phenyl 1-((4-(4-chloro-3,5-dimethylphenoxy)phenyl)sulfonyl)-1,2,3,4-tetrahydroquinoline-6-carboxylate,
1-((4-(4-chloro-3,5-dimethylphenoxy)phenyl)sulfonyl)-1,2,3,4-tetrahydroquinoline-6-carboxamide, methyl 1-((4-(4-chloro-3,5-dimethylphenoxy)phenyl)sulfonyl)-1,2,3,4-tetrahydroquinoline-6-carboxylate, acetoxymethyl 1-((4-(4-chloro-3,5-dimethylphenoxy)phenyl)sulfonyl)-1,2,3,4-tetrahydroquinoline-6-carboxylate, 1-((4-fluorophenyl)sulfonyl)-1,2,3,4-tetrahydroquinoline-6-carboxylic acid, 1-([1,1'-biphenyl]-4-ylsulfonyl)-1,2,3,4-tetrahydroquinoline-6-carboxylic acid, 1-((4-(p-tolyloxy)phenyl)sulfonyl)-1,2,3,4-tetrahydroquinoline-6-carboxylic acid, 1-(quinolin-8-ylsulfonyl)-1,2,3,4-tetrahydroquinoline-6-carboxylic acid, 1-((5-(dimethylamino)naphthalen-1-yl)sulfonyl)-1,2,3,4-tetrahydroquinoline-6-carboxylic acid, 1-((4-(4-chloro-3,5-dimethylphenoxy)phenyl)sulfonyl)-1,2,3,4-tetrahydroquinoline-6-carboxylic acid, (±)-1-(phenylsulfonyl)-1,2,3,4-tetrahydroquinoline-3-carboxylic acid, (±)-1-((4-bromophenyl)sulfonyl)-1,2,3,4-tetrahydroquinoline-3-carboxylic acid, (±)-1-((4-fluorophenyl)sulfonyl)-1,2,3,4-tetrahydroquinoline-3-carboxylic acid, (±)-1-([1,1'-biphenyl]-4-ylsulfonyl)-1,2,3,4-tetrahydroquinoline-3-carboxylic acid, (±)-1-(naphthalen-2-ylsulfonyl)-1,2,3,4-tetrahydroquinoline-3-carboxylic acid, (±)-1-((4-(4-chloro-3,5-dimethylphenoxy)phenyl)sulfonyl)-1,2,3,4-tetrahydroquinoline-3-carboxylic acid, (±)-1-(3-(4-chloro-3,5-dimethylphenoxy)propyl)-1,2,3,4-tetrahydroquinoline-3-carboxylic acid, 4-(N-isobutylphenylsulfonamido)benzoic acid, and the pharmaceutically acceptable salts, solvates, hydrates, cocrystals, or prodrugs thereof.

In an embodiment, the invention includes compounds of formula (IV):

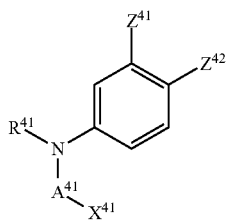

(IV)

wherein $R^{41}$ may be a substituent selected from the group consisting of H and optionally substituted alkyl, aryl, and cycloalkyl;

$Z^{41}$ and $Z^{42}$ each may independently represent a substituent selected from the group consisting of H, cyano, $OR^{42}$, $COOR^{42}$, $CONR^{42}OR^{42}$, $CONR^{42}R^{42}$, $CON(R^{42})$—$S(O)_2R^{42}$,

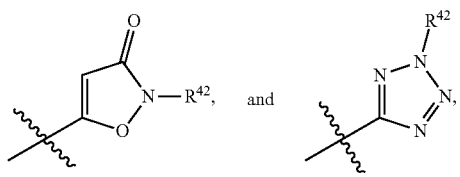

and optionally substituted alkyl and aryl;

each $R^{42}$ may independently represent a substituent selected from the group consisting of H and optionally substituted alkyl and aryl;

$A^{41}$ may be a bond or a substituent selected from the group consisting of $S(=O)$, $S(=O)_2$, and $C(=O)$;

$X^{41}$ may be a substituent selected from the group consisting of optionally substituted alkyl, aryl, cycloalkyl, and heterocycloalkyl; and pharmaceutically acceptable salts, solvates, hydrates, cocrystals, or prodrugs thereof.

In some embodiments of formula (IV) $Z^{41}$ and/or $Z^{42}$ may represent a carboxylic acid bioisostere which may, for example, be an optionally substituted alkyl ester, an acylsulfonamide, a hydroxamic acid, a hydroxamate, a tetrazole, a hydroxyisoxazole, an isoxazol-3-one, or a sulfonamide.

In some embodiments, the compound of formula (IV) may include one or more of:

4-(N-isobutyl-[1,1'-biphenyl]-4-ylsulfonamido)benzoic acid, 4-(N-isobutylnaphthalene-2-sulfonamido)benzoic acid, 2-hydroxy-4-(N-isobutylphenylsulfonamido)benzoic acid, 2-hydroxy-4-(N-isobutyl-4-methylphenylsulfonamido)benzoic acid, 4-(4-bromo-N-isobutylphenylsulfonamido)-2-hydroxybenzoic acid, 2-hydroxy-4-(N-isobutyl-4-(p-tolyloxy)phenylsulfonamido)benzoic acid, 4-(4-(3,5-dimethylphenoxy)-N-isobutylphenylsulfonamido)-2-hydroxybenzoic acid, 4-(4-(2,4-dichlorophenoxy)-N-isobutylphenylsulfonamido)-2-hydroxybenzoic acid, 2-hydroxy-4-(4-phenoxyphenylsulfonamido)benzoic acid, 3-(N-isobutylphenylsulfonamido)benzoic acid, 3-(N-isobutyl-4-methylphenylsulfonamido)benzoic acid, 2-hydroxy-5-(N-isobutylnaphthalene-2-sulfonamido)benzoic acid, 5-(4-(4-chloro-3,5-dimethylphenoxy)-N-isobutylphenylsulfonamido)-2-hydroxybenzoic acid, methyl 2-hydroxy-4-(N-isobutyl-4-phenoxyphenylsulfonamido)benzoate, 4-(N-benzyl-4-phenoxyphenylsulfonamido)-2-hydroxy-N-(phenylsulfonyl)benzamide, 4-(N-benzyl-4-phenoxyphenylsulfonamido)-2-hydroxy-N-(methylsulfonyl)benzamide, 4-(N-isobutyl-4-phenoxyphenylsulfonamido)-2-((4-(((3-nitro-4-(((tetrahydro-2H-pyran-4-yl)methyl)amino)phenyl)sulfonyl)carbamoyl)benzyl)oxy)benzoic acid, 4-(4-fluoro-N-isobutylphenylsulfonamido)benzoic acid, 4-(4-(4-chloro-3,5-dimethylphenoxy)-N-isobutylphenylsulfonamido)benzoic acid, 2-hydroxy-4-(N-isobutylnaphthalene-2-sulfonamido)benzoic acid, 2-hydroxy-4-(N-isobutyl-[1,1'-biphenyl]-4-ylsulfonamido)benzoic acid, 4-(N-cyclopentyl-[1,1'-biphenyl]-4-ylsulfonamido)-2-hydroxybenzoic acid, 4-(N-cyclopentylnaphthalene-2-sulfonamido)-2-hydroxybenzoic acid, 4-(4-(4-chloro-3,5-dimethylphenoxy)-N-cyclopentylphenylsulfonamido)-2-hydroxybenzoic acid, 3-(N-isobutylnaphthalene-2-sulfonamido)benzoic acid, 3-(N-isobutyl-[1,1'-biphenyl]-4-ylsulfonamido)benzoic acid, 3-(4-(4-chloro-3,5-dimethylphenoxy)-N-isobutylphenyl-sulfonamido)benzoic acid, phenyl 2-hydroxy-4-(N-isobutyl-4-phenoxyphenylsulfonamido)benzoate, acetoxymethyl 2-hydroxy-4-(N-isobutyl-4-phenoxyphenylsulfonamido)benzoate, N-(4-cyano-3-hydroxyphenyl)-N-isobutyl-4-phenoxybenzenesulfonamide, 4-(N-benzyl-4-phenoxyphenylsulfonamido)-2-hydroxy-N-((3-nitro-4-(((tetrahydro-2H-pyran-4-yl)methyl)amino)phenyl)sulfonyl)benzamide, 4-(N-benzyl-4-(4-chloro-3,5-dimethylphenoxy)phenyl-sulfonamido)-2-hydroxy-N-((3-nitro-4-(((tetrahydro-2H-pyran-4-yl)methyl)amino)phenyl)sulfonyl)benzamide, 3-(4-(4-chloro-3,5-dimethylphenoxy)-N-isobutylphenyl-sulfonamido)-2-hydroxybenzoic acid, 4-(4-fluoro-N-isobutylphenylsulfonamido)-2-hydroxy-benzoic acid, 2-hydroxy-4-(N-isobutyl-4-phenoxyphenylsulfonamido)benzoic acid, 4-(N-benzyl-[1,1'-biphenyl]-4-ylsulfonamido)-2-hydroxybenzoic acid, 4-(N-benzylnaphthalene-2-sulfonamido)-2-hydroxybenzoic acid, 4-(N-benzyl-4-(4-chloro-3,5-dimethylphenoxy)phenyl-sulfonamido)-2-hydroxybenzoic acid, 3-(4-fluoro-N-isobutylphenylsulfonamido)benzoic acid, 2-hydroxy-5-(N-isobutylphenylsulfonamido)benzoic acid, 2-hydroxy-5-(N-isobutyl-[1,1'-biphenyl]-4-ylsulfonamido)benzoic acid, N-(4-(2H-tetrazol-5-yl)phenyl)-N-isobutyl-4-phenoxybenzenesulfonamide, N,2-dihydroxy-4-(N-isobutyl-4-phenoxyphenylsulfonamido)benzamide, N-isobutyl-N-(4-(3-oxo-2,3-dihydroisoxazol-5-yl)phenyl)-4-phenoxybenzenesulfonamide, 5-(N-benzyl-4-(4-chloro-3,5-dimethylphenoxy)phenyl-sulfonamido)-2-hydroxybenzoic acid, 5-(N-benzyl-4-(4-chloro-3,5-dimethylphenoxy)phenyl-sulfonamido)-2-hydroxy-N-((3-nitro-4-(((tetrahydro-2H-pyran-4-yl)methyl)amino)phenyl)sulfonyl)benzamide, and the pharmaceutically acceptable salts, solvates, hydrates, cocrystals, or prodrugs thereof.

In some embodiments, the compounds of formula (IV) may include one or more compounds wherein $Z^{41}$ and $Z^{42}$ each may independently represent a substituent selected from the group consisting of $OR^{42}$ and $COOR^{42}$.

In an embodiment, the compound of the invention is selected from the group consisting of:

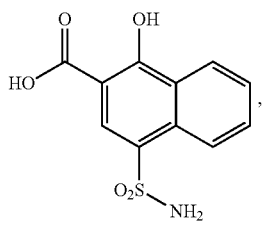

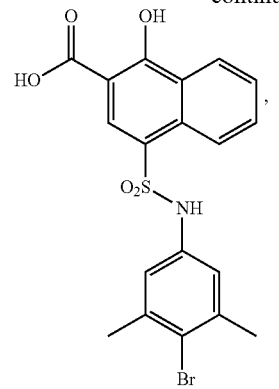

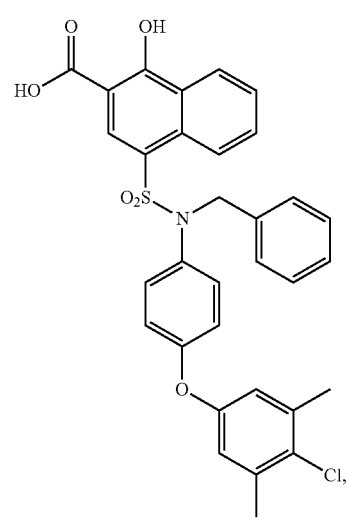

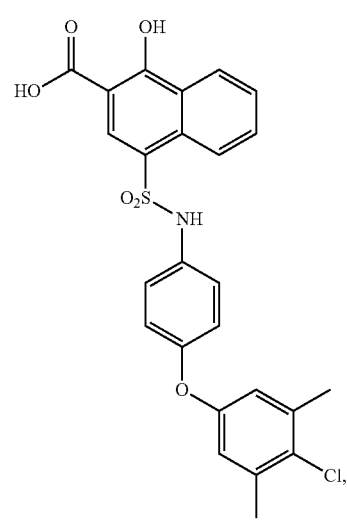

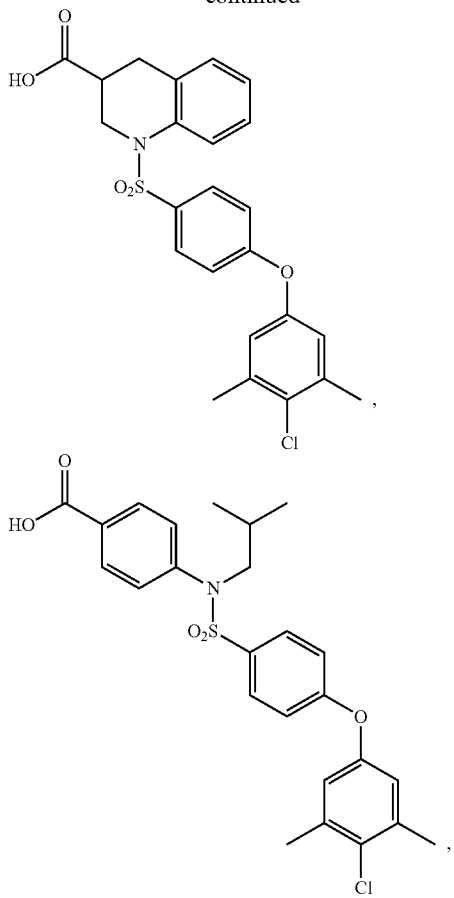

and the pharmaceutically acceptable salts, solvates, hydrates, cocrystals, or prodrugs thereof.

In an embodiment, the invention includes a method of treating a condition alleviated by inhibiting Mcl-1 protein activity in a patient in need of said treatment, the method including administering a therapeutically effective amount of a compound of formula (I) or a pharmaceutically acceptable salt, solvate, hydrate, cocrystal, or prodrug thereof.

In an embodiment, the invention includes a method of treating a condition alleviated by inhibiting Mcl-1 protein activity in a patient in need of said treatment, the method including administering a therapeutically effective amount of a compound of formula (II) or a pharmaceutically acceptable salt, solvate, hydrate, cocrystal, or prodrug thereof.

In an embodiment, the invention includes a method of treating a condition alleviated by inhibiting Mcl-1 protein activity in a patient in need of said treatment, the method including administering a therapeutically effective amount of a compound of formula (IIIa) or a pharmaceutically acceptable salt, solvate, hydrate, cocrystal, or prodrug thereof.

In an embodiment, the invention includes a method of treating a condition alleviated by inhibiting Mcl-1 protein activity in a patient in need of said treatment, the method including administering a therapeutically effective amount of a compound of formula (IIIb) or a pharmaceutically acceptable salt, solvate, hydrate, cocrystal, or prodrug thereof.

In an embodiment, the invention includes a method of treating a condition alleviated by inhibiting Mcl-1 protein activity in a patient in need of said treatment, the method including administering a therapeutically effective amount of a compound of formula (IV) or a pharmaceutically acceptable salt, solvate, hydrate, cocrystal, or prodrug thereof.

A method of treating a condition alleviated by inhibiting Mcl-1 protein activity in a patient in need of said treatment, the method including administering a therapeutically effective amount of one or more compounds selected from the group consisting of:

4-(N-(4-(4-chloro-3,5-dimethyl phenoxy)phenyl)sulfamoyl)-1-hydroxy-2-naphthoic acid, 4-(N-(4-(4-chloro-3,5-dimethylphenoxy)phenyl)-N-isobutylsulfamoyl)-1-hydroxy-2-naphthoic acid, 4-(N-(4-(4-chloro-3,5-dimethylphenoxy)phenyl)-N-cyclopentylsulfamoyl)-1-hydroxy-2-naphthoic acid, 4-(N-benzyl-N-(4-(4-chloro-3,5-dimethylphenoxy)phenyl)sulfamoyl)-1-hydroxy-2-naphthoic acid, 4-(N-benzylsulfamoyl)-1-hydroxy-2-naphthoic acid, 4-(N-(4-chlorophenyl)sulfamoyl)-1-hydroxy-2-naphthoic acid, 4-(N-(3-chlorobenzyl)sulfamoyl)-1-hydroxy-2-naphthoic acid, 1-hydroxy-4-(N-(4-(trifluoromethyl)phenyl)sulfamoyl)-2-naphthoic acid, 4-(N-(2-chlorobenzyl)sulfamoyl)-1-hydroxy-2-naphthoic acid, 1-hydroxy-4-(N-(p-tolyl)sulfamoyl)-2-naphthoic acid, 1-hydroxy-4-(N-(4-isopropylphenyl)sulfamoyl)-2-naphthoic acid, 4-(N-(3-cyanophenyl)sulfamoyl)-1-hydroxy-2-naphthoic acid, 4-(N-([1,1'-biphenyl]-2-yl)sulfamoyl)-1-hydroxy-2-naphthoic acid, 4-(N-([1,1'-biphenyl]-4-yl)sulfamoyl)-1-hydroxy-2-naphthoic acid, 4-(N-([1,1'-biphenyl]-3-yl)sulfamoyl)-1-hydroxy-2-naphthoic acid, 1-hydroxy-4-((4-phenylpiperazin-1-yl)sulfonyl)-2-naphthoic acid, 1-hydroxy-4-(N-(naphthalen-1-yl)sulfamoyl)-2-naphthoic acid, 1-hydroxy-4-(N-(naphthalen-2-yl)sulfamoyl)-2-naphthoic acid, 4-(N-(4-cyanophenyl)sulfamoyl)-1-hydroxy-2-naphthoic acid, 1-hydroxy-4-(N-(4-methoxyphenyl)sulfamoyl)-2-naphthoic acid, 1-hydroxy-4-(N-(2-(trifluoromethyl)phenyl)sulfamoyl)-2-naphthoic acid, 1-hydroxy-4-(N-(4-nitrophenyl)sulfamoyl)-2-naphthoic acid, 4-(N-(2-bromophenyl)sulfamoyl)-1-hydroxy-2-naphthoic acid, 4-(N-(3-bromophenyl)sulfamoyl)-1-hydroxy-2-naphthoic acid, 4-(N-(cyclohexylmethyl)sulfamoyl)-1-hydroxy-2-naphthoic acid, methyl 4-(N-(4-bromophenyl)-N-isobutylsulfamoyl)-1-methoxy-2-naphthoate, methyl 4-(N-(4-bromophenyl)-N-isobutylsulfamoyl)-1-hydroxy-2-naphthoate, 4-(N-(4-bromophenyl)-N-isobutylsulfamoyl)-1-methoxy-2-naphthoic acid, 1-hydroxy-4-(piperidin-1-ylsulfonyl)-2-naphthoic acid, 4-(N-(4-chlorobenzyl)sulfamoyl)-1-hydroxy-2-naphthoic acid, 4-(N-(2,4-dibromophenyl)sulfamoyl)-1-hydroxy-2-naphthoic acid,
1-hydroxy-4-(N-(4-isopropoxyphenyl)sulfamoyl)-2-naphthoic acid,
1-hydroxy-4-(N-(4-(naphthalen-1-yloxy)phenyl)sulfamoyl)-2-naphthoic acid,
4-(N,N-dimethylsulfamoyl)-1-hydroxy-2-naphthoic acid,
1-hydroxy-4-(N-(4-phenoxyphenyl)sulfamoyl)-2-naphthoic acid,
4-(N-(4-(3-bromophenoxy)phenyl)sulfamoyl)-1-hydroxy-2-naphthoic acid,
1-hydroxy-4-(N-(4-(p-tolyloxy)phenyl)sulfamoyl)-2-naphthoic acid,
4-(N-(4-(2,4-dichlorophenoxy)phenyl)sulfamoyl)-1-hydroxy-2-naphthoic acid,
4-((4-benzylpiperazin-1-yl)sulfonyl)-1-hydroxy-2-naphthoic acid,
4-(N-(4-(4-chlorophenoxy)phenyl)sulfamoyl)-1-hydroxy-2-naphthoic acid,
4-(N-(4-(3,5-dimethylphenoxy)phenyl)sulfamoyl)-1-hydroxy-2-naphthoic acid,
1-hydroxy-4-(N-phenylsulfamoyl)-2-naphthoic acid,
4-(N-(4-bromophenyl)-N-isobutylsulfamoyl)-1-hydroxy-2-naphthoic acid,
1-hydroxy-4-sulfamoyl-2-naphthoic acid,
1-hydroxy-4-(N-isobutyl-N-(4-isopropoxyphenyl)sulfamoyl)-2-naphthoic acid,
4-(N-(4-bromophenyl)sulfamoyl)-1-hydroxy-2-naphthoic acid,
methyl 1-hydroxy-4-(N-isobutyl-N-(4-isopropoxyphenyl)sulfamoyl)-2-naphthoate,
acetoxymethyl 1-hydroxy-4-(N-isobutyl-N-(4-isopropoxyphenyl)sulfamoyl)-2-naphthoate,
1-(phenylsulfonyl)-1,2,3,4-tetrahydroquinoline-6-carboxylic acid,
1-((4-bromophenyl)sulfonyl)-1,2,3,4-tetrahydroquinoline-6-carboxylic acid,
1-((4-phenoxyphenyl)sulfonyl)-1,2,3,4-tetrahydroquinoline-6-carboxylic acid,
1-(naphthalen-2-ylsulfonyl)-1,2,3,4-tetrahydroquinoline-6-carboxylic acid,
1-((4-(3,5-dimethylphenoxy)phenyl)sulfonyl)-1,2,3,4-tetrahydroquinoline-6-carboxylic acid,
1-((4-(p-tolylthio)phenyl)sulfonyl)-1,2,3,4-tetrahydroquinoline-6-carboxylic acid,
1-((benzyloxy)carbonyl)-1,2,3,4-tetrahydroquinoline-6-carboxylic acid,
1-(isobutoxycarbonyl)-1,2,3,4-tetrahydroquinoline-6-carboxylic acid,
1-(tert-butoxycarbonyl)-1,2,3,4-tetrahydroquinoline-6-carboxylic acid,
1-(4-phenoxybenzyl)-1,2,3,4-tetrahydroquinoline-6-carboxylic acid,
1-(3-(4-chloro-3,5-dimethylphenoxy)propyl)-1,2,3,4-tetrahydroquinoline-6-carboxylic acid,
phenyl 1-((4-(4-chloro-3,5-dimethylphenoxy)phenyl)sulfonyl)-1,2,3,4-tetrahydroquinoline-6-carboxylate,
1-((4-(4-chloro-3,5-dimethylphenoxy)phenyl)sulfonyl)-1,2,3,4-tetrahydroquinoline-6-carboxamide,
methyl 1-((4-(4-chloro-3,5-dimethylphenoxy)phenyl)sulfonyl)-1,2,3,4-tetrahydroquinoline-6-carboxylate,
acetoxymethyl 1-((4-(4-chloro-3,5-dimethylphenoxy)phenyl)sulfonyl)-1,2,3,4-tetrahydroquinoline-6-carboxylate,
1-((4-fluorophenyl)sulfonyl)-1,2,3,4-tetrahydroquinoline-6-carboxylic acid,
1-([1,1'-biphenyl]-4-ylsulfonyl)-1,2,3,4-tetrahydroquinoline-6-carboxylic acid,
1-((4-(p-tolyloxy)phenyl)sulfonyl)-1,2,3,4-tetrahydroquinoline-6-carboxylic acid,
1-(quinolin-8-ylsulfonyl)-1,2,3,4-tetrahydroquinoline-6-carboxylic acid,
1-((5-(dimethylamino)naphthalen-1-yl)sulfonyl)-1,2,3,4-tetrahydroquinoline-6-carboxylic acid,
1-((4-(4-chloro-3,5-dimethylphenoxy)phenyl)sulfonyl)-1,2,3,4-tetrahydroquinoline-6-carboxylic acid,
(±)-1-(phenylsulfonyl)-1,2,3,4-tetrahydroquinoline-3-carboxylic acid,
(±)-1-((4-bromophenyl)sulfonyl)-1,2,3,4-tetrahydroquinoline-3-carboxylic acid,
(±)-1-((4-fluorophenyl)sulfonyl)-1,2,3,4-tetrahydroquinoline-3-carboxylic acid,
(±)-1-([1,1'-biphenyl]-4-ylsulfonyl)-1,2,3,4-tetrahydroquinoline-3-carboxylic acid,
(±)-1-(naphthalen-2-ylsulfonyl)-1,2,3,4-tetrahydroquinoline-3-carboxylic acid,
(±)-1-((4-(4-chloro-3,5-dimethylphenoxy)phenyl)sulfonyl)-1,2,3,4-tetrahydroquinoline-3-carboxylic acid,
(±)-1-(3-(4-chloro-3,5-dimethylphenoxy)propyl)-1,2,3,4-tetrahydroquinoline-3-carboxylic acid,
4-(N-isobutylphenylsulfonamido)benzoic acid,
4-(N-isobutyl-[1,1'-biphenyl]-4-ylsulfonamido)benzoic acid,
4-(N-isobutylnaphthalene-2-sulfonamido)benzoic acid,
2-hydroxy-4-(N-isobutylphenylsulfonamido)benzoic acid,
2-hydroxy-4-(N-isobutyl-4-methylphenylsulfonamido)benzoic acid,
4-(4-bromo-N-isobutylphenylsulfonamido)-2-hydroxybenzoic acid,
2-hydroxy-4-(N-isobutyl-4-(p-tolyloxy)phenylsulfonamido)benzoic acid,
4-(4-(3,5-dimethylphenoxy)-N-isobutylphenylsulfonamido)-2-hydroxybenzoic acid,
4-(4-(2,4-dichlorophenoxy)-N-isobutylphenylsulfonamido)-2-hydroxybenzoic acid,
2-hydroxy-4-(4-phenoxyphenylsulfonamido)benzoic acid,
3-(N-isobutylphenylsulfonamido)benzoic acid,
3-(N-isobutyl-4-methylphenylsulfonamido)benzoic acid,
2-hydroxy-5-(N-isobutylnaphthalene-2-sulfonamido)benzoic acid,
5-(4-(4-chloro-3,5-dimethylphenoxy)-N-isobutylphenylsulfonamido)-2-hydroxybenzoic acid,
methyl 2-hydroxy-4-(N-isobutyl-4-phenoxyphenylsulfonamido)benzoate,
4-(N-benzyl-4-phenoxyphenylsulfonamido)-2-hydroxy-N-(phenylsulfonyl)benzamide,
4-(N-benzyl-4-phenoxyphenylsulfonamido)-2-hydroxy-N-(methylsulfonyl)benzamide,
4-(N-isobutyl-4-phenoxyphenylsulfonamido)-2-((4-(((3-nitro-4-(((tetrahydro-2H-pyran-4-yl)methyl)amino)phenyl)sulfonyl)carbamoyl)benzyl)oxy)benzoic acid,
4-(4-fluoro-N-isobutylphenylsulfonamido)benzoic acid,
4-(4-(4-chloro-3,5-dimethylphenoxy)-N-isobutylphenylsulfonamido)benzoic acid,
2-hydroxy-4-(N-isobutylnaphthalene-2-sulfonamido)benzoic acid,
2-hydroxy-4-(N-isobutyl-[1,1'-biphenyl]-4-ylsulfonamido)benzoic acid,
4-(N-cyclopentyl-[1,1'-biphenyl]-4-ylsulfonamido)-2-hydroxybenzoic acid, 4-(N-cyclopentylnaphthalene-2-sulfonamido)-2-hydroxybenzoic acid, 4-(4-(4-chloro-3,5-dimethylphenoxy)-N-cyclopentylphenylsulfonamido)-2-hydroxybenzoic acid, 3-(N-isobutylnaphthalene-2-sulfonamido)benzoic acid, 3-(N-isobutyl-[1,1'-biphenyl]-4-ylsulfonamido)benzoic acid, 3-(4-(4-chloro-3,5-dimethylphenoxy)-N-isobutylphenylsulfonamido)benzoic acid, phenyl 2-hydroxy-4-(N-isobutyl-4-phenoxyphenylsulfonamido)benzoate, acetoxymethyl 2-hydroxy-4-(N-isobutyl-4-phenoxyphenylsulfonamido)benzoate, N-(4-cyano-3-hydroxyphenyl)-N-isobutyl-4-phenoxybenzenesulfonamide, 4-(N-benzyl-4-phenoxyphenylsulfonamido)-2-hydroxy-N-((3-nitro-4-(((tetrahydro-2H-pyran-4-yl)methyl)amino)phenyl)sulfonyl)benzamide, 4-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide, 3-(4-(4-chloro-3,5-dimethylphenoxy)-N-isobutylphenylsulfonamido)-2-hydroxybenzoic acid, 4-(4-fluoro-N-isobutylphenylsulfonamido)-2-hydroxybenzoic acid, 2-hydroxy-4-(N-isobutyl-4-phenoxyphenylsulfonamido)benzoic acid, 4-(N-benzyl-[1,1'-biphenyl]-4-ylsulfonamido)-2-hydroxybenzoic acid, 4-(N-benzylnaphthalene-2-sulfonamido)-2-hydroxybenzoic acid, 4-(N-benzyl-4-(4-chloro-3,5-dimethylphenoxy)phenylsulfonamido)-2-hydroxybenzoic acid, 3-(4-fluoro-N-isobutylphenylsulfonamido)benzoic acid, 2-hydroxy-5-(N-isobutylphenylsulfonamido)benzoic acid, 2-hydroxy-5-(N-isobutyl-[1,1'-biphenyl]-4-ylsulfonamido)benzoic acid, N-(4-(2H-tetrazol-5-yl)phenyl)-N-isobutyl-4-phenoxybenzenesulfonamide, N,2-dihydroxy-4-(N-isobutyl-4-phenoxyphenylsulfonamido)benzamide, N-isobutyl-N-(4-(3-oxo-2,3-dihydroisoxazol-5-yl)phenyl)-4-phenoxybenzenesulfonamide, 5-(N-benzyl-4-(4-chloro-3,5-dimethylphenoxy)phenylsulfonamido)-2-hydroxybenzoic acid, 5-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide, and combinations thereof, or a pharmaceutically acceptable salt, solvate, hydrate, cocrystal, or prodrug thereof.

In some embodiments, the condition alleviated by inhibiting Mcl-1 protein may be selected from the group consisting of: pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

In some embodiments, the condition alleviated by inhibiting Mcl-1 protein may be selected from the group consisting of: myeloid leukemia, non-small cell lung cancer, pancreatic cancer, prostate cancer, and ovarian cancer.

In an embodiment, the invention may include a pharmaceutical composition for treating a condition alleviated by inhibiting Mcl-1 protein activity, the pharmaceutical composition including one or more compounds of formula (I), (II), (IIIa), (IIIb), and (IV), or a pharmaceutically acceptable salt, solvate, hydrate, cocrystal, or prodrug thereof, and a pharmaceutically acceptable carrier medium.

In some embodiments, the pharmaceutical composition may include one or more of: 4-(N-(4-(4-chloro-3,5-dimethyl phenoxy)phenyl)sulfamoyl)-1-hydroxy-2-naphthoic acid, 4-(N-(4-(4-chloro-3,5-dimethylphenoxy)phenyl)-N-isobutylsulfamoyl)-1-hydroxy-2-naphthoic acid, 4-(N-(4-(4-chloro-3,5-dimethylphenoxy)phenyl)-N-cyclopentylsulfamoyl)-1-hydroxy-2-naphthoic acid, 4-(N-benzyl-N-(4-(4-chloro-3,5-dimethylphenoxy)phenyl)sulfamoyl)-1-hydroxy-2-naphthoic acid, 4-(N-benzylsulfamoyl)-1-hydroxy-2-naphthoic acid, 4-(N-(4-chlorophenyl)sulfamoyl)-1-hydroxy-2-naphthoic acid, 4-(N-(3-chlorobenzyl)sulfamoyl)-1-hydroxy-2-naphthoic acid, 1-hydroxy-4-(N-(4-(trifluoromethyl)phenyl)sulfamoyl)-2-naphthoic acid, 4-(N-(2-chlorobenzyl)sulfamoyl)-1-hydroxy-2-naphthoic acid, 1-hydroxy-4-(N-(p-tolyl)sulfamoyl)-2-naphthoic acid, 1-hydroxy-4-(N-(4-isopropylphenyl)sulfamoyl)-2-naphthoic acid, 4-(N-(3-cyanophenyl)sulfamoyl)-1-hydroxy-2-naphthoic acid, 4-(N-([1,1'-biphenyl]-2-yl)sulfamoyl)-1-hydroxy-2-naphthoic acid, 4-(N-([1,1'-biphenyl]-4-yl)sulfamoyl)-1-hydroxy-2-naphthoic acid, 4-(N-([1,1'-biphenyl]-3-yl)sulfamoyl)-1-hydroxy-2-naphthoic acid, 1-hydroxy-4-((4-phenylpiperazin-1-yl)sulfonyl)-2-naphthoic acid, 1-hydroxy-4-(N-(naphthalen-1-yl)sulfamoyl)-2-naphthoic acid, 1-hydroxy-4-(N-(naphthalen-2-yl)sulfamoyl)-2-naphthoic acid, 4-(N-(4-cyanophenyl)sulfamoyl)-1-hydroxy-2-naphthoic acid, 1-hydroxy-4-(N-(4-methoxyphenyl)sulfamoyl)-2-naphthoic acid, 1-hydroxy-4-(N-(2-(trifluoromethyl)phenyl)sulfamoyl)-2-naphthoic acid, 1-hydroxy-4-(N-(4-nitrophenyl)sulfamoyl)-2-naphthoic acid, 4-(N-(2-bromophenyl)sulfamoyl)-1-hydroxy-2-naphthoic acid, 4-(N-(3-bromophenyl)sulfamoyl)-1-hydroxy-2-naphthoic acid, 4-(N-(cyclohexylmethyl)sulfamoyl)-1-hydroxy-2-naphthoic acid,
methyl 4-(N-(4-bromophenyl)-N-isobutylsulfamoyl)-1-methoxy-2-naphthoate,
methyl 4-(N-(4-bromophenyl)-N-isobutylsulfamoyl)-1-hydroxy-2-naphthoate,
4-(N-(4-bromophenyl)-N-isobutylsulfamoyl)-1-methoxy-2-naphthoic acid,
1-hydroxy-4-(piperidin-1-ylsulfonyl)-2-naphthoic acid,
4-(N-(4-chlorobenzyl)sulfamoyl)-1-hydroxy-2-naphthoic acid,
4-(N-(2,4-dibromophenyl)sulfamoyl)-1-hydroxy-2-naphthoic acid,
1-hydroxy-4-(N-(4-isopropoxyphenyl)sulfamoyl)-2-naphthoic acid,
1-hydroxy-4-(N-(4-(naphthalen-1-yloxy)phenyl)sulfamoyl)-2-naphthoic acid,
4-(N,N-dimethylsulfamoyl)-1-hydroxy-2-naphthoic acid,
1-hydroxy-4-(N-(4-phenoxyphenyl)sulfamoyl)-2-naphthoic acid,
4-(N-(4-(3-bromophenoxy)phenyl)sulfamoyl)-1-hydroxy-2-naphthoic acid,
1-hydroxy-4-(N-(4-(p-tolyloxy)phenyl)sulfamoyl)-2-naphthoic acid,
4-(N-(4-(2,4-dichlorophenoxy)phenyl)sulfamoyl)-1-hydroxy-2-naphthoic acid,
4-((4-benzylpiperazin-1-yl)sulfonyl)-1-hydroxy-2-naphthoic acid,
4-(N-(4-(4-chlorophenoxy)phenyl)sulfamoyl)-1-hydroxy-2-naphthoic acid,
4-(N-(4-(3,5-dimethylphenoxy)phenyl)sulfamoyl)-1-hydroxy-2-naphthoic acid,
1-hydroxy-4-(N-phenylsulfamoyl)-2-naphthoic acid,
4-(N-(4-bromophenyl)-N-isobutylsulfamoyl)-1-hydroxy-2-naphthoic acid,
1-hydroxy-4-sulfamoyl-2-naphthoic acid,
1-hydroxy-4-(N-isobutyl-N-(4-isopropoxyphenyl)sulfamoyl)-2-naphthoic acid,
4-(N-(4-bromophenyl)sulfamoyl)-1-hydroxy-2-naphthoic acid,
methyl 1-hydroxy-4-(N-isobutyl-N-(4-isopropoxyphenyl)sulfamoyl)-2-naphthoate,
acetoxymethyl 1-hydroxy-4-(N-isobutyl-N-(4-isopropoxyphenyl)sulfamoyl)-2-naphthoate,
1-(phenylsulfonyl)-1,2,3,4-tetrahydroquinoline-6-carboxylic acid,
1-((4-bromophenyl)sulfonyl)-1,2,3,4-tetrahydroquinoline-6-carboxylic acid,
1-((4-phenoxyphenyl)sulfonyl)-1,2,3,4-tetrahydroquinoline-6-carboxylic acid,
1-(naphthalen-2-ylsulfonyl)-1,2,3,4-tetrahydroquinoline-6-carboxylic acid,
1-((4-(3,5-dimethylphenoxy)phenyl)sulfonyl)-1,2,3,4-tetrahydroquinoline-6-carboxylic acid,
1-((4-(p-tolylthio)phenyl)sulfonyl)-1,2,3,4-tetrahydroquinoline-6-carboxylic acid,
1-((benzyloxy)carbonyl)-1,2,3,4-tetrahydroquinoline-6-carboxylic acid,
1-(isobutoxycarbonyl)-1,2,3,4-tetrahydroquinoline-6-carboxylic acid,
1-(tert-butoxycarbonyl)-1,2,3,4-tetrahydroquinoline-6-carboxylic acid,
1-(4-phenoxybenzyl)-1,2,3,4-tetrahydroquinoline-6-carboxylic acid,
1-(3-(4-chloro-3,5-dimethylphenoxy)propyl)-1,2,3,4-tetrahydroquinoline-6-carboxylic acid,
phenyl 1-((4-(4-chloro-3,5-dimethylphenoxy)phenyl)sulfonyl)-1,2,3,4-tetrahydroquinoline-6-carboxylate,
1-((4-(4-chloro-3,5-dimethylphenoxy)phenyl)sulfonyl)-1,2,3,4-tetrahydroquinoline-6-carboxamide,
methyl 1-((4-(4-chloro-3,5-dimethylphenoxy)phenyl)sulfonyl)-1,2,3,4-tetrahydroquinoline-6-carboxylate,
acetoxymethyl 1-((4-(4-chloro-3,5-dimethylphenoxy)phenyl)sulfonyl)-1,2,3,4-tetrahydroquinoline-6-carboxylate,
1-((4-fluorophenyl)sulfonyl)-1,2,3,4-tetrahydroquinoline-6-carboxylic acid,
1-([1,1'-biphenyl]-4-ylsulfonyl)-1,2,3,4-tetrahydroquinoline-6-carboxylic acid,
1-((4-(p-tolyloxy)phenyl)sulfonyl)-1,2,3,4-tetrahydroquinoline-6-carboxylic acid,
1-(quinolin-8-ylsulfonyl)-1,2,3,4-tetrahydroquinoline-6-carboxylic acid,
1-((5-(dimethylamino)naphthalen-1-yl)sulfonyl)-1,2,3,4-tetrahydroquinoline-6-carboxylic acid,
1-((4-(4-chloro-3,5-dimethylphenoxy)phenyl)sulfonyl)-1,2,3,4-tetrahydroquinoline-6-carboxylic acid,
(±)-1-(phenylsulfonyl)-1,2,3,4-tetrahydroquinoline-3-carboxylic acid,
(±)-1-((4-bromophenyl)sulfonyl)-1,2,3,4-tetrahydroquinoline-3-carboxylic acid,
(±)-1-((4-fluorophenyl)sulfonyl)-1,2,3,4-tetrahydroquinoline-3-carboxylic acid,
(±)-1-([1,1'-biphenyl]-4-ylsulfonyl)-1,2,3,4-tetrahydroquinoline-3-carboxylic acid,
(±)-1-(naphthalen-2-ylsulfonyl)-1,2,3,4-tetrahydroquinoline-3-carboxylic acid,
(±)-1-((4-(4-chloro-3,5-dimethylphenoxy)phenyl)sulfonyl)-1,2,3,4-tetrahydroquinoline-3-carboxylic acid,
(±)-1-(3-(4-chloro-3,5-dimethylphenoxy)propyl)-1,2,3,4-tetrahydroquinoline-3-carboxylic acid,
4-(N-isobutylphenylsulfonamido)benzoic acid,
4-(N-isobutyl-[1,1'-biphenyl]-4-ylsulfonamido)benzoic acid,
4-(N-isobutylnaphthalene-2-sulfonamido)benzoic acid,
2-hydroxy-4-(N-isobutylphenylsulfonamido)benzoic acid,
2-hydroxy-4-(N-isobutyl-4-methylphenylsulfonamido)benzoic acid,
4-(4-bromo-N-isobutylphenylsulfonamido)-2-hydroxybenzoic acid,
2-hydroxy-4-(N-isobutyl-4-(p-tolyloxy)phenylsulfonamido)benzoic acid,
4-(4-(3,5-dimethylphenoxy)-N-isobutylphenylsulfonamido)-2-hydroxybenzoic acid,
4-(4-(2,4-dichlorophenoxy)-N-isobutylphenylsulfonamido)-2-hydroxybenzoic acid,
2-hydroxy-4-(4-phenoxyphenylsulfonamido)benzoic acid,
3-(N-isobutylphenylsulfonamido)benzoic acid,
3-(N-isobutyl-4-methylphenylsulfonamido)benzoic acid,
2-hydroxy-5-(N-isobutylnaphthalene-2-sulfonamido)benzoic acid,
5-(4-(4-chloro-3,5-dimethylphenoxy)-N-isobutylphenylsulfonamido)-2-hydroxybenzoic acid,
methyl 2-hydroxy-4-(N-isobutyl-4-phenoxyphenylsulfonamido)benzoate,
4-(N-benzyl-4-phenoxyphenylsulfonamido)-2-hydroxy-N-(phenylsulfonyl)benzamide,
4-(N-benzyl-4-phenoxyphenylsulfonamido)-2-hydroxy-N-(methylsulfonyl)benzamide, 4-(N-isobutyl-4-phenoxyphenylsulfonamido)-2-((4-(((3-nitro-4-(((tetrahydro-2H-pyran-4-yl)methyl)amino)phenyl)sulfonyl)carbamoyl)benzyl)oxy)benzoic acid,
4-(4-fluoro-N-isobutylphenylsulfonamido)benzoic acid,
4-(4-(4-chloro-3,5-dimethylphenoxy)-N-isobutylphenylsulfonamido)benzoic acid,
2-hydroxy-4-(N-isobutylnaphthalene-2-sulfonamido)benzoic acid,
2-hydroxy-4-(N-isobutyl-[1,1'-biphenyl]-4-ylsulfonamido)benzoic acid,
4-(N-cyclopentyl-[1,1'-biphenyl]-4-ylsulfonamido)-2-hydroxybenzoic acid,
4-(N-cyclopentylnaphthalene-2-sulfonamido)-2-hydroxybenzoic acid,
4-(4-(4-chloro-3,5-dimethylphenoxy)-N-cyclopentylphenylsulfonamido)-2-hydroxybenzoic acid,
3-(N-isobutylnaphthalene-2-sulfonamido)benzoic acid,
3-(N-isobutyl-[1,1'-biphenyl]-4-ylsulfonamido)benzoic acid,
3-(4-(4-chloro-3,5-dimethylphenoxy)-N-isobutylphenylsulfonamido)benzoic acid,
phenyl 2-hydroxy-4-(N-isobutyl-4-phenoxyphenylsulfonamido)benzoate,
acetoxymethyl 2-hydroxy-4-(N-isobutyl-4-phenoxyphenylsulfonamido)benzoate,
N-(4-cyano-3-hydroxyphenyl)-N-isobutyl-4-phenoxybenzenesulfonamide,
4-(N-benzyl-4-phenoxyphenylsulfonamido)-2-hydroxy-N-((3-nitro-4-(((tetrahydro-2H-pyran-4-yl)methyl)amino)phenyl)sulfonyl)benzamide,
4-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide,
3-(4-(4-chloro-3,5-dimethylphenoxy)-N-isobutylphenylsulfonamido)-2-hydroxybenzoic acid,
4-(4-fluoro-N-isobutylphenylsulfonamido)-2-hydroxybenzoic acid,
2-hydroxy-4-(N-isobutyl-4-phenoxyphenylsulfonamido)benzoic acid,
4-(N-benzyl-[1,1'-biphenyl]-4-ylsulfonamido)-2-hydroxybenzoic acid,
4-(N-benzylnaphthalene-2-sulfonamido)-2-hydroxybenzoic acid,
4-(N-benzyl-4-(4-chloro-3,5-dimethylphenoxy)phenylsulfonamido)-2-hydroxybenzoic acid,
3-(4-fluoro-N-isobutylphenylsulfonamido)benzoic acid,
2-hydroxy-5-(N-isobutylphenylsulfonamido)benzoic acid,
2-hydroxy-5-(N-isobutyl-[1,1'-biphenyl]-4-ylsulfonamido)benzoic acid,
N-(4-(2H-tetrazol-5-yl)phenyl)-N-isobutyl-4-phenoxybenzenesulfonamide,
N,2-dihydroxy-4-(N-isobutyl-4-phenoxyphenylsulfonamido)benzamide,
N-isobutyl-N-(4-(3-oxo-2,3-dihydroisoxazol-5-yl)phenyl)-4-phenoxybenzenesulfonamide,
5-(N-benzyl-4-(4-chloro-3,5-dimethylphenoxy)phenylsulfonamido)-2-hydroxybenzoic acid,
5-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide, and combinations thereof.

BRIEF DESCRIPTION OF THE DRAWINGS

The foregoing summary, as well as the following detailed description of embodiments of the invention, will be better understood when read in conjunction with the appended drawings and figures.

In the drawings:

FIG. 5A illustrates a difference FragMap between Mcl-1 and Bcl-xL showing the favourable binding patterns for Mcl-1. The atom grid free energy (GFE) contributions to the binding affinity difference are also shown. FIG. 5B illustrates the experimental structures of Mcl-1 (A, 4HW4) and Bcl-$x_L$ (B, 1BXL) shows that the binding pocket between helix α4 (upper right) and α5 (bottom left) is larger for Mcl-1 than Bcl-$x_L$. The predicted binding modes of 3a for Mcl-1 (X) and Bcl-$x_L$ (Y) differs due to this p2 pocket difference. The 4-bromophenyl ring of 3a binds deeply to the opened pocket for Mcl-1 while it binds on the protein surface for Bcl-$x_L$. FIG. 5C illustrates binding orientations of 3bl to Mcl-1 (A, 4HW4) and Bcl-$x_L$ (B, 1BXL) along with the ΔFragMaps. The predicted binding modes of 3a for Mcl-1 (X) and Bcl-$x_L$ (Y) are also shown. FIG. 5D illustrates the binding orientations of 3bl to Bcl-$x_L$ (1BXL) along with the Bcl-$x_L$ APOLAR and NEG FragMaps.

DETAILED DESCRIPTION OF THE INVENTION

Figure 1:
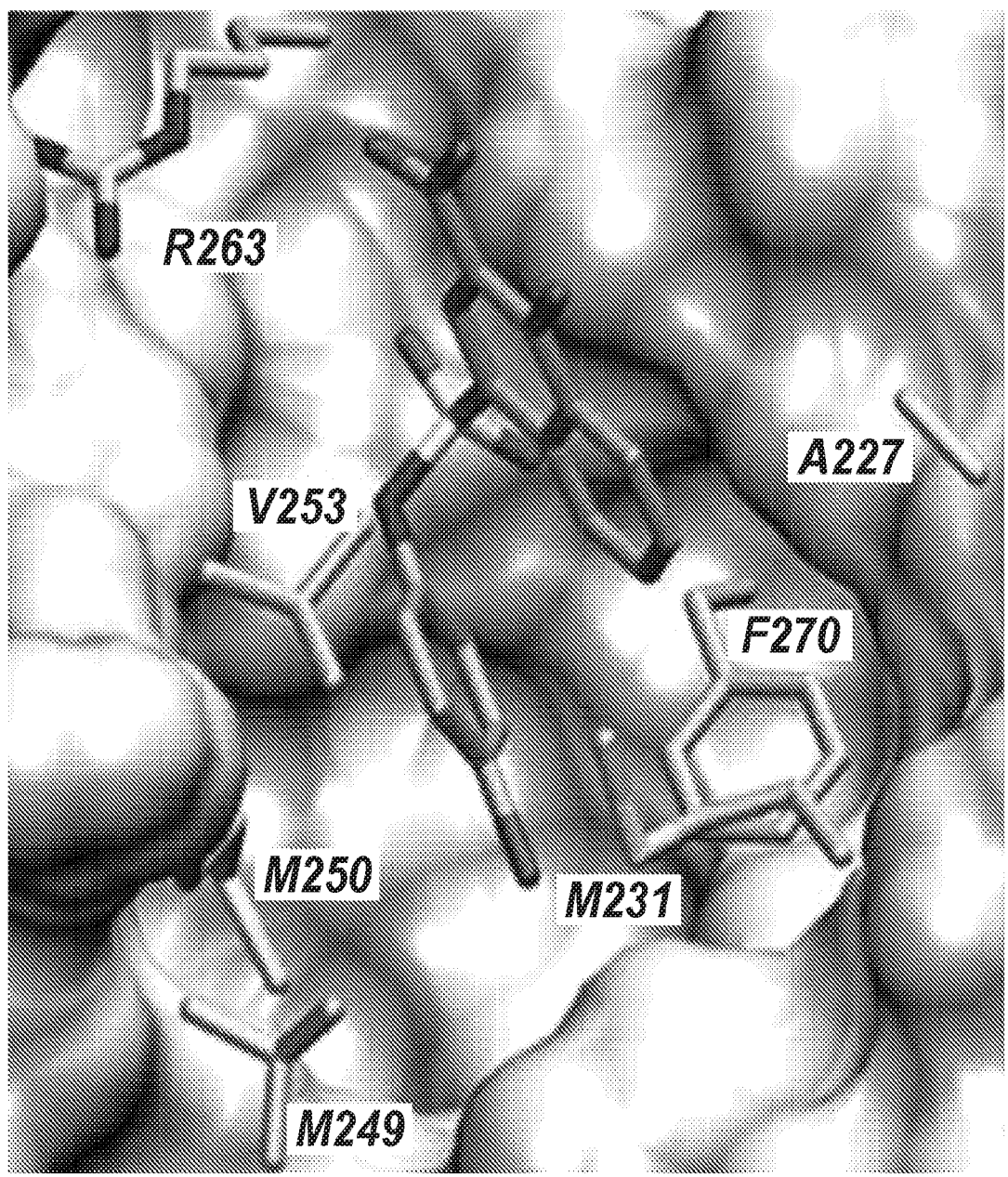
FIG. 1 illustrates the binding mode of 3a, as predicted by SILCS. Important residues within the p2 binding pocket are shown in stick representation.

Unless defined otherwise, all technical and scientific terms used herein have the same meaning as is commonly understood by one of skill in the art to which this invention belongs. All patents and publications referred to herein are incorporated by reference in their entireties.

Definitions

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The terms "active pharmaceutical ingredient" and "drug" include the Mcl-1 inhibitors described herein and, more specifically, the Mcl-1 inhibitors described by Formulas I, II, IIIa, IIIb, and IV. The terms "active pharmaceutical ingredient" and "drug" may also include those compounds described herein that bind Mcl-1 protein and thereby modulate Mcl-1 protein activity.

The term "isostere" refers to a group or molecule whose chemical and/or physical properties are similar to those of another group or molecule. A "bioisostere" is a type of isostere and refers to a group or molecule whose biological properties are similar to those of another group or molecule. For example, for the Mcl-1 inhibitors described herein, a carboxylic acid may be replaced by one of the following bioisosteres for carboxylic acids, including, without limitation, alkyl esters (COOR), acylsulfonamides (CONR—SO$_2$R), hydroxamic acids (CONR—OH), hydroxamates (CONR—OR), tetrazoles, hydroxyisoxazoles, isoxazol-3-ones, and sulfonamides (SO$_2$NR), where each R may independently represent hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "treat," "treatment," and/or "treating" may refer to the management of a disease, disorder, or pathological condition (e.g., pain, a neurological disorder, diarrhea, coughing, muscular tension, and glaucoma), or symptom thereof with the intent to cure, ameliorate, stabilize, prevent, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition).

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule. In some embodiments, the biological molecules modulated by the methods and compounds of the invention to effect treatment may include one or both of the δ-opioid receptor and the u-opioid receptor.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quarter in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

A "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of formulas I, II, IIIa, IIIb, and IV. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula I, II, IIIa, IIIb, and IV) is a prodrug within the scope of the invention. Various forms of prodrugs are well known in the art. A comprehensive description of pro drugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting, lymphocyte targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the invention.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (iso-propyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^aC(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., ($C_{2-10}$)alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Acylsulfonamide" refers to the group —C(=O)$NR^a$—S(=O)$R^a$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl, or heteroarylalkyl.

"Carboxaldehyde" refers to a —(C=O)H radical.

"Carbonyl" refers to the group —C(=O)—. Carbonyl groups may be substituted with the following exemplary substituents: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —NR$^a$—OR$^a$—, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. (C$_{3-10}$)cycloalkyl or C$_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, acylsulfonamido, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, amino, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, *Protective Groups in Organic Synthesis*, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, acylsulfonamido, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —$OR^a$, —$SR^a$, —$S(O)_tR^a$— (where t is 1 or 2), —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_tR^a$ (where t is 1 or 2), —S(O)$_tOR^a$ (where t is 1 or 2), —S(O)$_tN(R^a)_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, isoxazol-3-one, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —$OR^a$, —$SR^a$, —$S(O)_tR^a$— (where t is 1 or 2), —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_tR^a$ (where t is 1 or 2), —S(O)$_tOR^a$ (where t is 1 or 2), —S(O)$_tN(R^a)_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, a heterocycloalkyl moiety is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)$ $N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"hydroxamate" refers to the —$C(O)NR^aOR^a$ moiety, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Nitro" refers to the —$NO_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S-isomer. If that compound has one isomeric form predominant over the other, for example, 80% (S-isomer and 20% (R)-isomer, the enantiomeric purity of the compound with respect to the (S-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions*, Wiley Interscience, New York (1981); E. L. Eliel, *Stereochemistry of Carbon Compounds*, McGraw-Hill, New York (1962); and E. L. Eliel and S. H. Wilen, *Stereochemistry of Organic Compounds*, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S-enantiomer, means a preparation of the compound having greater than 50% by weight of the (S-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, *Protective Groups in Organic Synthesis*, 3rd Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxamate, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S($O_2$)—H, —S($O_2$)-(optionally substituted alkyl), —S($O_2$)-(optionally substituted amino), —S($O_2$)-(optionally substituted aryl), —S($O_2$)-(optionally substituted heteroaryl), and —S($O_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Methods of Treating Cancers and Other Diseases

The compounds and compositions described herein can be used in methods for treating diseases. In some embodiments, the compounds and compositions described herein can be used in methods for treating diseases associated with the upregulation of myeloid cell leukemia-1 (Mcl-1) oncoprotein. In some embodiments, the compounds and compositions described herein can be used for the treatment of hyperproliferative disorders, including those hyperproliferative disorders associated with the upregulation of Mcl-1. The compounds and compositions described herein may also be used in treating other disorders as described herein and in the following paragraphs.

In some embodiments, the hyperproliferative disorder is cancer. In some embodiments, the cancer is selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like.

In some embodiments, the hyperproliferative disorder treated by the compounds and compositions described herein includes cells having Mcl-1 protein and/or Mcl-1 related protein expression. In some embodiments, the disease treated by the compounds and compositions described herein is selected from the group consisting of myeloid leukemia, non-small cell lung cancer, pancreatic cancer, prostate cancer, and ovarian cancer.

In some embodiments, the compounds described herein may induce cell cycle arrest and/or apoptosis in cells containing functional Mcl-1 proteins. The compounds described herein may be used for sensitizing cells to additional agent(s), such as inducers of apoptosis and/or cell cycle arrest, and chemoprotection of normal cells through the induction of cell cycle arrest prior to treatment with chemotherapeutic agents.

In some embodiments, the compounds described herein may be useful for the treatment of disorders, such as those responsive to induction of apoptotic cell death, e.g., disorders characterized by dysregulation of apoptosis. In some embodiments, the compounds may be used to treat cancer that is characterized by resistance to cancer therapies (e.g., those cancer cells which are chemoresistant, radiation resistant, hormone resistant, and the like). In other embodiments, the compounds can be used to treat hyperproliferative diseases characterized by expression of functional Mcl-1 and/or Mcl-1 related proteins, which may or may not be resilient to Bcl-$x_L$ inhibitors.

Efficacy of the compounds and combinations of compounds described herein in treating the indicated diseases or disorders can be tested using various models known in the art, and described herein, which provide guidance for treatment of human disease.

MCL-1 Inhibitors

In an embodiment, the invention includes compounds that may be Mcl-1 inhibitors and/or modulators of Mcl-1 protein activity. In some embodiments, the compounds described herein may be selective inhibitors of Mcl-1 protein activity as compared to Bcl-$x_L$.

In some embodiments, the compounds described herein may selectively decrease the activity of Mcl-1 protein as compared to Bcl-$x_L$ protein in a ratio of at least about 1.5 to about 1, or at least about 2 to about 1, or at least about 3 to about 1, or at least about 4 to about 1, or at least about 5 to about 1, or at least about 10 to about 1, or at least about 15 to about 1, or at least about 20 to about 1, or at least about 25 to about 1, or at least about 30 to about 1, or at least about 35 to about 1, or at least about 40 to about 1, or at least about 45 to about 1, or at least about 50 to about 1, or at least about 100 to about 1, or at least about 200 to about 1, or at least about 300 to about 1, or at least about 400 to about 1, or at least about 500 to about 1, or at least about 600 to about 1, or at least about 700 to about 1, or least about 800 to about 1, or at least about 900 to about 1, or at least about 1000 to about 1, or at least about 10000 to about 1, or at least about 100000 to about 1, respectively.

In an embodiment, the Mcl-1 inhibitor may be a compound of formula I, or a pharmaceutically acceptable salt, solvate, hydrate, cocrystal, tautomer, or prodrug thereof. In some embodiments, the Mcl-1 inhibitor of formula I includes one or more of:

4-(N-(4-(4-chloro-3,5-dimethyl phenoxy)phenyl)sulfamoyl)-1-hydroxy-2-naphthoic acid, 4-(N-(4-(4-chloro-3,5-dimethylphenoxy)phenyl)-N-isobutylsulfamoyl)-1-hydroxy-2-naphthoic acid, 4-(N-(4-(4-chloro-3,5-dimethylphenoxy)phenyl)-N-cyclopentylsulfamoyl)-1-hydroxy-2-naphthoic acid, 4-(N-benzyl-N-(4-(4-chloro-3,5-dimethylphenoxy)phenyl)sulfamoyl)-1-hydroxy-2-naphthoic acid, 4-(N-benzylsulfamoyl)-1-hydroxy-2-naphthoic acid, 4-(N-(4-chlorophenyl)sulfamoyl)-1-hydroxy-2-naphthoic acid, 4-(N-(3-chlorobenzyl)sulfamoyl)-1-hydroxy-2-naphthoic acid, 1-hydroxy-4-(N-(4-(trifluoromethyl)phenyl)sulfamoyl)-2-naphthoic acid, 4-(N-(2-chlorobenzyl)sulfamoyl)-1-hydroxy-2-naphthoic acid, 1-hydroxy-4-(N-(p-tolyl)sulfamoyl)-2-naphthoic acid, 1-hydroxy-4-(N-(4-isopropylphenyl)sulfamoyl)-2-naphthoic acid, 4-(N-(3-cyanophenyl)sulfamoyl)-1-hydroxy-2-naphthoic acid, 4-(N-([1,1'-biphenyl]-2-yl)sulfamoyl)-1-hydroxy-2-naphthoic acid, 4-(N-([1,1'-biphenyl]-4-yl)sulfamoyl)-1-hydroxy-2-naphthoic acid, 4-(N-([1,1'-biphenyl]-3-yl)sulfamoyl)-1-hydroxy-2-naphthoic acid, 1-hydroxy-4-((4-phenylpiperazin-1-yl)sulfonyl)-2-naphthoic acid, 1-hydroxy-4-(N-(naphthalen-1-yl)sulfamoyl)-2-naphthoic acid, 1-hydroxy-4-(N-(naphthalen-2-yl)sulfamoyl)-2-naphthoic acid, 4-(N-(4-cyanophenyl)sulfamoyl)-1-hydroxy-2-naphthoic acid, 1-hydroxy-4-(N-(4-methoxyphenyl)sulfamoyl)-2-naphthoic acid, 1-hydroxy-4-(N-(2-(trifluoromethyl)phenyl)sulfamoyl)-2-naphthoic acid, 1-hydroxy-4-(N-(4-nitrophenyl)sulfamoyl)-2-naphthoic acid, 4-(N-(2-bromophenyl)sulfamoyl)-1-hydroxy-2-naphthoic acid, 4-(N-(3-bromophenyl)sulfamoyl)-1-hydroxy-2-naphthoic acid, 4-(N-(cyclohexylmethyl)sulfamoyl)-1-hydroxy-2-naphthoic acid, methyl 4-(N-(4-bromophenyl)-N-isobutylsulfamoyl)-1-methoxy-2-naphthoate, methyl 4-(N-(4-bromophenyl)-N-isobutylsulfamoyl)-1-hydroxy-2-naphthoate,
4-(N-(4-bromophenyl)-N-isobutylsulfamoyl)-1-methoxy-2-naphthoic acid,
1-hydroxy-4-(piperidin-1-ylsulfonyl)-2-naphthoic acid,
4-(N-(4-chlorobenzyl)sulfamoyl)-1-hydroxy-2-naphthoic acid,
4-(N-(2,4-dibromophenyl)sulfamoyl)-1-hydroxy-2-naphthoic acid,
1-hydroxy-4-(N-(4-isopropoxyphenyl)sulfamoyl)-2-naphthoic acid,
1-hydroxy-4-(N-(4-(naphthalen-1-yloxy)phenyl)sulfamoyl)-2-naphthoic acid,
4-(N,N-dimethylsulfamoyl)-1-hydroxy-2-naphthoic acid,
1-hydroxy-4-(N-(4-phenoxyphenyl)sulfamoyl)-2-naphthoic acid,
4-(N-(4-(3-bromophenoxy)phenyl)sulfamoyl)-1-hydroxy-2-naphthoic acid,
1-hydroxy-4-(N-(4-(p-tolyloxy)phenyl)sulfamoyl)-2-naphthoic acid,
4-(N-(4-(2,4-dichlorophenoxy)phenyl)sulfamoyl)-1-hydroxy-2-naphthoic acid,
4-((4-benzylpiperazin-1-yl)sulfonyl)-1-hydroxy-2-naphthoic acid,
4-(N-(4-(4-chlorophenoxy)phenyl)sulfamoyl)-1-hydroxy-2-naphthoic acid,
4-(N-(4-(3,5-dimethylphenoxy)phenyl)sulfamoyl)-1-hydroxy-2-naphthoic acid,
1-hydroxy-4-(N-phenylsulfamoyl)-2-naphthoic acid,
4-(N-(4-bromophenyl)-N-isobutylsulfamoyl)-1-hydroxy-2-naphthoic acid,
1-hydroxy-4-sulfamoyl-2-naphthoic acid,
1-hydroxy-4-(N-isobutyl-N-(4-isopropoxyphenyl)sulfamoyl)-2-naphthoic acid,
4-(N-(4-bromophenyl)sulfamoyl)-1-hydroxy-2-naphthoic acid,
methyl 1-hydroxy-4-(N-isobutyl-N-(4-isopropoxyphenyl)sulfamoyl)-2-naphthoate,
acetoxymethyl 1-hydroxy-4-(N-isobutyl-N-(4-isopropoxyphenyl)sulfamoyl)-2-naphthoate,
1-(phenylsulfonyl)-1,2,3,4-tetrahydroquinoline-6-carboxylic acid,
1-((4-bromophenyl)sulfonyl)-1,2,3,4-tetrahydroquinoline-6-carboxylic acid,
1-((4-phenoxyphenyl)sulfonyl)-1,2,3,4-tetrahydroquinoline-6-carboxylic acid,
1-(naphthalen-2-ylsulfonyl)-1,2,3,4-tetrahydroquinoline-6-carboxylic acid,
1-((4-(3,5-dimethylphenoxy)phenyl)sulfonyl)-1,2,3,4-tetrahydroquinoline-6-carboxylic acid,
1-((4-(p-tolylthio)phenyl)sulfonyl)-1,2,3,4-tetrahydroquinoline-6-carboxylic acid,
1-((benzyloxy)carbonyl)-1,2,3,4-tetrahydroquinoline-6-carboxylic acid,
1-(isobutoxycarbonyl)-1,2,3,4-tetrahydroquinoline-6-carboxylic acid,
1-(tert-butoxycarbonyl)-1,2,3,4-tetrahydroquinoline-6-carboxylic acid,
1-(4-phenoxybenzyl)-1,2,3,4-tetrahydroquinoline-6-carboxylic acid,
1-(3-(4-chloro-3,5-dimethylphenoxy)propyl)-1,2,3,4-tetrahydroquinoline-6-carboxylic acid,
phenyl 1-((4-(4-chloro-3,5-dimethylphenoxy)phenyl)sulfonyl)-1,2,3,4-tetrahydroquinoline-6-carboxylate,
1-((4-(4-chloro-3,5-dimethylphenoxy)phenyl)sulfonyl)-1,2,3,4-tetrahydroquinoline-6-carboxamide,
methyl 1-((4-(4-chloro-3,5-dimethylphenoxy)phenyl)sulfonyl)-1,2,3,4-tetrahydroquinoline-6-carboxylate,
acetoxymethyl 1-((4-(4-chloro-3,5-dimethylphenoxy)phenyl)sulfonyl)-1,2,3,4-tetrahydroquinoline-6-carboxylate,
1-((4-fluorophenyl)sulfonyl)-1,2,3,4-tetrahydroquinoline-6-carboxylic acid,
1-([1,1'-biphenyl]-4-ylsulfonyl)-1,2,3,4-tetrahydroquinoline-6-carboxylic acid,
1-((4-(p-tolyloxy)phenyl)sulfonyl)-1,2,3,4-tetrahydroquinoline-6-carboxylic acid,
1-(quinolin-8-ylsulfonyl)-1,2,3,4-tetrahydroquinoline-6-carboxylic acid,
1-((5-(dimethylamino)naphthalen-1-yl)sulfonyl)-1,2,3,4-tetrahydroquinoline-6-carboxylic acid,
1-((4-(4-chloro-3,5-dimethylphenoxy)phenyl)sulfonyl)-1,2,3,4-tetrahydroquinoline-6-carboxylic acid,
(±)-1-(phenylsulfonyl)-1,2,3,4-tetrahydroquinoline-3-carboxylic acid,
(±)-1-((4-bromophenyl)sulfonyl)-1,2,3,4-tetrahydroquinoline-3-carboxylic acid,
(±)-1-((4-fluorophenyl)sulfonyl)-1,2,3,4-tetrahydroquinoline-3-carboxylic acid,
(±)-1-([1,1'-biphenyl]-4-ylsulfonyl)-1,2,3,4-tetrahydroquinoline-3-carboxylic acid,
(±)-1-(naphthalen-2-ylsulfonyl)-1,2,3,4-tetrahydroquinoline-3-carboxylic acid,
(±)-1-((4-(4-chloro-3,5-dimethylphenoxy)phenyl)sulfonyl)-1,2,3,4-tetrahydroquinoline-3-carboxylic acid,
(±)-1-(3-(4-chloro-3,5-dimethylphenoxy)propyl)-1,2,3,4-tetrahydroquinoline-3-carboxylic acid,
4-(N-isobutylphenylsulfonamido)benzoic acid,
4-(N-isobutyl-[1,1'-biphenyl]-4-ylsulfonamido)benzoic acid,
4-(N-isobutylnaphthalene-2-sulfonamido)benzoic acid,
2-hydroxy-4-(N-isobutylphenylsulfonamido)benzoic acid,
2-hydroxy-4-(N-isobutyl-4-methylphenylsulfonamido)benzoic acid,
4-(4-bromo-N-isobutylphenylsulfonamido)-2-hydroxybenzoic acid,
2-hydroxy-4-(N-isobutyl-4-(p-tolyloxy)phenylsulfonamido)benzoic acid,
4-(4-(3,5-dimethylphenoxy)-N-isobutylphenylsulfonamido)-2-hydroxybenzoic acid,
4-(4-(2,4-dichlorophenoxy)-N-isobutylphenylsulfonamido)-2-hydroxybenzoic acid,
2-hydroxy-4-(4-phenoxyphenylsulfonamido)benzoic acid,
3-(N-isobutylphenylsulfonamido)benzoic acid,
3-(N-isobutyl-4-methylphenylsulfonamido)benzoic acid,
2-hydroxy-5-(N-isobutylnaphthalene-2-sulfonamido)benzoic acid,
5-(4-(4-chloro-3,5-dimethylphenoxy)-N-isobutylphenylsulfonamido)-2-hydroxybenzoic acid,
methyl 2-hydroxy-4-(N-isobutyl-4-phenoxyphenylsulfonamido)benzoate,
4-(N-benzyl-4-phenoxyphenylsulfonamido)-2-hydroxy-N-(phenylsulfonyl)benzamide,
4-(N-benzyl-4-phenoxyphenylsulfonamido)-2-hydroxy-N-(methylsulfonyl)benzamide,
4-(N-isobutyl-4-phenoxyphenylsulfonamido)-2-((4-(((3-nitro-4-(((tetrahydro-2H-pyran-4-yl)methyl)amino)phenyl)sulfonyl)carbamoyl)benzyl)oxy)benzoic acid,
4-(4-fluoro-N-isobutylphenylsulfonamido)benzoic acid,
4-(4-(4-chloro-3,5-dimethylphenoxy)-N-isobutylphenylsulfonamido)benzoic acid, 2-hydroxy-4-(N-isobutylnaphthalene-2-sulfonamido) benzoic acid,
2-hydroxy-4-(N-isobutyl-[1,1'-biphenyl]-4-ylsulfonamido)benzoic acid,
4-(N-cyclopentyl-[1,1'-biphenyl]-4-ylsulfonamido)-2-hydroxybenzoic acid,
4-(N-cyclopentylnaphthalene-2-sulfonamido)-2-hydroxybenzoic acid,
4-(4-(4-chloro-3,5-dimethylphenoxy)-N-cyclopentylphenylsulfonamido)-2-hydroxybenzoic acid,
3-(N-isobutylnaphthalene-2-sulfonamido)benzoic acid,
3-(N-isobutyl-[1,1'-biphenyl]-4-ylsulfonamido)benzoic acid,
3-(4-(4-chloro-3,5-dimethylphenoxy)-N-isobutylphenylsulfonamido)benzoic acid,
phenyl 2-hydroxy-4-(N-isobutyl-4-phenoxyphenylsulfonamido)benzoate,
acetoxymethyl 2-hydroxy-4-(N-isobutyl-4-phenoxyphenylsulfonamido)benzoate,
N-(4-cyano-3-hydroxyphenyl)-N-isobutyl-4-phenoxybenzenesulfonamide,
4-(N-benzyl-4-phenoxyphenylsulfonamido)-2-hydroxy-N-((3-nitro-4-(((tetrahydro-2H-pyran-4-yl)methyl)amino)phenyl)sulfonyl)benzamide,
4-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide,
3-(4-(4-chloro-3,5-dimethylphenoxy)-N-isobutylphenylsulfonamido)-2-hydroxybenzoic acid,
4-(4-fluoro-N-isobutylphenylsulfonamido)-2-hydroxybenzoic acid,
2-hydroxy-4-(N-isobutyl-4-phenoxyphenylsulfonamido)benzoic acid,
4-(N-benzyl-[1,1'-biphenyl]-4-ylsulfonamido)-2-hydroxybenzoic acid,
4-(N-benzylnaphthalene-2-sulfonamido)-2-hydroxybenzoic acid,
4-(N-benzyl-4-(4-chloro-3,5-dimethylphenoxy)phenylsulfonamido)-2-hydroxybenzoic acid,
3-(4-fluoro-N-isobutylphenylsulfonamido)benzoic acid,
2-hydroxy-5-(N-isobutylphenylsulfonamido)benzoic acid,
2-hydroxy-5-(N-isobutyl-[1,1'-biphenyl]-4-ylsulfonamido)benzoic acid,
N-(4-(2H-tetrazol-5-yl)phenyl)-N-isobutyl-4-phenoxybenzenesulfonamide,
N,2-dihydroxy-4-(N-isobutyl-4-phenoxyphenylsulfonamido)benzamide,
N-isobutyl-N-(4-(3-oxo-2,3-dihydroisoxazol-5-yl)phenyl)-4-phenoxybenzenesulfonamide,
5-(N-benzyl-4-(4-chloro-3,5-dimethylphenoxy)phenylsulfonamido)-2-hydroxybenzoic acid, and
5-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide.

In an embodiment, the Mcl-1 inhibitor may be a compound of formula II, or a pharmaceutically acceptable salt, solvate, hydrate, cocrystal, tautomer, or prodrug thereof. In some embodiments, the compounds of formula I include the compounds of formula II, and the pharmaceutically acceptable salts, solvates, hydrates, cocrystals, tautomers, or prodrugs thereof. In some embodiments, the Mcl-1 inhibitor of formula II includes one or more of:
4-(N-(4-(4-chloro-3,5-dimethyl phenoxy)phenyl)sulfamoyl)-1-hydroxy-2-naphthoic acid,
4-(N-(4-(4-chloro-3,5-dimethylphenoxy)phenyl)-N-isobutylsulfamoyl)-1-hydroxy-2-naphthoic acid,
4-(N-(4-(4-chloro-3,5-dimethylphenoxy)phenyl)-N-cyclopentyl sulfamoyl)-1-hydroxy-2-naphthoic acid,
4-(N-benzyl-N-(4-(4-chloro-3,5-dimethylphenoxy)phenyl)sulfamoyl)-1-hydroxy-2-naphthoic acid,
4-(N-benzylsulfamoyl)-1-hydroxy-2-naphthoic acid,
4-(N-(4-chlorophenyl)sulfamoyl)-1-hydroxy-2-naphthoic acid,
4-(N-(3-chlorobenzyl)sulfamoyl)-1-hydroxy-2-naphthoic acid,
1-hydroxy-4-(N-(4-(trifluoromethyl)phenyl)sulfamoyl)-2-naphthoic acid,
4-(N-(2-chlorobenzyl)sulfamoyl)-1-hydroxy-2-naphthoic acid,
1-hydroxy-4-(N-(p-tolyl)sulfamoyl)-2-naphthoic acid,
1-hydroxy-4-(N-(4-isopropylphenyl)sulfamoyl)-2-naphthoic acid,
4-(N-(3-cyanophenyl)sulfamoyl)-1-hydroxy-2-naphthoic acid,
4-(N-([1,1'-biphenyl]-2-yl)sulfamoyl)-1-hydroxy-2-naphthoic acid,
4-(N-([1,1'-biphenyl]-4-yl)sulfamoyl)-1-hydroxy-2-naphthoic acid,
4-(N-([1,1'-biphenyl]-3-yl)sulfamoyl)-1-hydroxy-2-naphthoic acid,
1-hydroxy-4-((4-phenylpiperazin-1-yl)sulfonyl)-2-naphthoic acid,
1-hydroxy-4-(N-(naphthalen-1-yl)sulfamoyl)-2-naphthoic acid,
1-hydroxy-4-(N-(naphthalen-2-yl)sulfamoyl)-2-naphthoic acid,
4-(N-(4-cyanophenyl)sulfamoyl)-1-hydroxy-2-naphthoic acid,
1-hydroxy-4-(N-(4-methoxyphenyl)sulfamoyl)-2-naphthoic acid,
1-hydroxy-4-(N-(2-(trifluoromethyl)phenyl)sulfamoyl)-2-naphthoic acid,
1-hydroxy-4-(N-(4-nitrophenyl)sulfamoyl)-2-naphthoic acid,
4-(N-(2-bromophenyl)sulfamoyl)-1-hydroxy-2-naphthoic acid,
4-(N-(3-bromophenyl)sulfamoyl)-1-hydroxy-2-naphthoic acid,
4-(N-(cyclohexylmethyl)sulfamoyl)-1-hydroxy-2-naphthoic acid,
methyl 4-(N-(4-bromophenyl)-N-isobutylsulfamoyl)-1-methoxy-2-naphthoate,
methyl 4-(N-(4-bromophenyl)-N-isobutylsulfamoyl)-1-hydroxy-2-naphthoate,
4-(N-(4-bromophenyl)-N-isobutylsulfamoyl)-1-methoxy-2-naphthoic acid,
1-hydroxy-4-(piperidin-1-ylsulfonyl)-2-naphthoic acid,
4-(N-(4-chlorobenzyl)sulfamoyl)-1-hydroxy-2-naphthoic acid,
4-(N-(2,4-dibromophenyl)sulfamoyl)-1-hydroxy-2-naphthoic acid,
1-hydroxy-4-(N-(4-isopropoxyphenyl)sulfamoyl)-2-naphthoic acid,
1-hydroxy-4-(N-(4-(naphthalen-1-yloxy)phenyl)sulfamoyl)-2-naphthoic acid,
4-(N,N-dimethylsulfamoyl)-1-hydroxy-2-naphthoic acid,
1-hydroxy-4-(N-(4-phenoxyphenyl)sulfamoyl)-2-naphthoic acid,
4-(N-(4-(3-bromophenoxy)phenyl)sulfamoyl)-1-hydroxy-2-naphthoic acid,
1-hydroxy-4-(N-(4-(p-tolyloxy)phenyl)sulfamoyl)-2-naphthoic acid, 4-(N-(4-(2,4-dichlorophenoxy)phenyl)sulfamoyl)-1-hydroxy-2-naphthoic acid, 4-((4-benzylpiperazin-1-yl)sulfonyl)-1-hydroxy-2-naphthoic acid, 4-(N-(4-(4-chlorophenoxy)phenyl)sulfamoyl)-1-hydroxy-2-naphthoic acid, 4-(N-(4-(3,5-dimethylphenoxy)phenyl)sulfamoyl)-1-hydroxy-2-naphthoic acid, 1-hydroxy-4-(N-phenylsulfamoyl)-2-naphthoic acid, 4-(N-(4-bromophenyl)-N-isobutylsulfamoyl)-1-hydroxy-2-naphthoic acid, 1-hydroxy-4-sulfamoyl-2-naphthoic acid, 1-hydroxy-4-(N-isobutyl-N-(4-isopropoxyphenyl)sulfamoyl)-2-naphthoic acid, 4-(N-(4-bromophenyl)sulfamoyl)-1-hydroxy-2-naphthoic acid, methyl 1-hydroxy-4-(N-isobutyl-N-(4-isopropoxyphenyl)sulfamoyl)-2-naphthoate, and acetoxymethyl 1-hydroxy-4-(N-isobutyl-N-(4-isopropoxyphenyl)sulfamoyl)-2-naphthoate.

In an embodiment, the Mcl-1 inhibitor may be a compound of formula IIIa or IIIb, or a pharmaceutically acceptable salt, solvate, hydrate, cocrystal, tautomer, or prodrug thereof. In some embodiments, the compounds of formula I include the compounds of formula IIIa or IIIb, and the pharmaceutically acceptable salts, solvates, hydrates, cocrystals, tautomers, or prodrugs thereof. In some embodiments, the Mcl-1 inhibitor of formula IIIa or IIIb includes one or more of:

1-(phenylsulfonyl)-1,2,3,4-tetrahydroquinoline-6-carboxylic acid, 1-((4-bromophenyl)sulfonyl)-1,2,3,4-tetrahydroquinoline-6-carboxylic acid, 1-((4-phenoxyphenyl)sulfonyl)-1,2,3,4-tetrahydroquinoline-6-carboxylic acid, 1-(naphthalen-2-ylsulfonyl)-1,2,3,4-tetrahydroquinoline-6-carboxylic acid, 1-((4-(3,5-dimethylphenoxy)phenyl)sulfonyl)-1,2,3,4-tetrahydroquinoline-6-carboxylic acid, 1-((4-(p-tolylthio)phenyl)sulfonyl)-1,2,3,4-tetrahydroquinoline-6-carboxylic acid, 1-((benzyloxy)carbonyl)-1,2,3,4-tetrahydroquinoline-6-carboxylic acid, 1-(isobutoxycarbonyl)-1,2,3,4-tetrahydroquinoline-6-carboxylic acid, 1-(tert-butoxycarbonyl)-1,2,3,4-tetrahydroquinoline-6-carboxylic acid, 1-(4-phenoxybenzyl)-1,2,3,4-tetrahydroquinoline-6-carboxylic acid, 1-(3-(4-chloro-3,5-dimethylphenoxy)propyl)-1,2,3,4-tetrahydroquinoline-6-carboxylic acid, phenyl 1-((4-(4-chloro-3,5-dimethylphenoxy)phenyl)sulfonyl)-1,2,3,4-tetrahydroquinoline-6-carboxylate, 1-((4-(4-chloro-3,5-dimethylphenoxy)phenyl)sulfonyl)-1,2,3,4-tetrahydroquinoline-6-carboxamide, methyl 1-((4-(4-chloro-3,5-dimethylphenoxy)phenyl)sulfonyl)-1,2,3,4-tetrahydroquinoline-6-carboxylate, acetoxymethyl 1-((4-(4-chloro-3,5-dimethylphenoxy)phenyl)sulfonyl)-1,2,3,4-tetrahydroquinoline-6-carboxylate, 1-((4-fluorophenyl)sulfonyl)-1,2,3,4-tetrahydroquinoline-6-carboxylic acid, 1-([1,1'-biphenyl]-4-ylsulfonyl)-1,2,3,4-tetrahydroquinoline-6-carboxylic acid, 1-((4-(p-tolyloxy)phenyl)sulfonyl)-1,2,3,4-tetrahydroquinoline-6-carboxylic acid, 1-(quinolin-8-ylsulfonyl)-1,2,3,4-tetrahydroquinoline-6-carboxylic acid, 1-((5-(dimethylamino)naphthalen-1-yl)sulfonyl)-1,2,3,4-tetrahydroquinoline-6-carboxylic acid, 1-((4-(4-chloro-3,5-dimethylphenoxy)phenyl)sulfonyl)-1,2,3,4-tetrahydroquinoline-6-carboxylic acid, (±)-1-(phenylsulfonyl)-1,2,3,4-tetrahydroquinoline-3-carboxylic acid, (±)-1-((4-bromophenyl)sulfonyl)-1,2,3,4-tetrahydroquinoline-3-carboxylic acid, (±)-1-((4-fluorophenyl)sulfonyl)-1,2,3,4-tetrahydroquinoline-3-carboxylic acid, (±)-1-([1,1'-biphenyl]-4-ylsulfonyl)-1,2,3,4-tetrahydroquinoline-3-carboxylic acid, (±)-1-(naphthalen-2-ylsulfonyl)-1,2,3,4-tetrahydroquinoline-3-carboxylic acid, (±)-1-((4-(4-chloro-3,5-dimethylphenoxy)phenyl)sulfonyl)-1,2,3,4-tetrahydroquinoline-3-carboxylic acid, (±)-1-(3-(4-chloro-3,5-dimethylphenoxy)propyl)-1,2,3,4-tetrahydroquinoline-3-carboxylic acid, and 4-(N-isobutylphenylsulfonamido)benzoic acid.

In an embodiment, the Mcl-1 inhibitor may be a compound of formula IV, or a pharmaceutically acceptable salt, solvate, hydrate, cocrystal, tautomer, or prodrug thereof. In some embodiments, the compounds of formula I include the compounds of formula IV, and the pharmaceutically acceptable salts, solvates, hydrates, cocrystals, tautomers, or prodrugs thereof. In some embodiments, the Mcl-1 inhibitor of formula IV may include one or more of:

4-(N-isobutyl-[1,1'-biphenyl]-4-ylsulfonamido)benzoic acid, 4-(N-isobutylnaphthalene-2-sulfonamido)benzoic acid, 2-hydroxy-4-(N-isobutylphenylsulfonamido)benzoic acid, 2-hydroxy-4-(N-isobutyl-4-methylphenylsulfonamido)benzoic acid, 4-(4-bromo-N-isobutylphenylsulfonamido)-2-hydroxybenzoic acid, 2-hydroxy-4-(N-isobutyl-4-(p-tolyloxy)phenylsulfonamido)benzoic acid, 4-(4-(3,5-dimethylphenoxy)-N-isobutylphenylsulfonamido)-2-hydroxybenzoic acid, 4-(4-(2,4-dichlorophenoxy)-N-isobutylphenylsulfonamido)-2-hydroxybenzoic acid, 2-hydroxy-4-(4-phenoxyphenylsulfonamido)benzoic acid, 3-(N-isobutylphenylsulfonamido)benzoic acid, 3-(N-isobutyl-4-methylphenylsulfonamido)benzoic acid, 2-hydroxy-5-(N-isobutylnaphthalene-2-sulfonamido)benzoic acid, 5-(4-(4-chloro-3,5-dimethylphenoxy)-N-isobutylphenylsulfonamido)-2-hydroxybenzoic acid, methyl 2-hydroxy-4-(N-isobutyl-4-phenoxyphenylsulfonamido)benzoate, 4-(N-benzyl-4-phenoxyphenylsulfonamido)-2-hydroxy-N-(phenylsulfonyl)benzamide, 4-(N-benzyl-4-phenoxyphenylsulfonamido)-2-hydroxy-N-(methylsulfonyl)benzamide, 4-(N-isobutyl-4-phenoxyphenylsulfonamido)-2-((4-(((3-nitro-4-(((tetrahydro-2H-pyran-4-yl)methyl)amino)phenyl)sulfonyl)carbamoyl)benzyl)oxy)benzoic acid, 4-(4-fluoro-N-isobutylphenylsulfonamido)benzoic acid, 4-(4-(4-chloro-3,5-dimethylphenoxy)-N-isobutylphenylsulfonamido)benzoic acid, 2-hydroxy-4-(N-isobutylnaphthalene-2-sulfonamido)benzoic acid, 2-hydroxy-4-(N-isobutyl-[1,1'-biphenyl]-4-ylsulfonamido)benzoic acid, 4-(N-cyclopentyl-[1,1'-biphenyl]-4-ylsulfonamido)-2-hydroxybenzoic acid, 4-(N-cyclopentylnaphthalene-2-sulfonamido)-2-hydroxybenzoic acid, 4-(4-(4-chloro-3,5-dimethylphenoxy)-N-cyclopentylphenylsulfonamido)-2-hydroxybenzoic acid, 3-(N-isobutylnaphthalene-2-sulfonamido)benzoic acid, 3-(N-isobutyl-[1,1'-biphenyl]-4-ylsulfonamido)benzoic acid, 3-(4-(4-chloro-3,5-dimethylphenoxy)-N-isobutylphenylsulfonamido)benzoic acid, phenyl 2-hydroxy-4-(N-isobutyl-4-phenoxyphenylsulfonamido)benzoate, acetoxymethyl 2-hydroxy-4-(N-isobutyl-4-phenoxyphenylsulfonamido)benzoate, N-(4-cyano-3-hydroxyphenyl)-N-isobutyl-4-phenoxybenzenesulfonamide, 4-(N-benzyl-4-phenoxyphenylsulfonamido)-2-hydroxy-N-((3-nitro-4-(((tetrahydro-2H-pyran-4-yl)methyl)amino)phenyl)sulfonyl)benzamide, 4-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide, 3-(4-(4-chloro-3,5-dimethylphenoxy)-N-isobutylphenylsulfonamido)-2-hydroxybenzoic acid, 4-(4-fluoro-N-isobutylphenylsulfonamido)-2-hydroxybenzoic acid, 2-hydroxy-4-(N-isobutyl-4-phenoxyphenylsulfonamido)benzoic acid, 4-(N-benzyl-[1,1'-biphenyl]-4-ylsulfonamido)-2-hydroxybenzoic acid, 4-(N-benzylnaphthalene-2-sulfonamido)-2-hydroxybenzoic acid, 4-(N-benzyl-4-(4-chloro-3,5-dimethylphenoxy)phenylsulfonamido)-2-hydroxybenzoic acid, 3-(4-fluoro-N-isobutylphenylsulfonamido)benzoic acid, 2-hydroxy-5-(N-isobutylphenylsulfonamido)benzoic acid, 2-hydroxy-5-(N-isobutyl-[1,1'-biphenyl]-4-ylsulfonamido)benzoic acid, N-(4-(2H-tetrazol-5-yl)phenyl)-N-isobutyl-4-phenoxybenzenesulfonamide, N,2-dihydroxy-4-(N-isobutyl-4-phenoxyphenylsulfonamido)benzamide, N-isobutyl-N-(4-(3-oxo-2,3-dihydroisoxazol-5-yl)phenyl)-4-phenoxybenzenesulfonamide, 5-(N-benzyl-4-(4-chloro-3,5-dimethylphenoxy)phenylsulfonamido)-2-hydroxybenzoic acid, and 5-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide.

In an embodiment, the Mcl-1 inhibitor may be one or more of the compounds set forth in the table below:

| Identifier | Compound Name | Structure |
|---|---|---|
| | Naphthoate Analogs | |
| JY-5-371 | 4-(N-(4-(4-chloro-3,5-dimethyl phenoxy)phenyl) sulfamoyl)-1-hydroxy-2-naphthoic acid | 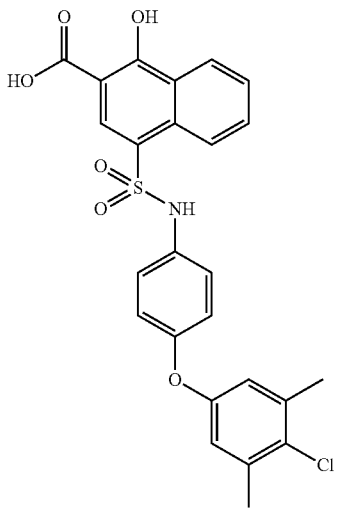 [SMILES: Cc1cc(Oc2ccc(NS(=O)(=O)c3cc(C(=O)O)c(O)c4ccccc34)cc2)cc(C)c1Cl] |

-continued

| Identifier | Compound Name | Structure |
| --- | --- | --- |
| JY-5-377 | 4-(N-(4-(4-chloro-3,5-dimethyl phenoxy)phenyl)-N-isobutylsulfamoyl)-1-hydroxy-2-naphthoic acid | 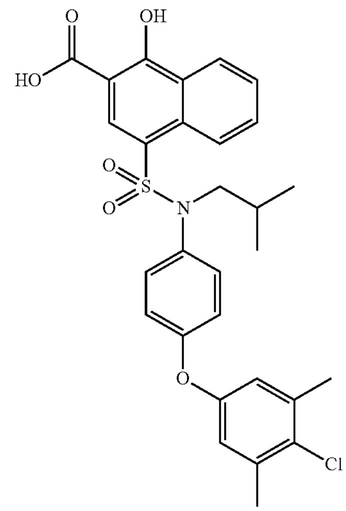 [SMILES: Cc1cc(Oc2ccc(N(CC(C)C)S(=O)(=O)c3cc(C(=O)O)c(O)c4ccccc34)cc2)cc(C)c1Cl] |
| JY-5-379 | 4-(N-(4-(4-chloro-3,5-dimethylphenoxy) phenyl)-N-cyclopentylsulfamoyl)-1-hydroxy-2-naphthoic acid | 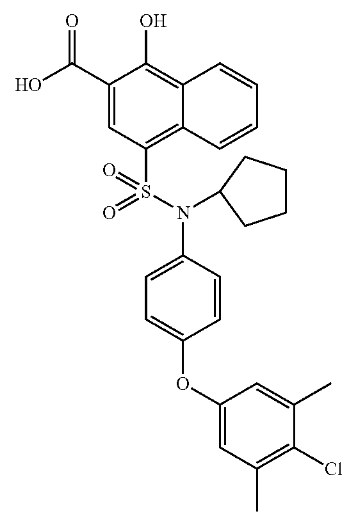 [SMILES: Cc1cc(Oc2ccc(N(C3CCCC3)S(=O)(=O)c3cc(C(=O)O)c(O)c4ccccc34)cc2)cc(C)c1Cl] |
| JY-5-380 | 4-(N-benzyl-N-(4-(4-chloro-3,5-dimethylphenoxy) phenyl) sulfamoyl)-1-hydroxy-2-naphthoic acid | 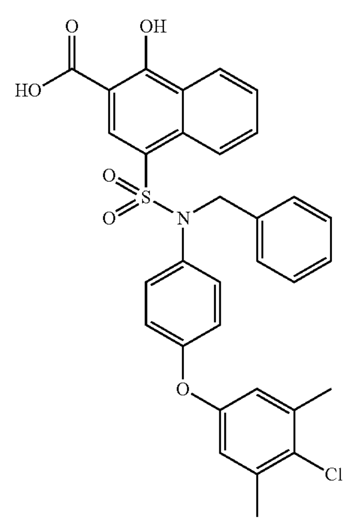 [SMILES: Cc1cc(Oc2ccc(N(Cc3ccccc3)S(=O)(=O)c3cc(C(=O)O)c(O)c4ccccc34)cc2)cc(C)c1Cl] |

-continued
| Identifier | Compound Name | Structure |
|---|---|---|
| 5jc65 | 4-(N-benzylsulfamoyl)-1-hydroxy-2-naphthoic acid | 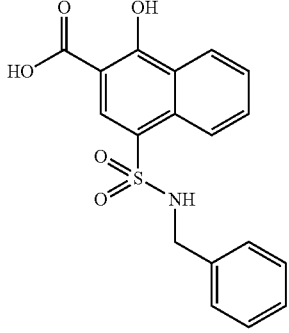 [SMILES: O=C(O)c1cc(S(=O)(=O)NCc2ccccc2)c2ccccc2c1O] |
| 5jc67 | 4-(N-(4-chlorophenyl)sulfamoyl)-1-hydroxy-2-naphthoic acid | 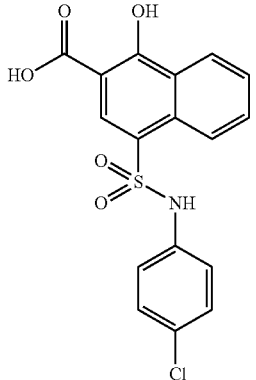 |
| 5jc71 | 4-(N-(3-chlorobenzyl)sulfamoyl)-1-hydroxy-2-naphthoic acid | 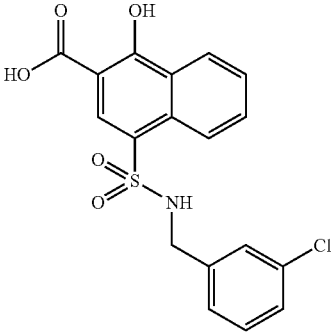 [SMILES: O=C(O)c1cc(S(=O)(=O)NCc2cccc(Cl)c2)c2ccccc2c1O] |
| 5jc73-1 | 1-hydroxy-4-(N-(4-(trifluoromethyl)phenyl)sulfamoyl)-2-naphthoic acid | 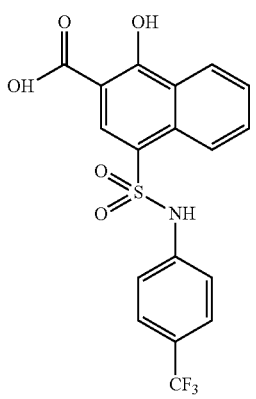 [SMILES: O=C(O)c1cc(S(=O)(=O)Nc2ccc(C(F)(F)F)cc2)c2ccccc2c1O] |

-continued

| Identifier | Compound Name | Structure |
|---|---|---|
| 5jc73-2 | 4-(N-(2-chlorobenzyl)sulfamoyl)-1-hydroxy-2-naphthoic acid | 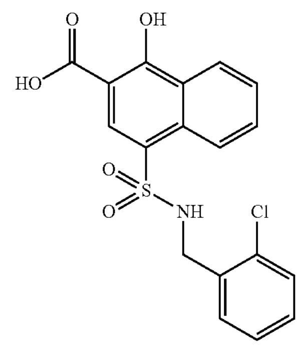 [SMILES: O=C(O)c1cc(S(=O)(=O)NCc2ccccc2Cl)c2ccccc2c1O] |
| 5jc74-1 | 1-hydroxy-4-(N-(p-tolyl)sulfamoyl)-2-naphthoic acid | 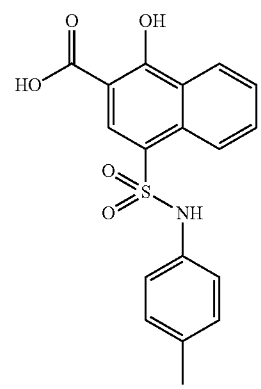 [SMILES: Cc1ccc(NS(=O)(=O)c2cc(C(=O)O)c(O)c3ccccc23)cc1] |
| 5jc74-2 | 1-hydroxy-4-(N-(4-isopropylphenyl)sulfamoyl)-2-naphthoic acid | 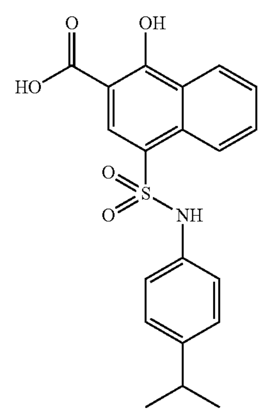 [SMILES: CC(C)c1ccc(NS(=O)(=O)c2cc(C(=O)O)c(O)c3ccccc23)cc1] |
| 5jc-75-2 | 4-(N-(3-cyanophenyl)sulfamoyl)-1-hydroxy-2-naphthoic acid | 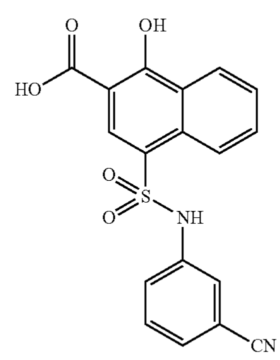 [SMILES: N#Cc1cccc(NS(=O)(=O)c2cc(C(=O)O)c(O)c3ccccc23)c1] |

-continued
| Identifier | Compound Name | Structure |
|---|---|---|
| LC-4-002 | 4-(N-([1,1'-biphenyl]-2-yl)sulfamoyl)-1-hydroxy-2-naphthoic acid | 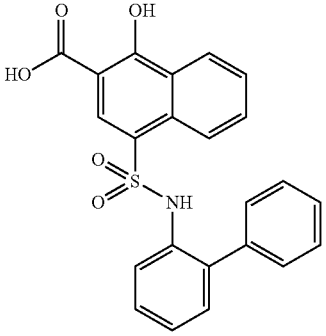 [SMILES: O=C(O)c1cc(S(=O)(=O)Nc2ccccc2-c2ccccc2)c2ccccc2c1O] |
| LC-3-191 | 4-(N-([1,1'-biphenyl]-4-yl)sulfamoyl)-1-hydroxy-2-naphthoic acid | 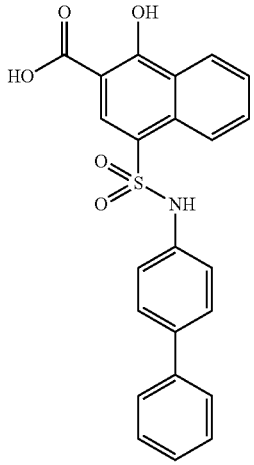 [SMILES: O=C(O)c1cc(S(=O)(=O)Nc2ccc(-c3ccccc3)cc2)c2ccccc2c1O] |
| LC-3-192 | 4-(N-([1,1'-biphenyl]-3-yl)sulfamoyl)-1-hydroxy-2-naphthoic acid | 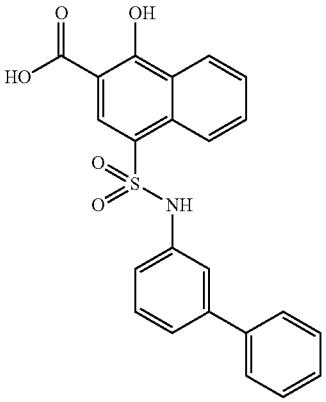 [SMILES: O=C(O)c1cc(S(=O)(=O)Nc2cccc(-c3ccccc3)c2)c2ccccc2c1O] |
| EW-2-051 | 1-hydroxy-4-((4-phenylpiperazin-1-yl)sulfonyl)-2-naphthoic acid | 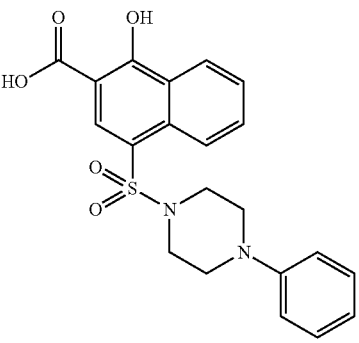 [SMILES: O=C(O)c1cc(S(=O)(=O)N2CCN(c3ccccc3)CC2)c2ccccc2c1O] |

-continued

| Identifier | Compound Name | Structure |
|---|---|---|
| EW-2-056 | 1-hydroxy-4-(N-(naphthalen-1-yl)sulfamoyl)-2-naphthoic acid | 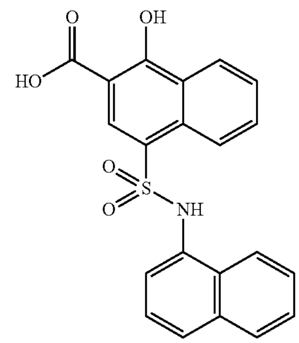 [SMILES: O=C(O)c1cc(S(=O)(=O)Nc2cccc3ccccc23)c2ccccc2c1O] |
| EW-2-057 | 1-hydroxy-4-(N-(naphthalen-2-yl)sulfamoyl)-2-naphthoic acid | 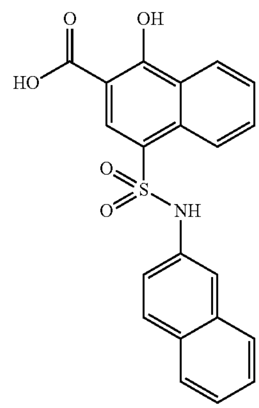 [SMILES: O=C(O)c1cc(S(=O)(=O)Nc2ccc3ccccc3c2)c2ccccc2c1O] |
| TA-1-018 | 4-(N-(4-cyanophenyl)sulfamoyl)-1-hydroxy-2-naphthoic acid | 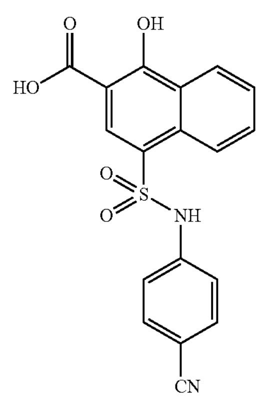 [SMILES: N#Cc1ccc(NS(=O)(=O)c2cc(C(=O)O)c(O)c3ccccc23)cc1] |
| MEL-3-018 | 1-hydroxy-4-(N-(4-methoxyphenyl)sulfamoyl)-2-naphthoic acid | 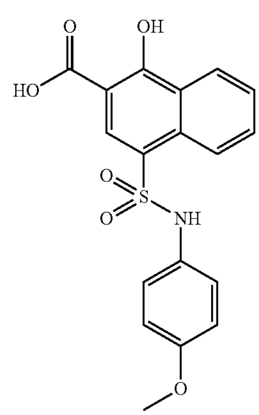 [SMILES: COc1ccc(NS(=O)(=O)c2cc(C(=O)O)c(O)c3ccccc23)cc1] |

-continued

| Identifier | Compound Name | Structure |
| --- | --- | --- |
| TA-1-017 | 1-hydroxy-4-(N-(2-(trifluoromethyl)phenyl)sulfamoyl)-2-naphthoic acid | 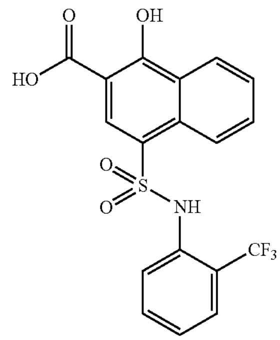 [SMILES: O=C(O)c1cc(S(=O)(=O)Nc2ccccc2C(F)(F)F)c2ccccc2c1O] |
| MEL-3-005 | 1-hydroxy-4-(N-(4-nitrophenyl)sulfamoyl)-2-naphthoic acid | 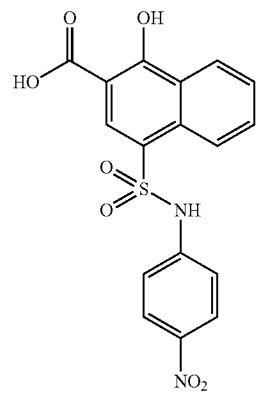 |
| TA-1-019 | 4-(N-(2-bromophenyl)sulfamoyl)-1-hydroxy-2-naphthoic acid | 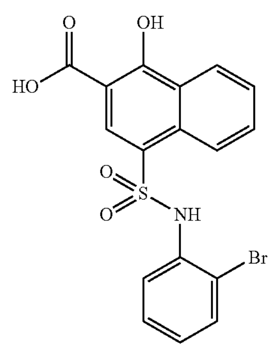 [SMILES: O=C(O)c1cc(S(=O)(=O)Nc2ccccc2Br)c2ccccc2c1O] |
| TA-1-020 | 4-(N-(3-bromophenyl)sulfamoyl)-1-hydroxy-2-naphthoic acid | 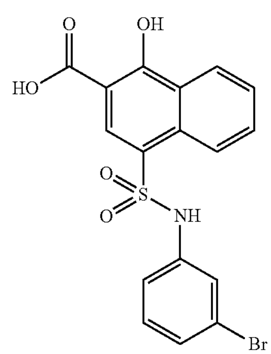 [SMILES: O=C(O)c1cc(S(=O)(=O)Nc2cccc(Br)c2)c2ccccc2c1O] |

-continued

| Identifier | Compound Name | Structure |
| --- | --- | --- |
| MEL-3-006 | 4-(N-(cyclohexylmethyl)sulfamoyl)-1-hydroxy-2-naphthoic acid | 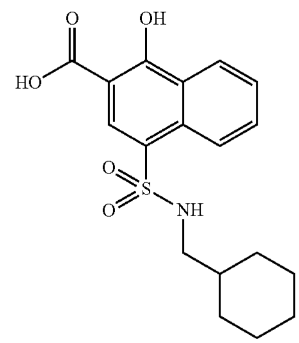 [SMILES: O=C(O)c1cc(S(=O)(=O)NCC2CCCCC2)c2ccccc2c1O] |
| MEL-3-009-A | methyl 4-(N-(4-bromophenyl)-N-isobutylsulfamoyl)-1-methoxy-2-naphthoate | 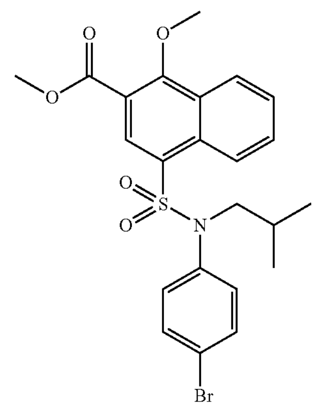 [SMILES: COC(=O)c1cc(S(=O)(=O)N(CC(C)C)c2ccc(Br)cc2)c2ccccc2c1OC] |
| MEL-3-009-B | methyl 4-(N-(4-bromophenyl)-N-isobutyl-sulfamoyl)-1-hydroxy-2-naphthoate | 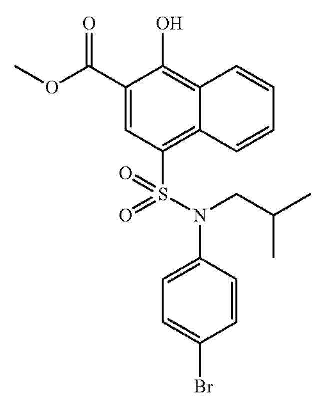 [SMILES: COC(=O)c1cc(S(=O)(=O)N(CC(C)C)c2ccc(Br)cc2)c2ccccc2c1O] |
| MEL-3-010 | 4-(N-(4-bromophenyl)-N-isobutylsulfamoyl)-1-methoxy-2-naphthoic acid | 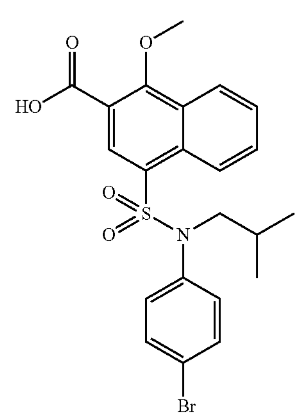 [SMILES: COc1c(C(=O)O)cc(S(=O)(=O)N(CC(C)C)c2ccc(Br)cc2)c2ccccc12] |

-continued

| Identifier | Compound Name | Structure |
|---|---|---|
| SF-5-263 | 1-hydroxy-4-(piperidin-1-ylsulfonyl)-2-naphthoic acid | 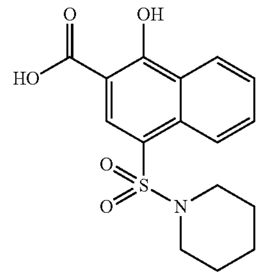 [SMILES: O=C(O)c1cc(S(=O)(=O)N2CCCCC2)c2ccccc2c1O] |
| SF-5-264 | 4-(N-(4-chlorobenzyl)sulfamoyl)-1-hydroxy-2-naphthoic acid | 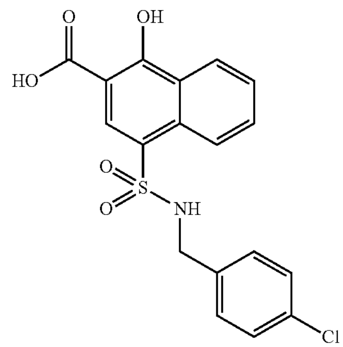 [SMILES: O=C(O)c1cc(S(=O)(=O)NCc2ccc(Cl)cc2)c2ccccc2c1O] |
| SF-5-290 | 4-(N-(2,4-dibromophenyl)sulfamoyl)-1-hydroxy-2-naphthoic acid | 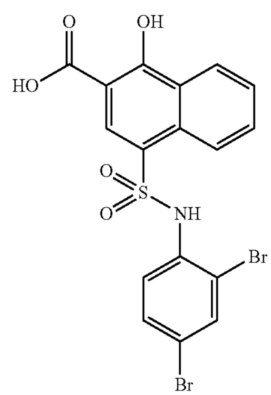 [SMILES: O=C(O)c1cc(S(=O)(=O)Nc2ccc(Br)cc2Br)c2ccccc2c1O] |
| SF-5-293 | 1-hydroxy-4-(N-(4-isopropoxyphenyl)sulfamoyl)-2-naphthoic acid | 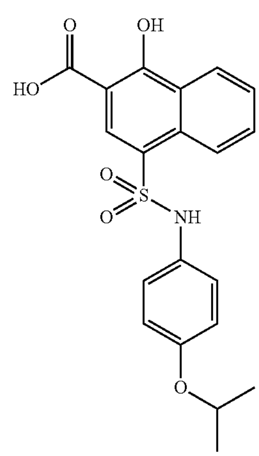 [SMILES: CC(C)Oc1ccc(NS(=O)(=O)c2cc(C(=O)O)c(O)c3ccccc23)cc1] |

-continued

| Identifier | Compound Name | Structure |
|---|---|---|
| SF-5-300 | 1-hydroxy-4-(N-(4-(naphthalen-1-yloxy)phenyl)sulfamoyl)-2-naphthoic acid | 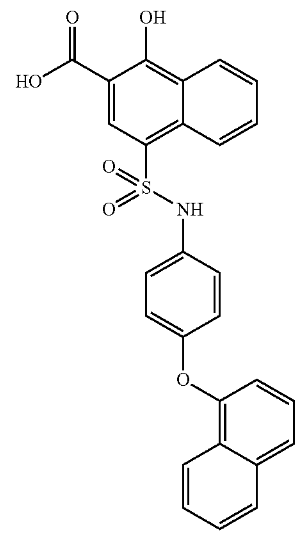 [SMILES: O=C(O)c1cc(S(=O)(=O)Nc2ccc(Oc3cccc4ccccc34)cc2)c2ccccc2c1O] |
| SF-5-295 | 4-(N,N-dimethyl-sulfamoyl)-1-hydroxy-2-naphthoic acid | 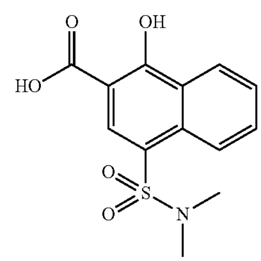 [SMILES: CN(C)S(=O)(=O)c1cc(C(=O)O)c(O)c2ccccc12] |
| SF-5-299 | 1-hydroxy-4-(N-(4-phenoxyphenyl)sulfamoyl)-2-naphthoic acid | 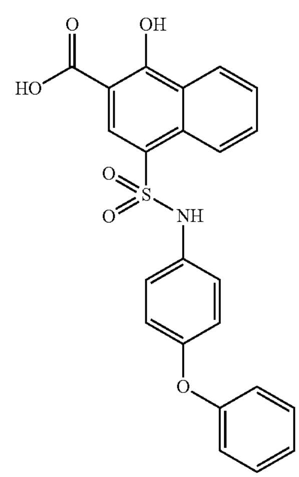 [SMILES: O=C(O)c1cc(S(=O)(=O)Nc2ccc(Oc3ccccc3)cc2)c2ccccc2c1O] |

| Identifier | Compound Name | Structure |
|---|---|---|
| SF-5-303 | 4-(N-(4-(3-bromophenoxy)phenyl)sulfamoyl)-1-hydroxy-2-naphthoic acid | 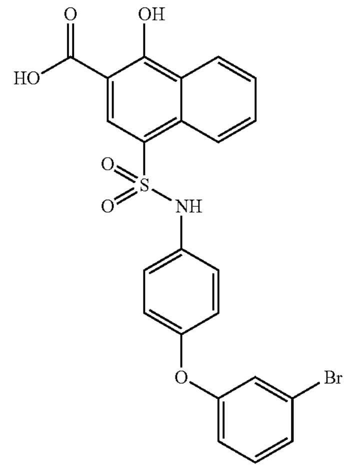 [SMILES: O=C(O)c1cc(S(=O)(=O)Nc2ccc(Oc3cccc(Br)c3)cc2)c2ccccc2c1O] |
| SF-5-301 | 1-hydroxy-4-(N-(4-(p-tolyloxy)phenyl)sulfamoyl)-2-naphthoic acid | 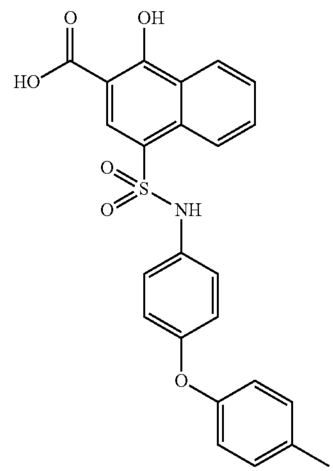 [SMILES: Cc1ccc(Oc2ccc(NS(=O)(=O)c3cc(C(=O)O)c(O)c4ccccc34)cc2)cc1] |
| SF-5-302 | 4-(N-(4-(2,4-dichlorophenoxy)phenyl)sulfamoyl)-1-hydroxy-2-naphthoic acid | 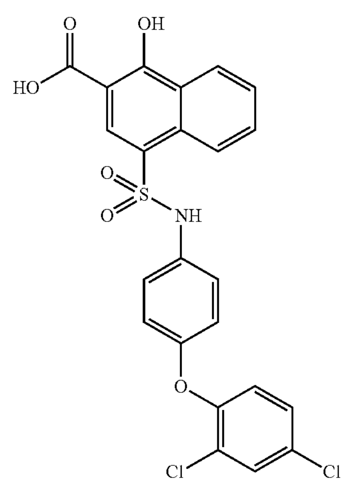 [SMILES: O=C(O)c1cc(S(=O)(=O)Nc2ccc(Oc3ccc(Cl)cc3Cl)cc2)c2ccccc2c1O] |

| Identifier | Compound Name | Structure |
|---|---|---|
| SF-5-307 | 4-((4-benzyl-piperazin-1-yl)sulfonyl)-1-hydroxy-2-naphthoic acid | 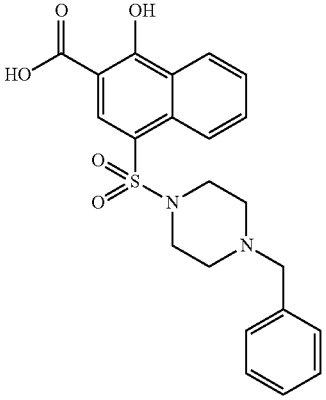 [SMILES: O=C(O)c1cc(S(=O)(=O)N2CCN(Cc3ccccc3)CC2)c2ccccc2c1O] |
| SF-5-304 | 4-(N-(4-(4-chlorophenoxy)phenyl)sulfamoyl)-1-hydroxy-2-naphthoic acid | 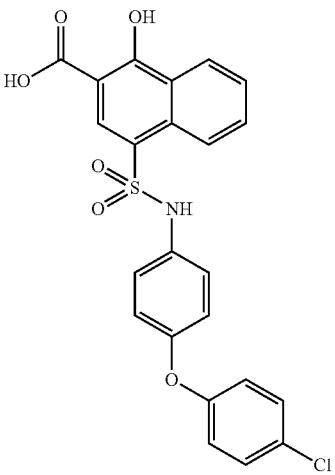 [SMILES: O=C(O)c1cc(S(=O)(=O)Nc2ccc(Oc3ccc(Cl)cc3)cc2)c2ccccc2c1O] |
| SF-5-306 | 4-(N-(4-(3,5-dimethylphenoxy)phenyl)sulfamoyl)-1-hydroxy-2-naphthoic acid | 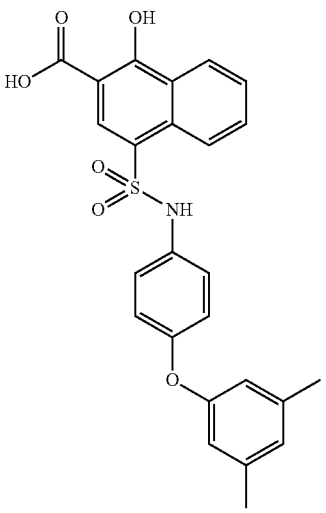 [SMILES: Cc1cc(C)cc(Oc2ccc(NS(=O)(=O)c3cc(C(=O)O)c(O)c4ccccc34)cc2)c1] |

-continued
| Identifier | Compound Name | Structure |
|---|---|---|
| SF-5-311 | 1-hydroxy-4-(N-phenylsulfamoyl)-2-naphthoic acid | 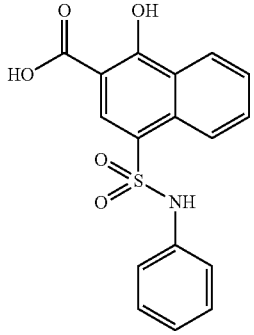 [SMILES: O=C(O)c1cc(S(=O)(=O)Nc2ccccc2)c2ccccc2c1O] |
| SF-5-308 | 4-(N-(4-bromophenyl)-N-isobutylsulfamoyl)-1-hydroxy-2-naphthoic acid | 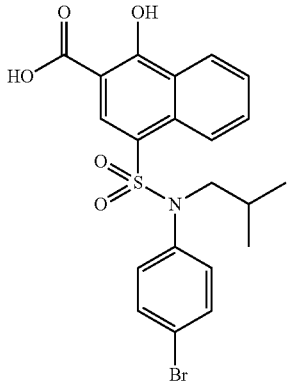 [SMILES: CC(C)CN(c1ccc(Br)cc1)S(=O)(=O)c1cc(C(=O)O)c(O)c2ccccc12] |
| SF-5-294 | 1-hydroxy-4-sulfamoyl-2-naphthoic acid | 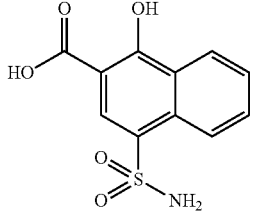 [SMILES: NS(=O)(=O)c1cc(C(=O)O)c(O)c2ccccc12] |
| MEL-2-116 | 1-hydroxy-4-(N-isobutyl-N-(4-isopropoxyphenyl)sulfamoyl)-2-naphthoic acid | 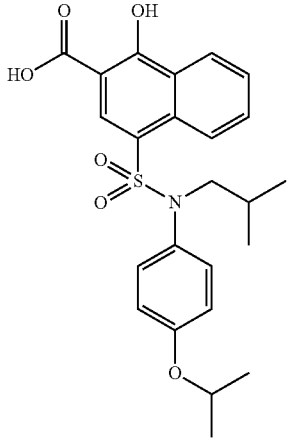 [SMILES: CC(C)CN(c1ccc(OC(C)C)cc1)S(=O)(=O)c1cc(C(=O)O)c(O)c2ccccc12] |

-continued

| Identifier | Compound Name | Structure |
|---|---|---|
| SF-5-180 | 4-(N-(4-bromophenyl)sulfamoyl)-1-hydroxy-2-naphthoic acid | 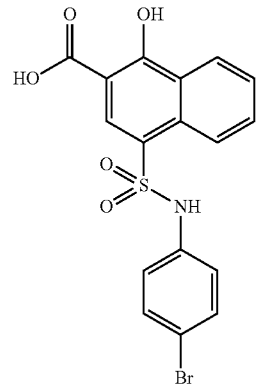 [SMILES: O=C(O)c1cc(S(=O)(=O)Nc2ccc(Br)cc2)c2ccccc2c1O] |
| MEL-3-118 | methyl 1-hydroxy-4-(N-isobutyl-N-(4-isopropoxyphenyl)sulfamoyl)-2-naphthoate | 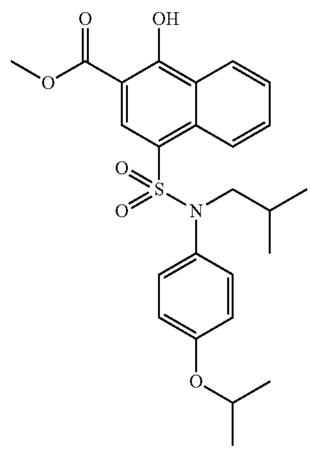 [SMILES: COC(=O)c1cc(S(=O)(=O)N(CC(C)C)c2ccc(OC(C)C)cc2)c2ccccc2c1O] |
| MEL-3-128 | acetoxymethyl 1-hydroxy-4-(N-isobutyl-N-(4-isopropoxyphenyl)sulfamoyl)-2-naphthoate | 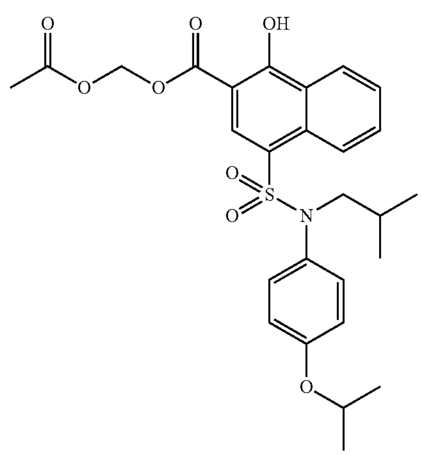 [SMILES: CC(=O)OCOC(=O)c1cc(S(=O)(=O)N(CC(C)C)c2ccc(OC(C)C)cc2)c2ccccc2c1O] |

Tetrahydroquinoline Analogs

-continued
| Identifier | Compound Name | Structure |
|---|---|---|
| SF-5-118 | 1-(phenylsulfonyl)-1,2,3,4-tetrahydroquinoline-6-carboxylic acid | 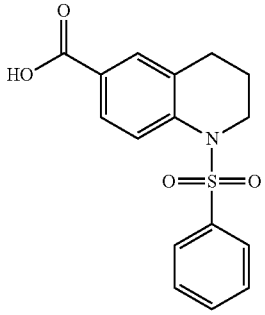 [SMILES: O=C(O)c1ccc2c(c1)CCCN2S(=O)(=O)c1ccccc1] |
| LC-3-004 | 1-((4-bromophenyl)sulfonyl)-1,2,3,4-tetrahydroquinoline-6-carboxylic acid | 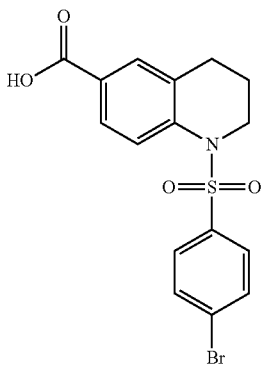 [SMILES: O=C(O)c1ccc2c(c1)CCCN2S(=O)(=O)c1ccc(Br)cc1] |
| LC-4-013 | 1-((4-phenoxyphenyl)sulfonyl)-1,2,3,4-tetrahydroquinoline-6-carboxylic acid | 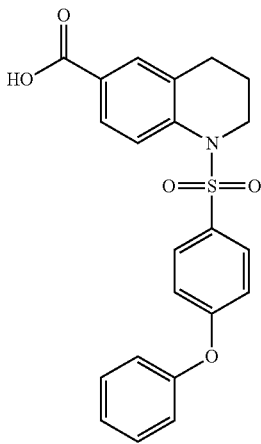 [SMILES: O=C(O)c1ccc2c(c1)CCCN2S(=O)(=O)c1ccc(Oc2ccccc2)cc1] |
| LC-3-006 | 1-(naphthalen-2-ylsulfonyl)-1,2,3,4-tetrahydroquinoline-6-carboxylic acid | 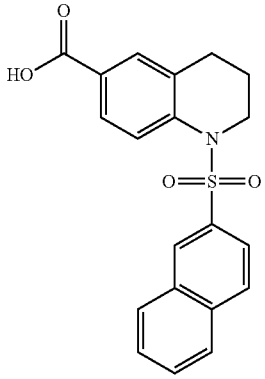 [SMILES: O=C(O)c1ccc2c(c1)CCCN2S(=O)(=O)c1ccc2ccccc2c1] |

-continued

| Identifier | Compound Name | Structure |
|---|---|---|
| LC-4-159 | 1-((4-(3,5-dimethylphenoxy)phenyl)sulfonyl)-1,2,3,4-tetrahydroquinoline-6-carboxylic acid | 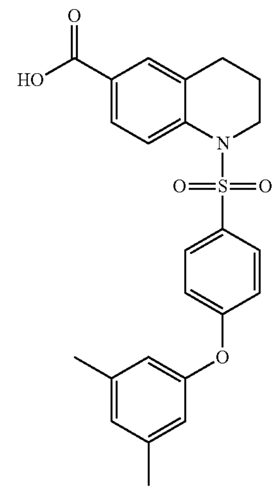 [SMILES: Cc1cc(C)cc(Oc2ccc(S(=O)(=O)N3CCCc4cc(C(=O)O)ccc43)cc2)c1] |
| LC-4-160 | 1-((4-(p-tolylthio)phenyl)sulfonyl)-1,2,3,4-tetrahydroquinoline-6-carboxylic acid | 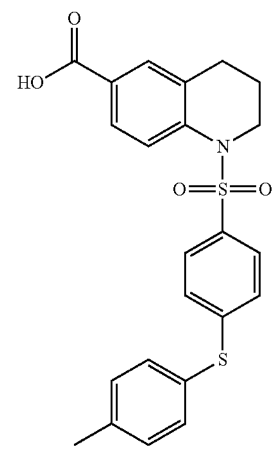 [SMILES: Cc1ccc(Sc2ccc(S(=O)(=O)N3CCCc4cc(C(=O)O)ccc43)cc2)cc1] |
| LC-3-182 | 1-((benzyloxy)carbonyl)-1,2,3,4-tetrahydroquinoline-6-carboxylic acid | 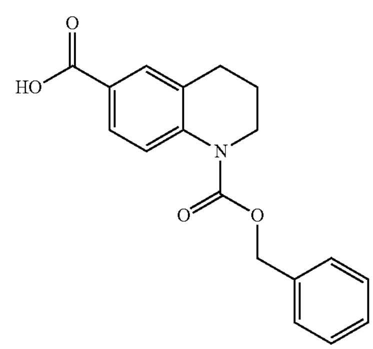 [SMILES: O=C(O)c1ccc2c(c1)CCCN2C(=O)OCc1ccccc1] |
| LC-3-177 | 1-(isobutoxycarbonyl)-1,2,3,4-tetrahydroquinoline-6-carboxylic acid | 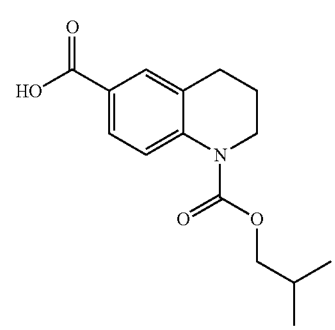 [SMILES: CC(C)COC(=O)N1CCCc2cc(C(=O)O)ccc21] |

-continued

| Identifier | Compound Name | Structure |
| --- | --- | --- |
| LC-3-178 | 1-(tert-butoxycarbonyl)-1,2,3,4-tetrahydroquinoline-6-carboxylic acid | 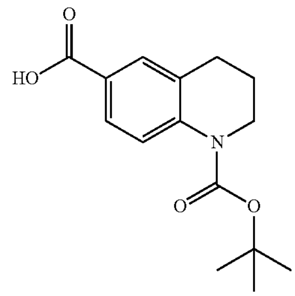 [SMILES: CC(C)(C)OC(=O)N1CCCc2cc(C(=O)O)ccc21] |
| LC-4-180 | 1-(4-phenoxybenzyl)-1,2,3,4-tetrahydroquinoline-6-carboxylic acid | 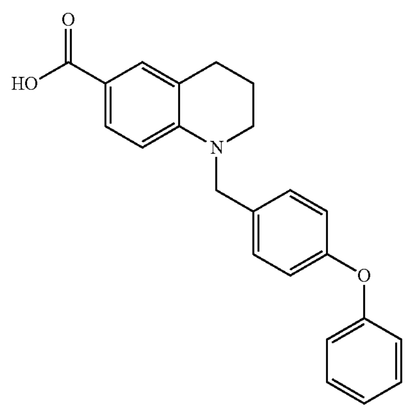 [SMILES: O=C(O)c1ccc2c(c1)CCCN2Cc1ccc(Oc2ccccc2)cc1] |
| LC-3-014 | 1-(3-(4-chloro-3,5-dimethylphenoxy)propyl)-1,2,3,4-tetrahydroquinoline-6-carboxylic acid | 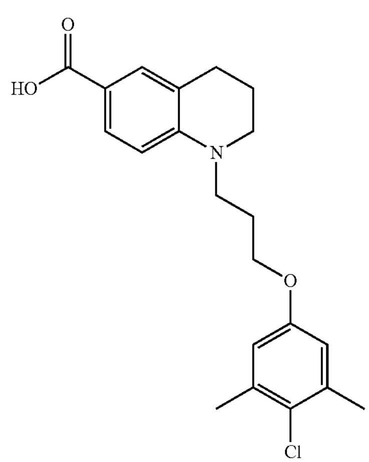 [SMILES: Cc1cc(OCCCN2CCCc3cc(C(=O)O)ccc32)cc(C)c1Cl] |

-continued

| Identifier | Compound Name |
|---|---|
| LC-3-122 | phenyl 1-((4-(4-chloro-3,5-dimethylphenoxy)phenyl)sulfonyl)-1,2,3,4-tetrahydroquinoline-6-carboxylate |
| LC-3-119 | 1-((4-(4-chloro-3,5-dimethylphenoxy)phenyl)sulfonyl)-1,2,3,4-tetrahydroquinoline-6-carboxamide |
| LC-3-121 | methyl 1-((4-(4-chloro-3,5-dimethylphenoxy)phenyl)sulfonyl)-1,2,3,4-tetrahydroquinoline-6-carboxylate |

-continued

| Identifier | Compound Name | Structure |
|---|---|---|
| LC-3-128 | acetoxymethyl 1-((4-(4-chloro-3,5-dimethylphenoxy)phenyl)sulfonyl)-1,2,3,4-tetrahydroquinoline-6-carboxylate | 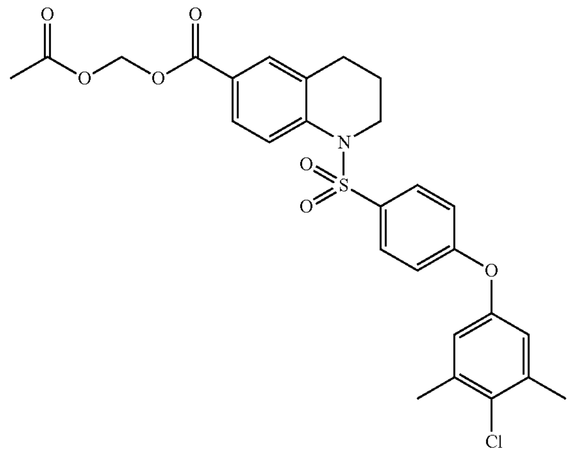 [SMILES: CC(=O)OCOC(=O)c1ccc2c(c1)CCCN2S(=O)(=O)c1ccc(Oc2cc(C)c(Cl)c(C)c2)cc1] |
| LC-3-010 | 1-((4-fluorophenyl)sulfonyl)-1,2,3,4-tetrahydroquinoline-6-carboxylic acid | 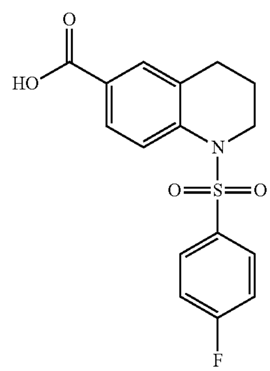 [SMILES: O=C(O)c1ccc2c(c1)CCCN2S(=O)(=O)c1ccc(F)cc1] |
| LC-3-002 | 1-([1,1'-biphenyl]-4-ylsulfonyl)-1,2,3,4-tetrahydroquinoline-6-carboxylic acid | 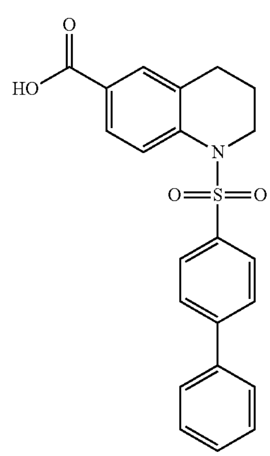 [SMILES: O=C(O)c1ccc2c(c1)CCCN2S(=O)(=O)c1ccc(-c2ccccc2)cc1] |

-continued

| Identifier | Compound Name | Structure |
|---|---|---|
| LC-4-158 | 1-((4-(p-tolyloxy)phenyl)sulfonyl)-1,2,3,4-tetrahydroquinoline-6-carboxylic acid | 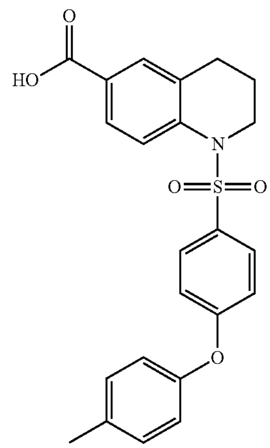 [SMILES: Cc1ccc(Oc2ccc(S(=O)(=O)N3CCCc4cc(C(=O)O)ccc43)cc2)cc1] |
| LC-4-172 | 1-(quinolin-8-ylsulfonyl)-1,2,3,4-tetrahydroquinoline-6-carboxylic acid | 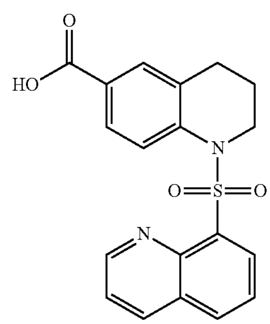 [SMILES: O=C(O)c1ccc2c(c1)CCCN2S(=O)(=O)c1cccc2cccnc12] |
| LC-4-165 | 1-((5-(dimethylamino)naphthalen-1-yl)sulfonyl)-1,2,3,4-tetrahydroquinoline-6-carboxylic acid | 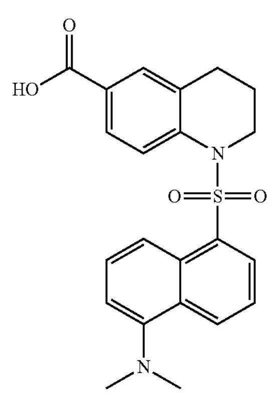 [SMILES: CN(C)c1cccc2c(S(=O)(=O)N3CCCc4cc(C(=O)O)ccc43)cccc12] |

-continued

| Identifier | Compound Name | Structure |
| --- | --- | --- |
| LC-3-012 | 1-((4-(4-chloro-3,5-dimethylphenoxy)phenyl)sulfonyl)-1,2,3,4-tetrahydroquinoline-6-carboxylic acid | 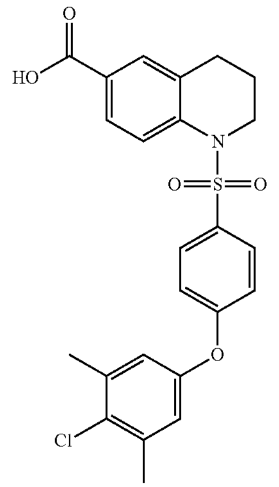 [SMILES: Cc1cc(Oc2ccc(S(=O)(=O)N3CCCc4cc(C(=O)O)ccc43)cc2)cc(C)c1Cl] |
| SF-5-103 | (±)-1-(phenylsulfonyl)-1,2,3,4-tetrahydroquinoline-3-carboxylic acid | 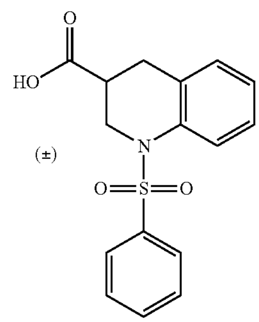 [SMILES: O=C(O)C1Cc2ccccc2N(S(=O)(=O)c2ccccc2)C1] |
| SF-5-135 | (±)-1-((4-bromophenyl)sulfonyl)-1,2,3,4-tetrahydroquinoline-3-carboxylic acid | 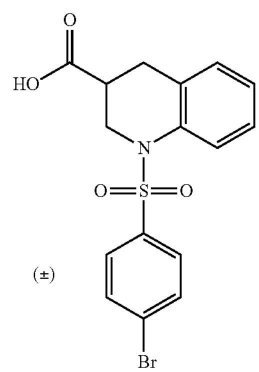 [SMILES: O=C(O)C1Cc2ccccc2N(S(=O)(=O)c2ccc(Br)cc2)C1] |
| SF-5-136 | (±)-1-((4-fluorophenyl)sulfonyl)-1,2,3,4-tetrahydroquinoline-3-carboxylic acid | 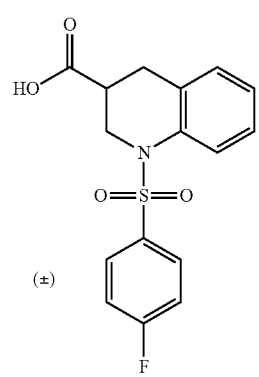 [SMILES: O=C(O)C1Cc2ccccc2N(S(=O)(=O)c2ccc(F)cc2)C1] |

-continued
| Identifier | Compound Name | Structure |
|---|---|---|
| SF-5-133 | (±)-1-([1,1'-biphenyl]-4-ylsulfonyl)-1,2,3,4-tetrahydroquinoline-3-carboxylic acid | 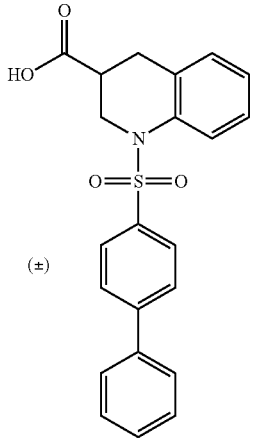 [SMILES: O=C(O)C1Cc2ccccc2N(S(=O)(=O)c2ccc(-c3ccccc3)cc2)C1] |
| SF-5-134 | (±)-1-(naphthalen-2-ylsulfonyl)-1,2,3,4-tetrahydroquinoline-3-carboxylic acid | 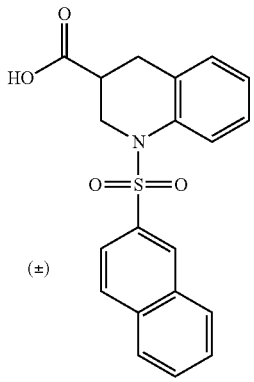 [SMILES: O=C(O)C1Cc2ccccc2N(S(=O)(=O)c2ccc3ccccc3c2)C1] |
| SF-5-141/ LC-3-115 | (±)-1-((4-(4-chloro-3,5-dimethylphenoxy)phenyl)sulfonyl)-1,2,3,4-tetrahydroquinoline-3-carboxylic acid | 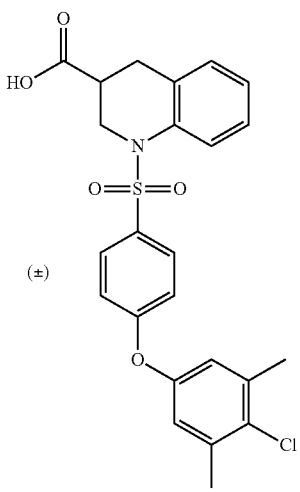 [SMILES: Cc1cc(Oc2ccc(S(=O)(=O)N3CC(C(=O)O)Cc4ccccc43)cc2)cc(C)c1Cl] |

-continued

| Identifier | Compound Name | Structure |
| --- | --- | --- |
| LC-3-016 | (±)-1-(3-(4-chloro-3,5-dimethylphenoxy)propyl)-1,2,3,4-tetrahydroquinoline-3-carboxylic acid | |
| Salicylate/Aminobenzoate Analogs | | |
| LC-3-029 | 4-(N-isobutylphenyl-sulfonamido)benzoic acid | 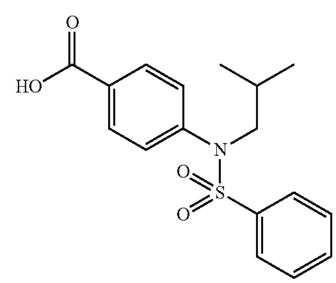 [SMILES: CC(C)CN(c1ccc(C(=O)O)cc1)S(=O)(=O)c1ccccc1] |
| LC-3-030 | 4-(N-isobutyl-[1,1'-biphenyl]-4-ylsulfonamido)benzoic acid | 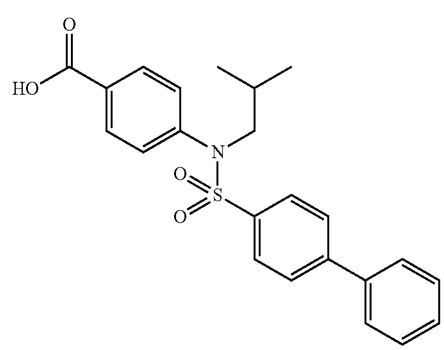 [SMILES: CC(C)CN(c1ccc(C(=O)O)cc1)S(=O)(=O)c1ccc(-c2ccccc2)cc1] |
| LC-3-031 | 4-(N-isobutylnaphthalene-2-sulfonamido)benzoic acid | 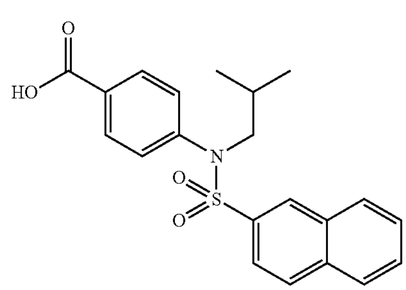 [SMILES: CC(C)CN(c1ccc(C(=O)O)cc1)S(=O)(=O)c1ccc2ccccc2c1] |

-continued

| Identifier | Compound Name | Structure |
|---|---|---|
| 4jc117-1 | 2-hydroxy-4-(N-isobutylphenyl-sulfonamido) benzoic acid | 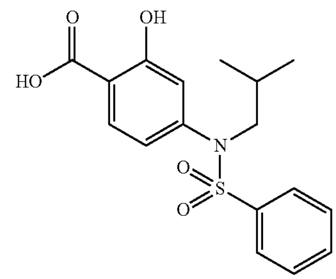 [SMILES: CC(C)CN(c1ccc(C(=O)O)c(O)c1)S(=O)(=O)c1ccccc1] |
| 4jc117-2 | 2-hydroxy-4-(N-isobutyl-4-methylphenyl-sulfonamido) benzoic acid | 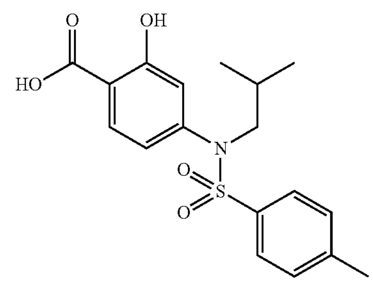 [SMILES: Cc1ccc(S(=O)(=O)N(CC(C)C)c2ccc(C(=O)O)c(O)c2)cc1] |
| LC-5-012 | 4-(4-bromo-N-isobutylphenyl-sulfonamido)-2-hydroxybenzoic acid | 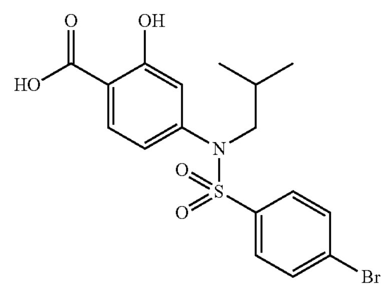 [SMILES: CC(C)CN(c1ccc(C(=O)O)c(O)c1)S(=O)(=O)c1ccc(Br)cc1] |
| LC-4-119 | 2-hydroxy-4-(N-isobutyl-4-(p-tolyloxy)phenyl-sulfonamido) benzoic acid | 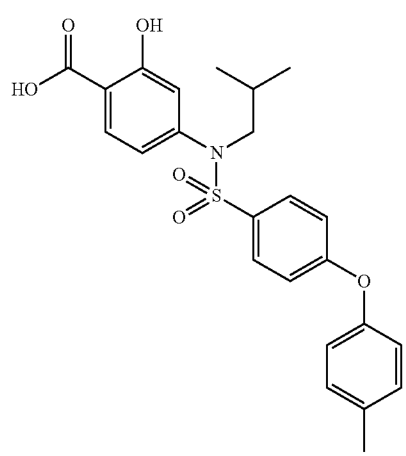 [SMILES: Cc1ccc(Oc2ccc(S(=O)(=O)N(CC(C)C)c3ccc(C(=O)O)c(O)c3)cc2)cc1] |

-continued

| Identifier | Compound Name | Structure |
|---|---|---|
| LC-4-100 | 4-(4-(3,5-dimethylphenoxy)-N-isobutylphenyl-sulfonamido)-2-hydroxybenzoic acid | 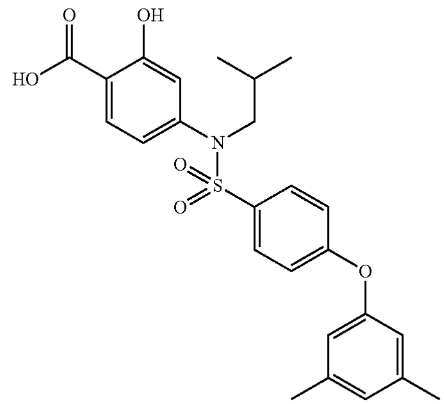 [SMILES: Cc1cc(C)cc(Oc2ccc(S(=O)(=O)N(CC(C)C)c3ccc(C(=O)O)c(O)c3)cc2)c1] |
| LC-4-111 | 4-(4-(2,4-dichlorophenoxy)-N-isobutylphenyl-sulfonamido)-2-hydroxybenzoic acid | 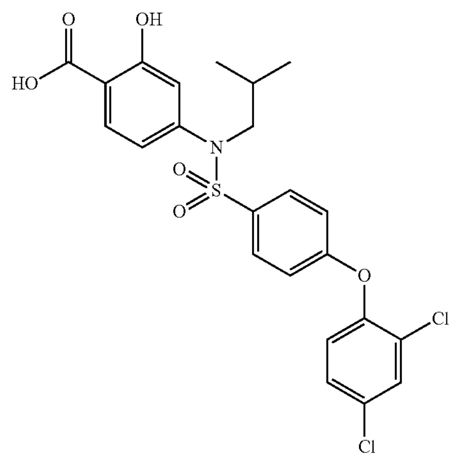 [SMILES: CC(C)CN(c1ccc(C(=O)O)c(O)c1)S(=O)(=O)c1ccc(Oc2ccc(Cl)cc2Cl)cc1] |
| LC-5-005 | 2-hydroxy-4-(4-phenoxyphenyl-sulfonamido)benzoic acid | 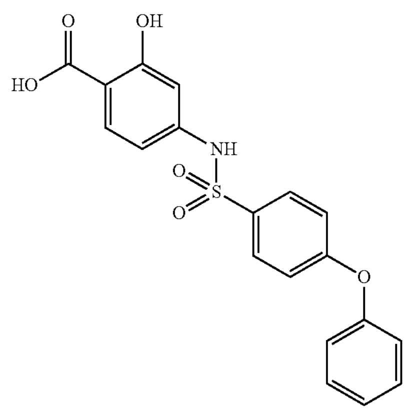 [SMILES: O=C(O)c1ccc(NS(=O)(=O)c2ccc(Oc3ccccc3)cc2)cc1O] |
| 4jc177-1 | 3-(N-isobutylphenyl-sulfonamido)benzoic acid | 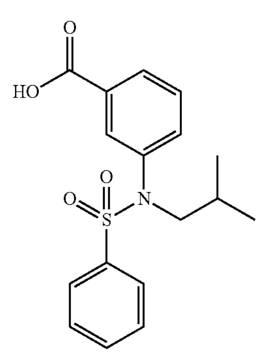 [SMILES: CC(C)CN(c1cccc(C(=O)O)c1)S(=O)(=O)c1ccccc1] |

-continued

| Identifier | Compound Name | Structure |
|---|---|---|
| 4jc177-2 | 3-(N-isobutyl-4-methylphenyl-sulfonamido)benzoic acid | 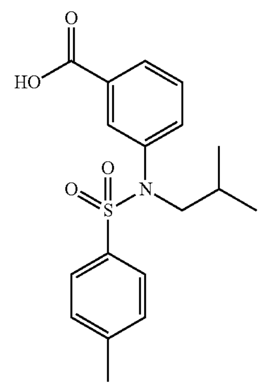 [SMILES: Cc1ccc(S(=O)(=O)N(CC(C)C)c2cccc(C(=O)O)c2)cc1] |
| JY-5-299 | 2-hydroxy-5-(N-isobutyl-naphthalene-2-sulfonamido)benzoic acid | 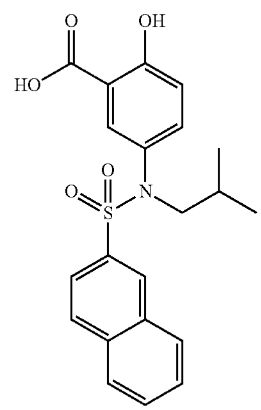 [SMILES: CC(C)CN(c1ccc(O)c(C(=O)O)c1)S(=O)(=O)c1ccc2ccccc2c1] |
| JY-5-304 | 5-(4-(4-chloro-3,5-dimethylphenoxy)-N-isobutylphenyl-sulfonamido)-2-hydroxybenzoic acid | 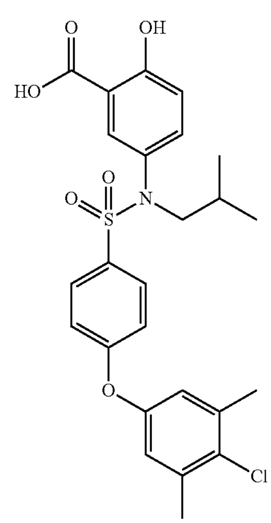 [SMILES: Cc1cc(Oc2ccc(S(=O)(=O)N(CC(C)C)c3ccc(O)c(C(=O)O)c3)cc2)cc(C)c1Cl] |

-continued
| Identifier | Compound Name | Structure |
|---|---|---|
| LC-4-131 | methyl 2-hydroxy-4-(N-isobutyl-4-phenoxyphenyl-sulfonamido)benzoate | 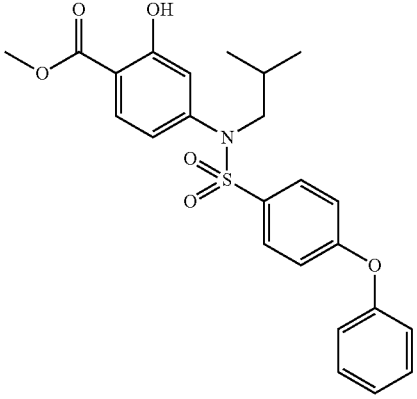 [SMILES: COC(=O)c1ccc(N(CC(C)C)S(=O)(=O)c2ccc(Oc3ccccc3)cc2)cc1O] |
| LC-5-096 | 4-(N-benzyl-4-phenoxyphenyl-sulfonamido)-2-hydroxy-N-(phenylsulfonyl)benzamide | 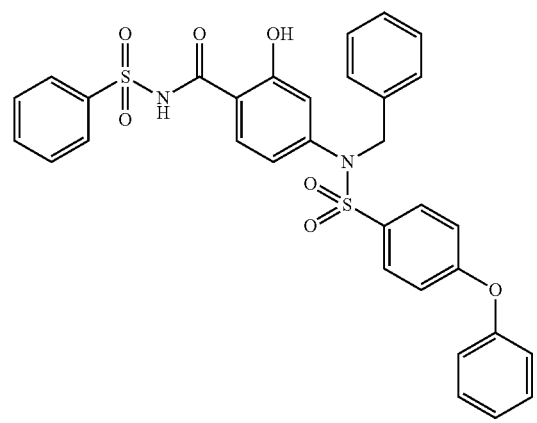 [SMILES: O=C(NS(=O)(=O)c1ccccc1)c1ccc(N(Cc2ccccc2)S(=O)(=O)c2ccc(Oc3ccccc3)cc2)cc1O] |
| LC-5-112 | 4-(N-benzyl-4-phenoxyphenyl-sulfonamido)-2-hydroxy-N-(methylsulfonyl)benzamide | 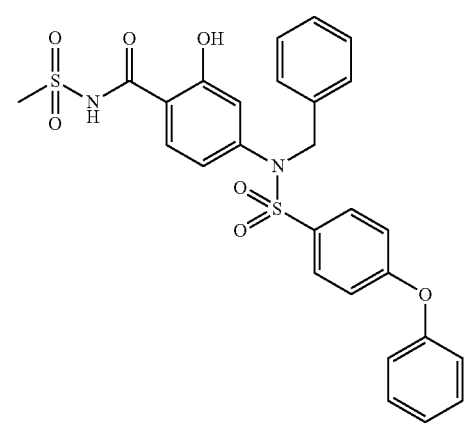 [SMILES: CS(=O)(=O)NC(=O)c1ccc(N(Cc2ccccc2)S(=O)(=O)c2ccc(Oc3ccccc3)cc2)cc1O] |

-continued

| Identifier | Compound Name | Structure |
|---|---|---|
| LC-5-111 | 4-(N-isobutyl-4-phenoxyphenyl-sulfonamido)-2-((4-(((3-nitro-4-(((tetrahydro-2H-pyran-4-yl)methyl)amino)phenyl)sulfonyl)carbamoyl)benzyl)oxy)benzoic acid | 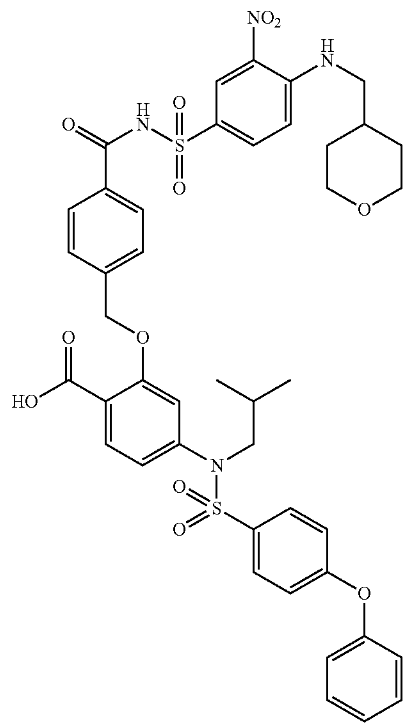 [SMILES: CC(C)CN(c1ccc(C(=O)O)c(OCc2ccc(C(=O)NS(=O)(=O)c3ccc(NCC4CCOCC4)c([N+](=O)[O-])c3)cc2)c1)S(=O)(=O)c1ccc(Oc2ccccc2)cc1] |
| LC-3-025 | 4-(4-fluoro-N-isobutylphenyl-sulfonamido)benzoic acid | 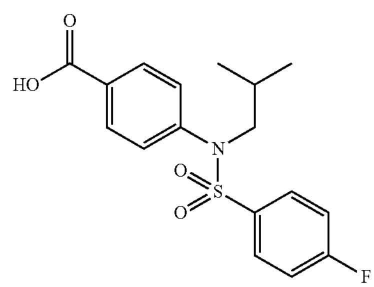 [SMILES: CC(C)CN(c1ccc(C(=O)O)cc1)S(=O)(=O)c1ccc(F)cc1] |
| LC-3-035 | 4-(4-(4-chloro-3,5-dimethylphenoxy)-N-isobutylphenyl-sulfonamido)benzoic acid | 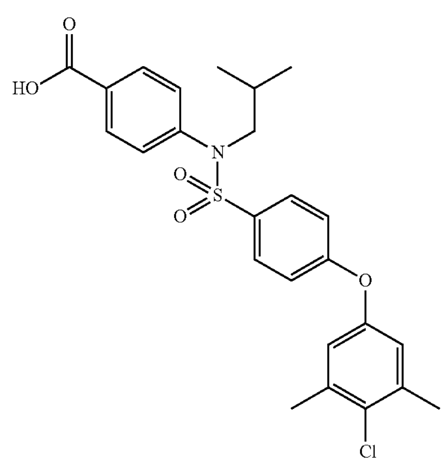 [SMILES: Cc1cc(Oc2ccc(S(=O)(=O)N(CC(C)C)c3ccc(C(=O)O)cc3)cc2)cc(C)c1Cl] |

-continued

| Identifier | Compound Name | Structure |
|---|---|---|
| 4jc117-3 | 2-hydroxy-4-(N-isobutylnaphthalene-2-sulfonamido) benzoic acid | 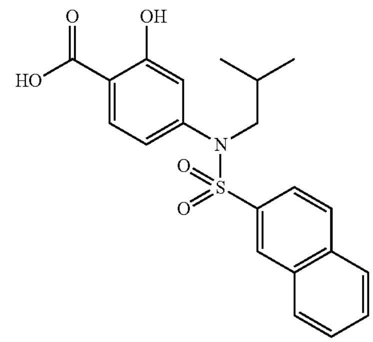 [SMILES: CC(C)CN(c1ccc(C(=O)O)c(O)c1)S(=O)(=O)c1ccc2ccccc2c1] |
| 4jc117-4 | 2-hydroxy-4-(N-isobutyl-[1,1'-biphenyl]-4-ylsulfonamido) benzoic acid | 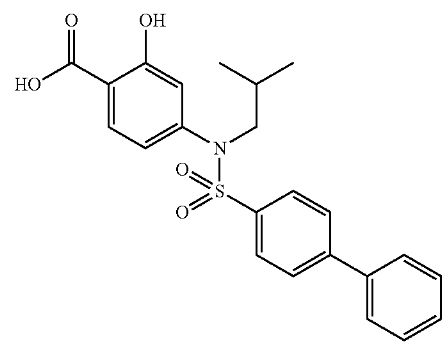 [SMILES: CC(C)CN(c1ccc(C(=O)O)c(O)c1)S(=O)(=O)c1ccc(-c2ccccc2)cc1] |
| LC-4-082 | 4-(N-cyclopentyl-[1,1'-biphenyl]-4-ylsulfonamido)-2-hydroxybenzoic acid | 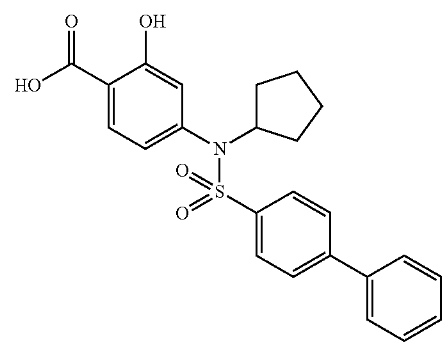 [SMILES: O=C(O)c1ccc(N(C2CCCC2)S(=O)(=O)c2ccc(-c3ccccc3)cc2)cc1O] |
| LC-4-083 | 4-(N-cyclopentyl-naphthalene-2-sulfonamido)-2-hydroxybenzoic acid | 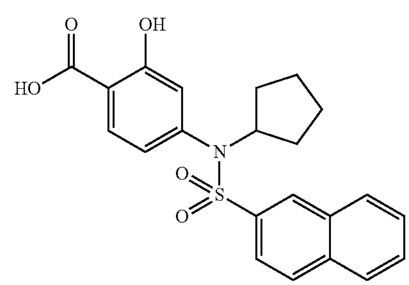 [SMILES: O=C(O)c1ccc(N(C2CCCC2)S(=O)(=O)c2ccc3ccccc3c2)cc1O] |
| LC-4-104 | 4-(4-(4-chloro-3,5-dimethylphenoxy)-N-cyclopentylphenyl-sulfonamido)-2-hydroxybenzoic acid | 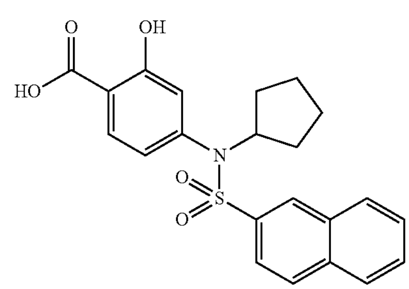 [SMILES: O=C(O)c1ccc(N(C2CCCC2)S(=O)(=O)c2ccc3ccccc3c2)cc1O] |

-continued

| Identifier | Compound Name | Structure |
|---|---|---|
| 4jc177-3 | 3-(N-isobutyl-naphthalene-2-sulfonamido)benzoic acid | 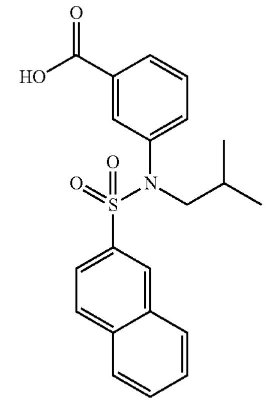 [SMILES: CC(C)CN(c1cccc(C(=O)O)c1)S(=O)(=O)c1ccc2ccccc2c1] |
| 4jc177-4 | 3-(N-isobutyl-[1,1'-biphenyl]-4-ylsulfonamido)benzoic acid | 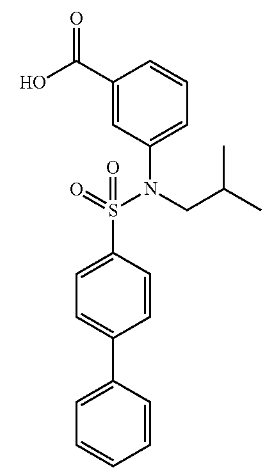 [SMILES: CC(C)CN(c1cccc(C(=O)O)c1)S(=O)(=O)c1ccc(-c2ccccc2)cc1] |
| 4jc177-5 | 3-(4-(4-chloro-3,5-dimethylphenoxy)-N-isobutylphenyl-sulfonamido)benzoic acid | 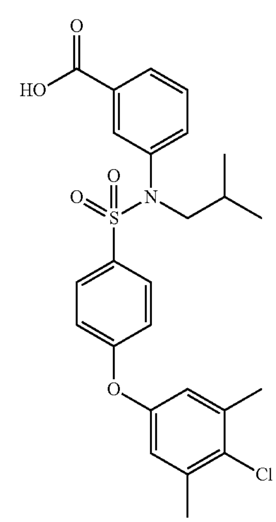 [SMILES: Cc1cc(Oc2ccc(S(=O)(=O)N(CC(C)C)c3cccc(C(=O)O)c3)cc2)cc(C)c1Cl] |

-continued

| Identifier | Compound Name | Structure |
|---|---|---|
| LC-4-134 | phenyl 2-hydroxy-4-(N-isobutyl-4-phenoxyphenyl-sulfonamido)benzoate | 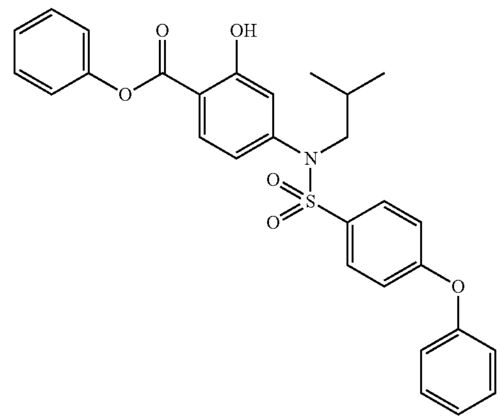 [SMILES: CC(C)CN(c1ccc(C(=O)Oc2ccccc2)c(O)c1)S(=O)(=O)c1ccc(Oc2ccccc2)cc1] |
| LC-4-141 | acetoxymethyl 2-hydroxy-4-(N-isobutyl-4-phenoxyphenyl-sulfonamido)benzoate | 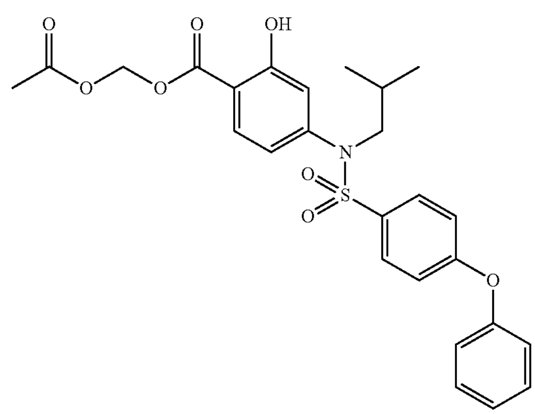 [SMILES: CC(=O)OCOC(=O)c1ccc(N(CC(C)C)S(=O)(=O)c2ccc(Oc3ccccc3)cc2)cc1O] |
| LC-5-050 | N-(4-cyano-3-hydroxyphenyl)-N-isobutyl-4-phenoxybenzene-sulfonamide | 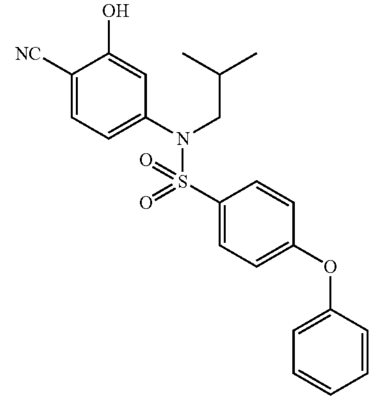 [SMILES: CC(C)CN(c1ccc(C#N)c(O)c1)S(=O)(=O)c1ccc(Oc2ccccc2)cc1] |

| Identifier | Compound Name | Structure |
|---|---|---|
| LC-5-107 | 4-(N-benzyl-4-phenoxyphenyl-sulfonamido)-2-hydroxy-N-((3-nitro-4-(((tetrahydro-2H-pyran-4-yl)methyl)amino)phenyl)sulfonyl)benzamide | 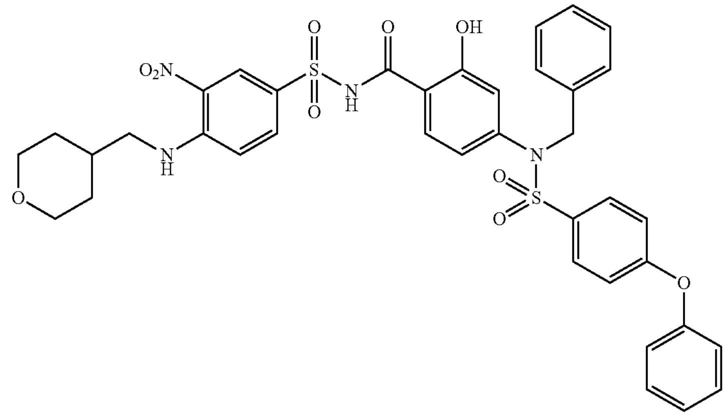 [SMILES: O=C(NS(=O)(=O)c1ccc(NCC2CCOCC2)c([N+](=O)[O-])c1)c1ccc(N(Cc2ccccc2)S(=O)(=O)c2ccc(Oc3ccccc3)cc2)cc1O] |
| LC-5-131 | 4-(N-benzyl-4-(4-chloro-3,5-dimethylphenoxy)phenyl-sulfonamido)-2-hydroxy-N-((3-nitro-4-(((tetrahydro-2H-pyran-4-yl)methyl)amino)phenyl)sulfonyl)benzamide | 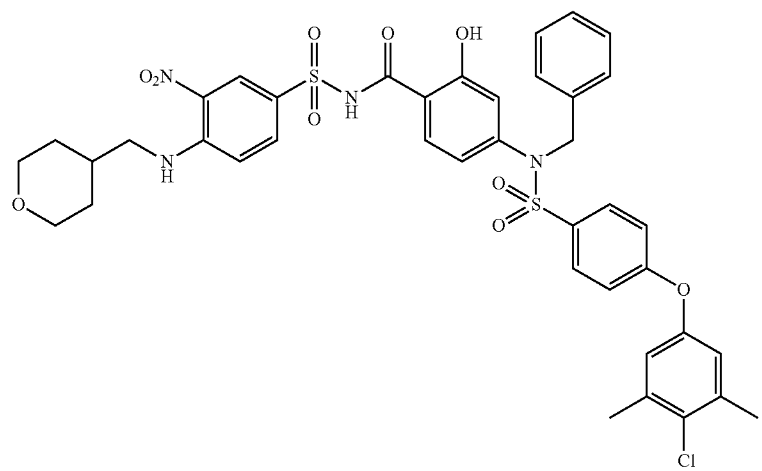 [SMILES: Cc1cc(Oc2ccc(S(=O)(=O)N(Cc3ccccc3)c3ccc(C(=O)NS(=O)(=O)c4ccc(NCC5CCOCC5)c([N+](=O)[O-])c4)c(O)c3)cc2)cc(C)c1Cl] |
| 4jc117-5 | 3-(4-(4-chloro-3,5-dimethylphenoxy)-N-isobutylphenyl-sulfonamido)-2-hydroxybenzoic acid | 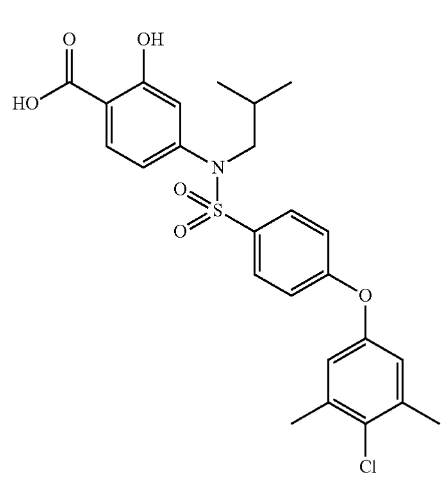 [SMILES: Cc1cc(Oc2ccc(S(=O)(=O)N(CC(C)C)c3ccc(C(=O)O)c(O)c3)cc2)cc(C)c1Cl] |

| Identifier | Compound Name | Structure |
| --- | --- | --- |
| LC-5-025 | 4-(4-fluoro-N-isobutylphenyl-sulfonamido)-2-hydroxybenzoic acid | 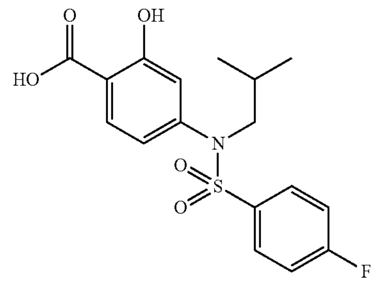 [SMILES: CC(C)CN(c1ccc(C(=O)O)c(O)c1)S(=O)(=O)c1ccc(F)cc1] |
| LC-4-099 | 2-hydroxy-4-(N-isobutyl-4-phenoxyphenyl-sulfonamido) benzoic acid | 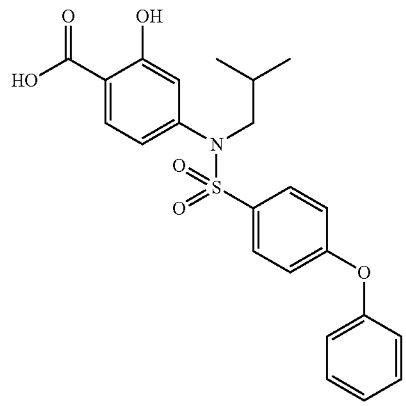 [SMILES: CC(C)CN(c1ccc(C(=O)O)c(O)c1)S(=O)(=O)c1ccc(Oc2ccccc2)cc1] |
| LC-4-112 | 4-(N-benzyl-[1,1'-biphenyl]-4-ylsulfonamido)-2-hydroxybenzoic acid | 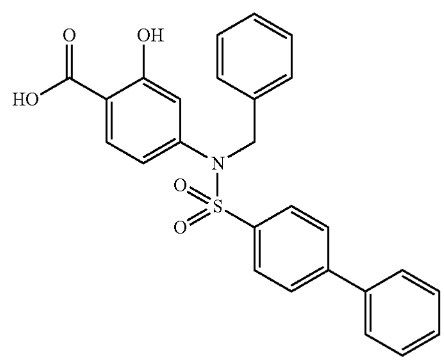 [SMILES: O=C(O)c1ccc(N(Cc2ccccc2)S(=O)(=O)c2ccc(-c3ccccc3)cc2)cc1O] |
| LC-4-113 | 4-(N-benzyl-naphthalene-2-sulfonamido)-2-hydroxybenzoic acid | 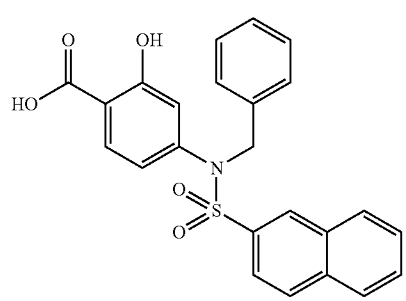 [SMILES: O=C(O)c1ccc(N(Cc2ccccc2)S(=O)(=O)c2ccc3ccccc3c2)cc1O] |

-continued

| Identifier | Compound Name | Structure |
|---|---|---|
| LC-4-118 | 4-(N-benzyl-4-(4-chloro-3,5-dimethylphenoxy)phenyl-sulfonamido)-2-hydroxybenzoic acid | 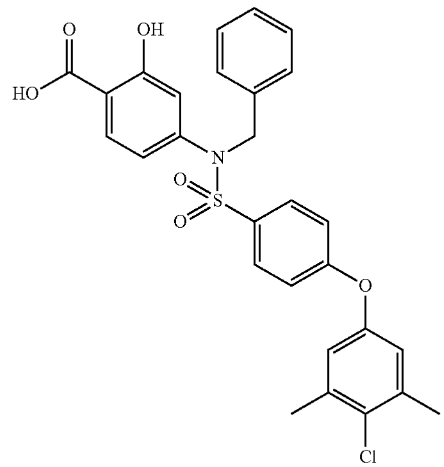 [SMILES: Cc1cc(Oc2ccc(S(=O)(=O)N(Cc3ccccc3)c3ccc(C(=O)O)c(O)c3)cc2)cc(C)c1Cl] |
| 4jc177-6 | 3-(4-fluoro-N-isobutylphenyl-sulfonamido)benzoic acid | 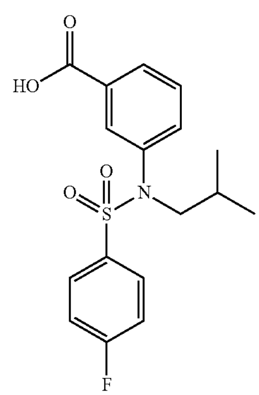 [SMILES: CC(C)CN(c1cccc(C(=O)O)c1)S(=O)(=O)c1ccc(F)cc1] |
| JY-5-296 | 2-hydroxy-5-(N-isobutylphenyl-sulfonamido)benzoic acid | 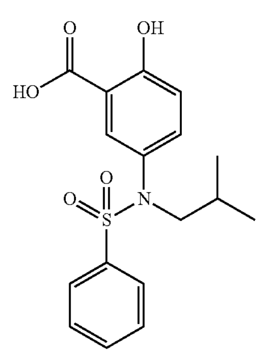 [SMILES: CC(C)CN(c1ccc(O)c(C(=O)O)c1)S(=O)(=O)c1ccccc1] |

-continued

| Identifier | Compound Name | Structure |
|---|---|---|
| JY-5-300 | 2-hydroxy-5-(N-isobutyl-[1,1'-biphenyl]-4-ylsulfonamido) benzoic acid | 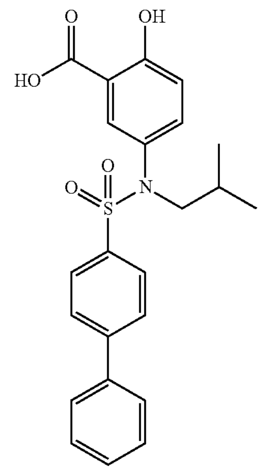 [SMILES: CC(C)CN(c1ccc(O)c(C(=O)O)c1)S(=O)(=O)c1ccc(-c2ccccc2)cc1] |
| LC-5-068 | N-(4-(2H-tetrazol-5-yl)phenyl)-N-isobutyl-4-phenoxybenzene-sulfonamide | 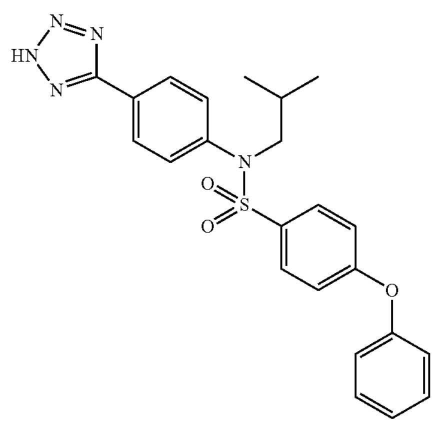 [SMILES: CC(C)CN(c1ccc(-c2nn[nH]n2)cc1)S(=O)(=O)c1ccc(Oc2ccccc2)cc1] |
| LC-5-062 | N,2-dihydroxy-4-(N-isobutyl-4-phenoxyphenyl-sulfonamido) benzamide | 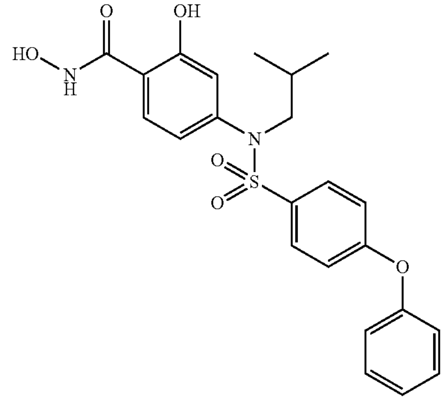 [SMILES: CC(C)CN(c1ccc(C(=O)NO)c(O)c1)S(=O)(=O)c1ccc(Oc2ccccc2)cc1] |

| Identifier | Compound Name | Structure |
|---|---|---|
| LC-5-069 | N-isobutyl-N-(4-(3-oxo-2,3-dihydroisoxazol-5-yl)phenyl)-4-phenoxybenzenesulfonamide | 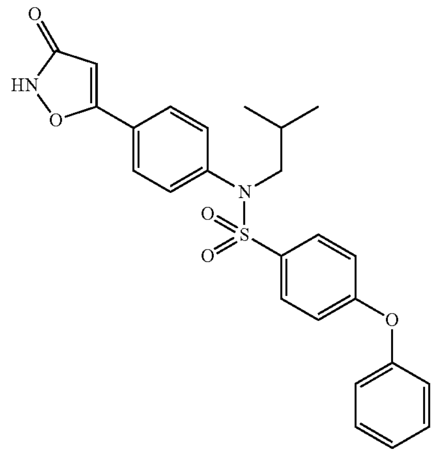 [SMILES: CC(C)CN(c1ccc(-c2cc(=O)[nH]o2)cc1)S(=O)(=O)c1ccc(Oc2ccccc2)cc1] |
| LC-5-129 | 5-(N-benzyl-4-(4-chloro-3,5-dimethylphenoxy)phenylsulfonamido)-2-hydroxybenzoic acid | 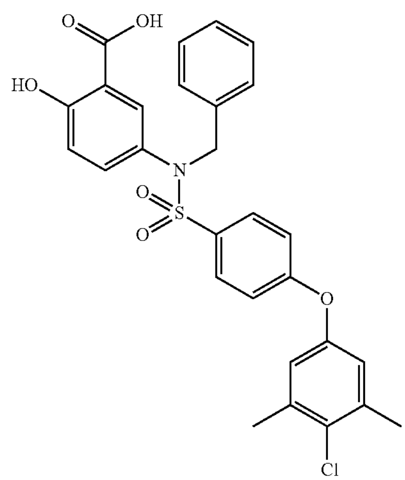 [SMILES: Cc1cc(Oc2ccc(S(=O)(=O)N(Cc3ccccc3)c3ccc(O)c(C(=O)O)c3)cc2)cc(C)c1Cl] |
| LC-5-132 | 5-(N-benzyl-4-(4-chloro-3,5-dimethylphenoxy)phenylsulfonamido)-2-hydroxy-N-((3-nitro-4-(((tetrahydro-2H-pyran-4-yl)methyl)amino)phenyl)sulfonyl)benzamide | 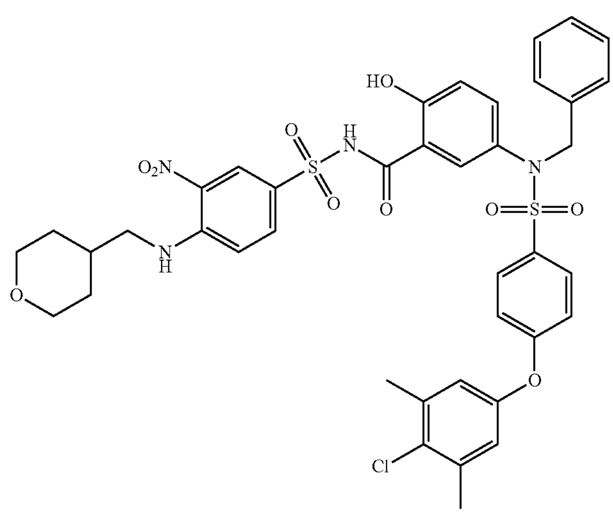 [SMILES: Cc1cc(Oc2ccc(S(=O)(=O)N(Cc3ccccc3)c3ccc(O)c(C(=O)NS(=O)(=O)c4ccc(NCC5CCOCC5)c([N+](=O)[O-])c4)c3)cc2)cc(C)c1Cl] |

In some embodiments, the Mcl-1 inhibitors described above may be delivered as listed or as a pharmaceutically acceptable salt, solvate, hydrate, cocrystal, tautomer, or prodrug thereof.

Pharmaceutical Compositions

In an embodiment, an active pharmaceutical ingredient or combination of active pharmaceutical ingredients, such as any of the foregoing Mcl-1 inhibitors, is provided as a pharmaceutically acceptable composition.

In some embodiments, the concentration of each of the active pharmaceutical ingredients provided in the pharmaceutical compositions of the invention, such as any of the foregoing Mcl-1 inhibitors, is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of each of the active pharmaceutical ingredients provided in the pharmaceutical compositions of the invention, such as any of the foregoing Mcl-1 inhibitors, is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the foregoing Mcl-1 inhibitors, is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of each of the active pharmaceutical ingredients provided in the pharmaceutical compositions of the invention, such as any of the foregoing Mcl-1 inhibitors, is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of each of the active pharmaceutical ingredients provided in the pharmaceutical compositions of the invention, such as any of the foregoing Mcl-1 inhibitors, is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the active pharmaceutical ingredients provided in the pharmaceutical compositions of the invention, such as any of the foregoing Mcl-1 inhibitors, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician. The clinically-established dosages of the foregoing Mcl-1 inhibitors may also be used if appropriate.

In an embodiment, the molar ratio of two active pharmaceutical ingredients in the pharmaceutical compositions is in the range from 10:1 to 1:10, preferably from 2.5:1 to 1:2.5, and more preferably about 1:1. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20.

In an embodiment, the pharmaceutical compositions described herein, such as any of the foregoing Mcl-1 inhibitors, are for use in the treatment of hyperproliferative disorders associated with the overexpression or upregulation of Mcl-1. In a some embodiments, the pharmaceutical compositions described herein are for use in the treatment of a cancer associated with overexpression or upregulation of Mcl-1 selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

In a some embodiments, the pharmaceutical compositions described herein are for use in the treatment of a cancer associated with overexpression or upregulation of Mcl-1 selected from the group consisting of myeloid leukemia, non-small cell lung cancer, pancreatic cancer, prostate cancer, and ovarian cancer.

Furthermore, the described methods of treatment may normally include medical follow-up to determine the therapeutic or prophylactic effect brought about in the subject undergoing treatment with the compound(s) and/or composition(s) described herein.

Described below are non-limiting pharmaceutical compositions and methods for preparing the same.

Pharmaceutical Compositions for Oral Administration

In an embodiment, the invention provides a pharmaceutical composition for oral administration containing the active pharmaceutical ingredient or combination of active pharmaceutical ingredients, such as the Mcl-1 inhibitors described herein, and a pharmaceutical excipient suitable for oral administration.

In some embodiments, the invention provides a solid pharmaceutical composition for oral administration containing: (i) an effective amount of an active pharmaceutical ingredient or combination of active pharmaceutical ingredients, and (ii) a pharmaceutical excipient suitable for oral administration. In selected embodiments, the composition further contains (iii) an effective amount of a third active pharmaceutical ingredient and optionally (iv) an effective amount of a fourth active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogs thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In some embodiments, a pharmaceutical composition is provided for injection containing an active pharmaceutical ingredient or combination of active pharmaceutical ingredients, such as an Mcl-1 inhibitor, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, a pharmaceutical composition is provided for transdermal delivery containing an active pharmaceutical ingredient or combination of active pharmaceutical ingredients, such as Mcl-1 inhibitors described herein, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of an active pharmaceutical ingredient or combination of active pharmaceutical ingredients in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139, the entirety of which are incorporated herein by reference. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra and the Mcl-1 inhibitors described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions of the Mcl-1 inhibitors described herein may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The active pharmaceutical ingredient or combination of active pharmaceutical ingredients can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit comprising a composition comprising a therapeutically effective amount of an active pharmaceutical ingredient or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides a kit comprising (1) a composition comprising a therapeutically effective amount of an active pharmaceutical ingredient or combination of active pharmaceutical ingredients or a pharmaceutically acceptable salt, solvate, hydrate, cocrystal, or prodrug thereof, and (2) a diagnostic test for determining whether a patient's cancer is a particular subtype of a cancer. Any of the foregoing diagnostic methods may be utilized in the kit.

The kits described above are preferably for use in the treatment of the diseases and conditions described herein. In a particular embodiment, the kits are for use in the treatment of hyperproliferative disorders.

In a particular embodiment, the kits described herein are for use in the treatment of cancer. In some embodiments, the kits described herein are for use in the treatment of a cancer selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In particular embodiments, the kits described herein are for use in the treatment of a cancer selected from the group consisting of myeloid leukemia, non-small cell lung cancer, pancreatic cancer, prostate cancer, and ovarian cancer.

Dosages and Dosing Regimens

The amounts of the pharmaceutical compositions administered using the methods herein, such as the dosages of Mcl-1 inhibitors, will be dependent on the human or mammal being treated, the severity of the disorder or condition, the rate of administration, the disposition of the active pharmaceutical ingredients and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in mg/m² of body surface area.

In some embodiments, the invention include methods of treating a cancer in a human subject suffering from the cancer in which cancer cells overexpress Mcl-1, the method comprising the steps of administering a therapeutically effective dose of an active pharmaceutical ingredient that is an Mcl-1 inhibitor to the human subject.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the preferred oral route, may be used as appropriate. A single dose of a pharmaceutical composition may also be used for treatment of an acute condition.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients may continue as long as necessary. In selected embodiments, a pharmaceutical composition is administered for more than 1, 2, 3, 4, 5, 6, 7, 14, or 28 days. In some embodiments, a pharmaceutical composition is administered for less than 28, 14, 7, 6, 5, 4, 3, 2, or 1 day. In some embodiments, a pharmaceutical composition is administered chronically on an ongoing basis—e.g., for the treatment of chronic effects. In some embodiments, the administration of a pharmaceutical composition continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of an active pharmaceutical ingredient disclosed herein is in the range of about 0.01 mg/kg to about 200 mg/kg, or about 0.1 to 100 mg/kg, or about 1 to 50 mg/kg.

In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect—by dividing such larger doses into several small doses for administration throughout the day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

In some embodiments, the compositions described herein further include controlled-release, sustained release, or extended-release therapeutic dosage forms for administration of the compounds described herein, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

The following examples describe the invention in further detail. These examples are provided for illustrative purposes only, and should in no way be considered as limiting the invention.

EXAMPLES

Example 1

Compound Scaffolds Including the 1-Hydroxy-2-Naphthoate Scaffold

Described herein are potent inhibitors of Mcl-1 based on a novel 1-hydroxy-2-naphthoate scaffold. This disclosure includes a 1-hydroxy-2-naphthoic acid core that would provide an alternative platform from which to inhibit Mcl-1, wherein the carboxylic acid was predicted to bind R263, and the distal phenyl ring the p3 pocket. Further engineering to gain access to the p2 pocket was driven by the hydroxyl group and the carboxylic acid whose ortho- and meta-directing effects, respectively, synergize to promote the regioselective 4-chlorosulfonylation of the scaffold; subsequent amination of this readily introduced functional group is expected to facilitate occupancy of the p2 pocket. The subject scaffold design is illustrated in Scheme 1-1, which permits access to Mcl-1 inhibitors in only two synthetic steps from commercially available starting materials.

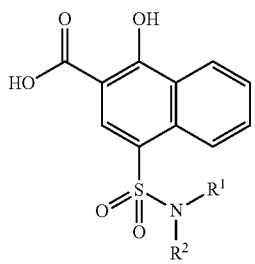

$R^1$ = H, alkyl
$R^2$ = H, alkyl, aryl

Scheme 1-1:

Structure-based design of novel 1-hydroxy-4-sulfamoyl-2-naphthoates (3) as Mcl-1 inhibitors.

To facilitate ligand design, the Site Identification by Ligand Competitive Saturation (SILCS) method was used. SILCS FragMaps represent the 3D grid free energy distribution of different types of functional groups around the protein. The FragMaps include contributions from solute-protein interactions, solute desolvation and protein desolvation in the context of protein flexibility. In addition, to assure that all regions accessible to solute atoms can be occupied by the studied ligands, the protein surface is defined based on SILCS exclusion maps.

Results and Discussion

Molecular modeling and SILCS functional group affinity mapping (FragMaps) of the Mcl-1 binding site indicated that the carboxylic acid of designed molecule 3a (FIG. 1C) would occupy an energetically favorable region, associated with a salt bridge interaction with R263 of the Mcl-1 binding site, while the ring of the naphthyl core would bind in the p3 pocket demarcated by a favorable non-polar FragMap. The aniline was directed into the hydrophobic p2 pocket, which is also demarcated by a nonpolar FragMap. With the molecular modeling data in hand, compound 3a was then synthesized according to Scheme 1-2.

Briefly, commercially available 1-hydroxy-2-naphthoic acid (4) was regioselectively 4-chlorosulfonylated to yield 5, which was isolated by pouring over ice and used without further purification. Sulfonyl chloride 5 was next reacted with 4-bromoaniline to furnish the target molecule 3a in excellent overall yield (83%). Evaluation of 3a in a fluorescence polarization competition assay (FPCA) indicated that it disrupted the Mcl-1-Bak-BH3 PPI with an $IC_{50}$ of 10.9 µM, corresponding to a $K_i$ of 2.76 µM. Given the ability of 3a to inhibit Mcl-1, a structure-activity relationship (SAR) study was developed, the results of which are presented in the tables below. The target molecules in Table 1-1 were all prepared according to the concise synthetic route depicted in Scheme 1-2, those in Table 1-2 were synthesized using anilines prepared as described in Scheme 1-3, whilst those in Table 1-3 were generated by following the synthetic route in Scheme 1-4.

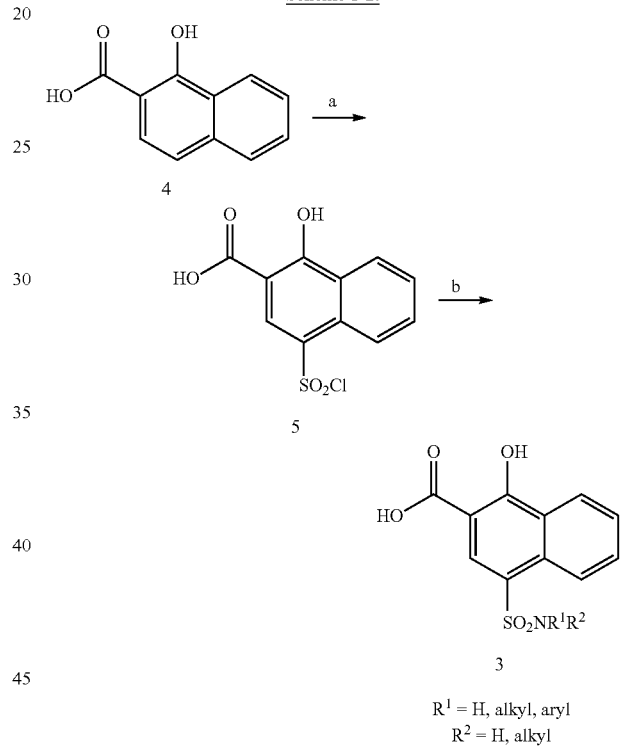

Scheme 1-2.

$R^1$ = H, alkyl, aryl
$R^2$ = H, alkyl (a) ClSO$_3$H, 0° C., 1 h; (b) ArNH$_2$, pyr, acetone, 50° C., 3 h or R$^1$NH$_2$/R$^1$R$^2$NH, DIPEA, acetone, RT, 5 h.

TABLE 1-1

Experimental and computational Mcl-1 and Bcl-x$_L$ inhibitory profiles of first generation inhibitors.

| Comp. | R$^1$ | R$^2$ | Mcl-1 K$_i$ (µM)$^a$ | Bcl-x$_L$ K$_i$ (µM)$^a$ | Selectivity | Mcl-1 LGFE (kcal mol$^{-1}$) | Bcl-xL LGFE (kcal mol$^{-1}$) |
|---|---|---|---|---|---|---|---|
| 3a | 4-Br—C$_6$H$_4$ | H | 2.76 ± 1.26 | 51.4 ± 31.3 | 19 | −39.46 | −36.20 |
| 3b | H | H | 99.0 ± 11.2 | NA | | −31.00 | |
| 3c | Bn | H | 56.3 ± 2.1 | NA | | −39.02 | |
| 3d | CH$_2$—(2-Cl—C$_6$H$_4$) | H | 50.3 ± 11.8 | — | — | −37.09 | |
| 3e | CH$_2$—(3-Cl—C$_6$H$_4$) | H | 5.03 ± 2.78 | — | — | −38.80 | |
| 3f | CH$_2$—(4-Cl—C$_6$H$_4$) | H | 21.0 ± 3.9 | 338 ± 203 | 16 | −41.13 | −38.60 |
| 3g | CH$_2$—C$_6$H$_{11}$ | H | 7.31 ± 1.42 | 77.6 ± 14.3 | 11 | −42.01 | −40.99 |

TABLE 1-1-continued

Experimental and computational Mcl-1 and Bcl-$x_L$ inhibitory profiles of first generation inhibitors.

| Comp. | R$^1$ | R$^2$ | Mcl-1 K$_i$ (μM)$^a$ | Bcl-x$_L$ K$_i$ (μM)$^a$ | Selectivity | Mcl-1 LGFE (kcal mol$^{-1}$) | Bcl-xL LGFE (kcal mol$^{-1}$) |
|---|---|---|---|---|---|---|---|
| 3h | Me | Me | 25.7 ± 4.86 | NA | | −35.73 | |
| 3i | —CH$_2$CH$_2$CH$_2$CH$_2$CH$_2$— | | 2.95 ± 0.43 | — | | −42.58 | |
| 3j | —CH$_2$CH$_2$N(Ph)CH$_2$CH$_2$— | | 4.54 ± 3.86 | — | | −44.80 | |
| 3k | —CH$_2$CH$_2$N(Bn)CH$_2$CH$_2$— | | 3.41 ± 0.37 | — | | −34.40 | |
| 3l | Ph | H | 106 ± 26 | NA | | −37.18 | |
| 3m | 2-Br—C$_6$H$_4$ | H | 6.84 ± 2.23 | — | | −36.80 | |
| 3n | 3-Br—C$_6$H$_4$ | H | 5.64 ± 1.76 | — | | −38.98 | |
| 3o | 2,4-di-Br—C$_6$H$_3$ | H | 0.420 ± 0.163 | 2.31 ± 1.35 | 5.5 | −39.00 | −37.67 |
| 3p | 1-Naphthyl | H | 11.2 ± 2.0 | 110 ± 45 | 10 | −39.78 | −38.34 |
| 3q | 2-Naphthyl | H | 4.58 ± 1.56 | 68.5 ± 36.3 | 15 | −38.84 | −37.24 |
| 3r | 2-Ph—C$_6$H$_4$ | H | 8.50 ± 1.34 | — | | −42.88 | |
| 3s | 3-Ph—C$_6$H$_4$ | H | 1.88 ± 0.62 | | | −41.08 | |
| 3t | 4-Ph—C$_6$H$_4$ | H | 1.54 ± 0.46 | — | | −43.70 | |
| 3u | 2-CF$_3$—C$_6$H$_4$ | H | 4.05 ± 2.11 | 19.3 ± 9.0 | 4.8 | −41.75 | −40.68 |
| 3v | 4-Cl—C$_6$H$_4$ | H | 1.91 ± 0.26 | — | | −39.51 | |
| 3w | 4-CF$_3$—C$_6$H$_4$ | H | 2.50 ± 0.65 | — | | −43.43 | |
| 3x | 4-Me—C$_6$H$_4$ | H | 34.3 ± 1.0 | — | | −38.82 | |
| 3y | 4-(iPr)—C$_6$H$_4$ | H | 3.86 ± 1.53 | — | | −41.58 | |
| 3z | 4-OMe—C$_6$H$_4$ | H | 11.9 ± 2.5 | 71.9 ± 21.0 | 6 | −38.27 | −36.46 |
| 3aa | 4-(OiPr)—C$_6$H$_4$ | H | 54.0 ± 4.6 | NA | | −40.81 | |
| 3ab | 4-CN—C$_6$H$_4$ | H | 22.2 ± 1.6 | — | | −36.95 | |
| 3ac | 4-NO2—C$_6$H$_4$ | H | 4.49 ± 1.20 | 23.3 ± 2.5 | 5.2 | −39.27 | −38.47 |
| 3ad | 3-CN—C$_6$H$_4$ | H | 26.9 ± 0.6 | | | −36.40 | |

$^a$K$_i$ values determined by Nikolovska-Coleska equation from IC$_{50}$ values. Data represent the average of at least two independent assays; errors are standard deviations.
$^b$Selectivity is defined as the K$_i$ (Bcl-x$_L$) divided by the Ki (Mcl-1).
NA, no activity.

Unsubstituted sulfonamide 3b was the weakest Mcl-1 inhibitor with a K$_i$ of 99.0 μM, which was consistent with the less favorable LGFE score (Table 1-1). Replacement of the NH$_2$ group with benzylic amines and anilines improved Mcl-1 inhibitory activity in every case, which is attributed to the occupancy of the apolar FragMaps with the apolar FragMap in the p2 pocket yielding more favourable LGFE scores. In addition, the FragMaps extend further towards the interior of the protein, suggesting that further hydrophobic extension of benzylic amines would improve activity. Indeed, chlorobenzylic amine derivatives 3d-3f were more potent than unsubstituted benzylic amine derivative 3c by up to 8-fold. Replacement of the benzyl group in 3c with a cyclohexylmethyl group (3g) also afforded an 8-fold improvement in inhibitory activity with a K$_i$ of 7.31 μM. Piperidine derivative 3i achieved good inhibition (K$_i$=2.95 μM), as did the neutral and the basic piperazines 3j and 3k, respectively, indicating a positively-charged group here is not detrimental to binding. Substitution of the aniline ring in 3l with bromine atoms afforded between 10 to 54-fold improvement in activity, with the most profound effect observed with para-substituted derivative 3a (K$_i$=2.76 μM, cf. 83.8 μM for 3l). Introduction of an additional bromine atom into the ortho position of 3a to afford 2,4-dibromo derivative 3o led to an even more potent inhibitor with a K$_i$ of 420 nM. Concomitantly, this change led to an erosion in selectivity of more than ten-fold for Mcl-1 over Bcl-x$_L$. Naphthalene derivatives 3p and 3q were also more active than unsubstituted 3l. Functionalization of the aniline ring in 3l with additional phenyl rings to afford biphenyls 3r-3t resulted in improved inhibition in each case, again with para-substituted derivative 3u the most potent of the series (K$_i$=1.54 μM). For the remainder of the compounds in Table 1-1, substitution of the aniline ring in 3l with hydrophobic and polar groups resulted in enhanced activities in all instances with the greatest improvements observed with hydrophobic groups in the para position.

Motivated by the improved activity of extended hydrophobic substituents on the sulfonamide phenyl ring (e.g. 3o and 3s) along with the extended apolar FragMap in the p2 pocket (FIG. 1B), we chose to expand our library of para-substituted anilines by introduction of various aryloxy groups into the para position. Requisite anilines were synthesized according to Scheme 1-3, and then coupled to sulfonyl chloride 5 according to Scheme 1-2. As shown in Table 1-2, compounds 3ba-3bi afforded potent inhibition of Mcl-1 with the tightest binder delivering a K$_i$ of 79 nM. This ~1000-fold enhancement in inhibitory activity relative to unsubstituted aniline 3l is associated with the increased overlap of the nonpolar groups with the second apolar FragMaps in the p2 pocket, as quantified by the systematically more favourable LGFE scores (Table 1-2).

TABLE 1-2

Experimental and computational Mcl-1 and Bcl-$x_L$ inhibitory profiles of second generation inhibitors.

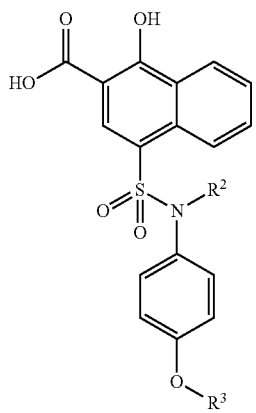

| Comp. | $R^2$ | $R^3$ | Mcl-1 $K_i$ (μM)[a] | Bcl-$x_L$ $K_i$ (μM)[a] | Selectivity[b] | Mcl-1 LGFE (kcal mol$^{-1}$) | Bcl-$x_L$ LGFE (kcal mol$^{-1}$) |
|---|---|---|---|---|---|---|---|
| 3ba | iBu | iPr | 0.487± | 6.08 ± 0.81 | 12 | −38.81 | −36.24 |
| 3bb | H | Ph | 1.15 ± 0.28 | ND | — | −43.68 | |
| 3bc | H | 4-Me-C$_6$H$_4$ | 0.335± | 0.84 ± 0.05 | 2.5 | −43.58 | −42.87 |
| 3bd | H | 1-Naphthyl | 0.082± | 0.22 ± 0.06 | 3.7 | −47.46 | −48.26 |
| 3be | H | 3-Br-C$_6$H$_4$ | 0.114± | 0.30 ± 0.04 | 3.8 | −44.65 | −44.31 |
| 3bf | H | 3,5-di-Me-C$_6$H$_3$ | 0.284± | 0.39 ± 0.10 | 1.4 | −46.21 | −45.53 |
| 3bg | H | 2,4-di-Cl-C$_6$H$_3$ | 0.079± | 0.19 ± 0.02 | 2.4 | −46.79 | −46.47 |
| 3bh | H | 4-Cl-C$_6$H$_4$ | 0.173± | ND | — | −45.94 | |
| 3bi | H | 4-Cl-3,5-di-Me—C$_6$H$_2$ | 0.117 ± 0.060 | 0.48 ± 0.05 | 4.1 | −47.29 | −46.68 |
| 3bj | iBu | 4-Cl-3,5-di-Me—C$_6$H$_2$ | 0.080 ± 0.019 | 0.17 ± 0.06 | 2.1 | −48.23 | −47.38 |
| 3bk | Cp | 4-Cl-3,5-di-Me—C$_6$H$_2$ | 0.033 ± 0.025 | 0.29 ± 0.05 | 8.8 | −40.05 | −38.93 |
| 3bl | Bn | 4-Cl-3,5-di-Me—C$_6$H$_2$ | 0.031 ± 0.017 | 0.34 ± 0.13 | 11 | −51.93 | −50.94 |

[a] $K_i$ values determined by Nikolovska-Coleska equation from IC$_{50}$ values. Data represent the average of at least two independent assays; errors are standard deviations.
[b] Selectivity is defined as the $K_i$ (Bcl-$x_L$) divided by the $K_i$ (Mcl-1).
ND, not determined.

Simultaneously, these modifications also greatly increased affinity of the compounds to Bcl-$x_L$. The sulfonamide NH group in 3bi offers an additional position from which further inhibitory activity might be acquired. Indeed, alkylation of this nitrogen atom with cyclopentyl (3bk) and benzyl (3bl) resulted in our most potent inhibitors yet with $K_i$s of 33 nM and 31 nM, respectively. These alkylations also led to a recovery of selectivity for Mcl-1 over Bcl-$x_L$ of up to eleven-fold.

Scheme 1-3.

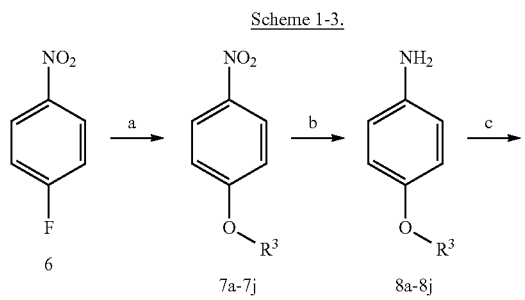

-continued

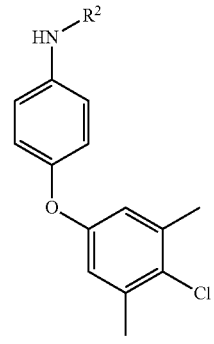

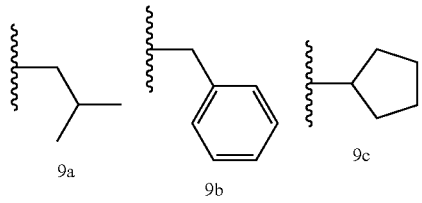

(a) ArOH, K$_2$CO$_3$, 100° C., 16 h; (b) SnCl$_2$•2H$_2$O, EtOAc, 50° C., 16 h;
(c) isobutyraldehyde, benzaldehyde or cyclopentanone, NaBH(OAc)$_3$, 1,2-dichloroethane, RT, 16 h.

Finally, the importance of the carboxylic acid and hydroxyl groups of the inhibitor scaffold was ascertained. Towards this goal, the compounds shown in Scheme 1-4 were synthesized. As seen in Table 1-3, the carboxylic acid is important to activity, which is consistent with its likelihood of binding R263. Methylation of the hydroxyl group to deliver compound 3cd resulted in around a 40-fold reduction in activity indicating its importance, too.

TABLE 1-3

Investigation into the significance of the inhibitor's carboxylic acid and hydroxyl group towards the inhibition of Mcl-1.

| Comp. | X | Y | Mcl-1 $K_i$ (µM)[a] | Mcl-1 LGFE (kcal mol$^{-1}$) |
|---|---|---|---|---|
| 3ca | CO2H | OH | 0.566± | −42.19 |
| 3cb | CO$_2$Me | OH | >500 | −34.23 |
| 3cc | CO$_2$Me | OMe | >500 | −35.45 |
| 3cd | CO$_2$H | OMe | 23.4 ± 2.6 | −42.41 |

[a]$K_i$ values determined by Nikolovska-Coleska equation from IC$_{50}$ values. Data represent the average of at least two independent assays; errors are standard deviations.

Although SILCS predicted the methoxy derivative 3cd (LGFE=−42.41 kcal/mol) to bind with slightly greater affinity than its hydroxy counterpart 3ca (LGFE=−42.19 kcal/mol), the observed disparity may be explained by an anticipated greater acidity for the latter through a six-membered intramolecular hydrogen bond between the hydroxyl and the carboxylate that affords a stronger salt bridge with R263.

Scheme 1-4.

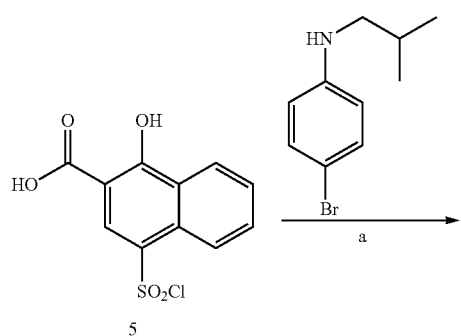

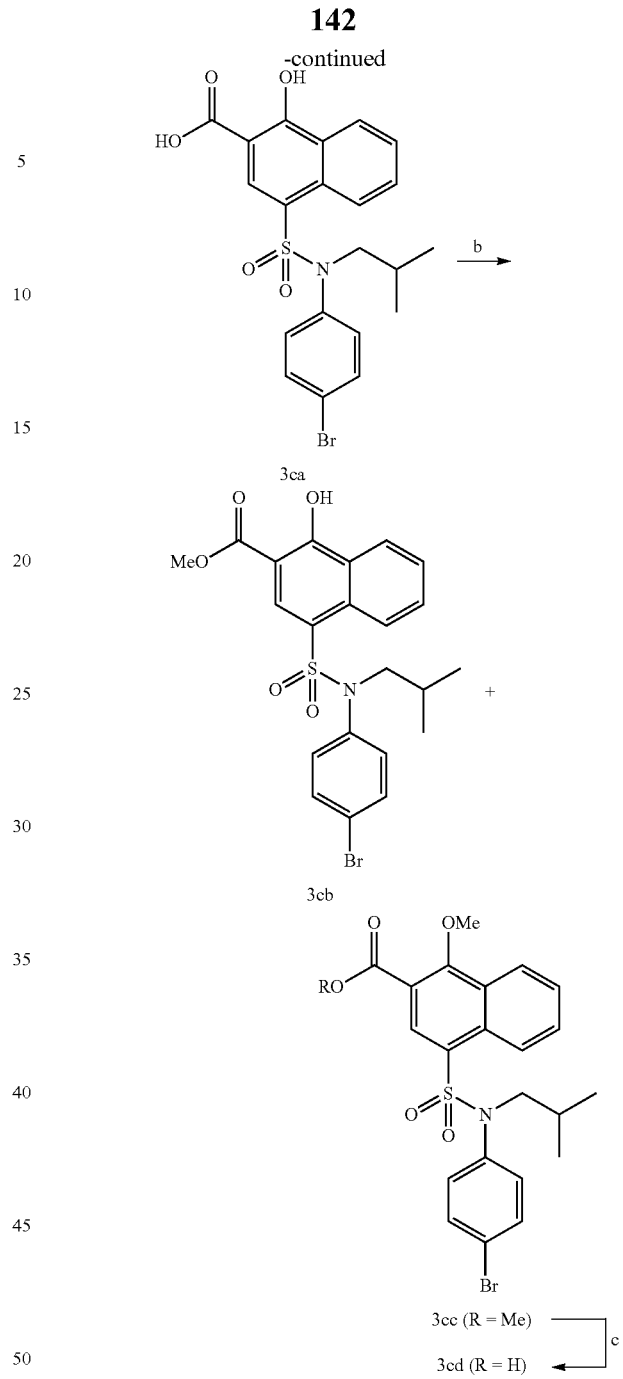

(a) ArNH$_2$, pyr, acetone, 50° C., 3 h; (b) MeI, K$_2$CO$_3$, DMF, rt, 16 h; (c) NaOH, MeOH/THF/H$_2$O, 3:1:1, rt, 16 h.

Figure 2:
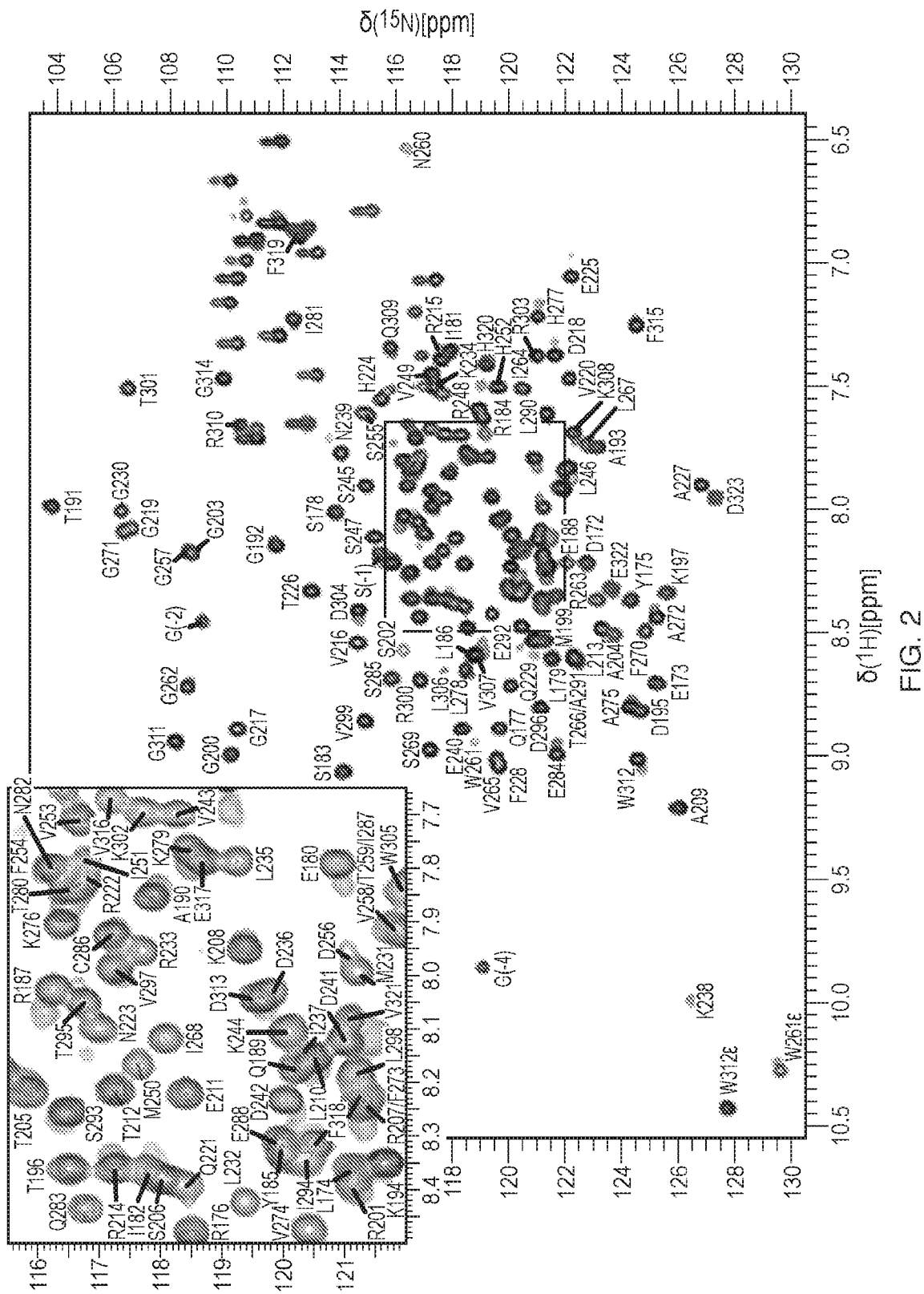
FIG. 2 illustrates a 2D NMR HSQC spectra, which shows chemical shift perturbations caused by the direct interaction of compound 3ba with Mcl-1. The spectrum of the control sample is overlaid with the spectrum of Mcl-1 bound to 3ba. Inset is enlargement of boxed region.
Figure 3:
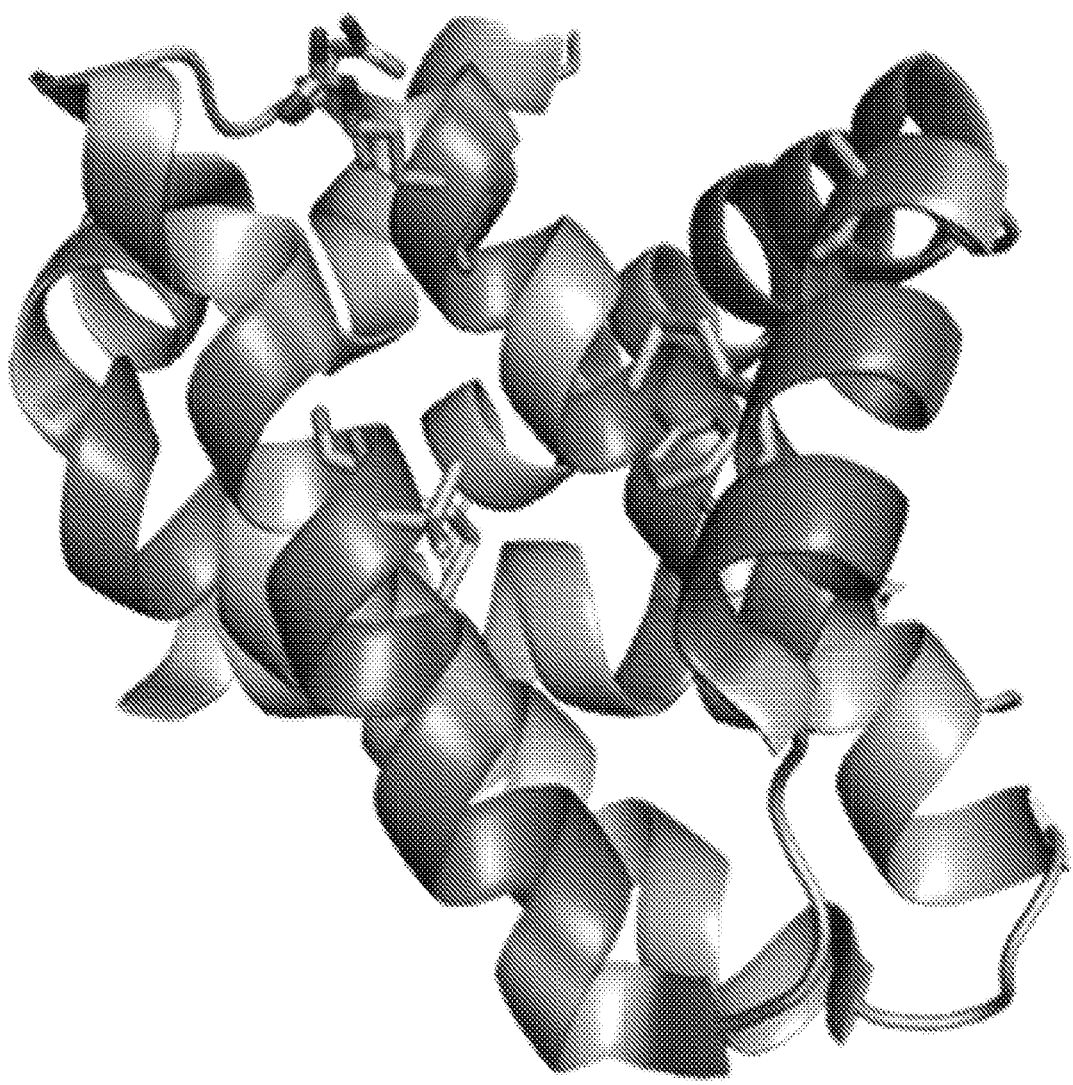
FIG. 3 illustrates Mcl-1 residues whose chemical shifts are perturbed in the presence of compound 3ba.

NMR HSQC experiments using $^{15}$N-labeled Mcl-1 (recombinant human Mcl-1 residues 172 to 327) confirmed the direct interaction of this class of compounds with the protein. Specifically, the HSQC of compound 3ba (FIG. 2) shows perturbation of the chemical shifts of Mcl-1 backbone $^1$H—$^{15}$N correlations consistent with the predicted binding mode of 3a shown in FIG. 1. Under the NMR experimental conditions the amino acid residues interacting with the compound are undergoing intermediate chemical exchange so their $^1$H—$^{15}$N correlation peaks are broadened or lost. Intermediate exchange was expected based on the binding affinity determined for 3ba, $K_i$ of 0.487 µM. Mapping the residues completely lost due to chemical exchange broadening on the 3D structure of Mcl-1 (FIG. 3) supports the model shown in FIG. 1. The majority of the changes occur in residues near the compound including R263 and N260, residues in the p2 pocket (V249, M250, and F270), and in the p3 pocket (A227 and M231).

Figure 6:
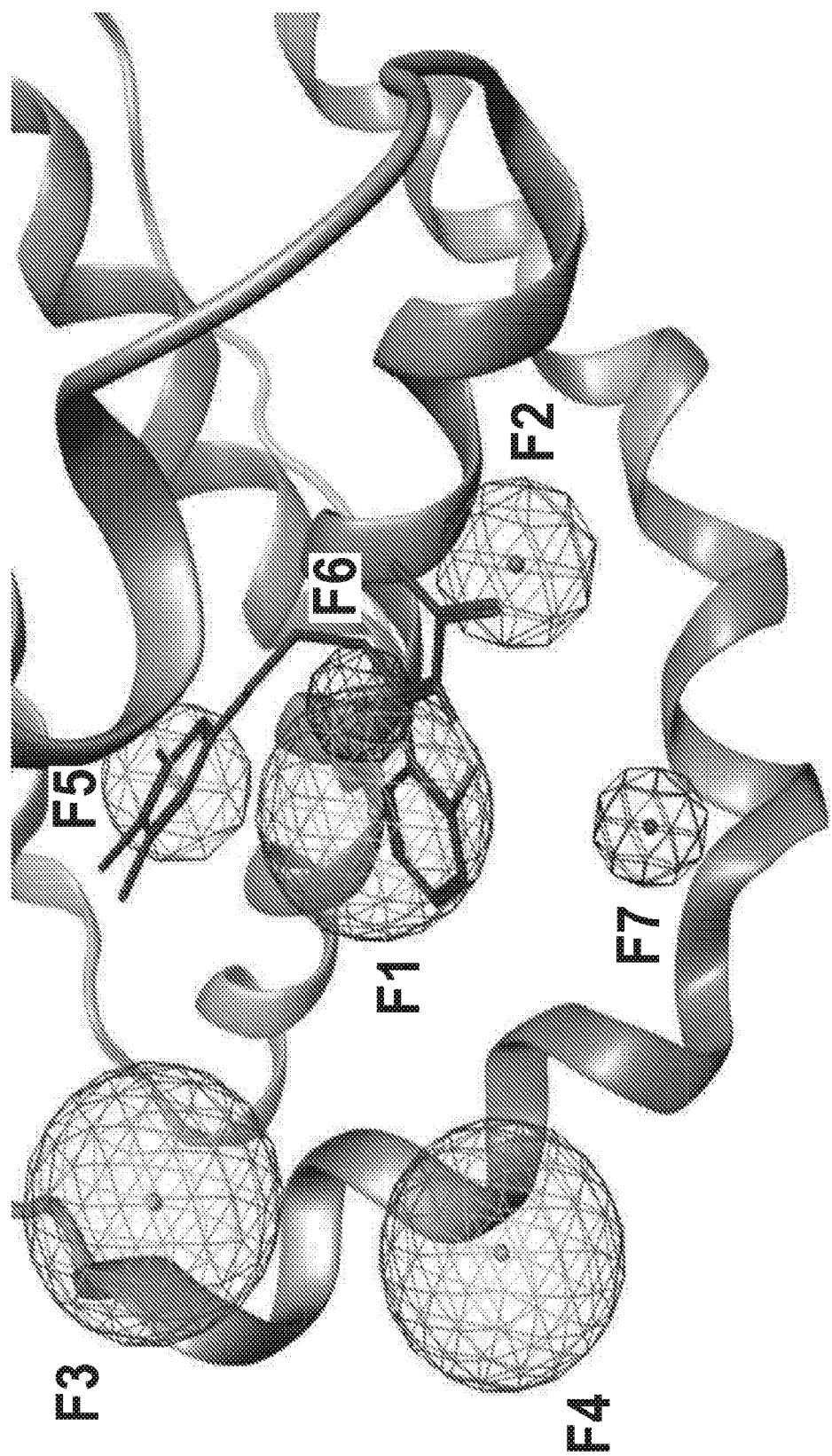
FIG. 6 illustrates pharmacophore features for the Mcl-1 binding site. The pharmacophore features developed from SILCS FragMaps are used to explore the binding conformation of the tested compounds. Crystal structure of Mcl-1 and the inhibitor Fesik60 from complex (PDBID:4HW3) are shown. Protein atoms occluding the view of the binding pocket were removed to facilitate visualization. Features APOLAR (i.e., F1, F3, F4, and F5), HBDON (i.e., F7), HBACC (i.e., F6), and NEG (i.e., F2) are marked.
Figure 7:
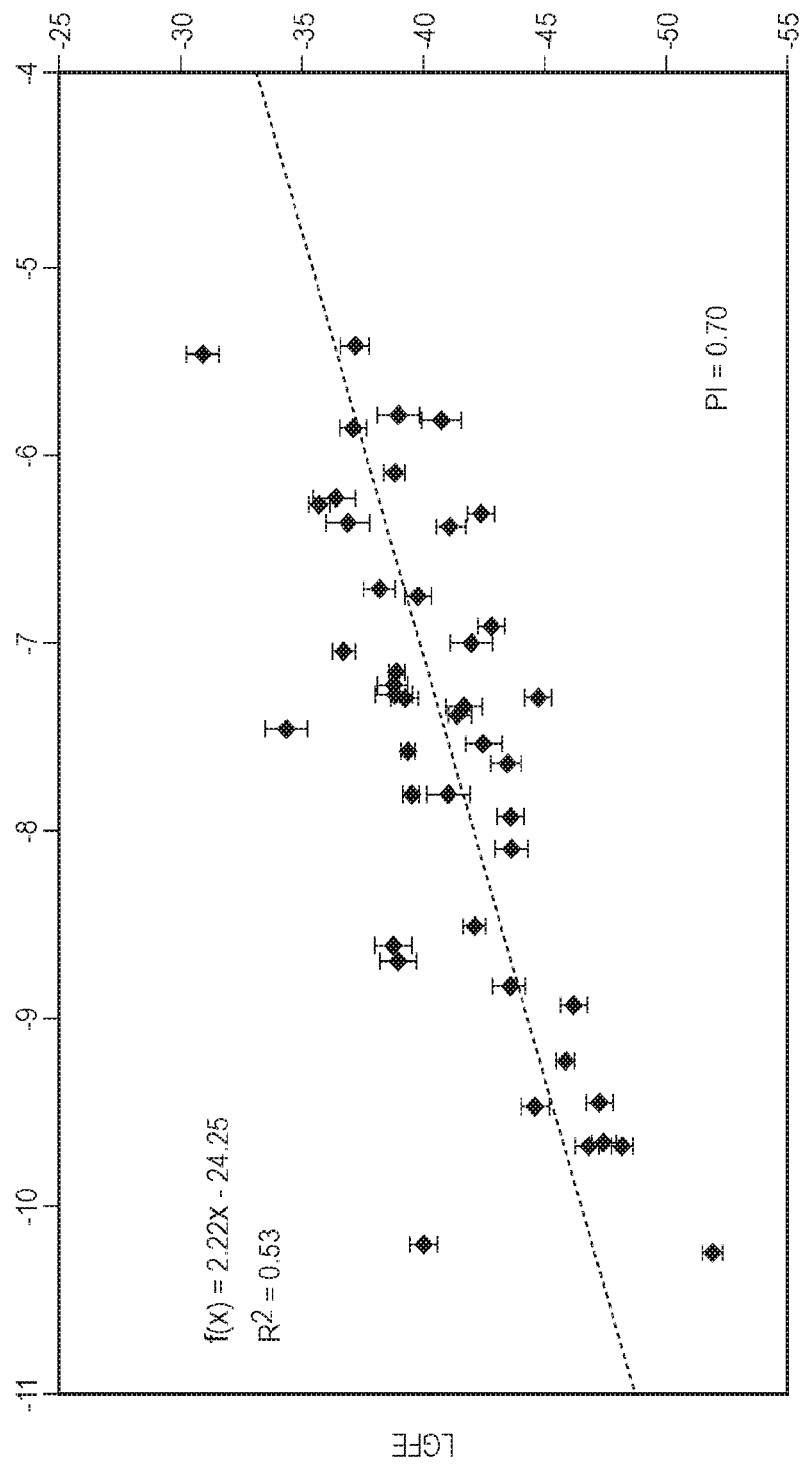
FIG. 7 illustrates a correlation plot of experimental binding affinity (from Ki) vs. predicted LGFE (standard deviations are shown by the error bars) for all the tested compounds of MCL-1. A correlation coefficient of 0.53 and a predictive index of 0.70 were obtained.

Comprehensive SILCS SAR Analysis of Mcl-1 Binding:

Additional SILCS based modeling was undertaken to predict the bound orientation of the active ligands, to better understand the contributions of the different regions of the ligands to binding to Mcl-1 as well as to differential binding of the compounds to Mcl-1 versus Bcl-$x_L$. This information would be of utility in designing ligands with improved potency and selectivity for Mcl-1. Thus, subsequent modeling involved docking of each studied compound using the SILCS-Pharm approach as described in FIG. 6. The docked orientation of each compound was then subjected to SILCS MC sampling to allow the molecules to sample to local region as defined by the FragMaps and the exclusion maps from which the LGFE scores were calculated. Comparison of the LGFE values for all the tested compounds with the experimental affinities converted to free energies ($\Delta G = -RT\ln K_i$, where R is the Boltzmann constant and T is the temperature) for Mcl-1 yields a correlation of $R^2=0.53$ and a high predictive index of 0.70, (FIG. 7). Thus, the LGFE scores correlate with the Mcl-1 experimental data, indicating the quality of the bound orientations from the SILCS-Pharm-SILCS-MC protocol.

Given the predictive capabilities of the LGFE scores, further analysis was undertaken to use the SILCS modeling to further interpret the experimental SAR data. This analysis focused on four compounds: 3b, 3a, 3bi and 3bl. These compounds differ in the number of phenyl rings attached to the sulfonamide moiety going from 0 to 3 rings, in that order, with the binding affinities varying from 99 μM down to 31 nM. For these compounds a correlation of $R^2=0.99$ between the LGFE and experimental G values is obtained.

The predicted conformation of 3a, 3b, 3bi, and 3bl was analyzed inside the Mcl-1 binding site. For all four compounds, the carboxylic acid overlaps with the negative FragMap, associated with its interaction with R263 of Mcl-1 and the aromatic rings suitably overlap with hydrophobic FragMaps, binding within the hydrophobic groove. For 3b, the sulfonamide group is placed outside of the hydrophobic binding pocket corresponding to an H-bond donor FragMap indicating its possible H-bonding interaction with residue H224. The hydroxyl group on the naphthalene ring overlaps with an H-bond acceptor FragMap, possibly making an H-bond to residue T266. For the other three compounds, the naphthalene group flipped over relative to 3b, maintaining the position of the carboxylic acid while allowing the additional aromatic groups to interact with the hydrophobic binding pocket. Notably the sulfonamide oxygen atoms in this orientation overlap with an acceptor FragMap associated with interactions with residue T266.

Figure 4:
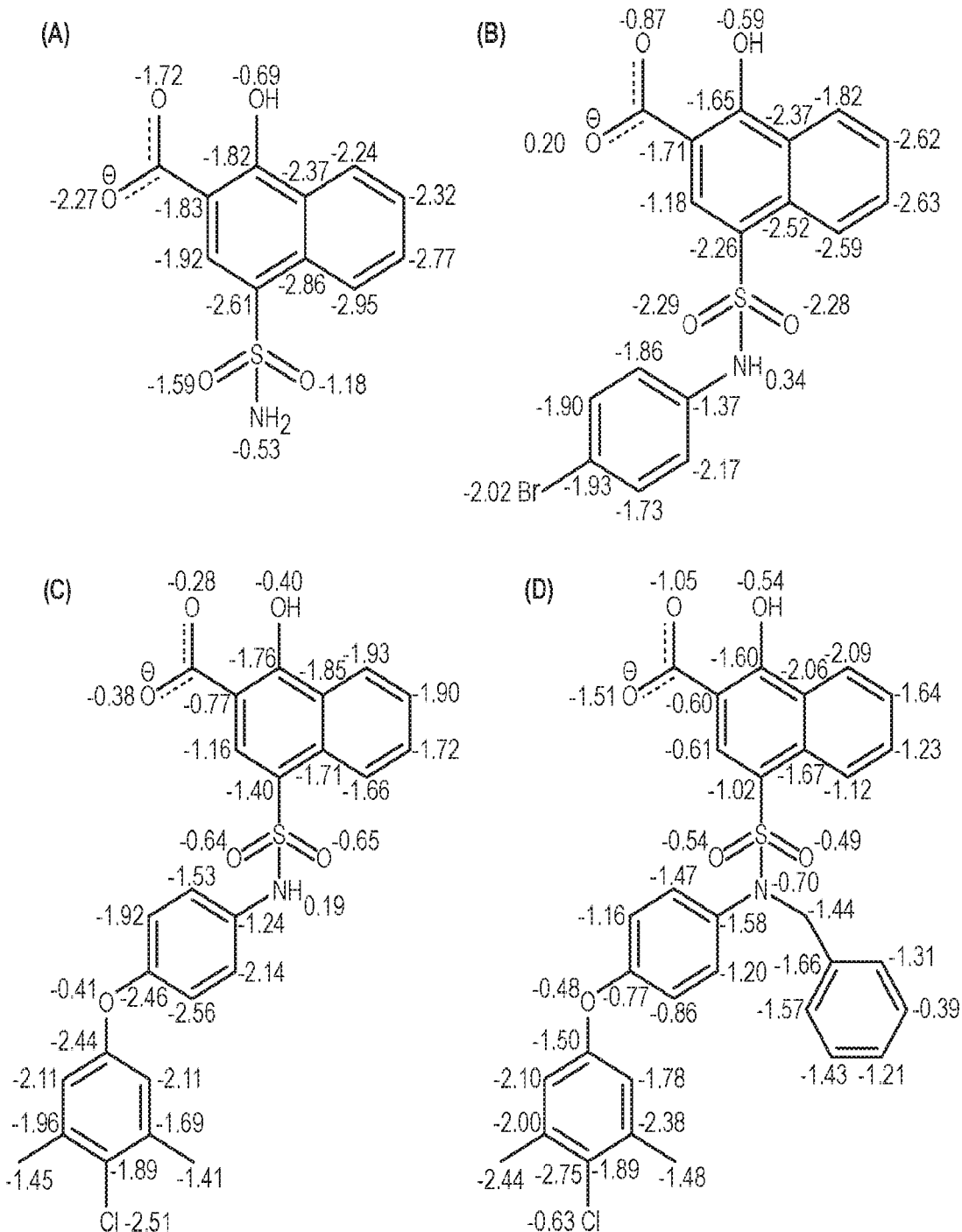
FIG. 4 illustrates atom GFE contributions for the most LGFE favorable binding conformation of the four compounds. Compound (A) is 3b; compound (B) is 3a; compound (C) is 3bi; and compound (D) is 3bl.
Figure 5A:
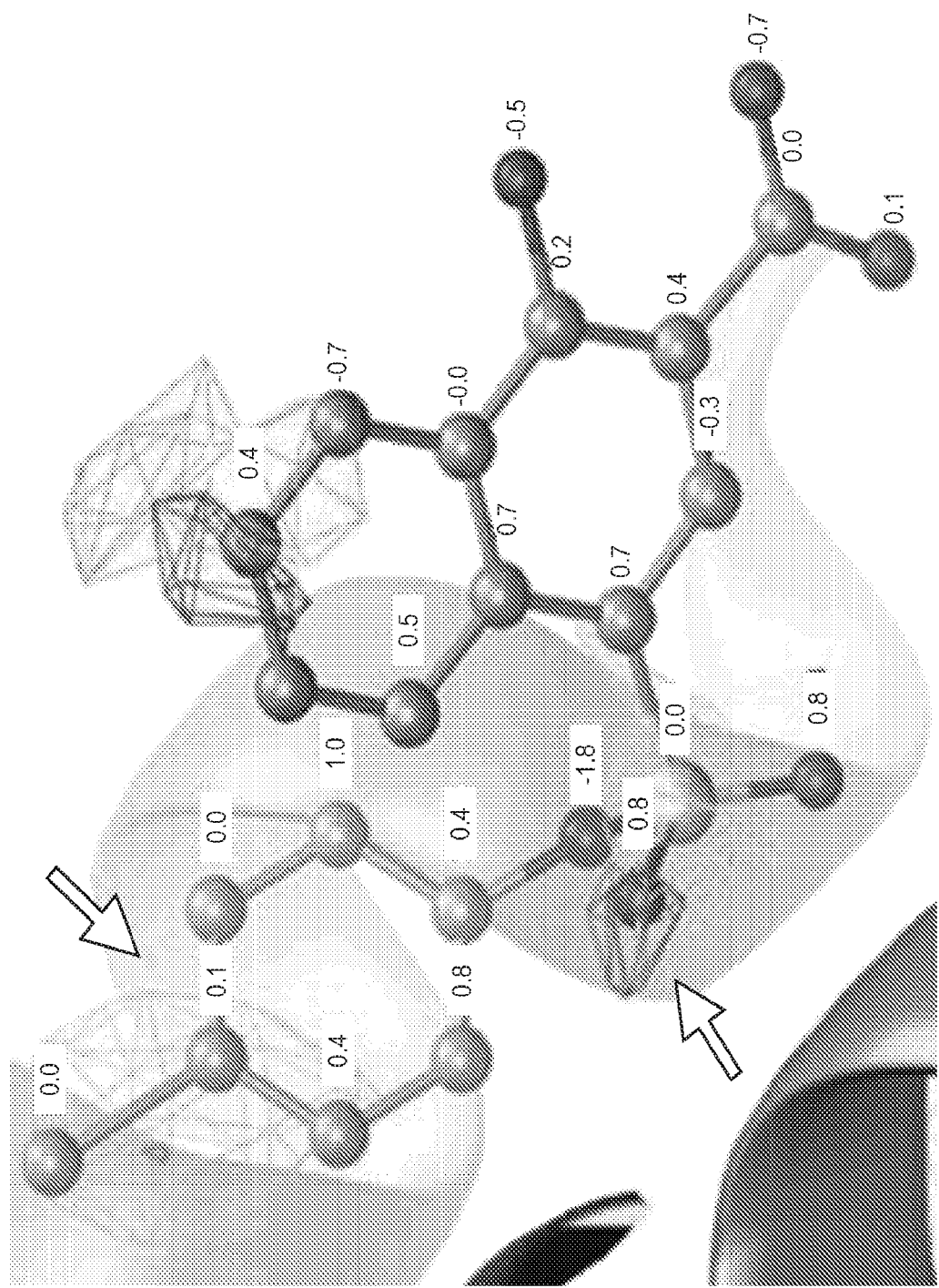
FIGS. 5A to 5D illustrate computational modeling studies of certain compounds described herein with Mcl-1 and Bcl-xL proteins.
Figure 5B:
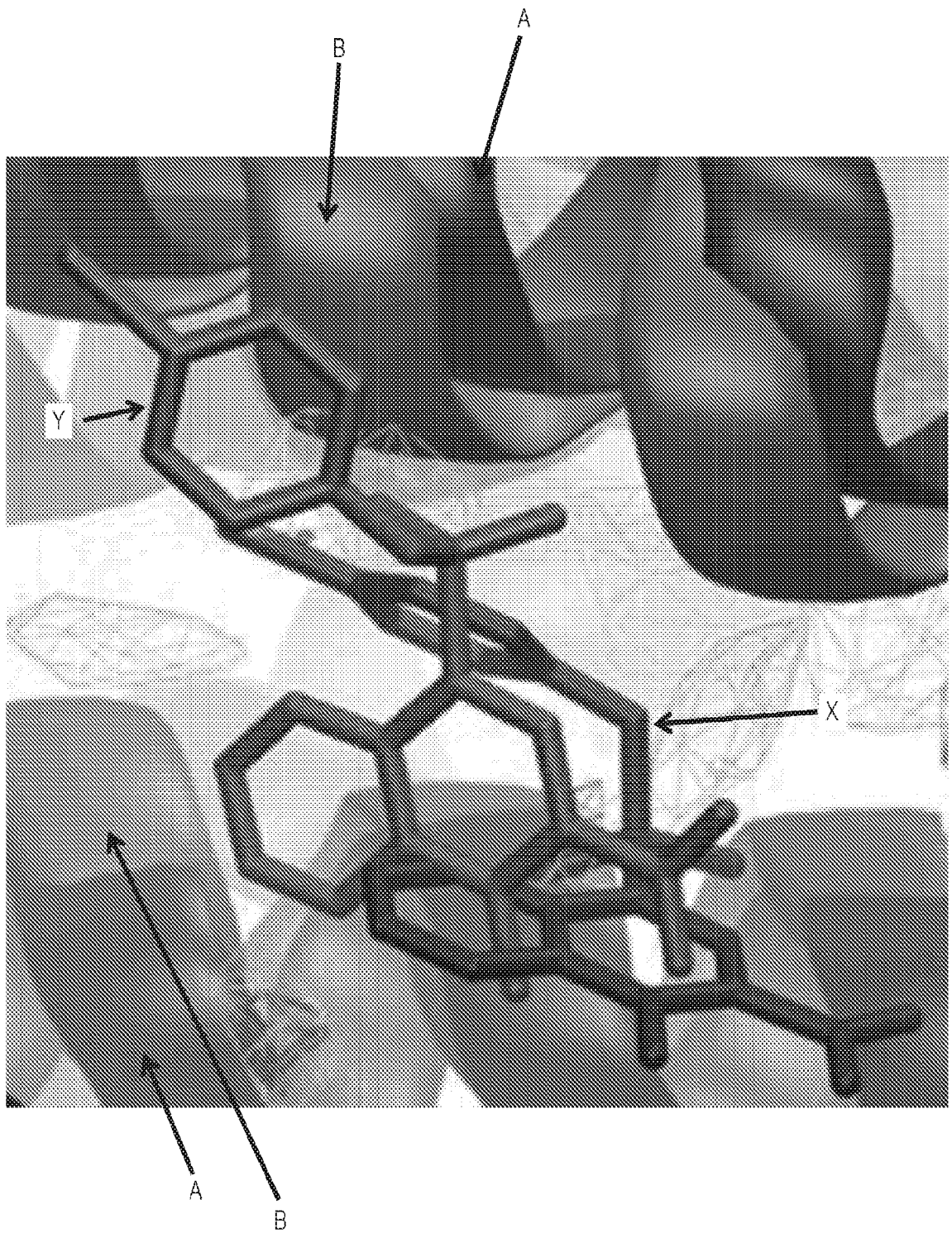
Figure 5C:
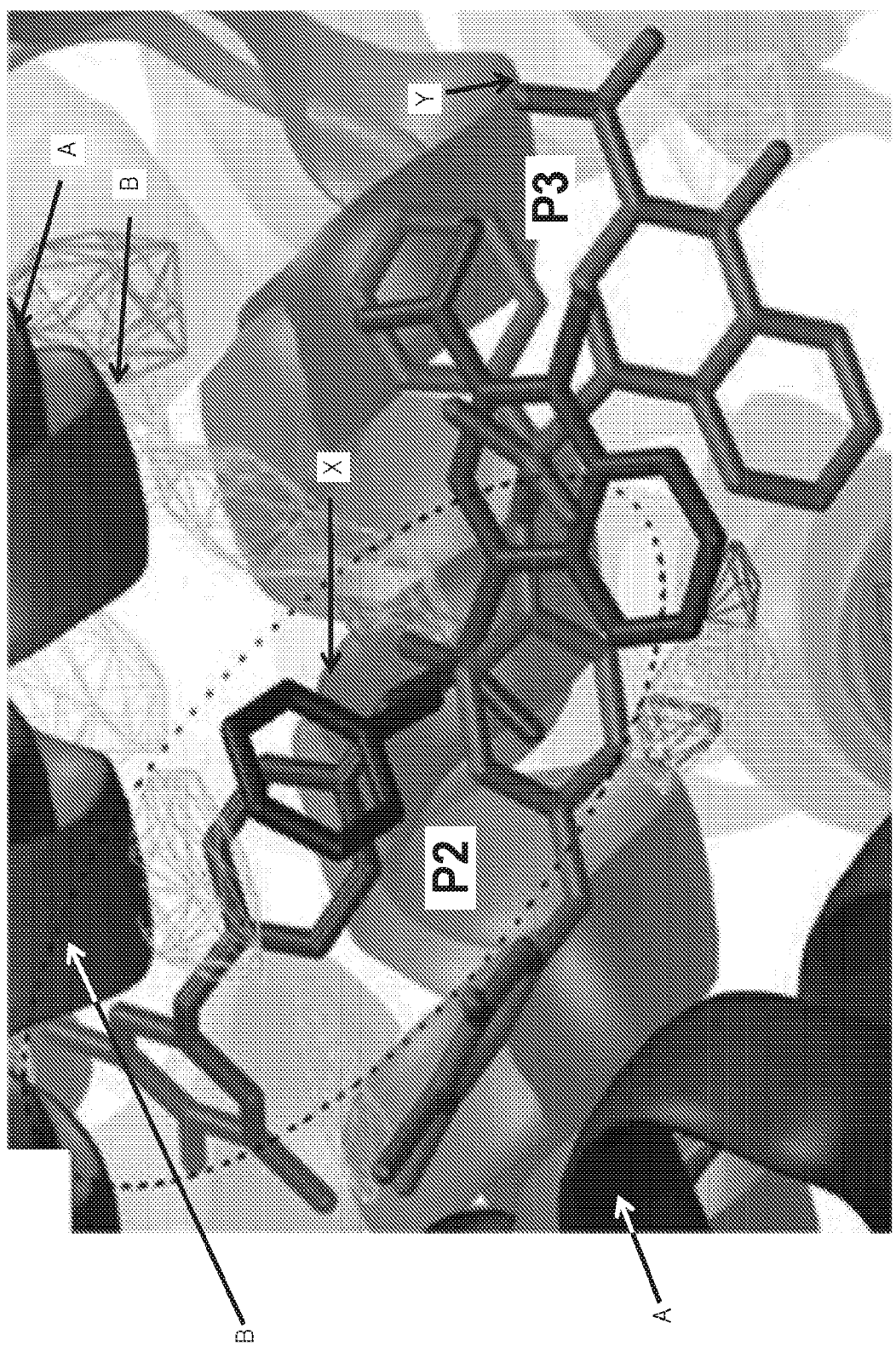
Figure 5D:
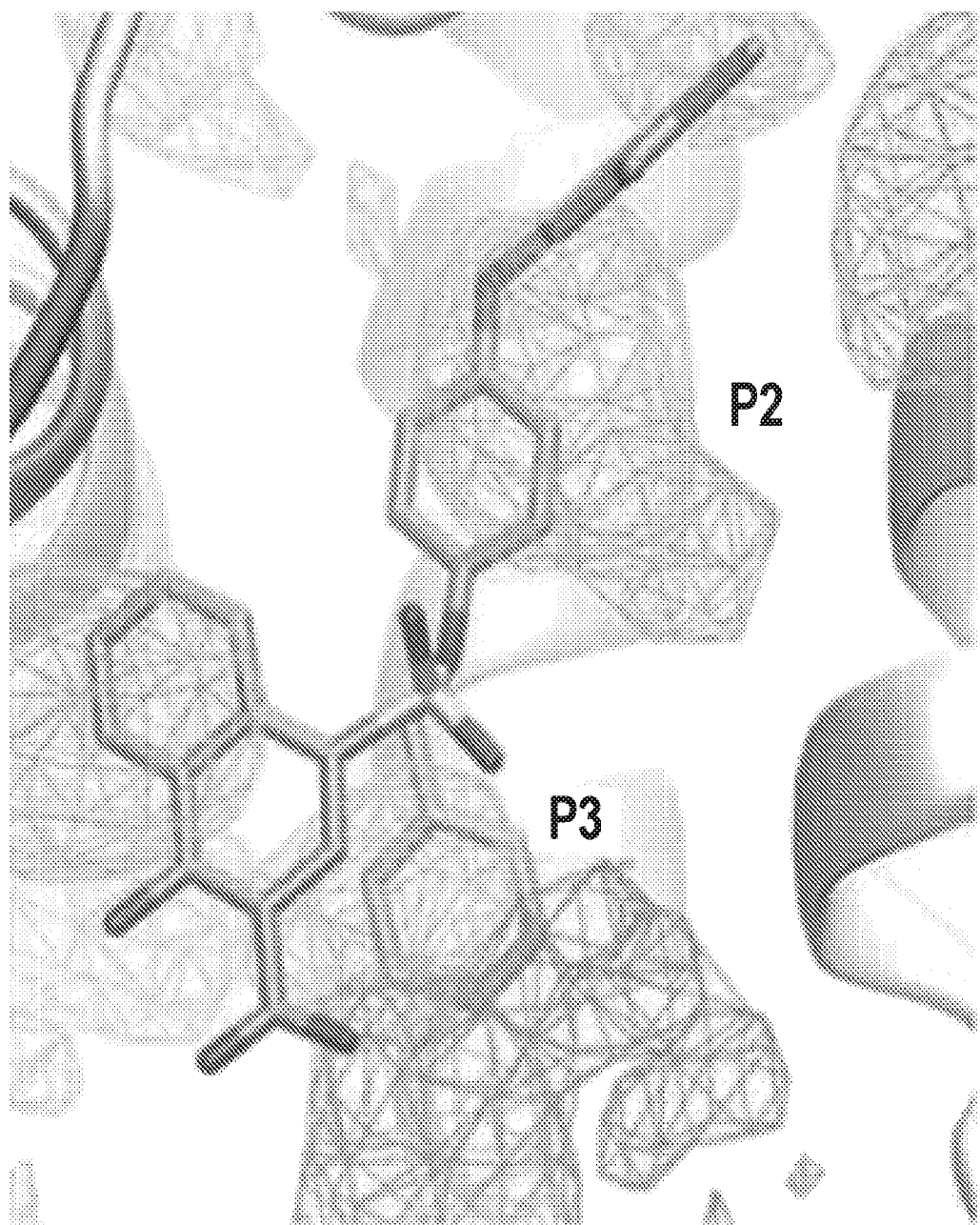

Additional analysis of the contribution of individual atoms and functional groups on the compounds to binding was performed by analyzing the atom-based GFE contributions of the individual atoms to the overall LGFEs. Presented in FIG. 4 are the GFE contributions for the most favorable binding conformations of the four compounds. For all compounds, the naphthyl and acid moieties make favorable contributions to binding. With 3b, significant favourable contributions occur with both the sulfonamide and hydroxyl moieties. In the remaining three compounds with the naphthyl moiety flipped, the sulfonamide and hydroxyl moieties make favourable contributions to binding though the magnitude is generally less than that of 3b. For example, while some of the sulfonamide oxygens make more favourable contributions with the larger compounds, the amide NH makes a very unfavourable contribution. However, the less favourable interactions of the hydroxyl and sulfonamide moieties are overcome by favorable contributions from the additional aromatic groups, which lead to the improved binding of the larger inhibitors. Interestingly, the quite favourable contributions from the second phenyl ring coming off the sulfonamide at the $R^2$ position was counterbalanced by decreased contributions from the aromatics group at the $R^1$ position upon going from 3bi to 3bl. This is consistent with the experimental free energy of binding changing by only −0.8 kcal/mol versus 3bi while differences going from 3b to 3a and 3a to 3bi are −2.1 and −1.9 kcal/mol, respectively. This atomic detailed interpretation of the experimental SAR data is anticipated to facilitate further improvements in the compounds.

SILCS Captures the Binding Specificity of Compounds for Mcl-1 Over Bcl-$x_L$

A long-standing challenge in targeting the anti-apoptotic Bcl-2 proteins is achieving family member specificity, particularly Mcl-1 specificity, although selective ligands are beginning to emerge.

Compound posing was performed using the SILCS Pharm approach. The SILCS Pharm method allows for well-defined pharmacophore features to be identified based on the SILCS FragMaps and used to direct ligand placement. As shown in FIG. 6 a total of seven pharmacophore features were located in the binding pocket. Three out of seven features (F1, F2 and F5) have good overlap with the corresponding functional groups in the crystal structure of Fesik60 bound to Mcl-1 (PDB: 4HW4). Notably, hydrophobic pharmacophore feature F5 was derived from the FragMap region, such that without the inclusion of protein flexibility in SILCS such an important feature for this series of compounds would likely not be captured. Based on the seven pharmacophore features, five pharmacophore models were developed. All five included two important features that overlap with Fesik60 (F1 and F2), one feature from the remaining five features (F3-F6) as another important feature, with the remaining features being marked as supplementary features. Docking of 250 conformations of the tested compounds in a partial matching mode was then performed against the pharmacophore models. In the partial matching mode all important features must to be matched by each ligand and supplementary features may be matched. In this matching mode, compounds that cannot match the important features are rejected. The best conformation based on RMS difference for each model was then subjected to the SILCS-MC approach, with the compound conformation with the most favorable LGFE selected for additional analysis.

To investigate the binding specificity of compounds for Mcl-1 versus Bcl-$x_L$, SILCS simulations and GFE FragMap generation followed by LGFE scoring were also done for Bcl-$x_L$ (Table 1-5).

TABLE 1-5

Experimental binding data ΔG and LGFE (kcal/mol) scores for all tested compounds for Mcl-1 and Bcl-xL.

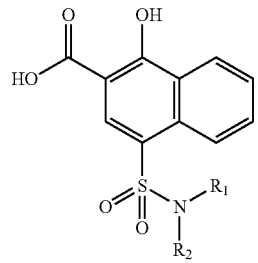

| Name | R¹ | R² | Mcl-1 Exp Δ G | Mcl-1 GFE | Bcl-xL Exp Δ G | Bcl-xL LGFE |
|---|---|---|---|---|---|---|
| 1; 3a | 4-Br—C₆H₄ | H | −7.58 | −39.46 | −5.85 | −36.20 |
| 3b; SF-5-294 | H | H | −5.46 | −31.00 | | |
| 3c; SF-5-311 | Bn | H | −5.79 | −39.02 | | |
| 3d; 5JC73-2 | CH₂-(2-Cl—C₆H₅) | H | −5.86 | −37.09 | | |
| 3e; 5JC71 | CH₂-(3-Cl—C₆H₅) | H | −7.22 | −38.80 | | |
| 3f; SF-5-264 | CH₂-(4-Cl—C₆H₅) | H | −6.38 | −41.13 | −4.73 | −38.60 |
| 3g; MEL-3-006 | CH₂—C₆H₁₁ | H | −7.00 | −42.01 | −5.60 | −40.99 |
| 3h; SF-5-295 | Me | Me | −6.26 | −35.73 | | |
| 3i; SF-5-263 | —CH₂CH₂CH₂CH₂CH₂— | | −7.54 | −42.58 | | |
| 3j; EW-2-051 | —CH₂CH₂N(Ph)CH₂CH₂— | | −7.29 | −44.80 | | |
| 3k; SF-5-307 | —CH₂CH₂N(Bn)CH₂CH₂— | | −7.45 | −34.40 | | |
| 3l; SF-5-311 | Ph | H | −5.42 | −37.18 | | |
| 3m; TA-1-019 | 2-Br—C₆H₅ | H | −7.04 | −36.80 | | |
| 3n; TA-1-020 | 3-Br—C₆H₅ | H | −7.16 | −38.98 | | |
| 3o; SF-5-290 | 2,4-di-Br—C₆H₄ | H | −8.69 | −39.00 | −7.68 | −37.67 |
| 3p; EW-2-056 | 1-Naphthyl | H | −6.75 | −39.78 | −5.40 | −38.34 |
| 3q; EW-2-057 | 2-Naphthyl | H | −7.28 | −38.84 | −5.68 | −37.24 |
| 3r; LC-4-002 | 2-Ph—C₆H₄ | H | −6.91 | −42.88 | | |
| 3s; LC-3-192 | 3-Ph—C₆H₄ | H | −7.81 | −41.08 | | |
| 3t; LC-3-192 | 4-Ph—C₆H₄ | H | −7.93 | −43.70 | | |
| 3u; TA-1-017 | 2-CF₃—C₆H₄ | H | −7.35 | −41.75 | −6.43 | −40.68 |
| 3v; 5JC67 | 4-Cl—C₆H₄ | H | −7.80 | −39.51 | | |
| 3w; 5JC73-1 | 4-CF₃—C₆H₄ | H | −7.64 | −43.43 | | |
| 3x; 5JC74-1 | 4-Me—C₆H₄ | H | −6.09 | −38.82 | | |
| 3y; 5JC74-2 | 4-(iPr)—C₆H₄ | H | −7.38 | −41.58 | | |
| 3z; MEL-3-018 | 4-OMe—C₆H₄ | H | −6.71 | −38.27 | −5.65 | −36.46 |
| 3aa; SF-5-293 | 4-(OiPr)—C₆H₄ | H | −5.82 | −40.81 | | |
| 3ab; TA-1-018 | 4-CN—C₆H₄ | H | −6.35 | −36.95 | | |
| 3ac; MEL-3-005 | 4-NO2—C₆H₄ | H | −7.29 | −39.27 | −6.31 | −38.47 |
| 3ad; 5JC75-2 | 3-CN—C₆H₄ | H | −6.23 | −36.40 | | |

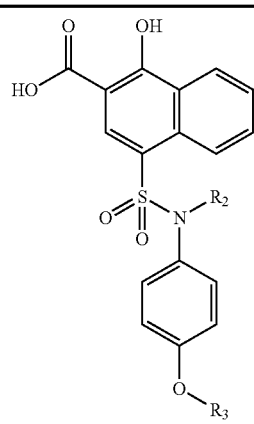

| Compound | R² | R³ | Mcl-1 Exp Δ G | Mcl-1 GFE | Bcl-xL Exp Δ G | Bcl-xL LGFE |
|---|---|---|---|---|---|---|
| 3ba; MEL-2-116 | iBu | iPr | −8.61 | −38.81 | −7.11 | −36.24 |
| 3bb; SF-5-299 | H | Ph | −8.10 | −43.68 | | |
| 3bc; SF-5-301 | H | 4-Me—C₆H₄ | −8.83 | −43.58 | −8.28 | −42.87 |
| 3bd; SF-5-300 | H | 1-Naphthyl | −9.66 | −47.46 | −9.08 | −48.26 |
| 3be; SF-5-303 | H | 3-Br—C₆H₄ | −9.47 | −44.65 | −8.89 | −44.31 |
| 3bf; SF-5-306 | H | 3,5-di-Me—C₆H₃ | −8.93 | −46.21 | −8.74 | −45.53 |

TABLE 1-5-continued

Experimental binding data ΔG and LGFE (kcal/mol) scores for all tested compounds for Mcl-1 and Bcl-xL.

| | | | | | | | |
|---|---|---|---|---|---|---|---|
| 3bg; SF-5-302 | H | 2,4-di-Cl—C$_6$H$_3$ | −9.68 | −46.79 | −9.16 | −46.47 |
| 3bh; SF-5-304 | H | 4-Cl—C$_6$H$_4$ | −9.22 | −45.94 | | |
| 3bi; JY-5-371 | H | 4-Cl-3,5-di-Me—C$_6$H$_2$ | −9.45 | −47.29 | −8.61 | −46.68 |
| 3bj; JY-5-377 | iBu | 4-Cl-3,5-di-Me—C$_6$H$_2$ | −9.68 | −48.23 | −9.23 | −47.38 |
| 3bk; JY-5-379 | Cp | 4-Cl-3,5-di-Me—C$_6$H$_2$ | −10.20 | −40.05 | −8.91 | −38.93 |
| 3bl; JY-5-380 | Bn | 4-Cl-3,5-di-Me—C$_6$H$_2$ | −10.24 | −51.93 | −8.82 | −50.94 |

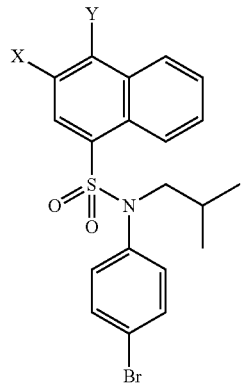

| Compound | X | Y | Mcl-1 Exp ΔG | Mcl-1 GFE |
|---|---|---|---|---|
| 3ca | CO$_2$H | OH | −8.52 | −42.19 |
| 3cb | CO$_2$Me | OH | >−4.50 | −34.23 |
| 3cc | CO$_2$Me | OMe | >−4.50 | −35.45 |
| 3cd | CO$_2$H | OMe | −6.31 | −42.41 |

Figure 8:
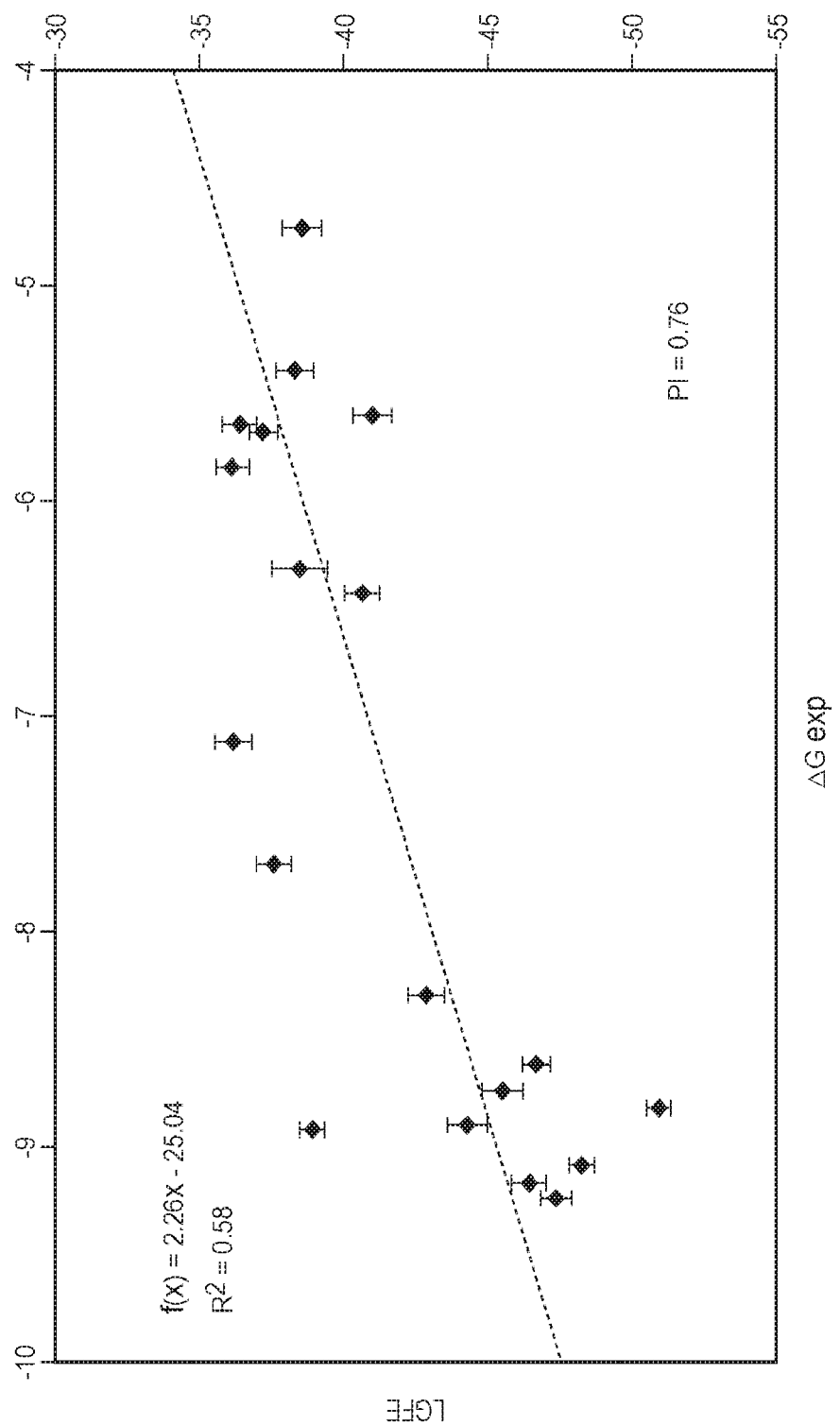
FIG. 8 illustrates a correlation plot of Bcl-xl experimental binding affinity (from Ki) vs. predicted LGFE (standard deviations are shown by the error bars) for all the compounds tested against Bcl-xL. A correlation coefficient of 0.58 and a predictive index of 0.76 were obtained.
Figure 9:
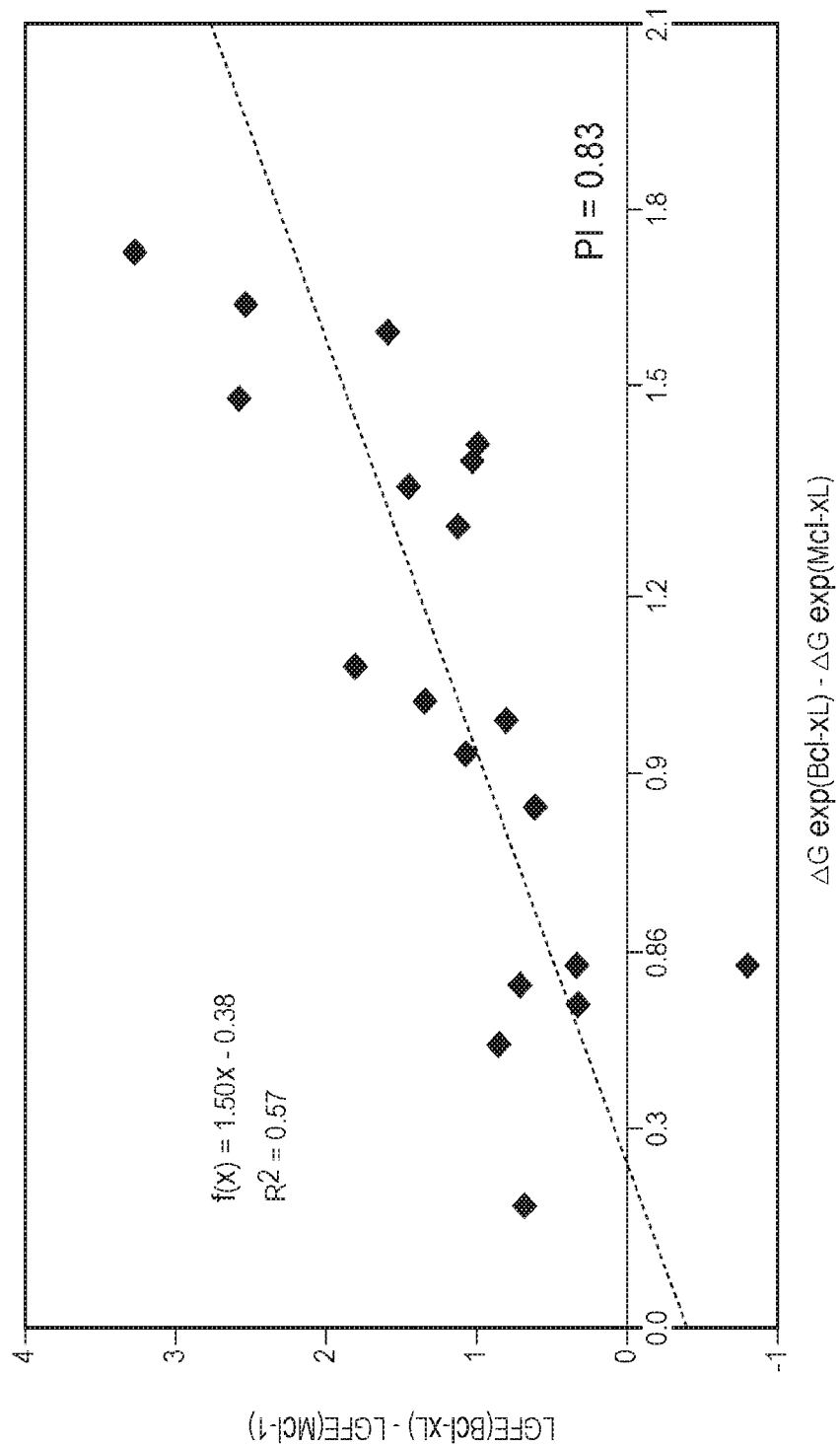
FIG. 9 illustrates a correlation plot of experimental binding affinity difference between Mcl-1 and Bcl-xL (from Ki) vs. predicted LGFE difference for all compounds tested against Bcl-x. A correlation coefficient of 0.57 and a predictive index of 0.83 were obtained.

A correlation of $R^2=0.58$ and a high predictive index of 0.76 was found between the LGFE and experimental binding data for Bcl-x$_L$ (FIG. 8). Difference FragMaps, ΔFragMaps, were then calculated as $GFE_{Bcl-xl}-GFE_{Mcl-1}$ such that positive ΔFragMaps favour Mcl-1 over Bcl-x$_L$. The ΔFragMaps may then be used to qualitatively understand the contributions driving specificity as well as quantitatively obtain difference LGFE scores (ΔLGFE). Correlation analysis between the ΔLGFE scores and the experimental differences in the binding affinities for Mcl-1 and Bcl-x$_L$ yielded an $R^2=0.57$ and predictive index of 0.83 (FIG. 9), indicating the quality of the SILCS ΔFragMaps in modeling the relative affinities for Mcl-1 versus Bcl-x$_L$. Additional analysis was therefore undertaken on 3a as this compound showed the largest specificity for Mcl-1 over Bcl-x$_L$. FIG. 5 (inset A) shows the ΔFragMaps between Mcl-1 and Bcl-x$_L$, and includes the docked orientation of 3a with the atom contributions to the ΔLGFE between Mcl-1 and Bcl-x$_L$ mapped onto this orientation. The p-bromophenyl group that binds deeply in the p2 pocket between helices α4 and α5 is in a Mcl-1 positive ΔFragMap indicating that region to favour binding to Mcl-1. Similarly, the sulfonamide oxygen contributes to the binding of 3a to Mcl-1 over Bcl-x$_L$. Alternatively, the NH moiety of the sulfonamide contributes to more favourable binding to Bcl-x$_L$ over Mcl-1. The acid moiety in the lower right of the figure is also predicted to favour binding to Bcl-x$_L$ over Mcl-1. Summing over the different ΔFragMap classes showed the overall ΔLGFE score of 3.0 kcal/mol favouring binding to Mcl-1 to have favourable contributions from the hydrophobic and neutral acceptor terms, 4.4 and 1.6 kcal/mol, respectively, while the neutral donor, negatively charged acceptor and hydroxyl groups favour Bcl-x$_L$ binding, with values of −1.8, −0.7 and −0.5 kcal/mol, respectively. Similar trends are observed for the other compounds for which a selectivity of Mcl-1 over Bcl-x$_L$ was found, as shown in Table 1-6.

TABLE 1-6

FragMap type contributions to the ΔLGFE scores between Mcl-1 and Bcl-xL using the most favorable binding conformations, where positive values favor binding to Mcl-1.

| Comp. | Exp. ΔG diff. | No. of heavy atoms | ΔLGFE | Hydrophobic | Hydroxyl group | Neutral Acceptor | Neutral Donor | Charged Acceptor |
|---|---|---|---|---|---|---|---|---|
| 1; 3a | 1.73 | 25 | 3.01 | 4.37 | −0.53 | 1.58 | −1.75 | −0.66 |
| 3f; SF-5-264 | 1.65 | 26 | 2.39 | 0.95 | −0.17 | −0.44 | −2.29 | 4.34 |
| 3g; MEL-3-006 | 1.40 | 25 | 1.56 | 3.03 | 0.80 | 0.54 | −3.71 | 0.90 |

TABLE 1-6-continued

FragMap type contributions to the ΔLGFE scores between Mcl-1 and Bcl-xL using the most favorable binding conformations, where positive values favor binding to Mcl-1.

| Comp. | Exp. ΔG diff. | No. of heavy atoms | ΔLGFE | Hydrophobic | Hydroxyl group | Neutral Acceptor | Neutral Donor | Charged Acceptor |
|---|---|---|---|---|---|---|---|---|
| 3o; SF-5-290 | 1.01 | 26 | 2.00 | 5.35 | −0.98 | 0.35 | −4.09 | 1.37 |
| 3p; EW-2-056 | 1.35 | 28 | 2.77 | 2.30 | −0.89 | −0.36 | 0.01 | 1.72 |
| 3q; EW-2-057 | 1.60 | 28 | 1.85 | 4.50 | 0.82 | 0.11 | −4.46 | 0.89 |
| 3u; TA-1-017 | 0.92 | 28 | 1.79 | −0.56 | 0.70 | 2.41 | −1.73 | 0.96 |
| 3z; MEL-3-018 | 1.06 | 26 | 2.27 | 0.72 | −0.25 | 1.81 | −1.39 | 1.38 |
| 3ac; MEL-3-005 | 0.98 | 27 | 0.88 | 2.94 | −0.55 | −0.09 | −1.40 | −0.02 |
| 3ba; MEL-2-116 | 1.50 | 32 | 3.11 | 0.49 | −0.14 | 0.43 | 0.00 | 2.33 |
| 3bc; SF-5-301 | 0.55 | 32 | 0.70 | 0.32 | 0.93 | −0.42 | −0.37 | 0.24 |
| 3bd; SF-5-300 | 0.58 | 35 | −0.58 | −0.96 | −0.15 | −0.23 | 0.04 | 0.72 |
| 3be; SF-5-303 | 0.58 | 32 | 0.43 | 0.44 | −0.20 | 0.50 | −0.18 | −0.14 |
| 3bf; SF-5-306 | 0.19 | 33 | 0.42 | −0.20 | −0.20 | 0.50 | −0.27 | 0.58 |
| 3bg; SF-5-302 | 0.52 | 33 | 0.77 | 1.37 | −0.21 | 0.20 | −0.27 | −0.32 |
| 3bi; JY-5-371 | 0.84 | 34 | 1.21 | 5.59 | −0.43 | −0.18 | −1.01 | −2.75 |
| 3bj; JY-5-377 | 0.45 | 38 | 0.64 | 3.32 | 0.27 | −0.58 | 0.00 | −2.36 |
| 3bk; JY-5-379 | 1.29 | 39 | 2.16 | 1.70 | 0.10 | −2.31 | 0.00 | 2.67 |
| 3bl; JY-5-380 | 1.42 | 41 | 1.34 | 1.17 | 0.00 | −0.85 | 0.00 | 1.02 |

Indeed, given that all the tested compounds favoured Mcl-1 binding over Bcl-x$_L$, these results indicate that the exploitation of the binding pocket inherently favours Mcl-1 binding, as previously discussed by Fesik. Without being limited to any one theory of the invention, the docked orientation of 3a in the two proteins indicates that this pocket is not being exploited with Bcl-x$_L$. This is consistent with the fact that Mcl-1 shows more opening at the p2 pocket as compared to Bcl-x$_L$ as illustrated in FIG. 5 (inset B), disallowing access of 3a deep into the hydrophobic pocket in the p2 site of Bcl-x$_L$.

However, further extension of the ligands (e.g. 3bl) leads to improved binding affinity, but not improved specificity. This may be explained by different predicted binding orientations of the compound to the two proteins. As seen in FIG. 5 (inset C), 3bl binds with its additional 4-chloro-3,5-dimethylphenyl $R^3$ group deep in the p2 pocket, and with the $R^2$ benzyl group occupying the upper region of the p2 pocket. In contrast, the orientation of 3bl bound to Bcl-x$_L$ shows the 4-chloro-3,5-dimethylphenyl to still interact with the p2 site, though not as deep as that occurring with Mcl-1. This leads to a shift in the location of the naphthyl ring as well as the $R^2$ phenyl group into the p3 site where they can exploit the hydrophobic character of that sub-pocket as well as interactions with R263, as indicated by the apolar and neg FragMaps in FIG. 5 (inset D), respectively. Thus, the significant increase in the size of 3bl leads to increased affinity with respect to both Mcl-1 and Bcl-x$_L$, with that larger size predicted to change the binding orientation with Bcl-x$_L$ such that increased specificity for Mcl-1 is not gained over 3a.

Conclusions

Described herein is a class of Mcl-1 inhibitors that target R263 and the p2 and p3 pockets within the hydrophobic BH3-binding crevice on the surface of the protein. SILCS analysis of this region of the BH3 binding site supported this strategy, with the use of the SILCS exclusion maps indicated significant additional opening of the p2 pocket that could be exploited in ligand design. Accordingly, a series of compounds were synthesized and subjected to experimental evaluation using a FP assay with binding of 3ba to targeted pocket of Mcl-1 verified using NMR. From this strategy, 3bl was identified with a $K_i$=31 nM for Mcl-1 with a specificity of 11-fold over Bcl-x$_L$.

The two-step synthesis then allowed the rapid synthesis and testing of over 40 analogs. This yielded compounds with affinities spanning over a 10,000 fold range. Detailed SILCS analysis of all of these compounds identified the moieties leading to improved affinity. These results suggest that fine tuning of interactions with the p2 pocket via appropriate modifications of the R3 ring (Table 1-2) as well as of the R1 ring will likely lead to improved affinity. Additional SILCS analysis on the differential binding of selected compounds to Mcl-1 versus Bcl-x$_L$ indicates that fine tuning of the $R^3$ ring occupying the p2 pocket may also improve specificity. Further modifications that may contribute to improved specificity include alkylation of the NH moiety of the sulfonamide moiety and additions of both hydrogen bond acceptor (e.g. OMe) or hydrophobic (e.g. Cl) functional groups to the naphthyl ring as indicated by the differential Fragmaps in the top, central region of FIG. 7A.

Experimental

Computational

Molecular modeling studies were initiated with the crystal structure of the Mcl-1-BH3 peptide complex (PDB ID: 4HW4), following removal of the 16mer BH3 peptide, and with the Bcl-xL-Bak complex structure (PDB ID: 1BXL), following removal of the Bak peptide. For both proteins, the Reduce software was used to choose optimal Asn, Gln, and His side-chain orientations and determine the optimal protonation states of His residues. The protein was immersed in a box of an aqueous solution containing eight small probe molecules at approximately 0.25 M each with water at ~55 M. The size of the simulation box was chosen so as to have the protein extrema separated from the edges by a minimum of 8 Å based on non-hydrogen atoms. The small molecules, or solutes, include benzene, propane, methanol, formamide, acetaldehyde, methylammonium and acetate, as previously used, along with imidazole. Ten such protein-small molecule aqueous systems were generated for each protein with each simulation system differing in the initial positions and orientations of the small molecules and water. The SILCS molecular dynamics (MD) simulations were performed using the GROMACS simulation program with the CHARMM36 force field, CHARMM general force field (CGenFF) and TIP3P water model to describe the protein, small molecules and water, respectively. The simulations were each extended for 40 ns, yielding a total of 400 ns of simulation time for each protein. Additional MD simulation details can be found in Reference.

From the simulation, 3D probability distributions of selected atoms from the small molecules were constructed to form the FragMaps, yielding a total of ten different FragMaps. The final FragMaps are converted to free energies, termed grid free energies (GFE), by normalizing the distributions with respect to the distributions of the solutes in an aqueous solution in the absence of the proteins followed by Boltzmann transformation to yield the GFE values. As the GFE FragMaps are normalized with respect to the fragment probabilities in solution, they contain both favorable regions as well as unfavorable regions. The unfavorable regions typically range from 0 to 3 kcal/mol, with the upper limit based on sampling issues. In addition to the FragMaps, exclusion maps were constructed by calculating the 3D probability distributions of all non-hydrogen atoms of the water and solutes together and identifying those voxels with zero occupancies, which defines the exclusion maps. This exclusion map represents regions forbidden to the small molecules and water and may be considered an alternate to more traditional representations of the protein surface. For quantitative analysis, these voxels were assigned a very high energetic penalty (1000 kcal/mol) while the remaining voxels were assigned energies associated with the specific FragMaps. The availability of the GFE FragMaps and the exclusion maps allows for quantitative estimates of binding affinities to be made referred to as ligand grid free energies (LGFE). These are a simple summation of the GFE energy contribution of all the atoms in each ligand that are classified with respect to the FragMap types followed by normalization of the summed energies by the number of classified ligands atoms and subsequent multiplication by the total number of non-hydrogen atoms, yielding the final LGFE values. Note that the LGFE scores are not directly equivalent to experimental free energies due to the additive approximation of the LGFE scores (i.e. the individual atom-based GFEs are summed to yield the LGFE), the lack of accounting for the energy cost of connecting the fragments that comprise the full compounds and issues associated with the standard state in the experimental and computational conditions.

In the present study the specific FragMaps were used for calculation of GFE and LGFE scores, while generic FragMaps are used for visualization. The specific and generic FragMap types that were used include: (1) aromatic, AROM (benzene carbons); (2) aliphatic, ALIP (propane carbons); (3) dual role hydrogen bond atom, MEOO (methanol oxygens); (4) FORN, (formamide nitrogen); (5) FORO, (formamide oxygen); (6) IMIN, (imidazole acceptor nitrogen); (7) IMIH, (imidazole donor nitrogen); (8) AALO, (acetaldehyde oxygen); (9) positive donor, POS (methylammonium nitrogen); (10) negative acceptor, NEG (acetate oxygens); (11) generic nonpolar, APOLAR (benzene and propane carbons); (12) generic neutral hydrogen-bond donor, HBDON (formamide and imidazole donor nitrogen); and (13) generic neutral hydrogen-hydrogen acceptor, HBACC (formamide, acetaldehyde oxygens and imidazole acceptor nitrogen). The convergence of the FragMaps was examined by calculating the overlap coefficient between two sections of the simulations (trajectories 1-5 and trajectories 6-10), as previously described. All the generic FragMaps show an overlap coefficient of greater than 0.6, indicating satisfactory convergence.

To identify the binding modes of the tested compounds with Mcl-1, the SILCS-Pharm protocol was used in which the FragMaps are used to define the pharmacophore features. The selected pharmacophore was used to direct docking of the studied compounds in the Mcl-1 binding pocket. Generation of 250 conformations of each compound and pharmacophore docking were conducted using MOE. For each compound, the best conformation, based on the smallest RMSD with the pharmacophore was retained for SILCS ligand grid free energy (LGFE) scoring. The compounds were locally relaxed and minimized using FragMap-based Monte Carlo (MC) sampling (SILCS-MC) from which the LGFE scores were obtained. The SILCS-MC was conducted for 50000 steps under slow cooling mode and was repeated 20 times for each conformation with different random seeds to get a Boltzmann averaged LGFE value, along with the corresponding standard deviation. The lowest energy LGFE conformation for each compound was chosen for visual presentation and analysis. The SILCS-MC was also performed in the same way using FragMaps of Bcl-$x_L$ to calculate Bcl-$x_L$ related LGFEs for the compounds that have available Bcl-$x_L$ experimental data. Bcl-$x_L$ SILCS-MC calculations were initiated from the Mcl-1 SILCS-PHARM orientations in the context of the Bcl-xL FragMaps and exclusion maps.

Chemistry

General.

Unless otherwise stated, all reactions were performed under an inert atmosphere ($N_2$). Reagents and solvents were ACS grade, and purchased from Sigma-Aldrich, Alfa Aesar, Oakwood and TCI America. Anhydrous solvents were used as provided without further purification. Reactions were monitored by thin-layer chromatography (TLC), visualizing with a UV lamp and/or $KMnO_4$ stain. Flash column chromatography was performed with silica gel 60 Å (70-230 mesh, Merck). $^1$H and $^{13}$C NMR spectra were recorded on a Varian INOVA 400 MHz NMR spectrometer at 25° C. Chemical shifts are reported in parts per million (ppm). Data for $^1$H NMR are reported as follows: chemical shift (δ ppm) (multiplicity, coupling constant (Hz), integration), where multiplicities are: s=singlet, d=doublet, t=triplet, sep=septet, m=multiplet. The residual solvent peak was used as an internal reference: CDCl$_3$ ($\delta_H$ 7.26; $\delta_C$ 77.21) and d$_6$-DMSO ($\delta_H$ 2.50; $\delta_C$ 39.51). Mass spectra were obtained on an Electrospray TOF (ESI-TOF) mass spectrometer (Bruker AmaZon X). All final molecules were deemed to be >95% pure by reversed-phased HPLC using a Waters 1525 analytical/preparative HPLC fitted with a C18 reversed-phase column (Atlantis T3: 4.6 mm×150 mm) according to the following conditions with solvents (A) H$_2$O/0.1% TFA, (B) CH$_3$CN—H$_2$O, 9:1 with 0.1% TFA at 1 ml min$^{-1}$: (I) a gradient of 100% A to 100% B over 22 min; (II) a gradient of 50% A to 100% B over 22 min; (III) a gradient of 25% A to 100% B over 22 min; (IV) an isocratic gradient of 100% B over 22 min. Data are presented as retention time (t$_R$ (min)), purity (%), condition (I or II).

4-Chlorosulfonyl-1-hydroxy-2-naphthoic Acid (5)

1-Hydroxy-2-naphthoic acid (4; 5 g, 26.6 mmol) was added portionwise with stirring over the course of 1 h to chlorosulfonic acid (25 mL) at −10° C. Once the addition was complete, TLC of the reaction mixture confirmed all starting material had been consumed (acetone/EtOAc, 1:1). The reaction mixture was carefully poured over ice. The resulting pinkish-grey solid was collected by vacuum filtration, washing several times with ice-cold water. After the product was allowed to dry on the filter for 1 h, it was transferred to a vacuum oven where it was dried further at 50° C. for 16 h.

General Procedure A: Amination with Anilines.

4-Chlorosulfonyl-1-hydroxy-2-naphthoic acid (5; 1 eq) was suspended in anhydrous acetone (0.2 M), and then the requisite aniline (1.2 eq) and pyridine (3 eq) were added under an inert (N$_2$) atmosphere. The reaction mixture was stirred at 50° C. for 3 h, by which time TLC (acetone/EtOAc, 1:1) indicated that the reaction was complete. The reaction was concentrated to dryness and then suspended in a 1:1 mixture of EtOAc and 1 M and was vigorously stirred for 5 min. The mixture was transferred to a separatory funnel, then partitioned between EtOAc and 1 M HCl. The organic layer was washed three times with 1 M HCl, dried over Na$_2$SO$_4$, filtered, concentrated to deliver a residue that was purified by column chromatography over silica gel using an eluent of CH$_2$Cl$_2$/MeOH/AcOH 92:7:1 to provide the title compound.

General Procedure B: Amination with Primary Aliphatic Amines.

4-Chlorosulfonyl-1-hydroxy-2-naphthoic acid (5; 1 eq) was suspended in anhydrous acetone (0.2 M). The requisite benzylic amine (1.2 eq) and DIPEA (2.5 eq) were added under an inert (N$_2$) atmosphere at room temperature (RT). The reaction was stirred at RT for 16 h. TLC (acetone/EtOAc, 1:1) indicated that reaction was complete. The reaction was concentrated to dryness and then suspended in a 1:1 mixture of EtOAc and 1 M and was vigorously stirred for 5 min. The mixture was transferred to a separatory funnel, then partitioned between EtOAc and 1 M HCl. The organic layer was washed three times with 1 M HCl, dried over Na$_2$SO$_4$, filtered, concentrated to deliver a residue that was purified by column chromatography over silica gel using an eluent of CH$_2$Cl$_2$/MeOH/AcOH 92:7:1 to provide the title compound.

General Procedure C: Amination with Secondary Aliphatic Amines.

4-Chlorosulfonyl-1-hydroxy-2-naphthoic acid (5; 1 eq) was suspended in anhydrous acetone (0.2 M), and then the requisite secondary amine (3 eq) was added under an inert (N$_2$) atmosphere at room temperature. After 1 h, TLC (acetone/EtOAc, 1:1) indicated that the reaction was complete. The reaction was concentrated to dryness and then suspended in a 1:1 mixture of EtOAc and 1 M and was vigorously stirred for 5 min. The mixture was transferred to a separatory funnel, then partitioned between EtOAc and 1 M HCl. The organic layer was washed three times with 1 M HCl, dried over Na$_2$SO$_4$, filtered, concentrated to deliver a residue that was purified by column chromatography over silica gel using an eluent of CH$_2$Cl$_2$/MeOH/AcOH 92:7:1 to provide the title compound.

General Procedure D: Nucleophilic Aromatic Substitution (S$_N$Ar).

4-Fluoronitrobenzene (1 eq) and the requisite phenol (1 eq) were dissolved in anhydrous DMSO (0.3 M). K$_2$CO$_3$ (2 eq) was added, and then the reaction was stirred at 120° C. for 16 h. The next day, TLC (Hex/EtOAc, 9:1) indicated the reaction was complete. The reaction was quenched with water and ice, which resulted in precipitation. The precipitate was collected by vacuum filtration and then dried overnight in a vacuum oven at 50° C. to furnish compounds 7 that were sufficiently pure to be advanced to the next step.

General Procedure E: Reduction of Nitro Group with SnCl$_2$.2H$_2$O.

The appropriate nitroarene 7 was dissolved in EtOAc (0.1 M), and then SnCl$_2$.2H$_2$O (5 eq) was added. The reaction mixture was stirred for 50° C. for 16 h, by which time TLC confirmed reaction completion. The reaction mixture was partitioned between EtOAc and sat. NaHCO$_3$. The organic layer was collected and the aqueous layer was extracted two times with EtOAc. The organics were combined, washed with sat. NaHCO$_3$, brine, dried with Na$_2$SO$_4$, filtered and concentrated. No further purification was required.

General Procedure F: Reductive Amination.

The aniline (1 eq) was dissolved in 1,2-dichloroethane (0.1 M) and the required aldehyde (1 eq) was added, followed by NaBH(OAc)$_3$ (2 eq). The reaction mixture stirred for 16 h at room temperature. TLC (Hex/EtOAc, 1:1) indicated that the reaction was complete. The reaction mixture was diluted with CH$_2$Cl$_2$ and then partitioned with sat. NaHCO$_3$. The aqueous layer was extracted with further CH$_2$Cl$_2$ (×2), and then the organic layers were combined, washed with brine, dried (Na$_2$SO$_4$) filtered and concentrated. The crude material was purified by flash column chromatography over silica gel using an eluent of Hex/EtOAc, 1:1 to provide the title compound.

4-(N-(4-bromophenyl)sulfamoyl)-1-hydroxy-2-naphthoic Acid (3a)

4-Chlorosulfonyl-1-hydroxy-2-naphthoic acid (5) was coupled to 4-bromoaniline according to General Procedure A on a 1 mmol scale to yield the title compound as an off-white solid (300 mg, 71%): $\delta_H$ (400 MHz, d$_6$-DMSO) 10.47 (s, 1H, SO$_2$NH), 8.48-8.45 (m, 2H, Ar), 8.32 (d, 1H, Ar, J=8.0 Hz), 7.67 (t, 1H, Ar, J=7.4 Hz), 7.49 (t, 1H, Ar, J=7.4 Hz), 7.31 (d, 2H, Ph, J=8.4 Hz), 6.93 (d, 2H, Ph, J=8.8 Hz); $\delta_C$ (100 MHz, d$_6$-DMSO) 171.0, 138.0, 133.8, 132.2, 131.5, 130.0, 128.0, 125.4, 125.2, 124.5, 120.7, 117.5, 115.3, 107.3, 95.9; Calcd (M$^+$): 421.0, Found: 420.0 ([M−H]$^-$); t$_R$=8.1 min (100%, III).

1-Hydroxy-4-sulfamoyl-2-naphthoic Acid (3b)

4-Chlorosulfonyl-1-hydroxy-2-naphthoic acid (5; 287 mg, 1 eq) was suspended in dioxane (5 mL) at 0° C., then NH$_4$OH (1 mL) was added dropwise. After 1 h, TLC confirmed the reaction was complete. The reaction mixture was concentrated to dryness, then partitioned between EtOAc (50 mL) and 1 M HCl (25 mL). The aqueous layer was extracted with further EtOAc (50 mL), then the organic layers were washed with brine, dried (Na$_2$SO$_4$), filtered and concentration to afford the title compound light orange solid (160 mg, 60%): $\delta_H$ (400 MHz, d$_6$-DMSO) 8.43-8.40 (m, 2H, Ar), 8.34 (d, 1H, Ar, J=8.4 Hz), 7.60 (t, 1H, Ar, J=7.4 Hz), 7.46 (t, 1H, Ar, J=8.0 Hz), 7.13 (s, 2H, SO$_2$NH$_2$); $\delta_C$ (100 MHz, d$_6$-DMSO) 171.3, 170.6, 131.5, 130.6, 128.9, 128.4, 125.3, 125.0, 124.6, 122.6, 107.9; Calcd (M$^+$): 267.0, Found: 266.0 ([M−H]$^-$).

4-(N-Benzylsulfamoyl)-1-hydroxy-2-naphthoic Acid (3c)

4-Chlorosulfonyl-1-hydroxy-2-naphthoic acid (5) was coupled to benzylamine according to General Procedure B on a 1 mmol scale to yield the title compound as a dark yellow solid (232 mg, 65%): $\delta_H$ (400 MHz, d$_6$-DMSO) 8.45 (d, J=8.0, 1 H, Ar), 8.43 (s, 1H, Ar), 8.36 (d, J=8.0, 1 H, Ar), 7.95 (t, J=6.4, 1 H, NH), 7.62 (t, J=8.0, 1 H, Ar), 7.48 (t, J=8.0, 1 H, Ar), 7.22-7.10 (m, 5H, Ar), 3.89 (d, J=6.4, 2 H, CH$_2$); $\delta_C$ (100 MHz, d$_6$-DMSO) 171.2, 138.6, 132.9, 131.7, 129.3, 128.4, 127.8, 127.3, 125.1, 125.0, 124.8, 46.2; Calcd (M$^+$): 357.1, Found: 356.0 ([M−H]$^-$); t$_R$=11.5 min (98.9%, II).

4-(N-(2-Chlorobenzyl)sulfamoyl)-1-hydroxy-2-naphthoic Acid (3d)

4-Chlorosulfonyl-1-hydroxy-2-naphthoic acid (5) was coupled to 2-chlorobenzylamine according to General Procedure B on a 1 mmol scale to yield the title compound as a light purple solid (274 mg, 70%): $\delta_H$ (400 MHz, d$_6$-DMSO) 8.45-8.33 (m, 2H, Ar), 8.35 (d, J=7.6, 1 H, Ar), 7.99 (t, J=6.0, 1 H, NH), 7.61 (t, J=7.6, 1 H, Ar), 7.46 (t, J=7.6, 1 H, Ar), 7.40-7.37 (m, 1H, Ar), 7.32-7.29 (m, 1H, Ar), 7.22-7.17 (m, 2H, Ar), 3.98 (d, J=6.0, 2 H, CH$_2$); $\delta_C$ (100 MHz, d$_6$-DMSO) 171.0, 135.7, 133.1, 132.2, 131.7, 129.9, 129.3, 129.1, 128.6, 127.2, 125.1, 125.0, 124.7, 107.8, 43.6; Calcd (M$^+$): 391.0, Found: 414.1 ([M+Na]$^+$); t$_R$=10.2 min (97.2%, II).

4-(N-(3-Chlorobenzyl)sulfamoyl)-1-hydroxy-2-naphthoic Acid (3e)

4-Chlorosulfonyl-1-hydroxy-2-naphthoic acid (5) was coupled to 3-chlorobenzylamine according to General Procedure B on a 1 mmol scale to yield the title compound as a dark purple solid (286 mg, 73%): $\delta_H$ (400 MHz, d$_6$-DMSO) 8.43-8.39 (m, 2H, Ar), 8.35 (d, J=7.6, 1 H, Ar), 8.04 (t, J=6.4, 1 H, NH), 7.63 (t, J=7.6, 1 H, Ar), 7.47 (t, J=7.6, 1 H, Ar), 7.21-7.15 (m, 3H, Ar), 7.13-7.09 (m, 1H, Ar), 3.91 (d, J=6.4, 2 H, CH$_2$); $\delta_C$ (100 MHz, d$_6$-DMSO) 171.2, 141.2, 133.1, 132.8, 131.6, 130.1, 129.4, 128.3, 127.6, 127.1, 126.4, 125.1, 125.0, 124.9, 107.6, 45.5; Calcd (M$^+$): 391.0. Found: 414.1 ([M+Na]$^+$); t$_R$=21.5 min (98.8%, I).

4-(N-(4-Chlorobenzyl)sulfamoyl)-1-hydroxy-2-naphthoic Acid (3f)

4-Chlorosulfonyl-1-hydroxy-2-naphthoic acid (5) was coupled to 4-chlorobenzylamine according to General Procedure B on a 1 mmol scale to yield the title compound as a light brown solid (294 mg, 75%): $\delta_H$ (400 MHz, d$_6$-DMSO) 8.56 (d, 1H, Ar, J=8.4 Hz), 8.46 (t, 1H, SO$_2$NH, J=5.8 Hz), 8.39 (d, 1H, Ar, J=8.8 Hz), 8.32 (s, 1H, Ar), 7.84 (t, 1H, Ar, J=7.6 Hz), 7.71 (t, 1H, Ar, J=7.4 Hz), 7.11, 7.06 (ABq, 4H, Ar, J$_{AB}$=8.8 Hz), 3.97 (d, 1H, Ar, J=6.4 Hz); $\delta_C$ (100 MHz, CDCl$_3$) 177.1, 169.4, 141.6, 136.7, 136.1, 136.0, 134.6, 134.4, 134.2, 132.3, 131.9, 130.6, 130.1, 129.1, 109.8, 50.3; Calcd (M$^+$): 391.0, Found: 392.0 ([M+H]$^+$); t$_R$=12.8 min (100%, II).

4-(N-(Cyclohexylmethyl)sulfamoyl)-1-hydroxy-2-naphthoic Acid (3g)

4-Chlorosulfonyl-1-hydroxy-2-naphthoic acid (5) was coupled to cyclohexylmethylamine according to General Procedure B on a 1 mmol scale to yield the title compound as a brown solid (218 mg, 60%): $\delta_H$ (400 MHz, d$_6$-DMSO) 8.61 (d, 1H, Ar, J=8.8 Hz), 8.42-8.39 (m, 3H, Ar), 7.86-7.81 (m, 2H, Ar, SO$_2$NH), 7.71 (m, 1H, Ar, J=7.4 Hz), 2.56 (t, 1H, CHC<u>H</u>$_2$, J=5.8 Hz), 1.55-1.45 (m, 5H, cyclohexyl), 1.30-1.18 (m, 1H, C<u>H</u>CH$_2$), 1.05-0.90 (m, 3H, cyclohexyl), 0.62-0.74 (m, 2H, cyclohexyl); $\delta_C$ (100 MHz, d$_6$-DMSO) 172.1, 164.1, 131.2, 130.8, 129.1, 126.8, 125.8, 125.2, 125.1, 124.0, 104.5, 48.6, 37.2, 30.1, 25.9, 25.3; Calcd (M$^+$): 363.1, Found: 386.3 ([M+Na]$^+$); t$_R$=13.7 min (98.2%, II).

4-(N,N-Dimethylsulfamoyl)-1-hydroxy-2-naphthoic Acid (3h)

4-Chlorosulfonyl-1-hydroxy-2-naphthoic acid (5) was coupled to dimethylamine hydrochloride according to General Procedure B on a 1 mmol scale to yield the title compound as a dark purple solid (170 mg, 58%): $\delta_H$ (400 MHz, d$_6$-DMSO) 8.58 (d, 1H, Ar, J=8.4 Hz), 8.43 (d, 1H, Ar, J=8.0 Hz), 8.40 (s, 1H, Ar), 7.86 (t, 1H, Ar, J=7.8 Hz), 7.71 (t, 1H, Ar, J=7.4 Hz), 2.70 (s, 6H, N(CH$_3$)$_2$); $\delta_C$ (100 MHz, d$_6$-DMSO) 172.2, 165.3, 132.3, 131.5, 127.3, 127.2, 125.7, 125.5, 124.5, 121.7, 105.6, 37.4; Calcd (M$^+$): 295.1, Found: 296.2 ([M+H]$^+$); t$_R$=20.5 min (98.3%, I).

1-Hydroxy-4-(piperidin-1-ylsulfonyl)-2-naphthoic Acid (3i)

4-Chlorosulfonyl-1-hydroxy-2-naphthoic acid (5) was coupled to piperidine according to General Procedure C on a 0.8 mmol scale to yield the title compound as a light brown solid (265 mg, 79%): $\delta_H$ (400 MHz, d$_6$-DMSO) 8.58 (d, 1H, Ar, J=8.4 Hz), 8.43 (d, 1H, Ar, J=8.8 Hz), 8.40 (s, 1H, Ar), 7.88 (t, 1H, Ar, J=7.8 Hz), 7.73 (t, 1H, Ar, J=7.6 Hz), 3.05-3.03 (m, 4H, CH$_2$NCH$_2$), 1.50-1.32 (m, 6H, piperidinyl); $\delta_C$ (100 MHz, d$_6$-DMSO) 172.3, 164.7, 132.1, 131.5, 131.2, 127.4, 125.5, 125.4, 124.5, 122.9, 105.4, 46.2, 25.4, 23.3; Calcd (M$^+$): 335.1, Found: 336.2 ([M+H]$^+$); t$_R$=16.5 min (95.1%, II).

1-Hydroxy-4-((4-phenylpiperazin-1-yl)sulfonyl)-2-naphthoic Acid (3j)

4-Chlorosulfonyl-1-hydroxy-2-naphthoic acid (5) was coupled to 1-phenylpiperizine according to General Procedure C on a 0.8 mmol scale to yield the title compound as a brown-orange solid (264 mg, 64%): $\delta_H$ (400 MHz, d$_6$-DMSO) 8.70 (d, 1H, Ar, J=8.8 Hz), 8.46-8.43 (m, 2H, Ar), 7.88 (t, 1H, Ar, J=8.0 Hz), 7.73 (t, 1H, Ar, J=7.4 Hz), 7.17 (t, 2H, Ph, J=7.8 Hz), 6.86 (d, 2H, Ph, J=8.0 Hz), 3.19-3.12 (m, 8H, piperazinyl); $\delta_C$ (100 MHz, d$_6$-DMSO) 171.9, 165.0, 150.4, 131.8, 131.5, 131.3, 129.0, 127.0, 125.3, 125.1, 124.2, 121.3, 119.8, 116.2, 105.3, 48.3, 45.2; Calcd (M$^+$): 412.1, Found: 413.3 ([M+H]$^+$); $t_R$=19.4 min (100%, II).

4-((4-Benzylpiperazin-1-yl)sulfonyl)-1-hydroxy-2-naphthoic Acid (3k)

4-Chlorosulfonyl-1-hydroxy-2-naphthoic acid (5) was coupled to N-benzylpiperazine according to General Procedure C on a 1 mmol scale to yield the title compound as a light yellow solid (303 mg, 71%): $\delta_H$ (400 MHz, d$_6$-DMSO) 8.41-8.37 (m, 3H, Ar), 7.62 (t, 1H, Ar, J=7.6 Hz), 7.47 (t, 1H, Ar, J=7.6 Hz), 7.43-7.36 (m, 5H, Ph), 4.22 (br s, 2H, CH$_2$Ph), 3.70-2.80 (m, 8H, piperazinyl); $\delta_C$ (100 MHz, d$_6$-DMSO) 173.4, 170.4, 158.7, 135.3, 132.6, 131.3, 131.0, 129.9, 129.2, 129.1, 125.6, 125.5, 124.9, 124.8, 107.9; Calcd (M$^-$): 426.1, Found: 427.2 ([M+H]$^+$); $t_R$=6.5 min (95.3%, II).

1-Hydroxy-4-(N-phenylsulfamoyl)-2-naphthoic acid (3l)

4-Chlorosulfonyl-1-hydroxy-2-naphthoic acid (5) was coupled to aniline according to General Procedure A on a 1 mmol scale to yield the title compound as a cream solid (275 mg, 80%): $\delta_H$ (400 MHz, d$_6$-DMSO) 10.58 (s, 1H, SO$_2$NH), 8.66 (d, 1H, Ar, J=8.4 Hz), 8.47 (s, 1H, Ar), 8.38 (d, 1H, Ar, J=8.8 Hz), 7.87 (t, 1H, Ar, J=8.0 Hz), 7.71 (t, 1H, Ar, J=7.8 Hz), 7.15 (t, 2H, Ph, J=7.8 Hz), 6.99 (d, 2H, Ph, J=8.0 Hz), 6.92 (t, 1H, Ph, J=7.0 Hz); $\delta_C$ (100 MHz, d$_6$-DMSO) 172.2, 164.9, 137.9, 131.6, 131.3, 130.9, 129.5, 127.4, 125.3, 125.0, 124.7, 124.6, 124.1, 119.7, 105.2; Calcd (M$^+$): 343.1, Found: 344.1 ([M+H]$^+$); $t_R$=3.9 min (100%, II).

4-(N-(2-bromophenyl)sulfamoyl)-1-hydroxy-2-naphthoic Acid (3m)

4-Chlorosulfonyl-1-hydroxy-2-naphthoic acid (5) was coupled to 2-bromoaniline according to General Procedure A on a 1 mmol scale to yield the title compound as a pink solid (287 mg, 68%): $\delta_H$ (400 MHz, d$_6$-DMSO) 10.07 (s, 1H, SO$_2$NH), 8.60 (d, 1H, Ar, J=8.4 Hz), 8.41 (d, 1H, Ar, J=8.4 Hz), 7.78 (t, 1H, Ar, J=7.4 Hz), 7.69 (t, 1H, Ar, J=7.4 Hz), 7.48 (d, 1H, Ar, J=7.6 Hz), 7.23 (t, 1H, Ar, J=7.4 Hz), 7.15 (d, 1H, Ar, J=8.0 Hz), 7.09 (t, 1H, Ar, J=7.4 Hz); $\delta_C$ (100 MHz, d$_6$-DMSO) 172.2, 165.2, 135.4, 133.5, 131.7, 131.1, 130.2, 128.9, 128.8, 128.7, 128.6, 127.2, 125.8, 125.6, 124.4, 120.9, 105.3; Calcd (M$^-$): Calcd (M$^+$): 421.0, Found: 420.2 ([M−H]$^-$); $t_R$=12.0 min (98.6%, II).

4-(N-(3-Bromophenyl)sulfamoyl)-1-hydroxy-2-naphthoic Acid (3n)

4-Chlorosulfonyl-1-hydroxy-2-naphthoic acid (5) was coupled to 3-bromoaniline according to General Procedure A on a 1 mmol scale to yield the title compound as a light pink solid (300 mg, 71%): $\delta_H$ (400 MHz, d$_6$-DMSO) 11.86 (s, 1H, SO$_2$NH), 8.61 (d, 1H, Ar, J=8.8 Hz), 8.51 (s, 1H, Ar), 8.38 (d, 1H, Ar, J=8.4 Hz), 7.87 (t, 1H, Ar, J=7.4 Hz), 7.69 (t, 1H, Ar, J=7.4 Hz), 7.18 (s, 1H, Ar), 7.14-7.00 (m, 3H, Ar); $\delta_C$ (100 MHz, d$_6$-DMSO) 172.1, 165.5, 139.7, 131.6, 131.5, 131.4, 131.2, 127.4, 126.5, 125.6, 125.5, 124.7, 123.5, 122.2, 121.4, 117.8, 105.4; Calcd (M$^+$): 421.0. Found: 420.2 ([M−H]$^-$); $t_R$=12.3 min (98.5%, II).

4-(N-(2,4-Dibromophenyl)sulfamoyl)-1-hydroxy-2-naphthoic Acid (3o)

4-Chlorosulfonyl-1-hydroxy-2-naphthoic acid (5) was coupled to 2,4-dibromoaniline according to General Procedure A on a 1 mmol scale to yield the title compound as a dark beige solid (291 mg, 58%): $\delta_H$ (400 MHz, d$_6$-DMSO) 10.15 (s, 1H, SO$_2$NH), 8.56 (d, 1H, Ar, J=8.4 Hz), 8.41 (d, 1H, Ar, J=8.4 Hz), 8.30 (s, 1H, Ar), 7.80-7.75 (m, 2H, Ar), 7.69 (t, 1H, Ar, J=7.4 Hz), 7.50 (dd, 1H, Ar, J=8.8, 1.6 Hz), 7.09 (d, 1H, Ar, J=8.4 Hz); $\delta_C$ (100 MHz, d$_6$-DMSO) 172.2, 165.3, 135.4, 135.1, 131.8, 131.6, 131.2, 130.3, 129.8, 127.3, 125.6, 125.5, 125.4, 124.5, 121.8, 120.0, 105.3; Calcd (M$^+$): 498.9, Found: 498.1 ([M−H]$^-$); $t_R$=18.2 min (97.0%, II).

1-Hydroxy-4-(N-(naphthalen-1-yl)sulfamoyl)-2-naphthoic Acid (3p)

4-Chlorosulfonyl-1-hydroxy-2-naphthoic acid (5) was coupled to 1-naphthylamine according to General Procedure A on a 1 mmol scale to yield the title compound as a dark purple solid (283 mg, 72%): $\delta_H$ (400 MHz, d$_6$-DMSO) 10.46 (s, 1H, SO$_2$NH), 8.74 (d, 1H, Ar, J=8.8 Hz), 8.38 (d, 1H, Ar, J=8.8 Hz), 8.26 (s, 1H, Ar), 7.96 (d, 1H, Ar, J=8.8 Hz), 7.85-7.83 (m, 2H, Ar), 7.73-7.68 (m, 2H, Ar), 7.41 (t, 1H, Ar, J=7.6 Hz), 7.34 (t, 1H, Ar, J=7.8 Hz), 7.28 (t, 1H, Ar, J=7.4 Hz), 7.12 (d, 1H, Ar, J=8.0 Hz); $\delta_C$ (100 MHz, d$_6$-DMSO) 171.8, 164.6, 134.7, 133.8, 132.2, 131.3, 130.9, 130.0, 129.4, 128.5, 128.0, 126.9, 126.7, 126.2, 125.9, 125.6, 125.0, 124.9, 124.1, 123.0, 104.8; Calcd (M$^-$): 393.1, Found: 416.2 ([M+Na]$^+$); $t_R$=9.7 min (100%, II).

1-Hydroxy-4-(N-(naphthalen-2-yl)sulfamoyl)-2-naphthoic Acid (3q)

4-Chlorosulfonyl-1-hydroxy-2-naphthoic acid (5) was coupled to 2-naphthylamine according to General Procedure A on a 1 mmol scale to yield the title compound as a grey-purple solid (303 mg, 77%): $\delta_H$ (400 MHz, d$_6$-DMSO) 10.83 (s, 1H, SO$_2$NH), 8.72 (d, 1H, Ar, J=7.6 Hz), 8.57 (s, 1H, Ar), 8.35 (d, 1H, Ar, J=8.4 Hz), 7.87 (t, 1H, Ar, J=8.0 Hz), 7.72-7.65 (m, 4H, Ar), 7.47 (s, 1H, Ar), 7.38 (t, 1H, J=7.0 Hz), 7.32 (t, 1H, Ar, J=7.0 Hz), 7.22 (d, 1H, Ar, J=8.8 Hz); $\delta_C$ (100 MHz, d$_6$-DMSO) 171.8, 164.9, 135.3, 133.2, 131.2, 131.0, 130.9, 129.8, 129.1, 127.5, 127.0, 126.9, 126.8, 125.2, 124.9, 124.6, 124.3, 123.7, 119.7, 115.0, 105.0; Calcd (M$^+$): 393.1. Found: 392.2 ([M−H]$^-$); $t_R$=12.7 min (94.5%, II).

4-(N-([1,1'-Biphenyl]-2-yl)sulfamoyl)-1-hydroxy-2-naphthoic Acid (3r)

4-Chlorosulfonyl-1-hydroxy-2-naphthoic acid (5) was coupled to 2-aminobiphenyl according to General Procedure A on a 1 mmol scale to yield the title compound as a beige solid (252 mg, 60%): $\delta_H$ (400 MHz, d$_6$-DMSO) 9.60 (s, 1H), 8.33-8.28 (m, 2H), 8.07 (s, 1H), 7.62-7.58 (m, 2H), 7.23 (t, J=4.8 Hz, 2H), 7.11 (t, J=4.8 Hz, 1H), 7.03-7.00 (m, 6H). $\delta_C$ (100 MHz, d$_6$-DMSO) 172.3, 164.9, 139.9, 138.6, 133.5, 131.4, 131.3, 130.9, 129.5, 129.1, 128.5, 127.8, 127.7, 126.9, 126.8, 126.4, 125.5, 125.4, 124.3, 105.1; Calcd (M$^-$): 419.1, Found: 442.2 ([M+Na]$^+$); $t_R$=14.6 min (98.7%, II).

4-(N-([1,1'-Biphenyl]-3-yl)sulfamoyl)-1-hydroxy-2-naphthoic Acid (3s)

4-Chlorosulfonyl-1-hydroxy-2-naphthoic acid (5) was coupled to 3-aminobiphenyl according to General Procedure A on a 1 mmol scale to yield the title compound as a dark brown solid (239 mg, 58%): $\delta_H$ (400 MHz, d$_6$-DMSO) 10.45 (s, 1H), 8.61 (s, 1H), 8.53 (d, J=8.8 Hz, 1H), 8.32 (d, J=8.8

Hz, 1H), 7.68 (t, J=8 Hz, 1H), 7.49 (t, J=7.6 Hz, 1H), 7.40 (m, 4H), 7.34 (m, 1H), 7.28 (s, 1H), 7.20 (t, J=7.6 Hz, 1H), 7.13 (d, J=8 Hz, 1H), 6.95 (d, J=8 Hz, 1H). $\delta_C$ (100 MHz, $d_6$-DMSO) 171.1, 141.3, 140.2, 139.2, 134.1, 131.6, 130.1, 129.9, 129.4, 128.0, 126.9, 125.4, 125.2, 124.6, 121.5, 117.7, 116.6, 107.1; Calcd (M$^+$): 419.1, Found: 418.3 ([M−H]$^-$); $t_R$=13.9 min (100%, II).

4-(N-([1,1'-Biphenyl]-4-yl)sulfamoyl)-1-hydroxy-2-naphthoic Acid (3t)

4-Chlorosulfonyl-1-hydroxy-2-naphthoic acid (5) was coupled to 4-aminobiphenyl according to General Procedure A on a 1 mmol scale to yield the title compound as a brown solid (260 mg, 62%): $\delta_H$ (400 MHz, $d_6$-DMSO) 10.37 (s, 1H), 8.54 (s, 1H), 8.47 (d, J=8 Hz, 1H), 8.31 (d, J=7.6 Hz, 1H), 7.62 (t, J=8 Hz, 1H), 7.51 (d, J=8 Hz, 2H), 7.44 (d, J=8.4 Hz, 3H), 7.35 (t, J=8 Hz, 2H), 7.25 (t, J=7.6 Hz, 1H), 7.05 (d, J=7.6 Hz, 2H). $\delta_C$ (100 MHz, $d_6$-DMSO) 172.5, 170.8, 139.9, 138.2, 134.8, 134.3, 131.6, 129.6, 129.2, 128.7, 127.6, 127.3, 126.6, 125.3, 124.8, 124.5, 118.8, 116.3, 107.9; Calcd (M$^-$): 419.5, Found: 418.3 ([M−H]$^-$); $t_R$=13.9 min (98.3%, II).

1-Hydroxy-4-(N-(2-(trifluoromethyl)phenyl)sulfamoyl)-2-naphthoic Acid (3u)

4-Chlorosulfonyl-1-hydroxy-2-naphthoic acid (5) was coupled to 2-trifluoromethylaniline according to General Procedure A on a 1 mmol scale to yield the title compound as a dark pink solid (222 mg, 54%): $\delta_H$ (400 MHz, $d_6$-DMSO) 10.06 (s, 1H, SO$_2$NH), 8.62 (d, 1H, Ar, J=8.0 Hz), 8.44 (d, 1H, Ar, J=8.8 Hz), 8.32 (s, 1H, Ar), 7.80 (t, 1H, Ar, J=7.4 Hz), 7.71-7.66 (m, 2H, Ar), 7.52 (t, 1H, Ar, J=7.2 Hz), 7.41 (t, 1H, Ar, J=7.0 Hz), 6.99 (d, 1H, Ar, J=7.6 Hz); $\delta_C$ (100 MHz, $d_6$-DMSO) 172.1, 166.2, 134.5, 133.8, 133.7, 131.5, 131.0, 130.7, 130.6, 129.5, 127.8, 127.4, 126.9, 126.2 (q, $^2J_{CF}$=40 Hz), 125.5 (q, $^1J_{CF}$=108 Hz), 125.5, 124.6, 105.6; Calcd (M$^+$): 411.0, Found: 410.2 ([M−H]$^-$); $t_R$=10.7 min (96.7%, II).

4-(N-(4-Chlorophenyl)sulfamoyl)-1-hydroxy-2-naphthoic Acid (3v)

4-Chlorosulfonyl-1-hydroxy-2-naphthoic acid (5) was coupled to 4-chloroaniline according to General Procedure A on a 1 mmol scale to yield the title compound as a light brown solid (189 mg, 50%): $\delta_H$ (400 MHz, $d_6$-DMSO) 10.74 (s, 1H, NH), 8.62 (d, J=8.8 Hz, 1 H, Ar), 8.46 (s, 1H, Ar), 8.39 (d, J=8.8 Hz, 1 H, Ar), 7.86 (t, J=8.8 Hz, 1 H, Ar), 7.71 (t, J=8.8, 1 H, Ar), 7.22 (d, J=8.4 Hz, 2 H, Ar), 7.00 (d, J=8.4 Hz, 2 H, Ar); $\delta_C$ (100 MHz, $d_6$-DMSO) 172.2, 165.0, 136.9, 131.7, 131.2, 131.1, 129.5, 128.1, 127.4, 125.4, 124.9, 124.6, 124.2, 121.1, 105.3; Calcd (M$^+$): 377.0. Found: 376.2 ([M−H]$^-$); $t_R$=12.2 min (95.7%, II).

1-Hydroxy-4-(N-(4-(trifluoromethyl)phenyl)sulfamoyl)-2-naphthoic Acid (3w)

4-Chlorosulfonyl-1-hydroxy-2-naphthoic acid (5) was coupled to 4-trifluoromethylaniline according to General Procedure A on a 1 mmol scale to yield the title compound as a light pink solid (218 mg, 53%): $\delta_H$ (400 MHz, $d_6$-DMSO) 11.13 (s, 1H, NH), 8.60 (d, J=8.8, 1 H, Ar), 8.57 (s, 1H, Ar), 8.39 (d, J=8.8, 1 H, Ar), 7.85 (t, J=8.8, 1 H, Ar), 7.68 (t, J=8.8, 1 H, Ar), 7.55 (d, J=8.8, 2 H, Ar), 7.19 (d, J=8.8, 2 H, Ar); $\delta_C$ (100 MHz, $d_6$-DMSO) 172.0, 165.7, 141.8, 131.7, 131.5, 131.2, 127.4, 127.0, 125.9, 125.7, 124.8, 124.7, 123.6, 118.2, 105.5; Calcd (M$^+$): 411.0, Found: 434.2 ([M+Na]$^+$); $t_R$=15.6 min (95.4%, II).

1-Hydroxy-4-(N-(p-tolyl)sulfamoyl)-2-naphthoic Acid (3x)

4-Chlorosulfonyl-1-hydroxy-2-naphthoic acid (5) was coupled to p-toluidine according to General Procedure A on a 1 mmol scale to yield the title compound as a beige solid (225 mg, 63%): $\delta_H$ (400 MHz, $d_6$-DMSO) 10.39 (s, 1H, NH), 8.65 (d, J=8.8, 1 H, Ar), 8.43 (s, 1H, Ar), 8.38 (d, J=8.8, 1 H, Ar), 7.86 (t, J=8.8, 1 H, Ar), 7.70 (t, J=8.8, 1 H, Ar), 6.95 (d, J=8.0, 2 H, Ar), 6.87 (d, J=8.0, 2 H, Ar), 2.11 (s, 3H, CH$_3$); $\delta_C$ (100 MHz, $d_6$-DMSO) 172.2, 165.0, 135.2, 133.4, 131.5, 131.4, 131.0, 129.9, 127.3, 125.4, 125.1, 124.5, 120.2, 105.3, 20.6; Calcd (M$^+$): 357.1, Found: 380.2 ([M+Na]$^+$); $t_R$=9.0 min (95.5%, II).

1-Hydroxy-4-(N-(4-isopropylphenyl)sulfamoyl)-2-naphthoic Acid (3y)

4-Chlorosulfonyl-1-hydroxy-2-naphthoic acid (5) was coupled top-isopropylaniline according to General Procedure A on a 1 mmol scale to yield the title compound as a beige solid (235 mg, 61%): $\delta_H$ (400 MHz, $d_6$-DMSO) 10.42 (s, 1H, NH), 8.63 (d, J=8.4, 1 H, Ar), 8.46 (s, 1H, Ar), 8.39 (d, J=8.4, 1 H, Ar), 7.84 (t, J=8.4, 1 H, Ar), 7.70 (t, J=8.4, 1 H, Ar), 7.02 (d, J=8.4, 2 H, Ar), 6.90 (d, J=8.0, 2 H, Ar), 2.71 (sept, J=7.2, 1 H, CH), 1.06 (d, J=7.2, 6 H, 2×CH$_3$); $\delta_C$ (100 MHz, $d_6$-DMSO) 172.2, 164.8, 144.3, 135.5, 131.5, 131.4, 130.8, 127.3, 125.3, 125.1, 124.5, 120.0, 105.2, 33.1, 24.2; Calcd (M$^+$): 385.1, Found: 408.3 ([M+Na]$^-$); $t_R$=15.3 min (95.9%, II).

1-Hydroxy-4-(N-(4-methoxyphenyl)sulfamoyl)-2-naphthoic Acid (3z)

4-Chlorosulfonyl-1-hydroxy-2-naphthoic acid (5) was coupled top-anisidine according to General Procedure A on a 1 mmol scale to yield the title compound as a light brown solid (281 mg, 75%): $\delta_H$ (400 MHz, $d_6$-DMSO) 10.18 (s, 1H, SO$_2$NH), 8.64 (d, 1H, Ar, J=8.8 Hz), 8.38 (d, 1H, Ar, J=8.4 Hz), 8.36 (s, 1H, Ar), 7.86 (t, 1H, Ar, J=7.4 Hz), 7.71 (t, 2H, Ar, J=7.6 Hz), 6.85 (d, 2H, Ar, J=9.2 Hz), 6.71 (d, 2H, Ar, J=8.8 Hz), 3.59 (s, 3H, OMe); $\delta_C$ (100 MHz, $d_6$-DMSO): 172.24, 164.74, 156.76, 131.48-131.44, 130.74, 130.27, 127.32, 125.29, 125.19, 124.82, 124.51, 123.33, 114.72, 105.19, 55.51; Calcd (M$^+$): 373.1, Found: 372.3 ([M−H—); $t_R$=8.7 min (99.6%, III).

1-Hydroxy-4-(N-(4-isopropoxyphenyl)sulfamoyl)-2-naphthoic Acid (3aa)

4-Chlorosulfonyl-1-hydroxy-2-naphthoic acid (5) was coupled to 4-isopropoxyaniline according to General Procedure A on a 1 mmol scale to yield the title compound as a white solid (289 mg, 72%): $\delta_H$ (400 MHz, $d_6$-DMSO) 10.15 (s, 1H, SO$_2$NH), 8.63 (d, 1H, Ar, J=8.8 Hz), 8.39 (d, 1H, Ar, J=8.0 Hz), 8.35 (s, 1H, Ar), 7.85 (t, 1H, Ar, J=7.4 Hz), 7.71 (t, 1H, Ar, J=7.8 Hz), 6.83 (d, 2H, Ar, J=9.6 Hz), 6.69 (d, 2H, Ar, J=8.8 Hz), 4.41 (hep, 1H, C$\underline{H}$(CH$_3$)$_2$, J=5.8 Hz), 1.14 (d, 6H, CH(C$\underline{H}_3$)$_2$, J=5.2 Hz); $\delta_C$ (100 MHz, $d_6$-DMSO) 172.2, 164.7, 155.0, 131.5, 131.4, 130.7, 130.1, 127.3, 125.3, 125.2, 124.9, 124.5, 123.4, 116.5, 105.2, 69.7, 22.1; Calcd (M$^+$): 401.1, Found: 402.0 ([M+H]$^+$); $t_R$=10.2 min (98.6%, II).

4-(N-(4-Cyanophenyl)sulfamoyl)-1-hydroxy-2-naphthoic Acid (3ab)

Chlorosulfonyl-1-hydroxy-2-naphthoic acid (5) was coupled to 4-aminobenzonitrile according to General Procedure A on a 1 mmol scale to yield the title compound as a light pink solid (254 mg, 69%): $\delta_H$ (400 MHz, $d_6$-DMSO) 11.32 (s, 1H, SO$_2$NH), 8.60-8.57 (m, 2H, Ar), 8.39 (d, 1H, Ar, J=8.8 Hz), 7.87 (t, 1H, Ar, J=7.4 Hz), 7.69 (t, 1H, Ar, J=7.8 Hz), 7.63 (d, 2H, Ar, J=8.4 Hz), 7.15 (d, 2H, Ar, J=8.8 Hz); $\delta_C$ (100 MHz, $d_6$-DMSO) 172.0, 166.1, 142.5, 134.1, 131.8, 131.7, 131.1, 127.3, 125.8, 124.8, 124.6, 122.9, 119.1, 118.1, 105.9, 105.3; Calcd (M$^+$): 368.1, Found: 367.1 ([M−H]$^−$); $t_R$=5.5 min (98.3%, II).

1-Hydroxy-4-(N-(4-nitrophenyl)sulfamoyl)-2-naphthoic Acid (3ac)

4-Chlorosulfonyl-1-hydroxy-2-naphthoic acid (5) was coupled to 4-nitroaniline according to General Procedure A on a 2 mmol scale to yield the title compound as a dark yellow solid (249 mg, 64%): $\delta_H$ (400 MHz, $d_6$-DMSO) 11.54 (s, 1H, SO$_2$NH), 8.61-8.58 (m, 2H, Ar), 8.38 (d, 1H, Ar, J=8.0 Hz), 8.07 (d, 2H, Ar, J=8.4 Hz), 7.86 (t, 1H, Ar, J=7.6 Hz), 7.68 (t, 1H, Ar, J=7.6 Hz), 7.20 (d, 2H, Ar, J=9.2 Hz); $\delta_C$ (100 MHz, $d_6$-DMSO) 171.5, 166.2, 144.1, 142.2, 131.8, 131.3, 130.8, 126.9, 125.6, 125.5, 124.5, 124.1, 121.9, 117.2, 105.4; Calcd (M$^+$): 388.0, Found: 387.3 ([M−H]$^−$); $t_R$=4.8 min (97.4%, I).

4-(N-(3-Cyanophenyl)sulfamoyl)-1-hydroxy-2-naphthoic Acid (3ad)

4-Chlorosulfonyl-1-hydroxy-2-naphthoic acid (5) was coupled to 3-aminobenzonitrile according to General Procedure A on a 1 mmol scale to yield the title compound as a reddish-purple solid (188 mg, 61%): $\delta_H$ (400 MHz, $d_6$-DMSO) 10.71 (s, 1H, NH), 8.54 (s, 1H, Ar), 8.40 (d, J=8.4, 1 H, Ar), 8.32 (d, J=8.4, 1 H, Ar), 7.63 (t, J=8.4, 1 H, Ar), 7.44 (t, J=8.4, 1 H, Ar), 7.39-7.27 (m, 4H, Ar); $\delta_C$ (100 MHz, $d_6$-DMSO) 173.3, 170.5, 139.9, 134.7, 131.5, 130.9, 129.7, 129.0, 126.5, 125.5, 124.9, 124.2, 122.7, 120.7, 118.8, 114.8, 112.1, 107.8; Calcd (M$^+$): 368.1, Found: 367.1 ([M−H]$^−$); $t_R$=7.4 min (97.2%, II).

1-Hydroxy-4-(N-isobutyl-N-(4-isopropoxyphenyl)sulfamoyl)-2-naphthoic Acid (3ba)

4-Chlorosulfonyl-1-hydroxy-2-naphthoic acid (5) was coupled to 4-isopropoxyaniline (8a) according to General Procedure A on a 1 mmol scale to yield the title compound as a beige solid (350 mg, 69%): $\delta_H$ (400 MHz, $d_6$-DMSO) 8.32 (d, 1H, Ar, J=8.4 Hz), 8.30 (s, 1H, Ar), 8.10 (, 1H, Ar, J=7.6 Hz), 7.49-8.39 (m, 2H, Ar), 6.96 (d, 2H, Ph, J=8.8 Hz), 6.77 (d, 2H, Ph, J=8.8 Hz), 7.06 (t, 1H, Ar, J=7.4 Hz), 4.56-4.50 (m, 1H, OCH), 3.25 (d, 2H, CH$_2$CH, J=6.8 Hz) 1.39-1.34 (m, 1H, CH$_2$CH) 1.22 (d, 6H, OCH(CH$_3$)$_2$, J=6.4 Hz), 0.73 (d, 6H, CH$_2$CH(CH$_3$)$_2$, J=6.8 Hz); $\delta_C$ (100 MHz, $d_6$-DMSO) 172.4, 170.8, 156.9, 134.7, 132.3, 131.9, 130.2, 128.9, 128.6, 125.1, 125.0 124.6, 115.9, 115.4, 108.0, 69.7, 57.5, 26.7, 22.2, 20.1; Calcd (M$^+$): 457.2, Found: 456.2 ([M−H]−); $t_R$=16.7 min (99.5%, III).

1-Hydroxy-4-(N-(4-phenoxyphenyl)sulfamoyl)-2-naphthoic Acid (3bb)

4-Chlorosulfonyl-1-hydroxy-2-naphthoic acid (5) was coupled to 4-phenoxyaniline (8b) according to General Procedure A on a 1 mmol scale to yield the title compound as a beige solid (340 mg, 78%): $\delta_H$ (400 MHz, $d_6$-DMSO) 10.41 (s, 1H, SO$_2$NH), 8.63 (d, 1H, Ar, J=8.8 Hz), 8.40-8.38 (m, 2H, Ar), 7.85 (t, 1H, Ar, J=7.6 Hz), 7.71 (t, 1H, Ar, J=7.6 Hz), 7.31 (t, 2H, Ar, J=8.0 Hz), 7.06 (t, 1H, Ar, J=7.4 Hz), 6.96 (d, 2H, Ar, J=8.8 Hz), 6.84-6.81 (m, 4H, Ar); $\delta_C$ (100 MHz, $d_6$-DMSO) 172.2, 165.1, 158.2, 157.4, 133.5, 131.5, 131.0, 130.4, 127.3, 125.4, 125.1, 124.6, 123.5, 122.8, 120.2, 118.3, 116.0, 114.9, 105.3; Calcd (M$^+$): 435.1, Found: 436.0 ([M+H]$^+$); $t_R$=14.4 min (100%, II).

1-Hydroxy-4-(N-(4-(p-tolyloxy)phenyl)sulfamoyl)-2-naphthoic Acid (3bc)

4-Chlorosulfonyl-1-hydroxy-2-naphthoic acid (5) was coupled to 4-(p-tolyloxy)aniline (8c) according to General Procedure A on a 1 mmol scale to yield the title compound as a beige solid (342 mg, 76%): $\delta_H$ (400 MHz, $d_6$-DMSO) 10.37 (s, 1H, SO$_2$NH), 8.63 (d, 1H, Ar, J=8.8 Hz), 8.41-8.39 (m, 2H, Ar), 7.85 (t, 1H, Ar, J=7.4 Hz), 7.71 (t, 1H, Ar, J=7.8 Hz), 7.11 (d, 2H, Ar, J=8.8 Hz), 6.94 (d, 2H, Ar, J=8.4 Hz), 6.78 (d, 2H, Ar, J=8.8 Hz), 6.74 (d, 1H, Ar, J=8.0 Hz), 2.24 (s, 3H, CH$_3$); $\delta_C$ (100 MHz, $d_6$-DMSO) 172.2, 164.5, 154.9, 153.9, 133.0, 132.7, 131.5, 130.9, 130.7, 127.3, 125.3, 125.1, 124.6, 122.8, 119.6, 118.6, 105.2, 20.6; Calcd (M$^+$): 449.1, Found: 472.3 ([M+Na]$^+$); $t_R$=9.3 min (100%, III).

1-Hydroxy-4-(N-(4-(naphthalen-1-yloxy)phenyl)sulfamoyl)-2-naphthoic Acid (3bd)

4-Chlorosulfonyl-1-hydroxy-2-naphthoic acid (5) was coupled to 4-(naphthalen-1-yloxy)aniline (8d) according to General Procedure A on a 1 mmol scale to yield the title compound as a light purple solid (351 mg, 70%): $\delta_H$ (400 MHz, $d_6$-DMSO) 10.42 (s, 1H, SO$_2$NH), 8.63 (d, 1H, Ar, J=8.8 Hz), 8.42-8.39 (m, 2H, Ar), 7.99 (d, 1H, Ar, J=8.8 Hz), 7.94 (d, 1H, Ar, J=8.0 Hz), 7.86 (t, 1H, Ar, J=7.4 Hz), 7.72 (t, 1H, Ar, J=7.8 Hz), 7.66 (d, 1H, Ar, J=8.8 Hz), 7.55 (t, 1H, Ar, J=7.4 Hz), 7.49 (t, 1H, Ar, J=7.0 Hz), 7.38 (t, 1H, Ar, J=7.8 Hz), 6.98, 6.88 (ABq, 4H, Ar, $J_{AB}$=8.4 Hz), 6.73 (d, 1H, Ar, J=8.0 Hz); $\delta_C$ (100 MHz, $d_6$-DMSO) 172.2, 165.2, 153.9, 153.0, 147.4, 134.9, 133.5, 131.4, 131.3, 131.0, 128.3, 127.3, 127.2, 126.6, 126.5, 125.5, 125.1, 124.6, 124.3, 123.5, 122.8, 121.7, 119.8, 113.1, 105.3; Calcd (M$^+$): 485.1, Found: 508.3 ([M+Na]$^+$); $t_R$=11.2 min (100%, III).

4-(N-(4-(3-Bromophenoxy)phenyl)sulfamoyl)-1-hydroxy-2-naphthoic Acid (3be)

4-Chlorosulfonyl-1-hydroxy-2-naphthoic acid (5) was coupled to 4-(3-bromophenoxy)aniline (8e) according to General Procedure A on a 1 mmol scale to yield the title compound as a beige solid (334 mg, 65%): $\delta_H$ (400 MHz, $d_6$-DMSO) 10.45 (s, 1H, SO$_2$NH), 8.62 (d, 1H, Ar, J=8.8 Hz), 8.43 (s, 1H, Ar), 8.40 (d, 1H, Ar, J=8.8 Hz), 7.86 (t, 1H, Ar, J=7.4 Hz), 7.71 (t, 1H, Ar, J=7.4 Hz), 7.26-7.25 (m, 2H, Ar), 7.01-6.99 (m, 3H, Ar), 6.90 (d, 2H, Ar, J=8.4 Hz), 6.83-6.80 (m, 1H, Ar); $\delta_C$ (100 MHz, $d_6$-DMSO) 172.2, 165.2, 158.7, 152.2, 134.2, 132.1, 131.4, 131.0, 127.3, 126.2, 125.6, 125.1, 124.6, 122.6, 122.5, 120.9, 120.8, 117.0, 115.9, 112.5, 105.3; Calcd (M$^+$): 513.0, Found: 513.9 ([M+H]$^+$); $t_R$=10.7 min (99.6%, III).

4-(N-(4-(3,5-Dimethylphenoxy)phenyl)sulfamoyl)-1-hydroxy-2-naphthoic Acid (3bf)

4-Chlorosulfonyl-1-hydroxy-2-naphthoic acid (5) was coupled to 4-(3,5-dimethylphenoxy)aniline (8f) according to General Procedure A on a 1 mmol scale to yield the title compound as a cream solid (306 mg, 66%): $\delta_H$ (400 MHz, d$_6$-DMSO) 10.40 (s, 1H, SO$_2$NH), 8.62 (d, 1H, Ar, J=8.8 Hz), 8.41-8.39 (m, 3H, Ar), 7.85 (t, 1H, Ar, J=7.4 Hz), 7.71 (t, 1H, Ar, J=7.4 Hz), 6.95, 6.79 (ABq, 4H, Ar, J$_{AB}$=9.0 Hz), 6.70 (s, 1H, Ar), 6.43 (s, 2H, Ar), 2.18 (s, 6H, 2×CH$_3$); $\delta_C$ (100 MHz, d$_6$-DMSO) 172.2, 157.4, 153.4, 139.7, 133.3, 131.6, 131.4, 130.9, 129.9, 127.4, 127.3, 125.5, 125.1, 124.6, 124.5, 122.7, 120.1, 116.1, 105.3, 21.3; Calcd (M$^+$): 463.1, Found: 463.91 ([M+H]$^+$); t$_R$=19.8 min (98.9%, II).

4-(N-(4-(2,4-Dichlorophenoxy)phenyl)sulfamoyl)-1-hydroxy-2-naphthoic Acid (3bg)

4-Chlorosulfonyl-1-hydroxy-2-naphthoic acid (5) was coupled to 4-(2,4-dichlorophenoxy)aniline (8g) according to General Procedure A on a 1 mmol scale to yield the title compound as a beige solid (297 mg, 66%): $\delta_H$ (400 MHz, d$_6$-DMSO) 10.46 (s, 1H, SO$_2$NH), 8.62 (d, 1H, Ar, J=8.8 Hz), 8.41-8.39 (m, 2H, Ar), 7.85 (t, 1H, Ar, J=7.4 Hz), 7.73-7.70 (m, 2H, Ar), 7.34 (dd, 1H, Ar, J=8.8, 2.4 Hz), 6.97 (d, 2H, Ar, J=8.8 Hz), 6.88-6.82 (m, 3H, Ar); $\delta_C$ (100 MHz, d$_6$-DMSO) 172.1, 165.3, 151.6, 148.8, 133.9, 131.4, 131.0, 130.5, 129.1, 127.4, 127.3, 125.5, 125.0, 124.2, 124.1, 122.6, 121.6, 119.3, 105.3; Calcd (M$^-$): 503.0, Found: 503.9 ([M+H]$^+$); t$_R$=12.3 min (100%, III).

4-(N-(4-(4-Chlorophenoxy)phenyl)sulfamoyl)-1-hydroxy-2-naphthoic Acid (3bh)

4-Chlorosulfonyl-1-hydroxy-2-naphthoic acid (5) was coupled to 4-(4-chlorophenoxy)aniline (8h) according to General Procedure A on a 1 mmol scale to yield the title compound as a beige solid (291 mg, 62%): $\delta_H$ (400 MHz, d$_6$-DMSO) 10.45 (s, 1H, SO$_2$NH), 8.63 (d, 1H, Ar, J=8.8 Hz), 8.41-8.39 (m, 2H, Ar), 7.86 (t, 1H, Ar, J=7.4 Hz), 7.72 (t, 1H, Ar, J=7.4 Hz), 7.35 (d, 1H, Ar, J=9.2 Hz), 6.98 (d, 1H, Ar, J=8.4 Hz), 6.85 (app t, 4H, Ar, J=8.6 Hz); $\delta_C$ (100 MHz, d$_6$-DMSO) 172.2, 165.0, 156.4, 152.8, 133.9, 131.5, 131.4, 130.9, 130.2, 127.4, 127.2, 125.4, 125.1, 124.6, 124.5, 122.7, 120.4, 119.9, 105.2; Calcd (M$^-$): 469.0, Found: 469.91 ([M+H]$^+$); t$_R$=19.5 min (98.8%, II).

4-(N-(4-(4-Chloro-3,5-dimethylphenoxy)phenyl)sulfamoyl)-1-hydroxy-2-naphthoic Acid (3bi)

4-Chlorosulfonyl-1-hydroxy-2-naphthoic acid (5) was coupled to 4-(4-chloro-3,5-dimethylphenoxy)aniline (8i) according to General Procedure A on a 1 mmol scale to yield the title compound as an off-white solid (374 mg, 75%): $\delta_H$ (400 MHz, d$_6$-DMSO, TMS) $\delta_H$ 10.41 (s, 1H, NH), 8.61 (d, 1H, Ar—H, J=8.8 Hz), 8.42 (s, 1H, Ar—H), 8.39 (d, 1H, Ar—H, J=8.4 Hz), 7.84 (t, 1H, Ar—H, J=7.6 Hz), 7.69 (t, 1H, Ar—H, J=7.6 Hz), 6.96 (d, 2H, Ar—H, J=8.8 Hz), 6.82 (d, 2H, Ar—H, J=8.8 Hz), 6.70 (s, 2H, Ar—H), 2.24 (s, 6H, Ar—CH$_3$). $\delta_C$ (100 MHz, d$_6$-DMSO) 172.2, 164.8, 155.2, 153.2, 137.6, 133.4, 131.5, 130.8, 128.2, 127.3, 125.3, 125.1, 124.7, 124.5, 122.5, 119.9, 118.6, 105.2, 20.7; Calcd (M$^+$): 497.1, Found: 496.2 ([M-H]$^-$); t$_R$=4.0 min (95.0%, IV).

4-(N-(4-(4-Chloro-3,5-dimethylphenoxy)phenyl)-N-isobutylsulfamoyl)-1-hydroxy-2-naphthoic Acid (3bj)

4-Chlorosulfonyl-1-hydroxy-2-naphthoic acid (5) was coupled to 4-(4-chloro-3,5-dimethylphenoxy)-N-isobutylaniline (9a) according to General Procedure A on a 1 mmol scale to yield the title compound as a cream solid (399 mg, 72%): $\delta_H$ (400 MHz, d$_6$-DMSO, TMS) $\delta_H$ 8.37 (d, 1H, Ar—H, J=8 Hz), 8.27 (s, 1H, Ar—H), 8.14 (d, 1H, Ar—H, J=8 Hz), 7.62 (t, 1H, Ar—H, J=7.4 Hz), 7.56 (t, 1H, Ar—H, J=7.4 Hz), 7.06 (d, 2H, Ar—H, J=8.8 Hz), 6.86 (s, 2H, Ar—H), 6.85 (d, 2H, Ar—H, J=8.8 Hz), 3.32 (d, 2H, NCH$_2$, J=7.2 Hz), 2.31 (s, 6H, Ar—CH$_3$), 1.42 (m, 1H, CH$_2$CH(CH$_3$)$_2$), 0.78 (d, 6H, CH(CH$_3$)$_2$, J=6.4 Hz) $\delta_C$ (100 MHz, d$_6$-DMSO) 156.3, 154.3, 137.9, 134.2, 132.9, 132.2, 130.6, 130.2, 128.9, 126.7, 126.1, 125.2, 124.7, 119.7, 118.7, 57.3, 26.8, 20.7, 20.2; Calcd (M$^+$): 553.1, Found: 552.2 ([M-H]$^-$); t$_R$=8.0 min (96.8%, IV).

4-(N-(4-(4-Chloro-3,5-dimethylphenoxy)phenyl)-N-cyclopentylsulfamoyl)-1-hydroxy-2-naphthoic Acid (3bk)

4-Chlorosulfonyl-1-hydroxy-2-naphthoic acid (5) was coupled to 4-(4-chloro-3,5-dimethylphenoxy)-N-isobutylaniline (9b) according to General Procedure A on a 1 mmol scale to yield the title compound as a white solid (396 mg, 70%): $\delta_H$ (400 MHz, d$_6$-DMSO, TMS) $\delta_H$ 8.44 (app. t, 2H, Ar—H, J=7.2 Hz), 8.27 (s, 1H, Ar—H), 7.90 (t, 1H, Ar—H, J=7.8 Hz), 7.74 (t, 1H, Ar—H, J=7.6 Hz), 6.94 (d, 2H, Ar—H, J=8.8 Hz), 6.88 (d, 4H, Ar—H, J=8.4 Hz), 4.54 (m, 1H, NCH(CH$_2$)$_2$, J=8.2 Hz), 2.30 (s, 6H, Ar—CH$_3$), 1.80-1.68 (m, 2H, (CHCH$_2$CH$_2$)), 1.50-1.17 (m, 6H, 3 (CHCH$_2$CH$_2$)) $\delta_C$ (100 MHz, d$_6$-DMSO) 172.2, 165, 157.3, 153.9, 138, 134, 131.6, 131.5, 130.2, 129.2, 127.3, 125.4, 125.2, 124.6, 124.4, 119.9, 118.3, 105.3, 59.9, 30.3, 22.4, 20.7; Calcd (M$^+$): 565.1, Found: 564.3 ([M-H]$^-$); t$_R$=8.5 min (95.4%, IV).

4-(N-Benzyl-N-(4-(4-chloro-3,5-dimethylphenoxy)phenyl)sulfamoyl)-1-hydroxy-2-naphthoic Acid (3bl)

4-Chlorosulfonyl-1-hydroxy-2-naphthoic acid (5) was coupled to 4-(4-chloro-3,5-dimethylphenoxy)-N-isobutylaniline (9c) according to General Procedure A on a 1 mmol scale to yield the title compound as a white solid (423 mg, 72%): $\delta_H$ (400 MHz, d$_6$-DMSO, TMS) $\delta_H$ 8.43 (d, 1H, Ar—H, J=8 Hz), 8.39 (s, 1H, Ar—H), 8.26 (d, 1H, Ar—H, J=8 Hz), 7.73 (m, 2H, Ar—H, J=7.2 Hz), 7.24-7.17 (m, 5H, Ph), 7.02 (d, 2H, Ar—H, J=8.8 Hz), 6.77 (m, 3H, Ar—H), 4.78 (s, 2H, NCH$_2$), 2.28 (s, 6H, (Ar—CH$_3$)$_2$) $\delta_C$ (100 MHz, d$_6$-DMSO) 172.2, 165.2, 156.3, 154.2, 137.9, 136.5, 133.6, 132, 131.9, 131.2, 130.9, 128.9, 128.6, 127.8, 127.2, 125.5, 125.4, 124.5, 123.1, 119.6, 118.5, 105.5, 53.8, 20.7; Calcd (M$^+$): 587.1, Found: 586.2 ([M-H]$^-$); t$_R$=5.7 min (95.9%, IV).

4-(N-(4-Bromophenyl)-N-isobutylsulfamoyl)-1-hydroxy-2-naphthoic Acid (3ca)

4-chlorosulfonyl-1-hydroxy-2-naphthoic acid (5) was coupled to 4-bromo-N-isobutylaniline (8j) according to General Procedure A on a 6 mmol scale to yield the title compound as a light pink solid (393 mg, 68%): $\delta_H$ (400 MHz, d$_6$-DMSO, TMS) $\delta_H$ 8.41-8.39 (m, 1H, Ar), 8.29 (s, 1H, Ar), 8.15-8.13 (m, 1H, Ar), 7.68-7.65 (m, 2H, Ar), 7.48 (d, 2H, Ph, J=8.8 Hz), 7.07 (d, 2H, Ph, J=8.4 Hz), 3.36 (d, 2H, NCH$_2$, J=7.2 Hz), 1.44-1.37 (m, 1H, CH$_2$CH), 0.77 (d, 6H, CH(CH$_3$)$_2$, J=6 Hz) $\delta_C$ (100 MHz, d$_6$-DMSO) 172.0, 165.8, 138.5, 132.4, 132.1, 131.9, 131.1, 130.8, 127.1, 125.7, 125.2, 124.5, 122.8, 120.9, 105.6, 57.1, 26.9, 19.9; Calcd (M+): 477.0. Found: 476.0 ([M−H]−); $t_R$=16.3 min (99.5%, III).

Methyl 4-(N-(4-bromophenyl)-N-isobutylsulfamoyl)-1-hydroxy-2-naphthoate (3cb) and Methyl 4-(N-(4-bromophenyl)-N-isobutylsulfamoyl)-1-methoxy-2-naphthoate (3cc)

Compound 3ca (752 mg, 1.3 mmol, 1 eq) was treated with MeI (2.2 eq) and $K_2CO_3$ (3 eq) in DMF (13 mL) at RT. After 16 h, the reaction was incomplete, yielding two products. Water (150 mL) was added to the reaction mixture, which was subsequently extracted with EtOAc (30 mL×3). The EtOAc extractions were combined, washed with water (100 mL×3), brine, dried ($Na_2SO_4$), filtered and concentrated. The residue was adsorbed onto silica gel and purified by flash column chromatography, eluting with a gradient of EtOAc in hexanes to deliver first 3cc (395 mg, 60%) and second 3cb (211 mg, 33%) as cream-coloured solids. 3cb: $\delta_H$ (400 MHz, $d_6$-DMSO) 12.28 (s, 1H, OH), 8.40 (d, 1H, Ar, J=8.4 Hz), 8.27 (s, 1H, Ar), 8.11 (d, 2H, Ar, J=8.4 Hz), 7.70-7.45 (m, 2H, Ar), 7.46 (d, 2H, Ar, J=8.4 Hz), 7.05 (d, 2H, Ar, J=8.4 Hz), 3.96 (s, 3H, $CO_2CH_3$), 3.34 (d, 1H, C$\underline{H}_2$CH(CH$_3$)$_2$), J=7.6 Hz), 1.38 (hep, 1H, C$\underline{H}$(CH$_3$)$_2$, J=6.9 Hz), 0.75 (d, 6H, CH(C$\underline{H}_3$)$_2$, J=6.0 Hz); $\delta_C$ (100 MHz, $d_6$-DMSO) 174.3, 168.2, 143.1, 137.2, 136.5, 136.3, 135.7, 135.6, 132.5, 130.0, 129.9, 129.3, 129.2, 125.9, 109.8, 61.9, 58.4, 31.6, 24.7; Calcd (M+): 491.0, Found: 514.0 ([M+Na]+); $t_R$=9.5 min (95.1%, IV). 3cc: $\delta_H$ (400 MHz, $d_6$-DMSO) 8.37 (d, 1H, Ar, J=7.6 Hz), 8.31 (s, 1H, Ar), 8.15 (d, 1H, Ar, J=8.8 Hz), 7.75 (t, 1H, Ar, J=7.6 Hz), 7.67 (t, 1H, Ar, J=7.4 Hz), 7.50 (d, 2H, Ar, J=8.4 Hz), 7.08 (d, 2H, Ar, J=8.4 Hz), 4.05 (s, 3H, CH$_3$), 3.93 (s, 3H, CH$_3$), 3.39 (d, 1H, C$\underline{H}_2$CH(CH$_3$)$_2$, J=6.8 Hz), 1.43 (hep, 1H, CH(CH$_3$)$_2$, J=6.7 Hz), 0.79 (d, 6H, CH(C$\underline{H}_3$)$_2$, J=5.2 Hz); $\delta_C$ (100 MHz, $d_6$-DMSO) 165.1, 162.1, 138.2, 132.5, 132.2, 131.3, 130.9, 130.7, 129.3, 128.8, 128.3, 125.3, 124.7, 121.2, 117.1, 64.2, 57.2, 53.2, 26.9, 19.9; Calcd (M+): 505.1, Found: 528.1 ([M+Na]+).

4-(N-(4-Bromophenyl)-N-isobutylsulfamoyl)-1-methoxy-2-naphthoic Acid (3cd)

Compound 3cc was saponified using LiOH.H$_2$O (3eq) in a mixture of THF/H$_2$O/MeOH (3:1:1) on a 0.2 mmol scale to deliver the title compound as a white solid (79 mg, 80%): $\delta_H$ (400 MHz, $d_6$-DMSO) 13.5 (br s, 1H, CO$_2$H), 8.36 (d, 1H, Ar, J=8.4 Hz), 8.32 (s, 1H, Ar), 8.15 (d, 1H, Ar, J=8.0 Hz), 7.73 (t, 1H, Ar, J=7.8 Hz), 7.65 (t, 1H, Ar, J=7.6 Hz), 7.49 (d, 2H, Ar, J=8.4 Hz), 7.07 (d, 2H, Ar, J=8.4 Hz), 4.06 (s, 3H, OMe), 3.40 (d, 2H, C$\underline{H}_2$CH(CH$_3$)$_2$), J=6.8 Hz), 1.43 (hep, 1H, C$\underline{H}$(CH$_3$)$_2$, J=6.8 Hz), 0.80 (d, 6H, CH(C$\underline{H}_3$)$_2$, J=6.4 Hz); $\delta_C$ (100 MHz, $d_6$-DMSO) 166.0, 161.6, 137.9, 132.5, 132.1, 130.8, 130.6, 130.0, 129.0, 128.2, 127.8, 124.9, 124.3, 120.8, 117.9, 63.6, 56.8, 26.5, 19.6; Calcd (M+): 491.0, Found: 490.0 ([M−H]−); $t_R$=15.3 min (98.5%, III).

Biology
General.

All chemical reagents were ACS grade or higher unless otherwise indicated. All buffers were passed through Chelex-100 (Bio-Rad, Hercules, Calif.) to remove trace metals. The D$_2$O, d$_6$-DMSO, $^{15}$NH$_4$Cl, and $^{13}$C-labeled glucose were purchased from Cambridge Isotope Laboratories, Inc. (Andover, Mass.).

Protein Production

A His6-MBP tagged recombinant human Mcl-1 residues 172 to 327 was produced in E. coli in either lysogeny broth (LB) or minimal media supplemented with $^{15}$NH$_4$Cl to produce unlabeled or $^{15}$N-labeled Mcl-1. The tagged protein was initially purified from the crude cell lysate by immobilized metal affinity chromatography (IMAC) chromatography (GE Healthcare Life Sciences), and after dialysis to remove the imidazole the affinity tag was cleaved using PreScission Protease (GE Healthcare Life Sciences). A Sephacryl S-200 size exclusion column was used as a final purification step before the protein was concentrated with a 10,000 MWCO centifugal filter concentrator (Millipore). The protein purity was shown to be >98% by Coomassie Brilliant Blue (Bio-Rad) stained SDS-PAGE gel and the final concentration was determined using the Bradford protein assay (Bio-Rad) with bovine serum albumin (BSA) standards (Pierce).

Peptide

A 6-aminohexanoic acid linker was conjugated to the N-terminus of the Bak BH3 peptide (GQVGRQLAIIGD-DINR), capped with fluorescein (on the amino group of the linker), and the peptide was amidated on the C-terminus to give FITC-Ahx-GQVGRQLAIIGDDINR-CONH$_2$, hereafter referred to as "FITC-Bak" (synthesized by Neo BioScience in >95% purity).

Fluorescence Polarization Experiments

Fluorescence polarization experiments were conducted using a BMG PHERAstar FS multimode microplate reader equipped with two PMTs for simultaneous measurements of the perpendicular and parallel fluorescence emission. The assays were performed in black polypropylene 384-well microplate (Costar) with a final volume of 20 microliter. Initially the affinity ($K_D$) of the FITC-Bak peptide was determined by titrating Mcl-1$^{172\text{-}327}$ into 10 nM FITC-Bak peptide in 20 mM HEPES, pH 6.8, 50 mM NaCl, 3 mM DTT, 0.01% Triton X-100 and 5% DMSO at room temperature while monitoring the perpendicular and parallel fluorescence emission with a 485 nm excitation and 520 nm emission filters. The fluorescence polarization competition assay (FPCA) was performed using 100 nM Mcl-1$^{172\text{-}327}$ in the same buffer (thus, 15 nM FITC-Bak) with varying concentrations of either unlabeled peptide or experimental. Regression analysis was carried out using Origin (Origin-Lab, Northampton, Mass.) to fit the data to the Hill equation (1) to determine the initial binding affinity ($K_D$) and the IC$_{50}$ in the FPCA. For the fluorescence polarization competition titrations, an equation derived by Nikolovska-Coleska et al. was used to calculate the $K_i$ from the IC$_{50}$ data. The affinity of FITC-Bak for Mcl-1$^{172\text{-}327}$ was determined to be 33.8±0.50 nM in the assay conditions used.

Nuclear Magnetic Resonance Spectroscopy

NMR spectra was collected at 25° C. with a Bruker AVANCE 800 NMR spectrometer (800.27 MHz for protons) equipped with pulsed-field gradients, four frequency channels, and triple resonance, z-axis gradient cryogenic probes. A one-second relaxation delay was used, and quadrature detection in the indirect dimensions was obtained with states-TPPI phase cycling; initial delays in the indirect dimensions were set to give zero- and first-order phase corrections of 90° and −180°, respectively. Data were processed using the processing program nmrPipe on Linux workstations. All proton chemical shifts are reported with respect to the H$_2$O or HDO signal, taken to be 4.658 ppm relative to external TSP (0.0 ppm) at 37° C. The $^{15}$N chemical shifts were indirectly referenced using the zero-point frequency at 37° C. of 0.10132905 for $^{15}$N—$^1$H, as previously described.

Uniformly $^{15}$N-labeled Mcl-1 was used to collect two-dimensional $^1$H, $^{15}$N-fast HSQC (heteronuclear single quantum coherence) spectra of Mcl-1 with and without compound to detect changes in the backbone $^{15}$N and $^1$H resonances of Mcl-1 due to the direct interaction with the compound. All compounds used for NMR were initially suspended in 100% $d_6$-DMSO. The NMR samples contained 131 µM $^{15}$N-labeled Mcl-1, 182 µM compound, 20 mM HEPES, pH 6.8, 50 mM NaCl, 3 mM DTT, 20% $D_2O$, and 5% $D_6$-DMSO.

Example 2

Synthesis of 1-hydroxy-4-sulfamoyl-2-napthoates and Cell Growth Inhibitory Activities of the Same Following onto Example 1, additional naphthoate Mcl-1 inhibitors were prepared to probe various aspects of the Mcl-1 binding site. And, unless specified otherwise, the compound numbering in Example 2 is equivalent to the compound numbering in Example 1. Naphthoates 13 and 14 were prepared as shown in scheme 2-1.

Scheme 2-1.

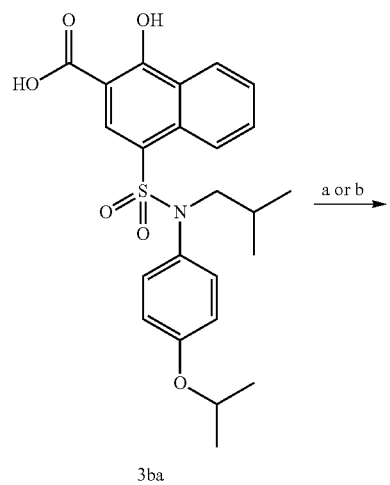

3ba

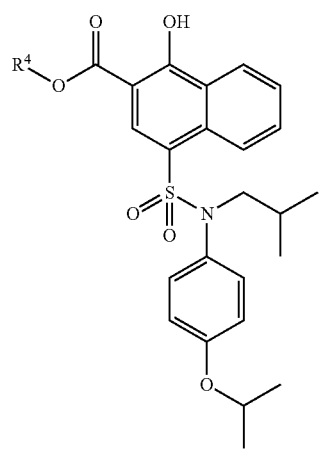

13 (R$^4$ = Me)
14 (R$^4$ = CH$_2$OCOCH$_3$)

(a) SOCl2, MeOH, rt, 48 h; (b) BrCH2OCOCH3, K2CO3, MeCN, 0° C., 16 h.

TABLE 2-1

Inhibition of cell proliferation by select compounds, as determined by a cell titer blue assay.

| | IC$_{50}$ (µM) | |
| Compound | A375 | SK-MEL-5 |
| --- | --- | --- |
| 3a | ~300 | ~300 |
| 3bl | 50 | 90 |
| 3ba | 150 | ~300 |
| 13 | ~300 | ~300 |
| 14 | 15 | 15 |

A long-standing challenge in targeting the anti-apoptotic Bcl-2 proteins is achieving family member specificity, particularly Mcl-1 specificity, although selective ligands are beginning to emerge.

To investigate the cellular activity of selected Mcl-1 inhibitors, the potent compound 3bl was evaluated for its ability to inhibit the proliferation of A375 and SK-MEL-5 melanoma cells, both of which express high levels of Mcl-1. Unfortunately, the IC$_{50}$ for 3bl was 50 µM and 90 µM in A375 and SK-MEL-5 cells, respectively (Table 2-1). Without being limited to any one theory, the poor efficacy in cells may be attributed to the charged carboxylic acid of 3bl. To test this hypothesis, two ester prodrugs were prepared of the potent, but more hydrophilic, inhibitor 3ba, methyl ester 13 and acetoxymethyl ester 14, according to Scheme 3. As expected, both prodrugs 13 and 14 demonstrated no binding affinity to Mcl-1 in vitro. Naphthoate derivative 3ba exhibited worse activity than 3bl in cells, consistent with its weaker affinity to Mcl-1. However, the acetoxymethyl ester 14 displayed an IC$_{50}$ of 15 µM in both A375 and SK-MEL-5 cells, presumably due to improved cell penetration and then intracellular hydrolysis to the active metabolite 3ba (Table 2-1). It is postulated that the lack of cellular activity for methyl ester 13 may be due to limited hydrolysis to 3ba. These results suggest a path forward with respect to rationally improving the cell penetration capabilities of this class of compounds based on a prodrug strategy.

Example 3

Figure 10:
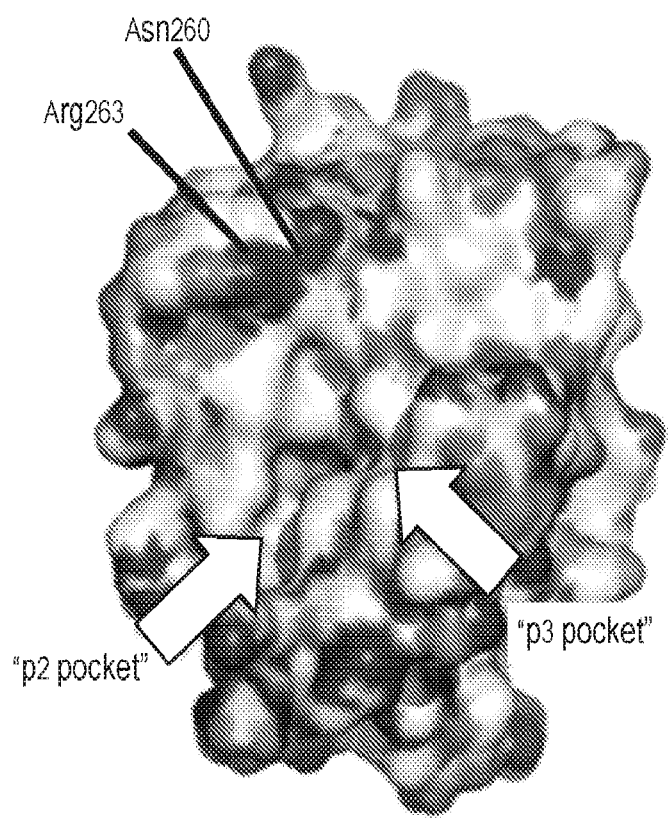
FIG. 10 illustrates the relative locations of Asn260 and Arg263 on the tertiary structure of the Mcl-1 protein in addition to the locations of the p2 and p3 pockets.
Figure 11:
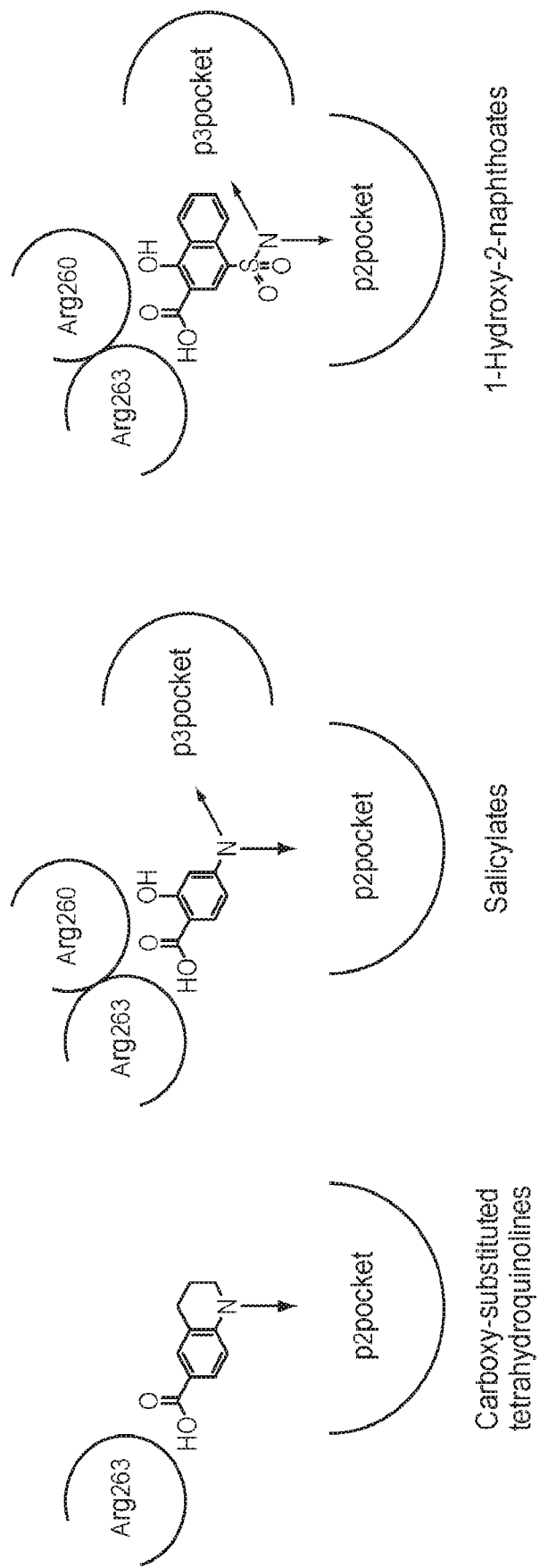
FIG. 11 illustrates the proposed Mcl-1 binding orientations for the tetrahydroquinoline, salicylate, and naphthoate Mcl-1 inhibitors described herein.

Inhibitors of the Mcl-1 Oncoprotein Based on Carboxy-Substituted Tetrahydroquinolines, Salicylate- and 1-Hydroxy-2-Naphthoate-Based Scaffolds Indoles, benzothiophenes and benzofurans appropriately functionalized with a carboxylic acid and a flexible hydrophobic group may be potent inhibitors of the Mcl-1 oncoprotein through recognition of Arg263 and occupancy of the p2 pocket, respectively. Three families are provided herein as Mcl-1 inhibitors based on a carboxy-substituted tetrahydroquinoline (THQ) scaffold, a salicylate scaffold and a 1-hydroxy-2-naphthoate scaffold that are proposed to bind these sites as well as Asn260 and the p3 pocket (FIGS. 10 and 11).

Several of the carboxy-substituted tetrahydroquinolines (THQs) described herein are shown to inhibit the Mcl-1 oncoprotein, as determined by a fluorescence polarization competition assay (Table 3-1).

TABLE 3-1

Mcl-1 and Bcl-x$_L$ inhibitory activity for various THQ compounds.

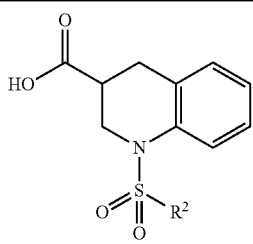

| Code Number | R$^1$ | K$_i$ (μM) Bcl-x$_L$ | K$_i$ (μM) Mcl-1 |
|---|---|---|---|
| SF-5-135 | 4-Br-phenyl | ND | >1000 |
| SF-5-133 | biphenyl-4-yl | ND | 12 |
| SF-5-134 | naphthalen-2-yl | ND | 30 |
| SF-5-136 | 4-F-phenyl | ND | >1000 |
| SF-5-141 | 4-(4-chloro-3,5-dimethylphenoxy)phenyl | ND | 0.286 |

(3-carboxy THQ scaffold)

| Code Number | R$^2$ | K$_i$ (μM) Bcl-x$_L$ | K$_i$ (μM) Mcl-1 |
|---|---|---|---|
| LC-3-004 | 4-Br-phenyl | ND | 203 |
| LC-3-002 | biphenyl-4-yl | ND | 14 |
| LC-3-006 | naphthalen-2-yl | ND | 22 |
| LC-3-010 | 4-F-phenyl | ND | >1000 |
| LC-3-012 | 4-(4-chloro-3,5-dimethylphenoxy)phenyl | ND | 0.332 |

Example 4

Structure-Based Design of 3-carboxy-substituted 1,2,3,4-tetrahydroquinolines Mcl-1 has emerged as an attractive target to expand the armamentarium in the war on cancer. Using structure-based design, 3-carboxy-substituted 1,2,3,4-tetrahydroquinolines were developed as a new chemotype to inhibit the Mcl-1 oncoprotein. The most potent compound inhibited Mcl-1 with a Ki of 120 nM, as determined by a fluorescence polarization competition assay. Direct binding was confirmed by 2D 1H-15N HSQC NMR spectroscopy with 15N-Mcl-1, which indicated interactions with R263 and T266, and occupation of the p2 pocket are likely responsible for the potent binding affinity. The short and facile synthetic chemistry is expected to mediate future compound optimization.

The intrinsic apoptosis pathway is activated when a cell undergoes stress, which leads to the homodimerization of the pro-apoptotic Bcl-2 proteins Bak and Bax at the outer mitochondrial membrane, and, in turn, a caspase cascade ensues that results in the formation of apoptosomes. The net result of this process is programmed cell death, or apoptosis. In many human cancers, anti-apoptotic members of the Bcl-2 family, which include Bcl-xL, Bcl-2 and Mcl-1, are over-expressed, immortalizing the cancer cells. Whilst inhibitors of Bcl-xL and Bcl-2 have advanced to clinical trials (dual Bcl-xL/Bcl-2: ABT-263 (navitoclax); Bcl-2 specific: ABT-199), progress in the development of specific Mcl-1 inhibitors has been less successful and there currently exists no drug to inhibit this protein. Upregulation of Mcl-1 specifically has been associated with the development and progression of several cancers that include acute myeloid leukemia, melanoma, non-small-cell lung, pancreatic, prostate, and ovarian cancers. Moreover, it is known that cancers dependent on Bcl-xL can exhibit resistance to the Bcl-xL inhibitor ABT-737 (a variant of ABT-263) through upregulation of Mcl-1. Therefore, the development of inhibitors of Mcl-1, either as single agents or as adjuvant therapies, represents an unmet medical need.

By virtue of a hydrophobic groove on its surface, Mcl-1 directly antagonizes the pro-apoptotic Bcl-2 proteins, which include Bak, Bax and Bim, through capturing their BH3 α-helical "death" domains, effectively "neutralizing" the cell-killing role of these proteins. More specifically, BH3 domains project four conserved hydrophobic side chains from one face of the α-helix that recognize sub-pockets on the surface of Mcl-1, which are termed p1 through p4. Additionally, a conserved aspartate residue on the opposite face of the helix recognizes R263. α-helix mimetics have been developed of the BH3 "death" domains to inhibit Mcl-1, as well as the family members Bcl-2 and Bcl-xL. Similarly, a complementary strategy to inhibit Mcl-1 through a more traditional small-molecule approach has begun to emerge. However, the discovery of clinical candidates remains elusive, and so new Mcl-1 inhibitors fashioned from novel scaffolds are essential. Furthermore, synthetic routes to access these inhibitors should be as short and simple as possible to expedite compound synthesis and keep costs to a minimum. In light of these considerations, we present our progress on the discovery of novel Mcl-1 inhibitors based on a simple and synthetically-accessible THQ scaffold.

As depicted in Scheme 4-1, quinoline-3-carboxylic acid 3 was esterified with thionyl chloride in methanol to yield ester 4. Reduction of the pyridine ring of 4 with pyridine-borane complex in glacial acetic acid then delivered racemic THQ 5 whose methyl ester was saponified to yield ±-6. Alternatively, sulfonylation of ±-5 furnished compounds ±-7, which were also saponified with lithium hydroxide to afford the 3-carboxy target compounds ±-8. Further elaboration of the phenylsulfonyl group in ±-7c was accomplished by an SNAr reaction with 4-chloro-3,5-dimethylphenol followed by ester hydrolysis to afford compound ±-2, as shown in Scheme 4-2. In addition, the phenylsulfonyl moiety in ±-2 was replaced with a more flexible propylene group through a reductive amination-saponification sequence to yield ±-11.

Scheme 4-1.

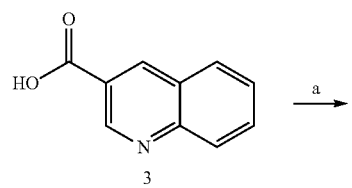

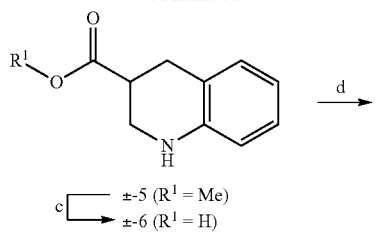

±-5 (R$^1$ = Me)
±-6 (R$^1$ = H)

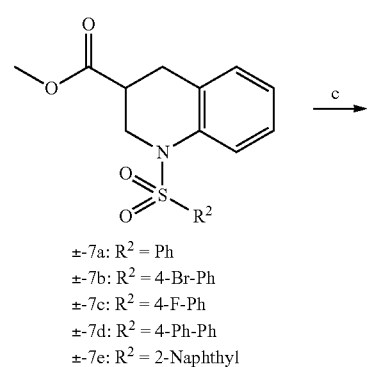

±-7a: R$^2$ = Ph
±-7b: R$^2$ = 4-Br-Ph
±-7c: R$^2$ = 4-F-Ph
±-7d: R$^2$ = 4-Ph-Ph
±-7e: R$^2$ = 2-Naphthyl

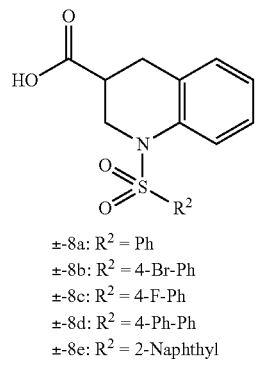

±-8a: R$^2$ = Ph
±-8b: R$^2$ = 4-Br-Ph
±-8c: R$^2$ = 4-F-Ph
±-8d: R$^2$ = 4-Ph-Ph
±-8e: R$^2$ = 2-Naphthyl (a) SOCl2, MeOH, 0° C. to reflux, overnight; (b) Pyr—BH3, AcOH, RT, overnight; (c) LiOH•H2O, THF—MeOH—H2O 3:1:1, RT, overnight; (d) R1SO2Cl, DIPEA, cat. DMAP, CHCl3, reflux, overnight.

Scheme 4-2:

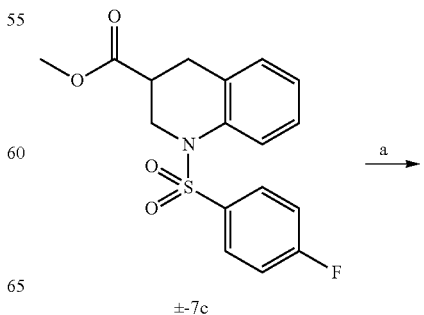

±-7c

-continued

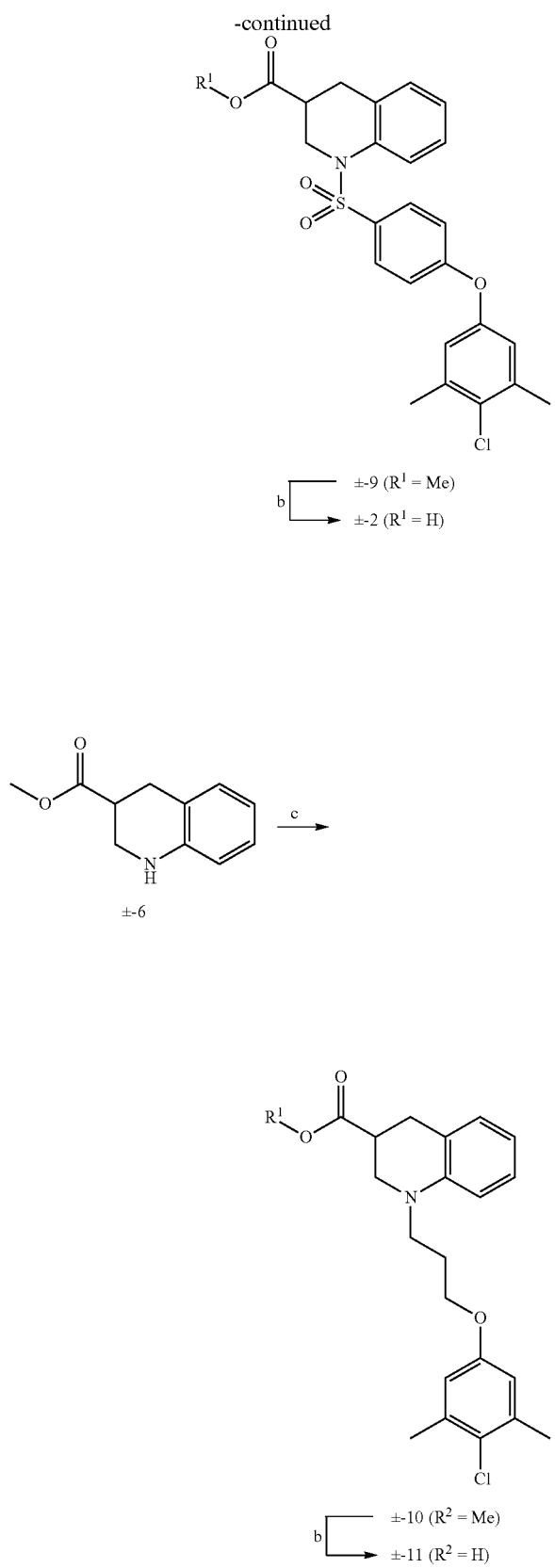

(a) 4-Chloro-3,5-dimethylphenol, K2CO3, DMF, 100° C., 48 h; (b) LiOH•H2O, THF—MeOH—H2O, 3:1:1, RT, overnight; (c) 4-chloro-3,5-dimethylphenoxypropaldehyde, NaBH(OAc)3, DCE, 35° C., overnight.

TABLE 4-1

Fluorescence polarization competition assay with Mcl-1 and FITC-labeled Bak-BH3 peptide ("FITC-Bak").

| Compd | $R^1$ | $R^2$ | $K_i$ (μM) |
|---|---|---|---|
| ±-6 | —H | —H | >500 |
| ±-8a | —H | phenylsulfonyl | 193 ± 24 |
| ±-8b | —H | 4-bromophenylsulfonyl | 117 ± 19 |
| ±-8c | —H | 4-fluorophenylsulfonyl | 176 ± 115 |
| ±-8d | —H | 4-biphenylsulfonyl | >500 |
| ±-8e | —H | 2-naphthylsulfonyl | 59.0 ± 6.0 |
| ±-9 | —Me | 4-(4-chloro-3,5-dimethylphenoxy)phenylsulfonyl | >500 |

TABLE 4-1-continued

Fluorescence polarization competition assay with Mcl-1 and FITC-labeled Bak-BH3 peptide ("FITC-Bak").

| Compd | R¹ | R² | $K_i$ (μM) |
|---|---|---|---|
| ±-2 | —H | 4-(4-chloro-3,5-dimethylphenoxy)phenylsulfonyl | 0.120 ± 0.053 |
| ±-11 | —H | 3-(4-chloro-3,5-dimethylphenoxy)propyl | 7.77 ± 1.39 |

In Table 4-1, the $IC_{50}$ data, which refers to the concentration of inhibitor that results in 50% displacement of FITC-Bak from Mcl-1, were converted to $K_i$ values using the Nikolovska-Coleska equation.

The target molecules were assayed for their abilities to disrupt the Mcl-1-Bak-BH3 PPI in a fluorescence polarization competition (FPC) assay with Mcl-1 and FITC-labeled Bak-BH3 peptide. Further details on the FPC assay can be found in the Supporting Information. As expected, unsubstituted racemic 1,2,3,4-tetrahydroquinoline-3-carboxylic acid (±-6) did not show any inhibitory effect ($K_i$>500 uM), which may, for example, be due to an inability to reach into the p2 pocket. Substitution of the THQ nitrogen with a phenylsulfonyl group (±-8) resulted in the discovery of a weak inhibitor of Mcl-1 ($K_i$=193 uM), whose activity was further enhanced by the addition of a bulky, hydrophobic bromine atom in the para position of the phenyl ring (±-8b: $K_i$=117 uM). However, there appears to be a geometrical constraint on the nature of the para hydrophobic group, since a phenyl ring here was not tolerated ((±-8d: $K_i$>500 uM). On the other hand, a 2-naphthylsulfonyl group (±-8e) afforded a two-fold increase in affinity to Mcl-1 over ±-8b indicating that large groups can be accommodated in the pocket binding the sulfonyl substituent. Gratifyingly, the originally designed molecule ±-2 exhibited the most potent binding of the series with a $K_i$ of 120 nM. We surmise this dramatic improvement in binding affinity is due to efficient and deep occupation of the p2 pocket by the 4-chloro-3,5-dimethylphenyl moiety that is facilitated by the ether oxygen providing increased structural flexibility not available to biphenyl ±-8d. A similarly impressive enhancement in the $K_i$ value of about three orders of magnitude exists for ±-8a as compared to ±-2. Compound ±-11 was a weaker inhibitor than ±-2 by over an order of magnitude, demonstrating the positive contribution made by the phenylsulfonyl group likely achieving favourable interactions at the top of the p2 pocket. Finally, the methyl ester of ±-2, i.e., compound ±-9, had no appreciable affinity to Mcl-1 indicating the significance of the carboxylic acid, which presumably binds R263 as proposed.

Figure 12:
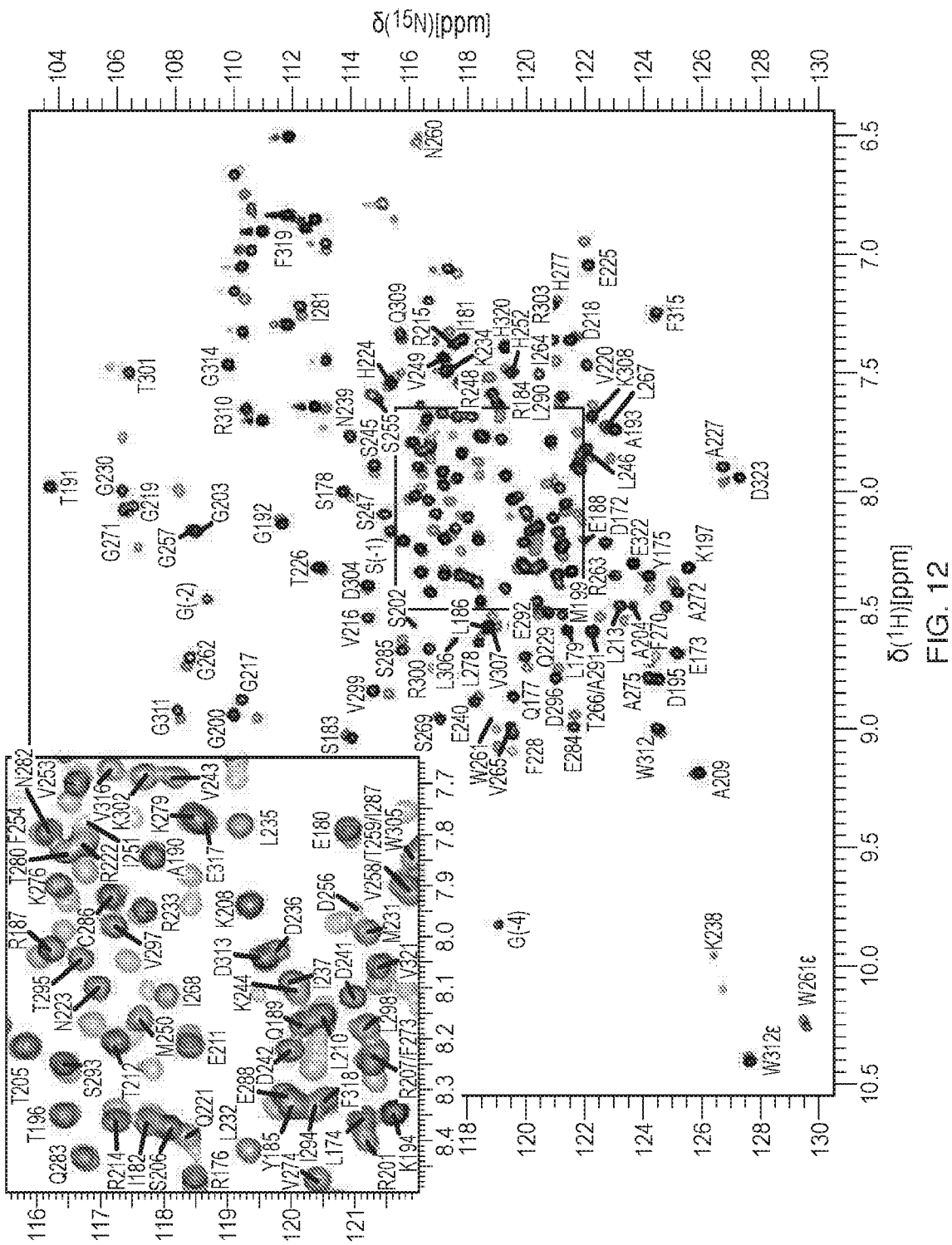
FIG. 12 illustrates a 2D 1H-15N HSQC spectra of Mcl-1 collected in the absence and presence of ±-2 from Example 4.
Figure 13:
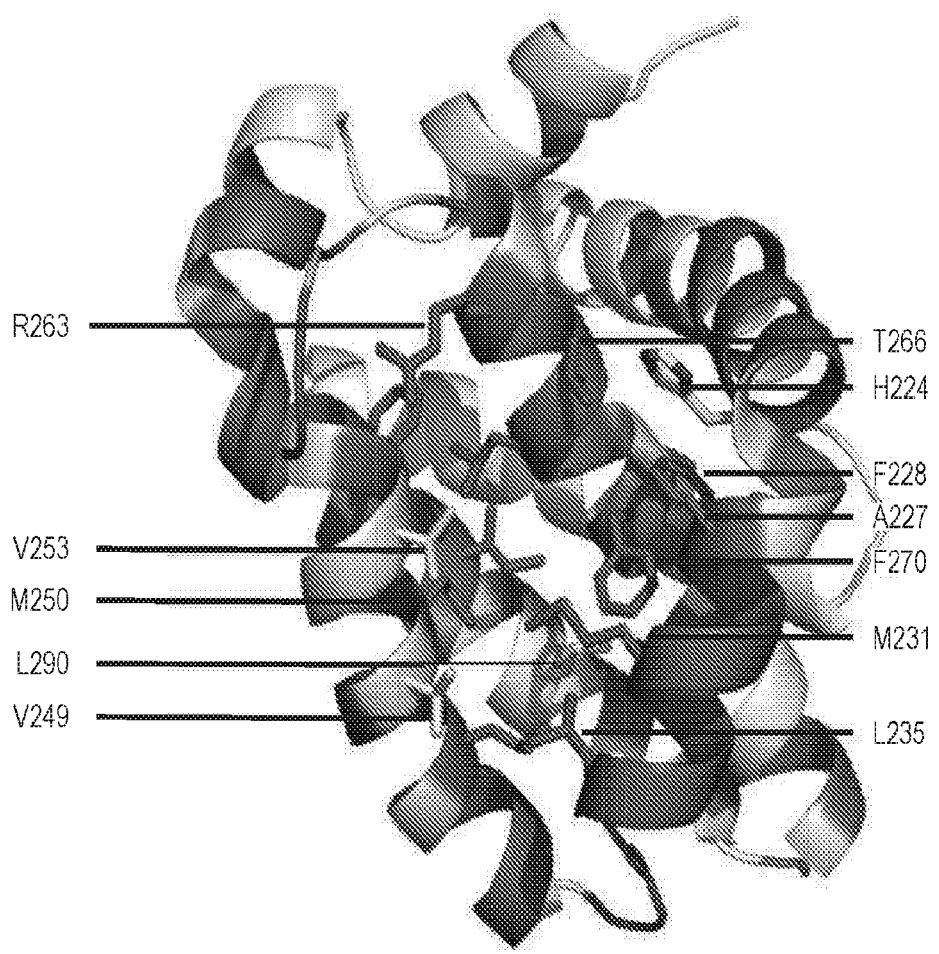
FIG. 13 illustrates resonance variations that were mapped onto the Mcl-1 crystal structure after calculating the chemical shift perturbations for each amino acid following the 2D 1H-15N HSQC analysis with ±-2 from Example 4.

Confirmation of the direct binding of ±-2 to Mcl-1 was afforded by heteronuclear NMR studies. 2D 1H-15N HSQC spectra of Mcl-1 were collected in the absence and presence of ±-2 (FIG. 12). An overlay of the two spectra revealed significant chemical shift changes and negligible peak broadening, characteristics of a fast exchange regime, and consistent with the nanomolar affinity observed in the FPC assay. Chemical shift perturbations were calculated for each amino acid and the resonance variation was mapped onto the Mcl-1 crystal structure, 3WIX in FIG. 13. Residues that experienced significant chemical shifts in the presence of ±-2 are shown in red and cluster around the p2 pocket, in support of the docking model presented above. More particularly, considerable shifts were observed among residues predicted to bind the carboxylate anion (R263 and T266) and 4-chloro-3,5-dimethylphenyl moiety (M250 and F270). On the other hand, the NMR data argues against a model in which H224 participates in π-π ring stacking with the benzene ring of the THQ.

The activity of ±-2 on the viability of human A375 melanoma cells that demonstrate increased expression of Mcl-1 was investigated next. A modest $GI_{50}$ of 50 uM for +-2 was observed (Table 4-2), which is more than two orders of magnitude less potent than the in vitro FP data. The moderate cellular activity of ±-2 may, for instance, be due to limited cell penetration owing to the charged carboxylic acid. Thus, the acetoxymethyl ester ±-12 (R1=CH2OCOCH3) was prepared as a neutral prodrug of ±-2. Like methyl ester ±-9, ±-12 was inactive in the FPC assay (Ki>500 uM), consistent with the requirement of the carboxylic acid function to engage R263. Surprisingly, however, the highly labile ester ±-12 did not yield a more potent cellular agent, which may, for instance, suggest that the charged carboxylic acid of ±-2 might not be a limiting factor in the translation of in vitro to cellular activity.

TABLE 4-2

Biological activity of select compounds.

| Compd | $K_i$ (μM)[a] | $GI_{50}$ (μM)[b] |
|---|---|---|
| ±-2 | 0.120 ± 0.053 | 50 |
| ±-12 | >500 | 73 |

[a]In vitro activity determined as described in Table 1.
[b]Viability of A375 cells as determined by a CellTiter-Blue ® assay.

In conclusion, a new chemotype to inhibit Mcl-1 has been discovered based on a THQ core. Compound ±-2 has a $K_i$ of 120 nM. The direct interaction of ±-2 with Mcl-1 was confirmed with 2D $^1H$—$^{15}N$ HSQC NMR data. Unlike the binding modes of the BH3 peptides with Mcl-1 in which all four hydrophobic pockets are bound, GOLD docking studies indicated that, whilst ±-2 interacts with the p2 pocket, no significant interactions with the p3 or p4 pockets were observed, which was largely substantiated by the HSQC NMR data. Thus, future analogs of ±-2 will focus on targeting the p3 and p4 pockets in addition to further exploration of the p2 pocket. Furthermore, docking studies suggested that the S-enantiomer is likely a stronger binder than its R counterpart, and so both enantiomers of ±-2 will be synthesized and evaluated to interrogate the impact of the chiral centre.

Example 5

Simplifying THQ Scaffold with the 4-Aminobenzoate Moiety

Figure 14:
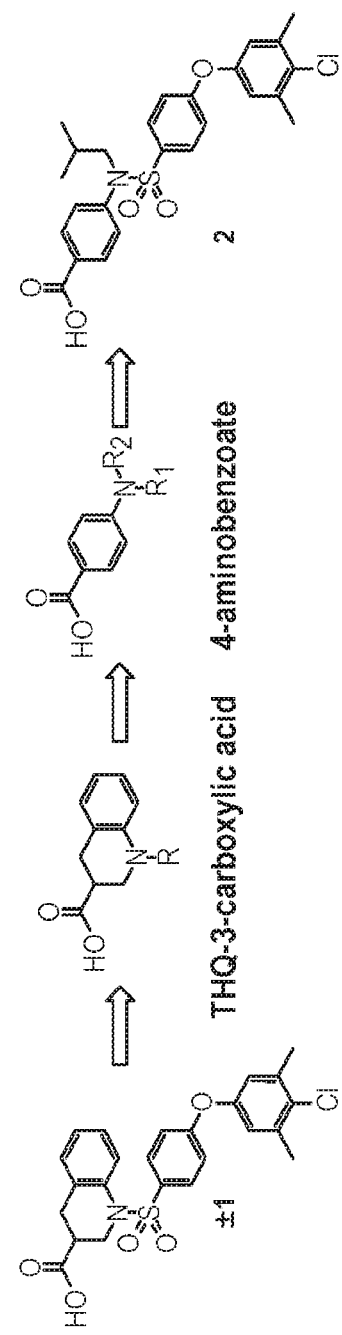
FIG. 14 illustrates the design of a 4-aminobenzoate analog based on the THQ scaffold.

A class of Mcl-1 inhibitors based on 3-carboxy-substituted 1,2,3,4-tetrahydroquinolines (THQ) scaffold has been described. The molecule presented a carboxylic acid to engage R263 and form a salt bridge, as well as various hydrophobic groups functionalized the N-position on the ring, which probe deep into the p2 pocket. A structural activity relationship (SAR) analysis has been performed by varying R groups, as shown in FIG. 14.

Due to the rigid nature of the THQ scaffold, it was synthetically challenging to systematically investigate the SAR regarding varying functional groups on the benzene ring, as well as installing additional moieties on the piperidine ring. Therefore, the THQ ring was simplified with a 4-aminobenzoate scaffold, as it offers a nitrogen atom that can be bi-functionalized by different $R_1$ and $R_2$ groups, as well as further decoration potential on the aromatic ring. For example, compound 2 possessed $R_1$ as an isobutyl group to mimicking part of the hydrophobic core from THQ, and $R_2$ as the 3,5-dimethyl-4-chloro-phenoxy benzene sulfonamide group, which has significantly contributed to the most potent THQ compound ±1.

Figure 15:
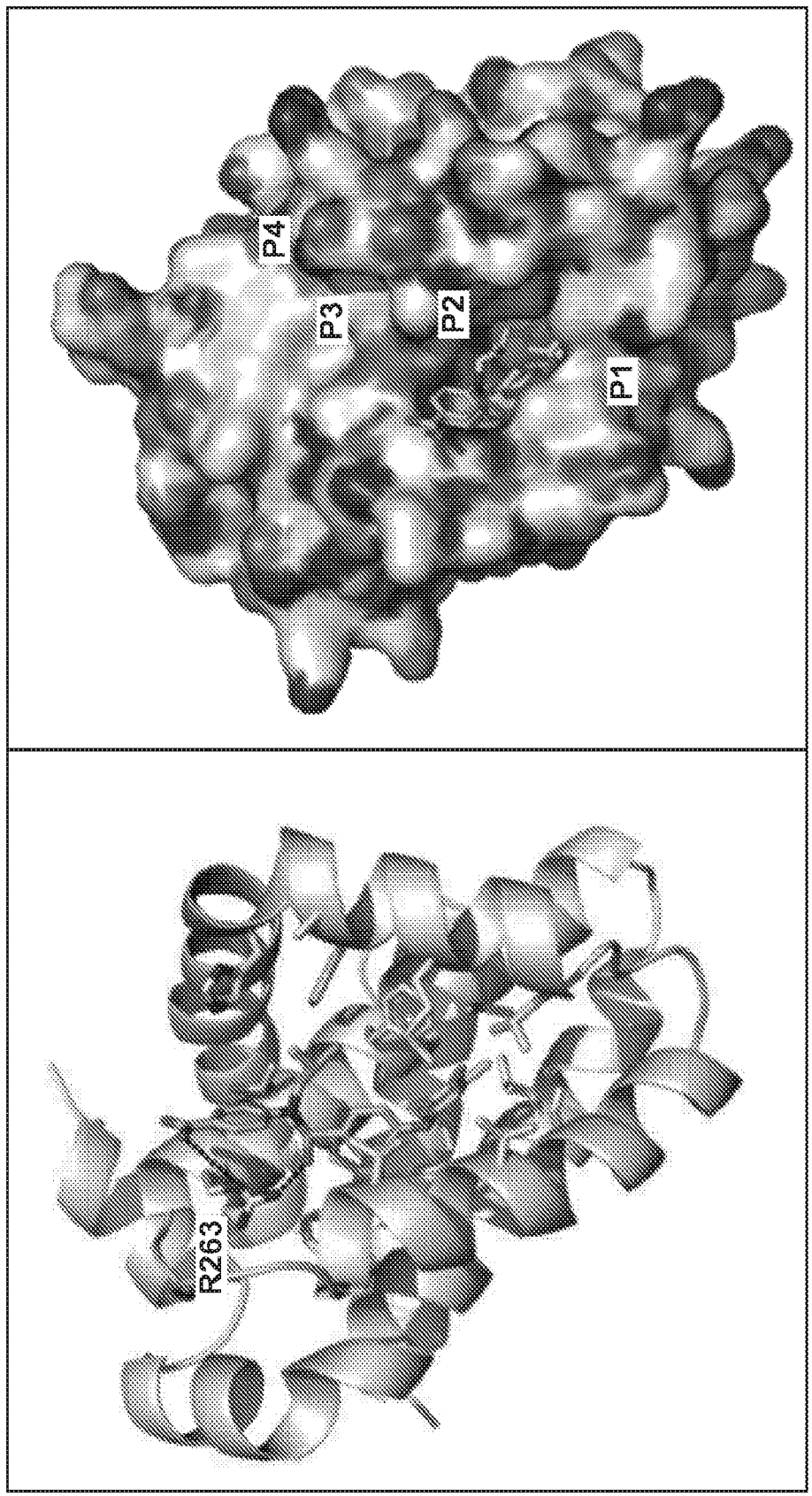
FIG. 15 illustrates the predicted binding of 4-aminobenzoate to Mcl-1.

To verify the design of the molecule, a GOLD docking experiment was run to test the possibility of compound 2 to bind to the Mcl-1 protein. As shown in FIG. 15, compound 2 was successfully docked into the p2 binding pocket of Mcl-1 protein. Key interactions were observed between the ligand and the protein including: the polar interaction between carboxylic acid and R263, the hydrophobic interaction between 3,5-dimethyl-4-chlorophenol and the deep portion of p2 hydrophobic binding site, and also the hydrophobic interaction between isobutyl group and the subtle hydrophobic pocket formed by A227, F228, M231 and F270.

To further validate the design of 4-aminobenzoates, a concise SAR library was synthesized according to general procedure shown in scheme 5-1. 4-nitrobenzoic acid 3 was esterified with sulfuric acid and methanol to yield ester 4. The nitro group of compound 4 was reduced with tin chloride dihydrate to deliver compound 5, which further underwent reductive amination with isobutyraldehyde to afford compound 6. Compound 6 was coupled to different aromatic sulfonyl chlorides to generate compounds library 7a-7d, which were saponified using lithium hydroxide to yield 4-aminobenzoate compounds 8a-8d. Additionally, compound 7d can be further elaborated with 3,5-dimethyl-4-chloro-phenol by $S_NAr$ reaction, followed by saponification to give compound 8e.

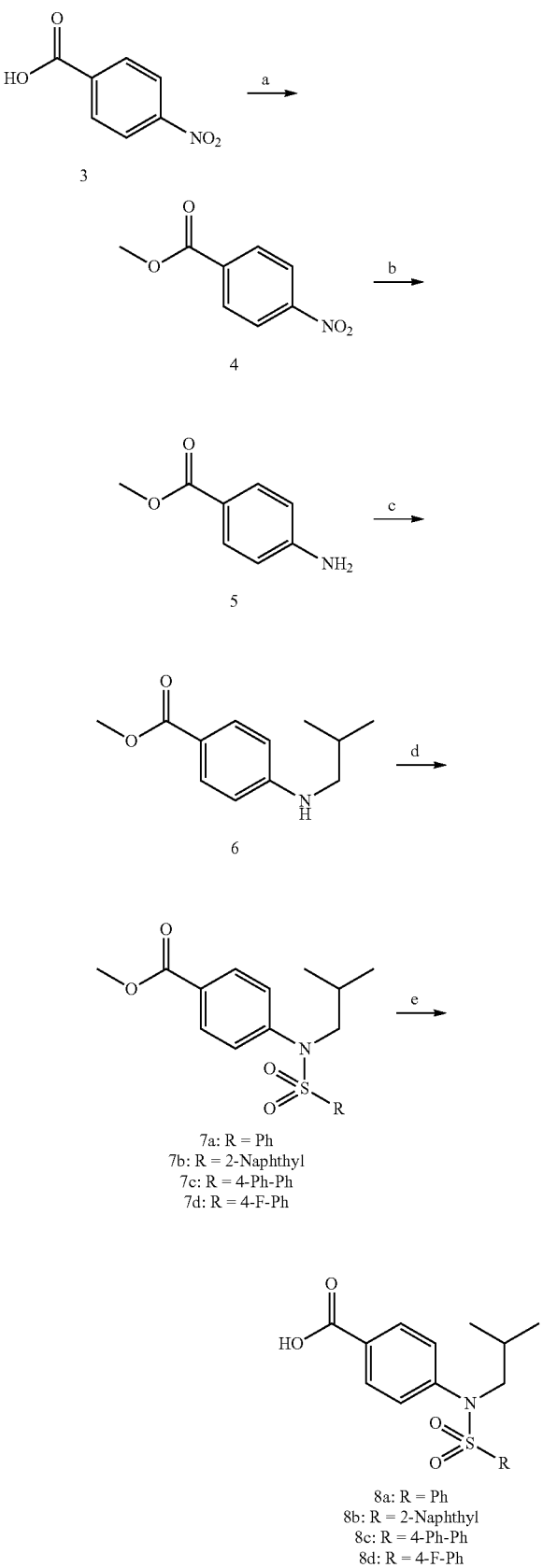

Scheme 5-1

TABLE 5-1

Mcl-1 binding affinity of 4-aminobenzoate analogs

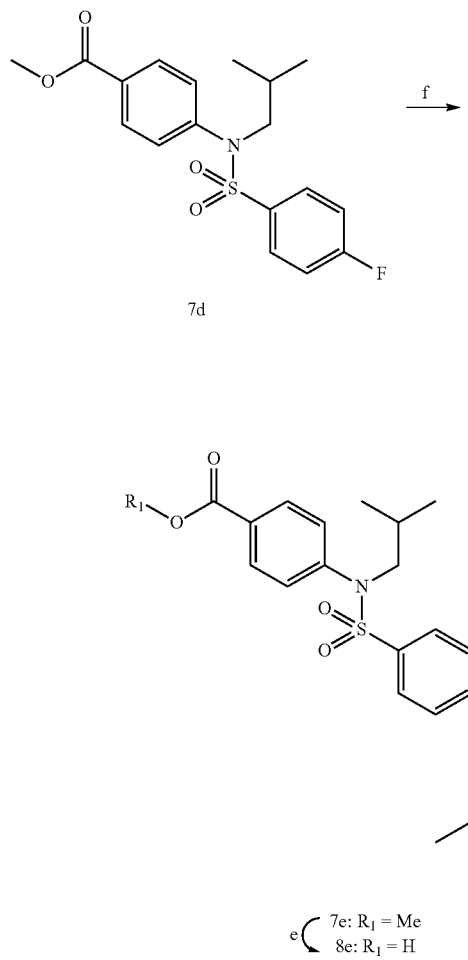

| Comp | R | Mcl-1 $K_i$ (μM) |
|---|---|---|
| LC-3-029 8a | phenyl | >500 |
| LC-3-031 8b | 2-naphthyl | >500 |
| LC-3-030 8c | biphenyl | 16.712 ± 2.284 |
| LC-3-025 8d | 4-fluorophenyl | >500 |
| LC-3-035 8e | 4-(4-chloro-3,5-dimethylphenoxy)phenyl | 2.058 ± 0.118 |

Synthesis of 4-aminobenzoate analogs. Reagents and conditions: (a) H₂SO₄, MeOH, 80° C., overnight; (b) SnCl₂•2H₂O, EtOAc, 50° C., overnight; (c) Isobutyraldehyde, NaBH(OAc)₃, DCE, RT, overnight; (d) RSO₂Cl, DIPEA, DMAP, CHCl₃, 60° C., overnight; (e) LiOH•H₂O, THF—MeOH—H₂O, 3:1:1, RT, overnight; (f) 4-chloro-3,5-dimethylphenol, K₂CO₃, DMSO, 100° C., overnight.

The potency of the molecules were evaluated by using a fluorescent polarization competition assay (FPCA) where the compounds were titrated into the mixture of Mcl-1 and FITC-Bak BH3 peptide to monitor their capability to disrupt the interaction between Mcl-1 and FITC-Bak BH3 peptide.

The inhibition constant for Mcl-1 ($K_i$) of each compound was shown in table 5-1. The biphenyl analog 8c was a moderate inhibitor with $K_i$=16.71 μM while the naphthyl analog 8b became a much weaker binder. The data indicated the significant influence on $K_i$ when using geometrically different rigid hydrophobic moieties. Therefore, if the binding pattern of these compounds were similar to the predicted mode from GOLD docking result, it can be inferred that the pocket accommodating R group can be a relatively small pocket, and hence the geometric shape of R moieties can play an important role to generate the best fit. Similar with what we found in the THQ library, further extension of the R group with the 3,5-dimethyl-4-chloro phenoxy group 8e rendered a more than 10-fold stronger binder comparing to 8c.

Figure 16:
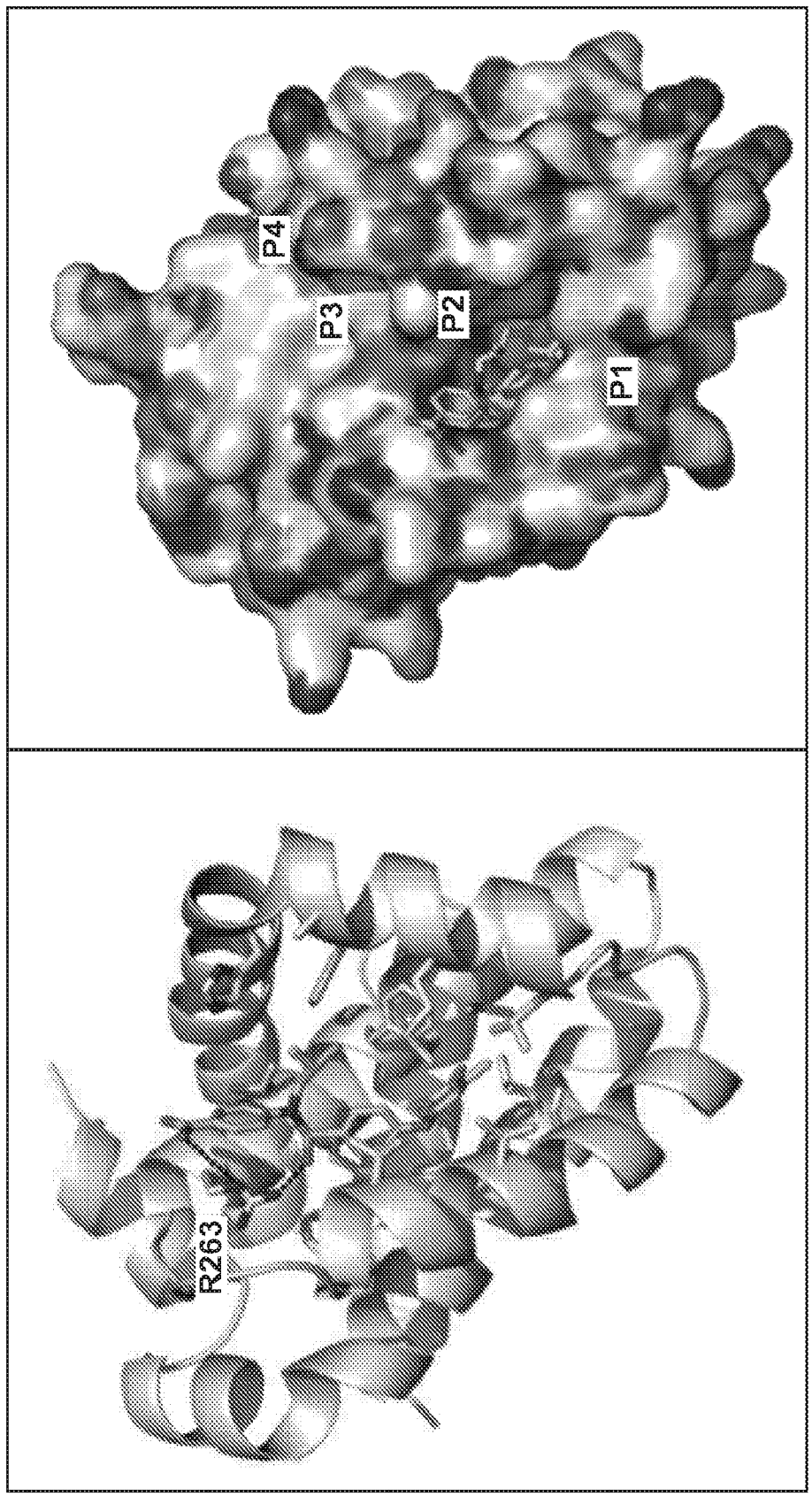
FIG. 16 illustrates the predicted binding of 4-aminobenzoate to Mcl-1 after the installation of a hydroxyl group ortho to the carboxylic acid (i.e., converting the 4-aminobenzoate into a 4-aminosalicylate).

With further investigation of the docking result demonstrated in FIG. 15, it is suspected that installing additional polar function groups onto the ortho position of carboxylic acid could potentially form favorable polar interactions with either R263 or T266 depending on the direction of the benzene ring. A GOLD docking experiment was done to show the possible binding pattern after installing a hydroxyl group ortho to the carboxylic acid, which converted the 4-aminobenzoate into a 4-aminosalicylate scaffold (FIG. 16). In this particular conformation, the hydroxyl group successfully recognized the R263, and also turned the carboxylic acid to a position where it was close enough to H-bond with T266.

To test this hypothesis, a library of analogs was designed and synthesized analog based on the 4-aminosalicylate scaffold according to scheme 5-2. 4-aminosalicylate was esterified under sulfuric acid and methanol condition to yield compound 10, which was further O-benzylated by reacting with benzyl bromide to afford compound 11. Reductive aminated compound 11 with different aldehydes and ketones (R₁) afforded compounds set 12a-12c. Sulfonylation of 12a-12c with various $R_2$—$SO_2Cl$ delivered compounds 12aa-12ag, 12ba-12bc, and 12ca-12cc. These compounds were further deprotected by saponification and TFA debenzylation to yield analogs of 13aa-13ag, 13ba, 13bb, and 13ca, 13cc. Alternatively, compound 12ad, 12bc and 12cc can be further elaborated with different substituted aromatic groups ($R_3$) by $S_NAr$ mechanism to afford compounds 12ah-12ak, 12bd and 12cd, which were deprotected using the same saponification followed by TFA debenzylation to generate final molecules 13ah-13ak, 13bd and 13cd. Additionally, compound 11 can also be directly sulfonylated by 4-phenoxybenzene sulfonylchloride to yield compound (12da), and then deprotected to give compound (13da).

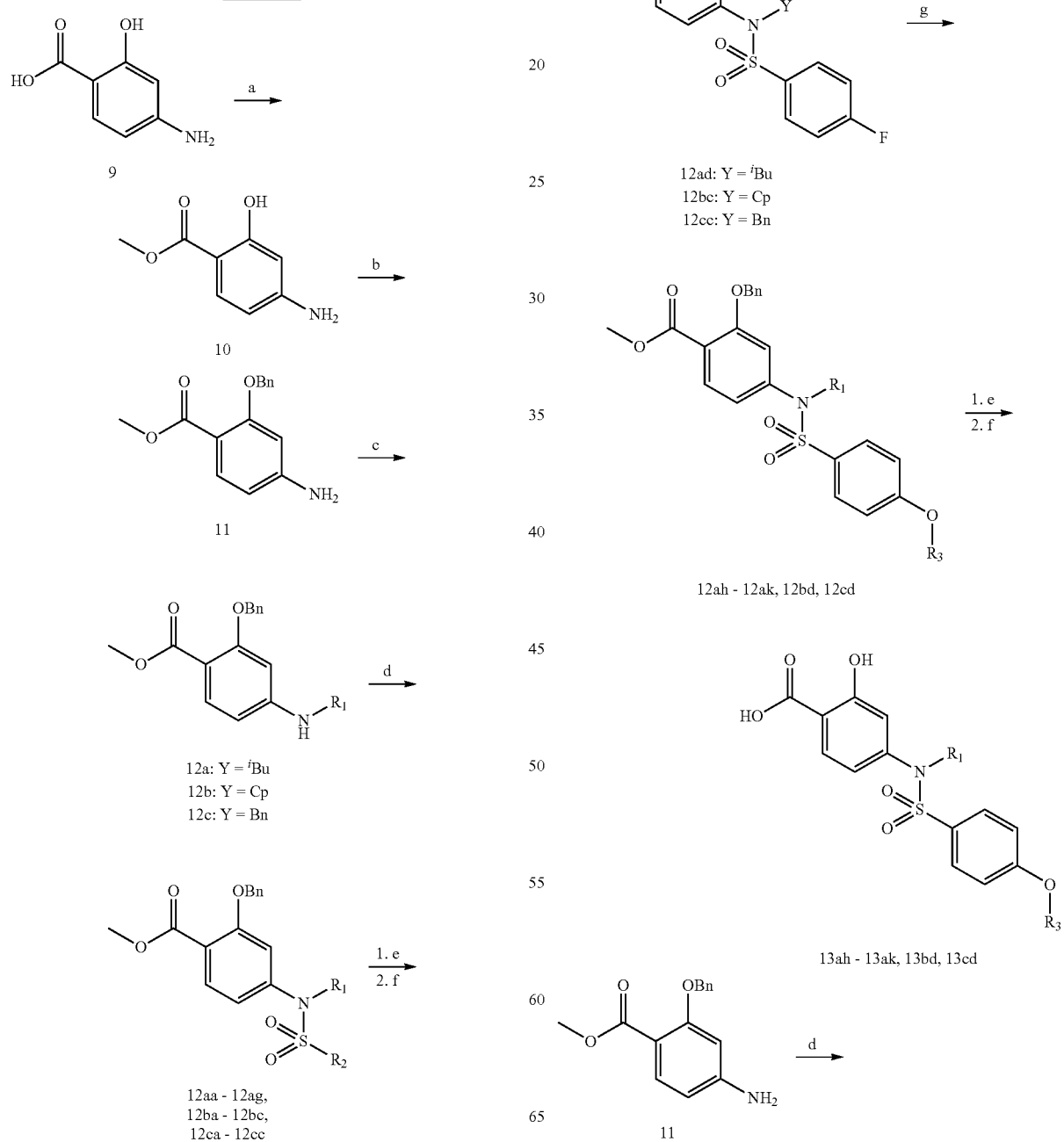

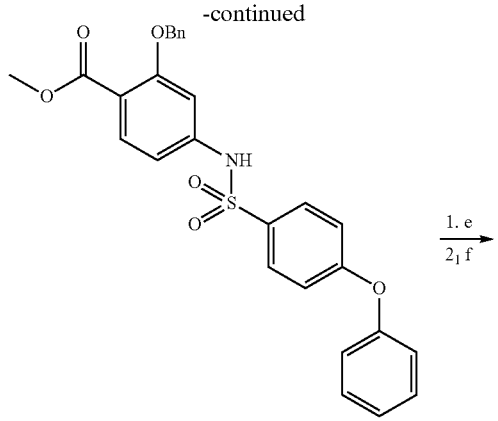

12da

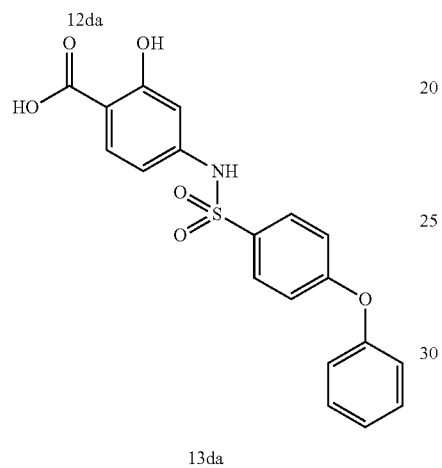

13da

Synthesis of 4-aminosalicylate analogs, Reagents and conditions: (a) H₂SO₄, MeOH, 80° C., overnight; (b) BnBr, KOᵗBu, DMF, RT, overnight; (c) R₁-aldehyde or R₁-ketone, NaBH(OAc)₃, DCE, RT, overnight; (d) R₂—SO₂Cl, DIPEA, DMAP, CHCl₃, 60° C., overnight; (e) LiOH•H₂O, THF—MeOH—H2O, 3:1:1, RT, overnight, (f) TFA, toluene, RT, overnight; (g) R₃-phenol, K₂CO₃, DMSO, 100° C., overnight.

Using the same FPCA experiment, the potencies of the analogs were determined and their structure activity relationships were examined in Tables 5-2 and 5-3. Excitingly, all of 4-aminosalicylate analogs in Table 5-2 exhibited stronger Mcl-1 binding affinities compared to their corresponding 4-aminobenzoates derivatives in Table 5-1, demonstrating the significant contribution from the OH group to the Mcl-1 binding.

With this expanded library shown in Table 5-2 compared to Table 5-1, it is clearer to see the increased hydrophobicity of R₂ substitution yielded stronger inhibitors, as illustrated by the decreasing K$_i$s from the phenyl 13aa, 4-flurophenyl 13ad, 4-methylphenyl 13af, 4-bromophenyl 13ae, 2-naphthyl 13ab to 4-biphenyl 13ac compounds with almost 50-fold improvement in binding affinity. Further expanding the R₂ moiety from the para position of the benzene sulfonamide with an oxygen linker rendered a group of tighter binders 13ag-13ak. The subtle structural changes on the phenoxy group were reflected well by their corresponding K$_i$, indicating the sensitivity of the binding region on the protein. Again, the most potent analog 13ak presented the key moiety of 3,5-dimethyl-4-chloro-phenoxy group, contributing to its Ki=778 nM.

Various R₁ substitutions were also made to further investigate the hydrophobic interactions between the N-substitutions and the Mcl-1 protein as shown in Table 5-3. When vertically comparing the analogs in Table 5-3, it is noticeable the consistent trend in K$_i$ from naphthyl, p-biphenyl to 3,5-dimethyl-4-chloro-phenoxy benzene group. On the other hand, when horizontally comparing the analogs in Table 5-3 with their corresponding derivatives in Table 5-2, the alterations of R₁ group have a significant impact on the potencies of these molecules. Completely deleting the hydrophobicity turned the compound 13da into a much weaker binder, indicating the importance of hydrophobic group on R₁ position. Comparing the K$_i$ among compounds where R₁=isobutyl (ⁱBu), cyclopentyl (Cp) and Benzyl (Bn), it is apparent that R₁=Cp rendered the least potent binders (13ab, 13ac, 13ak), R₁=ⁱBu gave the moderate potent binders 13ba-13bc, and R₁=Bn contributed to the most potent binders 13ca-13cc.

TABLE 5-2

Mcl-1 binding affinity of 4-aminosalicylate analogs.

| Compd | R₁ | R₂ | Mcl-1 K$_i$ (μM) |
|---|---|---|---|
| 4jc117-1 13aa | isobutyl | phenyl | 192.038 ± 37.534 |
| 4jc117-3 13ab | isobutyl | 2-naphthyl | 13.821 ± 1.325 |
| 4jc117-4 13ac | isobutyl | 4-biphenyl | 4.109 ± 0.245 |
| LC-5-025 13ad | isobutyl | 4-fluorophenyl | 99.372 ± 9.374 |
| LC-5-012 13ae | isobutyl | 4-bromophenyl | 16.980 ± 1.504 |
| 4jc117-2 13af | isobutyl | 4-methylphenyl | 61.243 ± 4.490 |

TABLE 5-2-continued
Mcl-1 binding affinity of 4-aminosalicylate analogs.
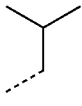
| Compd | R₁ | R₂ | Mcl-1 $K_i$ (μM) |
|---|---|---|---|
| LC-4-099 13ag | 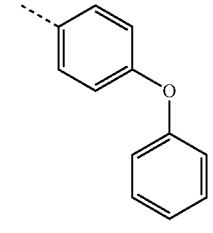 | 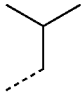 | 5.766 ± 0.458 |
| LC-4-119 13ah | 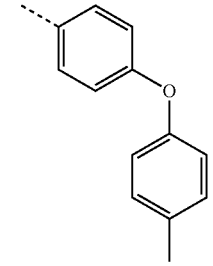 | 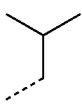 | 2.255 ± 0.168 |
| LC-4-100 13ai | 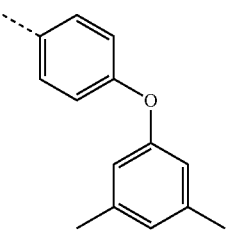 | 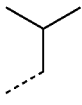 | 2.964 ± 0.286 |
| LC-4-111 13aj | 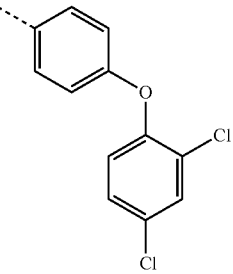 | 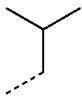 | 2.738 ± 0.258 |
| 4jc117-5 13ak | 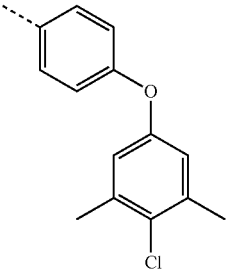 | 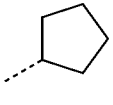 | 0.778 ± 0.050 |
TABLE 5-3
Mcl-1 binding affinity of 4-aminosalicylate analogs (continued).
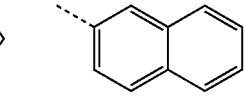
| Compd | R₁ | R₂ | Mcl-1 $K_i$ (μM) |
|---|---|---|---|
| LC-4-083 13ba | 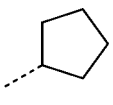 | 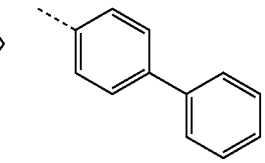 | 24.749 ± 9.449 |
| LC-4-082 13bb | 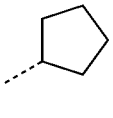 | 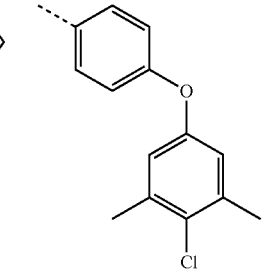 | 5.244 ± 0.694 |
| LC-4-104 13bc | 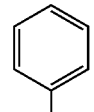 | 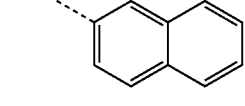 | 1.762 ± 0.208 |
| LC-4-113 13ca | 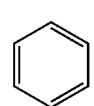 | 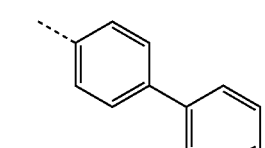 | 11.395 ± 1.572 |
| LC-4-112 13cb | 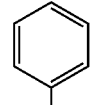 | 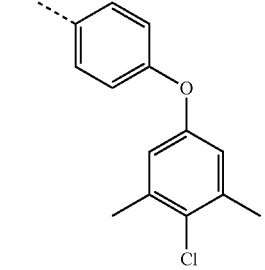 | 1.712 ± 0.144 |
| LC-4-118 13cc |  |  | 0.659 ± 0.040 |

TABLE 5-3-continued

Mcl-1 binding affinity of 4-aminosalicylate analogs (continued).

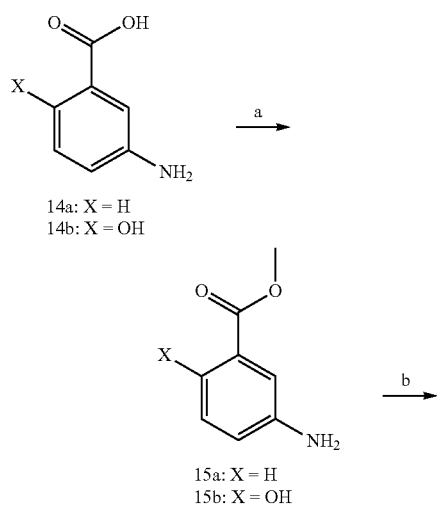

| Compd | $R_1$ | $R_2$ | Mcl-1 $K_i$ (μM) |
|---|---|---|---|
| LC-5-005 13da | H | (4-phenoxyphenyl) | 13.722 ± 1.050 |

Figure 17:
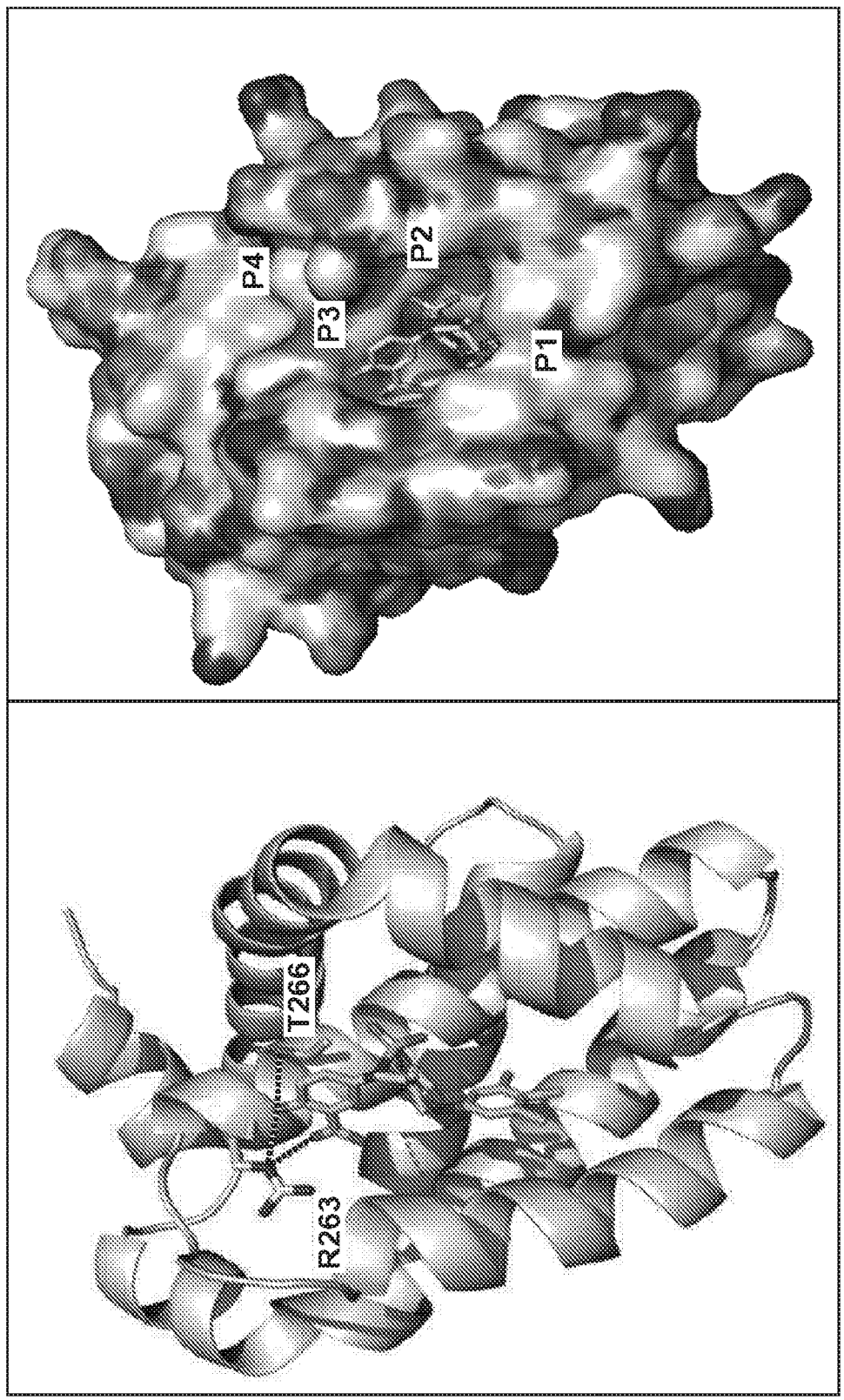
FIG. 17 illustrates the predicted binding of 5-aminosalicylate to Mcl-1.

Next, the relative position of carboxylic acid and hydroxyl group was further adjusted to investigate their impact on Mcl-1 binding affinity. Based on the predicted binding mode from FIG. 16, it seems legitimate to switch the position of carboxylic acid and hydroxyl group yet still maintaining the same polar contact with 8263 and T266, which rendered a new scaffold: 5-aminosalicylate. Another GOLD docking experiment was then conducted with the result shown in FIG. 17.

The 5-aminosalicylate molecule favorably fitted into the Mcl-1 binding pocket and developed polar interaction with R263 and T266 similar to the 4-aminosalicylate analog. Therefore, a library of 5-aminosalicylate analogs was designed and synthesized to validate the in silico model according to Scheme 5-3. Moreover, the hydroxyl group was also deleted, which converted them into 5-aminobenzoate molecules, to assess its contribution in this binding mode.

Scheme 5-3.

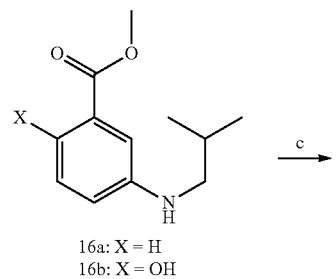

16a: X = H
16b: X = OH

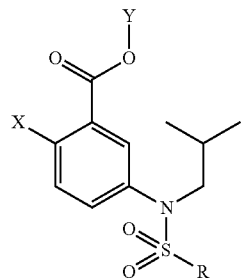

d ⎰ 17aa - 17ae: X = H, Y = Me
  ⎱ 18aa - 18ae: X = H, Y = H d ⎰ 17ba - 17bc: X = OH, Y = Me
  ⎱ 18ba - 18ac: X = OH, Y = H

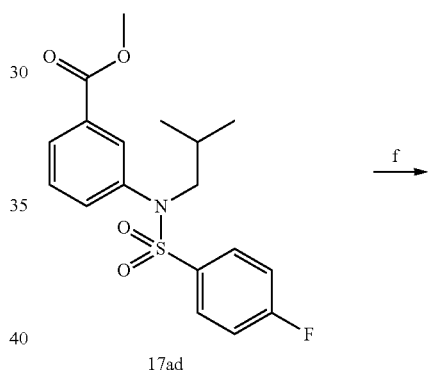

17ad

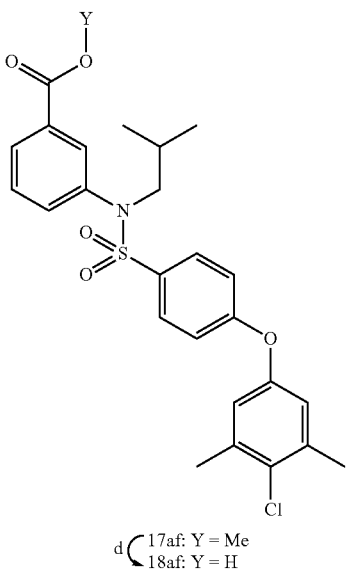

d ⎰ 17af: Y = Me
  ⎱ 18af: Y = H

189
-continued

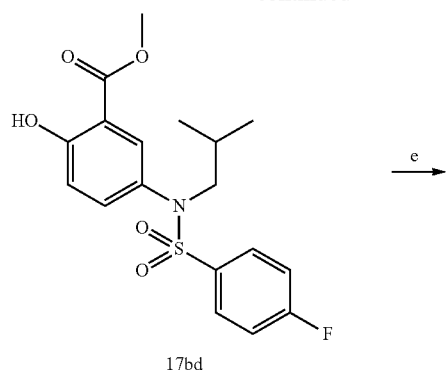

17bd

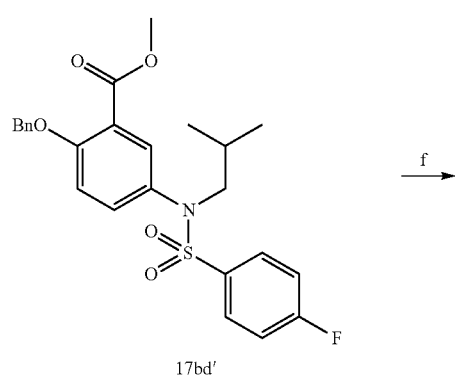

17bd'

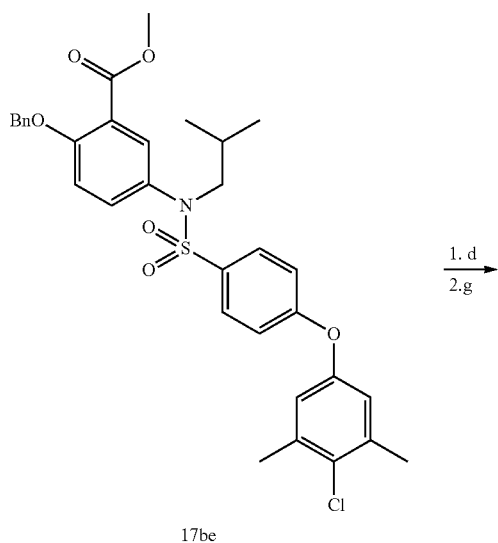

17be

190
-continued

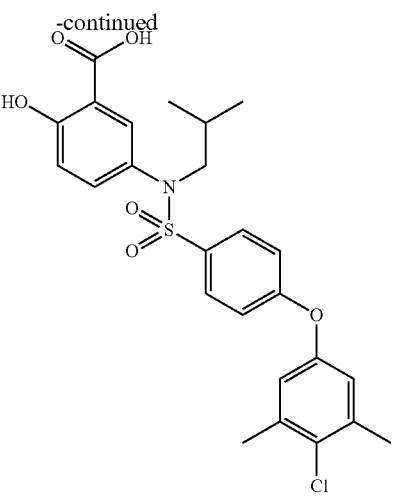

18be

Synthesis of 5-aminobenzoate and 5-aminosalicylate analogs. Reagents and conditions: (a) $H_2SO_4$, MeOH, 80° C., overnight; (b) Isobutyraldehyde, NaBH(OAc)$_3$, DCE, RT, overnight; (c) R—SO$_2$Cl, DIPEA, DMAP, CHCl$_3$, 60° C., overnight; (d) LiOH•H$_2$O, THF—MeOH—H$_2$O, 3:1:1, RT, overnight; (e) BnBr, KOtBu, DMF, RT, overnight; (f) 4-chloro-3, 5-dimethylphenol, K$_2$CO$_3$, DMSO, 100° C., overnight. (g) TFA, toluene, RT, overnight;

Esterification of 5-aminobenzoic acid 14a and 5-aminosalicylic acid 14b afforded compounds 15a and 15b. Reductive amination with isobutyraldehyde formed compounds 16a and 16b, which were further furnished by different R-sulfonyl chlorides to yield 17aa-17ad, and 17ba-17bc. The compounds were then subjected to saponification to yield final molecules 18aa-18ad, and 18ba-18bc. Also, compound 17ad was further elaborated on the fluorine by $S_NAr$ with 3,5-dimethyl-4-chloro-phenol, followed by basic hydrolysis to afford compound 18ae. In the case of 5-aminosalicylate, compound 17bd was first O-benzylated to give compound 17bd' before coupled with 3,5-dimethyl-4-chloro-phenol to afford 17be, and then underwent saponification and TFA debenzylation to yield final compound 18be.

The SAR analysis of both 5-aminobenzoate and 5-aminosalicylate derivatives were reported in Table 5-4. Comparing the left column of 5-aminobenzoates with the right column of 5-aminosalicylates, the pronounced differences of their $K_i$s demonstrate the compelling effect generated from hydroxyl group. Interestingly, in both classes, the 2-naphthyl analogs (18ab, 18bb) exhibited stronger binding affinity compared to 4-biphenyl analogs (18ac, 18bc), which was in a sharp contrast to the relationships in 4-aminobenzoate and 4-aminosalicylate scaffold. This may, for instance, be explained possibly by the change of binding direction potentially caused a collision of the 4-biphenyl moiety with the Mcl-1 hydrophobic pocket, while it guided the 2-naphthyl group to a favorable direction towards the pocket. The most potent compounds (18af and 18bd), which exhibited the $K_i$=1.45 µM and 586 nM, respectively, again carried the 3,5-dimethyl-4-chloro-phenoxy group.

TABLE 5-4

Mcl-1 binding affinity of 5-aminobenzoate and 5-aminosalicylate analogs.

| Compd | X | R | Mcl-1 $K_i$ (µM) |
|---|---|---|---|
| 4jc177-1 18aa | H | phenyl | >500 |
| 4jc177-3 18ab | H | 2-naphthyl | 61.659 ± 4.730 |
| 4jc177-4 18ac | H | 4-biphenyl | >500 |
| 4jc177-6 18ad | H | 4-fluorophenyl | >500 |
| 4jc177-2 18ae | H | 4-methylphenyl | 154.766 ± 14.670 |
| 4jc177-5 18af | H | 4-(4-chloro-3,5-dimethylphenoxy)phenyl | 1.454 ± 0.890 |
| JY-5-296 18ba | OH | phenyl | 46.468 ± 9.816 |
| jy-5-299 18bb | OH | 2-naphthyl | 7.509 ± 0.840 |
| JY-5-300 18bc | OH | 4-biphenyl | 8.704 ± 2.049 |
| JY-5-304 18bd | OH | 4-(4-chloro-3,5-dimethylphenoxy)phenyl | 0.586 ± 0.041 |

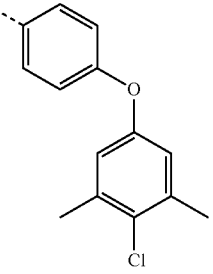

The carboxylic acid moiety may be an important factor in facilitating the MCL-1 protein binding. Therefore, it was anticipated that the carboxylic acid moiety on the benzoate and salicylate compounds may also be important for their potency. Also, the improved potency from 4/5-aminobenzoate to 4/5-aminosalicylate scaffold illustrated the contribution from hydroxyl group. Therefore, the function of carboxylic acid in the binding was explored by synthesizing its ester prodrugs as well as bioisosteres, and the hydroxyl group was methylated to test its impact on the compound's activity in Table 5-5. Apparently, substitution of the hydroxyl group (13ag) with methoxyl group (19) dramatically diminished the Mcl-1 binding affinity, suggesting that the H-bond donating effect from the hydroxyl group was more responsible for the polar interaction with Mcl-1 protein rather than H-bond accepting effect. Conversion of anionic carboxylic acid 13ag into neutral esters 20-22 negatively impacted their binding affinity, confirming its dominance in the formation of protein-ligand complex. On the contrary, bioisosteric replacement of carboxylic acid with different ionizable moieties yielded analogs with a wide range of potencies. Two of the most competent binders were the tetrazole analog 24 and the acyl sulfonamide analogs 27 and 28. Neither of salicylic nitrile 23 nor 3-hydroxyisoxazole 26 exhibited desirable potencies, while hydroxamic acid analog 25 turned out to be a moderate binder. These data indicated that the recognition of these different anionic moieties was associated with their conformational shapes, which is determined by the pointing direction acidic proton, as well as the distance between the proton and R263.

TABLE 5-5

Mcl-1 binding affinity of 4-aminosalicylates esters and bioisosteres.

| Compd | X | Y | R₁ | R₂ | Mcl-1 $K_i$ (μM) |
|---|---|---|---|---|---|
| LC-4-099 13ag | OH | HOOC- | isopropyl | phenyl | 5.8 ± 0.46 |
| LC-5-106 19 | OMe | HOOC- | isopropyl | phenyl | 106.70 ± 31.12 |
| LC-4-131 20 | OH | MeOOC- | isopropyl | phenyl | >500 |
| LC-4-134 21 | OH | PhOOC- | isopropyl | phenyl | >500 |
| LC-4-141 22 | OH | AcOCH₂OOC- | isopropyl | phenyl | >500 |
| LC-5-050 23 | OH | N≡C- | isopropyl | phenyl | >500 |
| LC-5-068 24 | H | tetrazolyl | isopropyl | phenyl | 3.3 ± 0.26 |
| LC-5-061 25 | OH | HO-NH-C(O)- | isopropyl | phenyl | 71 ± 5.8 |
| LC-5-069Toptop 26 | H | isoxazolone | isopropyl | phenyl | >500 |
| LC-5-112 27 | OH | MeSO₂-NH-C(O)- | benzyl | phenyl | 2.94 ± 0.35 |

TABLE 5-5-continued

Mcl-1 binding affinity of 4-aminosalicylates esters and bioisosteres.

| Compd | X | Y | R₁ | R₂ | Mcl-1 $K_i$ (μM) |
|---|---|---|---|---|---|
| LC-5-096 28 | OH | phenylsulfonyl-NH-C(O)- | benzyl | phenyl | 1.9 ± 0.22 |

Figure 18:
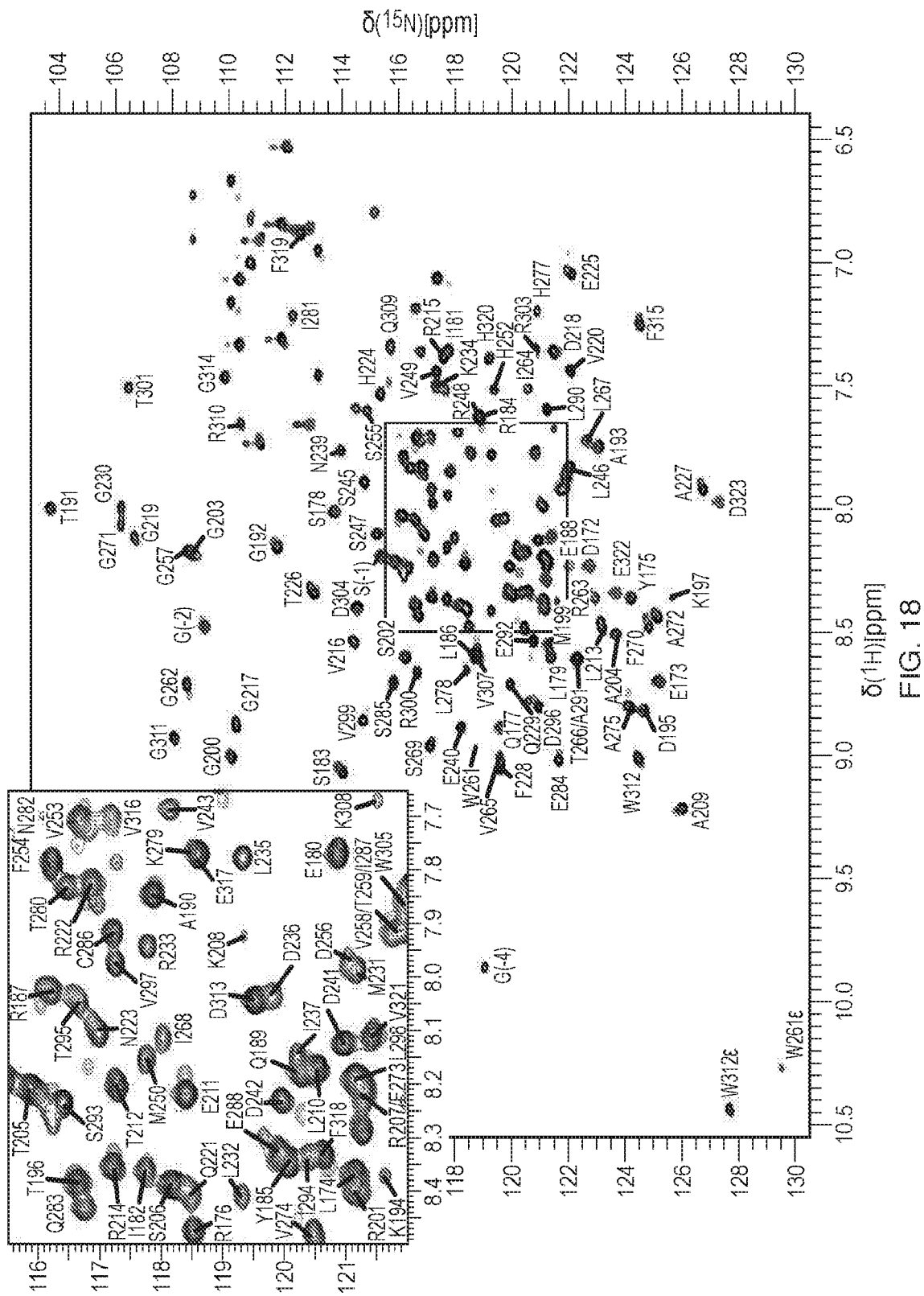
FIG. 18 illustrates a 2D 1H-15N HSQC spectra of apo-Mcl-1 collected in the absence and presence of 13ak.
Figure 19:
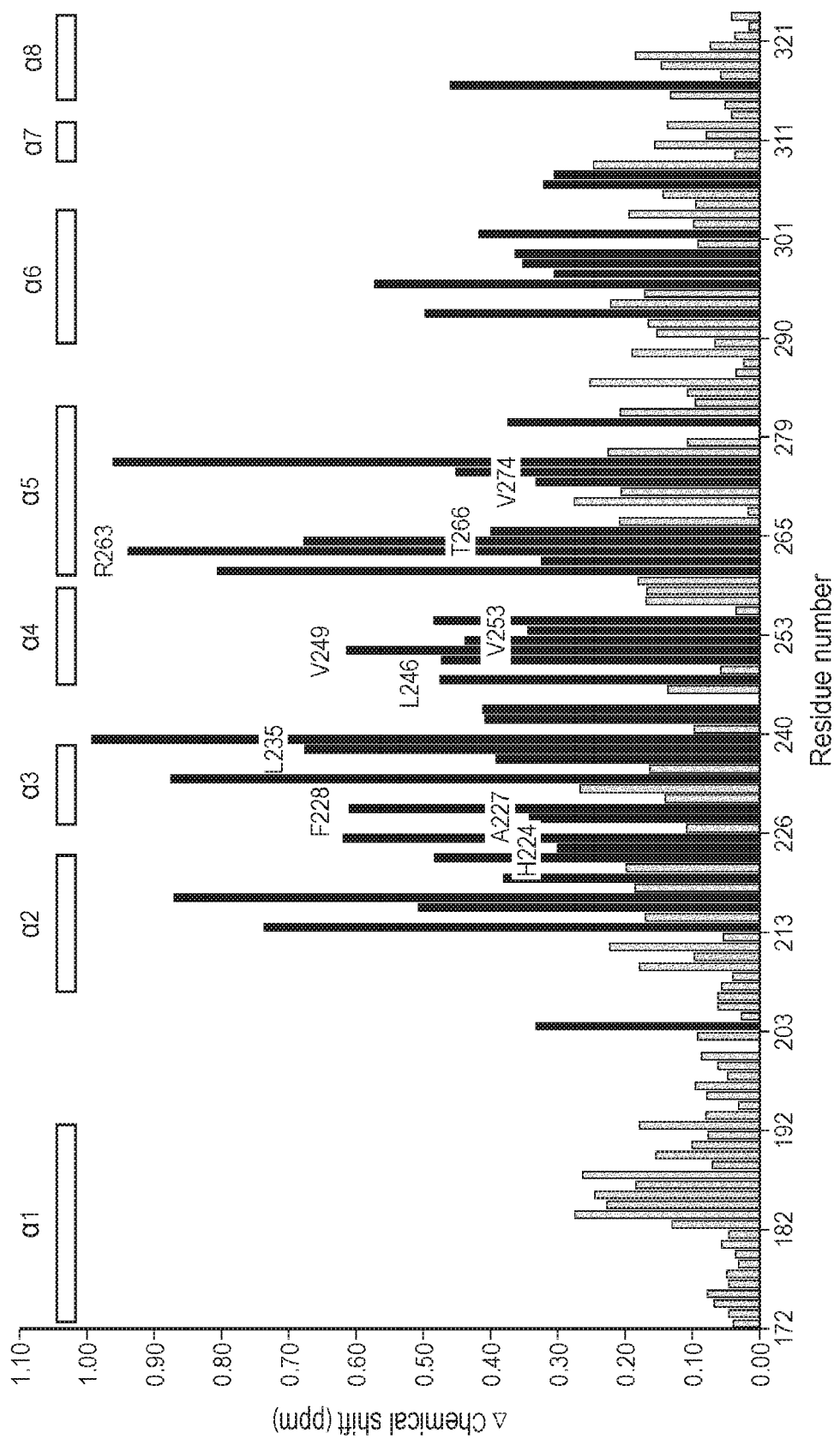
FIG. 19 illustrates a plot of chemical shift of Mcl-1 protein upon 13ak binding, where black columns are the amino residues that were significantly perturbed (Δ chemical shift >0.3 ppm).
Figure 20:
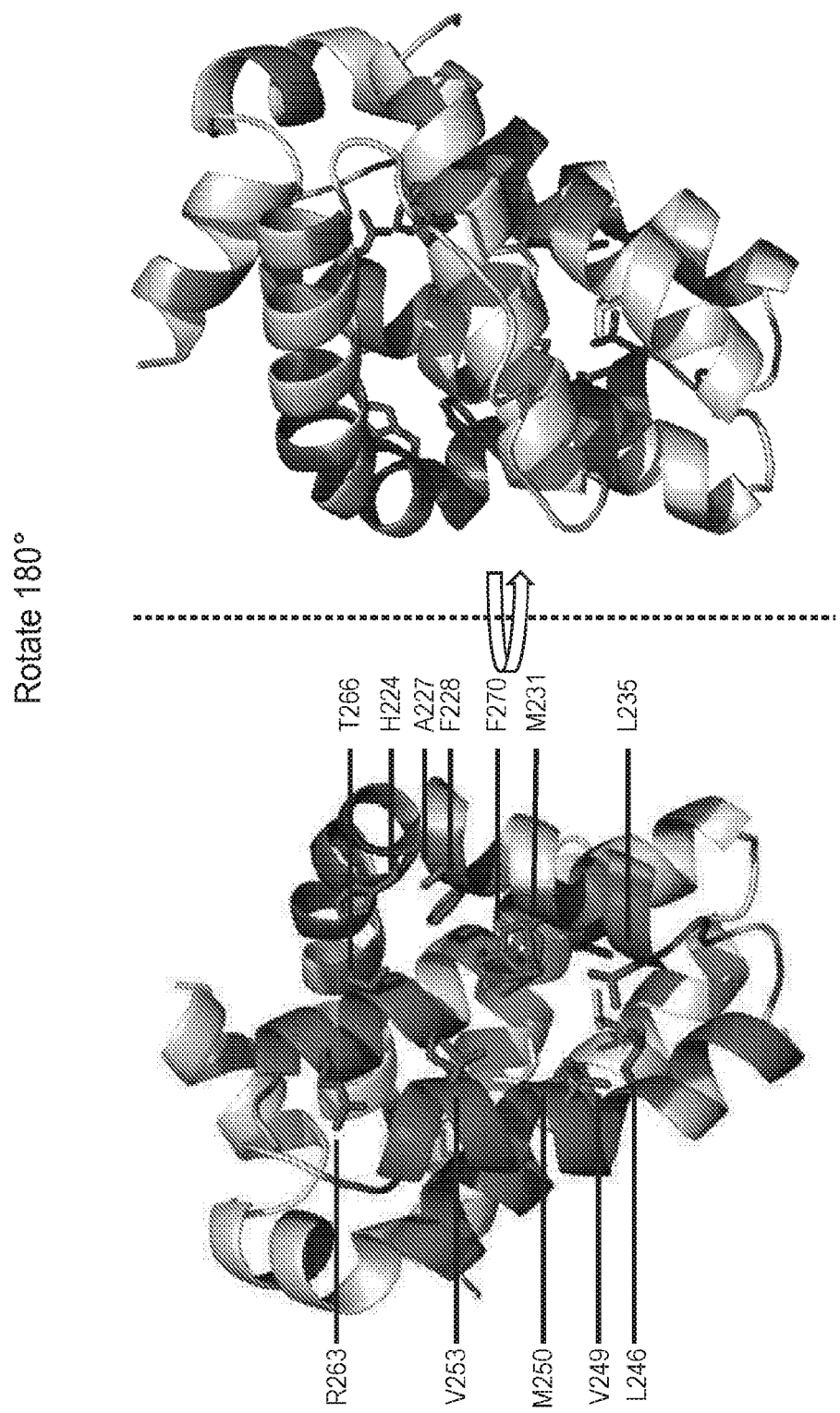
FIG. 20 illustrates NMR chemical shift perturbations of the MCL-1/13ak complex mapped onto MCL-1 crystal coordinates (PDB ID: 4HW3) in PyMOL. Residues experiencing chemical shifts of at least 0.3 ppm are shaded.

To further validate the Mcl-1 binding pattern of the molecules discussed above, one representative compound 13ak was examined by HSQC-NMR studies with Mcl-1 and the result was shown in FIGS. 18, 19, and 20. The 2D $^1$H—$^{15}$N HSQC spectra of Mcl-1 was collected with 13ak and without 13ak. It clearly showed that R263 and T266 were both perturbed upon the binding of the compound. Moreover, the majority of hydrophobic residues in the p2 binding pocket, which was formed by Mcl-1 protein helixes α2 to α6, were heavily perturbed as showing in red (Δ chemical shift >0.3 ppm). In the meantime, the rest of residues located far from the p2 pocket were not interfere as showing gray, further confirming the proposed binding pattern in FIG. 16.

The selectivity of 4-aminosalicylate and 5-aminosalicylate analogs is shown in Table 5-6. Most compounds exhibited weak to moderate selectivity against Bcl-$x_L$, indicating their dual Mcl-1/Bcl-$x_L$ inhibition profile. Generally, the compounds' binding affinity for Bcl-$x_L$ increased along with the development of stronger potency for Mcl-1 inhibition. Comparing the 4-aminosalicylate analogs, changing R₂ group (13aa, 13ab, 13ac, 13ag and 13ak) had little effects on selectivity. Substitution of R₁ group (13ak, 13bc, and 13cc) exhibited a very subtle response on the selectivity as well, with the benzyl substitution analog 13cc being the most selective inhibitor and the cyclopentyl analog 13bc being an equal potent inhibitor for both proteins. For the 5-aminosalicylate analogs, the R₂ group had a slightly greater impact on the selectivity, particularly when R₂ were 2-naphthyl 18bb and 3,5-dimethyl-4-chloro-phenoxyl group (18bd). Contrastingly, substituting the R₁ with a benzyl group on the 5-aminosalicylate scaffold (29) decreased the selectivity dramatically to yield a Mcl-1/Bcl-$x_L$ dual inhibitor.

TABLE 5-6

The selectivity of Mcl-1 against Bcl-xL for 4-aminosalicylate and 5-aminosalicylate analogs.

| Compd | X | Y | R₁ | R₂ | Mcl-1 $K_i$ (μM) | Bcl-xL $K_i$ (μM) | $K_i$(Mcl-1): $K_i$(Bcl-xL) |
|---|---|---|---|---|---|---|---|
| 4jc117-1 13aa | OH | HOOC-CH< | isobutyl | H | 192.038 ± 37.534 | 154.181 ± 27.596 | 1:0.80 |

TABLE 5-6-continued

The selectivity of Mcl-1 against Bcl-xL for 4-aminosalicylate and 5-aminosalicylate analogs.

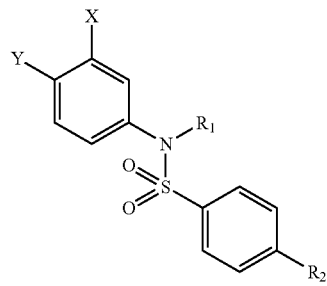

| Compd | X | Y | R₁ | R₂ | Mcl-1 K$_i$ (μM) | Bcl-xL K$_i$ (μM) | K$_i$(Mcl-1):K$_i$(Bcl-xL) |
|---|---|---|---|---|---|---|---|
| 4jc117-3 13ab | OH | HOOC- | isobutyl | phenyl | 13.821 ± 1.325 | 43.130 ± 14.668 | 1:3.12 |
| 4jc117-4 13ac | OH | HOOC- | isobutyl | phenyl | 4.109 ± 0.245 | 10.781 ± 2.553 | 1:2.63 |
| LC-4-099 13ag | OH | HOOC- | isobutyl | phenoxy | 5.766 ± 0.458 | 17.996 ± 4.602 | 1:3.12 |
| 4jc117-5 13ak | OH | HOOC- | isobutyl | 4-Cl-3,5-dimethylphenoxy | 0.778 ± 0.050 | 1.629 ± 0.177 | 1:2.09 |
| LC-4-104 13bc | OH | HOOC- | cyclopentylmethyl | 4-Cl-3,5-dimethylphenoxy | 1.762 ± 0.208 | 1.911 ± 0.117 | 1:1.08 |
| LC-4-118 13cc | OH | HOOC- | benzyl | 4-Cl-3,5-dimethylphenoxy | 0.629 ± 0.040 | 1.672 ± 0.351 | 1:2.65 |
| jy-5-296 18ba | HOOC- | OH | isobutyl | H | 46.468 ± 9.816 | 49.331 ± 5.026 | 1:1.06 |
| jy-5-299 18bb | HOOC- | OH | isobutyl | phenyl | 7.509 ± 0.840 | 44.636 ± 5.929 | 1:5.94 |

TABLE 5-6-continued

The selectivity of Mcl-1 against Bcl-xL for 4-aminosalicylate and 5-aminosalicylate analogs.

| Compd | X | Y | R$_1$ | R$_2$ | Mcl-1 K$_i$ (μM) | Bcl-xL K$_i$ (μM) | K$_i$(Mcl-1): K$_i$(Bcl-xL) |
|---|---|---|---|---|---|---|---|
| JY-5-300 18bc | HOOC- | OH | isopropyl | phenyl | 8.704 ± 2.049 | 13.851 ± 3.364 | 1:1.59 |
| JY-5-304 18bd | HOOC- | OH | isopropyl | 3,5-dimethyl-4-chlorophenoxy | 0.586 ± 0.041 | 2.905 ± 0.191 | 1:4.96 |
| LC-5-129 29 | HOOC- | OH | benzyl | 3,5-dimethyl-4-chlorophenoxy | 1.40 ± 0.47 | 1.816 ± 0.234 | 1:1.30 |

Additionally, a new hybrid molecule that fuses a Bcl-2 p4 moiety with a Mcl-1 p2 binding moiety through an acyl sulfonamide bond was developed.

In order to explore the SAR of this hybrid molecule, a library of analogs have been designed and synthesized in Table 5-7. First of all, various acyl sulfonamides were installed to compare their activity on both Mcl-1 and Bcl-x$_L$ (27, 28, 30, 31 and 32). Expansion of moiety size on the Y-position can completely revert the analog's selectivity profile, from selective against Bcl-xL (27), to dual Mcl-1/Bcl-xL inhibitor (28) and selective against Mcl-1 (29). During this process, the potency for both Mcl-1 and Bcl-x$_L$ was also increased from compound 27 to 30. Therefore, further optimization on the R$_2$ group with 3,5-dimethyl-4-phenol was expected to afford a more potent compound 31, with K$_i$ (Mcl-1)=800 nM and a slightly increased selectivity against Bcl-x$_L$. The identical Mcl-1/Bcl-x$_L$ inhibition profile between acyl sulfonamide compound 31 and carboxylic acid compound 13cc again demonstrated the bioisosteric character of acyl sulfonamide group. Further extending the Bcl-2 p4 moiety through an additional benzene sulfonamide linker generated the most potent dual Mcl-1/Bcl-x$_L$ inhibitor 32, with K$_i$ (Mcl-1)=493 nM and K$_i$ (Bcl-x$_L$)=835 nM. This suggested that the length of p4 moiety can be further optimized to improve the potency of these molecules. Also, the corresponding hybrid compound for 5-aminosalicylate compound was also synthesized (33) and exhibited very similar potency compared to its carboxylic acid analog 29. Finally, the different merging location was tested by synthesizing compound 34, which the Bcl-2 p4 moiety was merged onto the hydroxyl group position, similar to the merging position of Tanaka's molecule. However, this method of merging lessened the compound's Mcl-1 and Bcl-xL binding affinity compared to compound 13cc, suggesting that the carboxylic acid is the optimal position for this hybridization strategy.

TABLE 5-7
The selectivity of Mcl-1 over Bcl-xL when substituting carboxylic acid with various acyl sulfonamides.
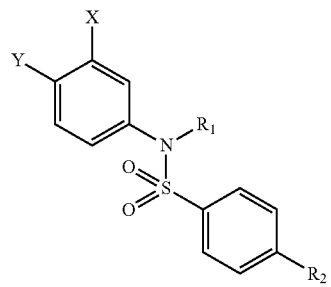
| Compd | X | Y | R₁ |
|---|---|---|---|
| LC-4-118 13cc | OH | HOOC– | phenyl (benzyl) |
| LC-5-112 27 | OH | CH₃SO₂NHC(O)– | phenyl (benzyl) |
| LC-5-096 28 | OH | PhSO₂NHC(O)– | phenyl (benzyl) |
| LC-5-107 30 | OH | 4-((tetrahydropyran-4-yl)methylamino)-3-nitrophenyl-SO₂NHC(O)– | phenyl (benzyl) |
| LC-5-131 31 | OH | 4-((tetrahydropyran-4-yl)methylamino)-3-nitrophenyl-SO₂NHC(O)– | phenyl (benzyl) |

TABLE 5-7-continued
The selectivity of Mcl-1 over Bcl-xL when substituting carboxylic acid with various acyl sulfonamides.
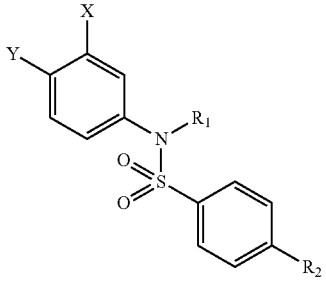
| Compd | X | Y | R₁ | R₂ | Mcl-1 K_i(μM) | Bcl-xL K_i(μM) | K_i(Mcl-1):K_i(Bcl-xL) |
|---|---|---|---|---|---|---|---|
| LC-5-175 32 | OH | | 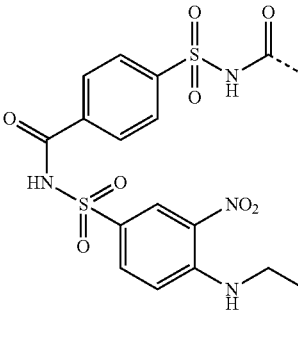 |  | | | |
| LC-5-129 29 |  | | OH | 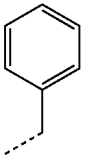 | | | |
| LC-5-132 33 | 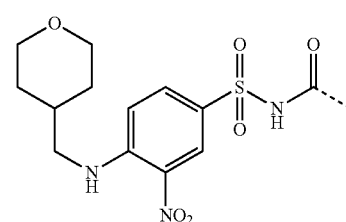 | | OH | 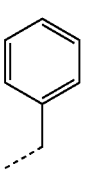 | | | |
| LC-5-111 34 | 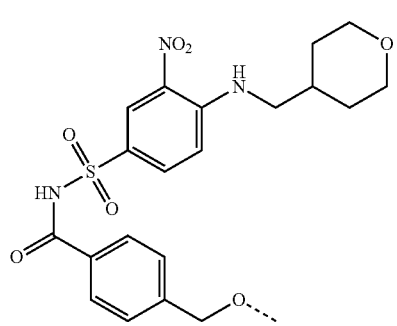 | |  | 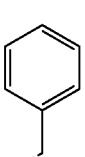 | | | |
| LC-4-118 13cc | | | | 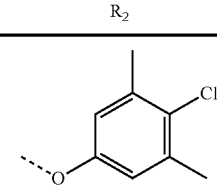 | 0.629 ± 0.040 | 1.672 ± 0.351 | 1:2.65 |

TABLE 5-7-continued
The selectivity of Mcl-1 over Bcl-xL when substituting carboxylic acid with various acyl sulfonamides.
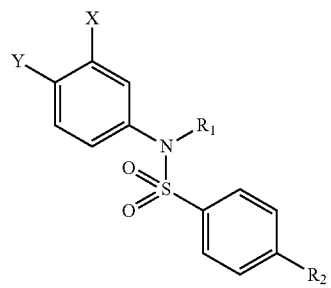
| | | | | |
|---|---|---|---|---|
| LC-5-112 27 | (phenoxy) | 2.94 ± 0.35 | 7.223 ± 1.072 | 1:2.45 |
| LC-5-096 28 | (phenoxy) | 1.945 ± 0.222 | 2.336 ± 0.221 | 1:1.20 |
| LC-5-107 30 | (phenoxy) | 1.232 ± 0.152 | 1.053 ± 0.146 | 1:0.85 |
| LC-5-131 31 | (4-chloro-3,5-dimethylphenoxy) | 0.80 ± 0.07 | 1.615 ± 0.176 | 1:2.02 |
| LC-5-175 32 | (4-chloro-3,5-dimethylphenoxy) | 0.493 ± 0.031 | 0.835 ± 0.086 | 1:1.69 |
| LC-5-129 29 | (4-chloro-3,5-dimethylphenoxy) | 1.40 ± 0.47 | 1.816 ± 0.234 | 1:1.30 |
| LC-5-132 33 | (4-chloro-3,5-dimethylphenoxy) | 1.01 ± 0.08 | 1.535 ± 0.226 | 1:1.52 |
| LC-5-111 34 | (4-chloro-3,5-dimethylphenoxy) | 8.55 ± 1.53 | 3.196 ± 1.883 | 1:0.37 |

TABLE 5-8

Selectivity of Mcl-1 against Bcl-xL when varying the linker.

| Compd | R₁ | L | Mcl-1K$_i$ (μM) | Bcl-xLK$_i$ (μM) | K$_i$ (Mcl-1):K$_i$ (Bcl-xL) |
|---|---|---|---|---|---|
| LC-4-118 13cc | benzyl | -SO₂-(p-phenylene)- | 0.629 ± 0.040 | 1.672 ± 0.351 | 1:2.66 |
| LC-5-188 35 | benzyl | -(CH₂)₃- | 1.445 ± 16.644 | 2.984 ± 0.406 | 1:2.06 |
| LC-5-184 36 | H | -(CH₂)₃- | 15.247 ± 1.891 | 22.713 ± 4.083 | 1:1.49 |

The impact of using a different linker group was also evaluated by replacing the sulfonamide group with a C-3 alkyl linker (35). Similar to the Mcl-1 inhibition resulting from the THQ scaffold, a sulfonamide linker increased the binding affinity for Mcl-1 from the C-3 alkyl linker. It also improved the compound's Bcl-x$_L$ binding affinity at the same time. Again, a hydrophobic R₁ group was desirable for the potency as compared to a hydrogen atom (36).

TABLE 5-9

Cell viability of HL-60 cell line after treating with inhibitors for 24 hrs.

| Compd | X | Y | R₁ | R₂ |
|---|---|---|---|---|
| LC-4-099 13ag | OH | -C(O)OH | isopropyl | -O-phenyl |

TABLE 5-9-continued

Cell viability of HL-60 cell line after treating with inhibitors for 24 hrs.

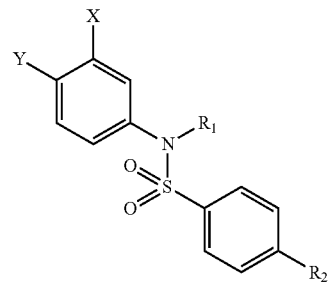

| | | | | |
|---|---|---|---|---|
| LC-4-131 20 | OH | methyl ester | isobutyl | phenoxy |
| LC-4-141 21 | OH | acetoxymethyl ester | isobutyl | phenoxy |
| LC-4-118 13cc | OH | COOH | benzyl | 4-chloro-3,5-dimethylphenoxy |
| LC-5-188 35 | OH | COOH | benzyl | 4-chloro-3,5-dimethyl-(propyl)phenyl |
| JY-5-304 18bd | COOH | OH | isobutyl | 4-chloro-3,5-dimethylphenoxy |
| LC-5-131 31 | OH | tetrahydropyranylmethylamino-nitro-phenyl sulfonamide acyl | benzyl | 4-chloro-3,5-dimethylphenoxy |

TABLE 5-9-continued

Cell viability of HL-60 cell line after treating with inhibitors for 24 hrs.

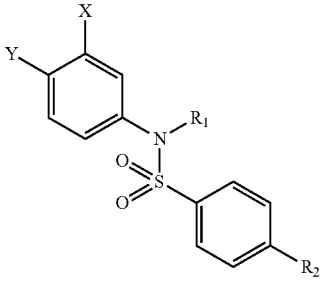

| Compd | Mcl-1 $K_i$ (µM) | Bcl-xL$K_i$ (µM) | HL-60 IC$_{50}$ (µM) 0.5% FBS | HL-60 IC$_{50}$ (µM) 10% FBS |
|---|---|---|---|---|
| LC-4-099 13ag | 5.766 ± 0.458 | 17.996 ± 4.602 | 18.51 | >120 |
| LC-4-131 20 | >500 | N.A | 68.07 | 76.42 |
| LC-4-141 21 | >500 | N.A | 46.42 | >120 |
| LC-4-118 13cc | 0.629 ± 0.040 | 1.672 ± 0.351 | <7.5 | 53.2 |
| LC-5-188 35 | 1.445 ± 16.644 | 2.984 ± 0.406 | 7.359 | 88.01 |
| JY-5-304 18bd | 0.586 ± 0.041 | 2.905 ± 0.191 | 9.817 | >120 |
| LC-5-131 31 | 0.80 ± 0.07 | 1.615 ± 0.176 | 9.965 | >120 |
| LC-5-175 32 | 0.493 ± 0.031 | 0.835 ± 0.086 | 16.74 | >120 |

Next, the most potent compounds were evaluated for their ability to kill human acute promyelocytic leukemia cell line HL-60, which has been reported to be more sensitive to Mcl-1 blockade than Bcl-2/Bcl-xL blockade, and most sensitive when a broad range of Bcl-2 pro-apoptotic proteins were inhibited including Bcl-2, Bcl-xL and Mcl-1. All the carboxylic acid and acyl sulfonamide compounds showed dose dependent cell growth inhibition with IC$_{50}$ ranging from less than 7.5 µM to 18.51 µM in the 0.5% fetal bovine serum environment. They all showed heavy serum binding when 10% of FBS was added to the culture environment, with a 10-fold or more drop in IC$_{50}$. The moderate cell grow inhibition ability for the two carboxylic acid ester prodrugs 20 and 21 could be attributed to the enzymatic hydrolysis that generated a free acid molecule (13ag) to function as an Mcl-1 inhibitor in the cells. The data also suggested that the acidic salicylate analogs were cell penetrable, which can be due to the formation of an intramolecular hydrogen bond with the ortho position phenol group to mask the negative charge and make the molecule less polar and more cell penetrable. Interestingly, the most potent Mcl-1/Bcl-xL dual inhibitor 32 was less effective in cell growth inhibition than compound 13cc, indicating other survival proteins might also affected with these inhibitors, Example 6

Inhibitors of the Mcl-1 Oncoprotein Based on Carboxy-Substituted Salicyclate Scaffolds Salicylate Functionalized salicylates inhibit the Mcl-1 oncoprotein, as determined by the fluorescence polarization competition assay as described herein. Various functionalized salicylates were prepared and tested as provided hereinbelow in Tables 6-1, 6-2, and 6-3.

Table 6-1. Exemplary functionalized salicylate analogs with their associated Mcl-1 and Bcl-x$_L$ inhibitory activities.

TABLE 6-2

Exemplary functionalized salicylate analogs with their associated Mcl-1 and Bcl-x$_L$ inhibitory activities.

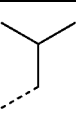

| Compd | R² | R¹ | K$_i$ (μM) Mcl-1 | Bcl-xL |
|---|---|---|---|---|
| LC-3-029 | 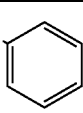 |  | ND | ND |
| LC-3-031 | 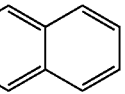 |  | ND | ND |
| LC-3-030 | 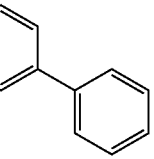 | 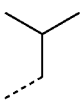 | ND | ND |
| LC-3-025 | 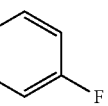 | 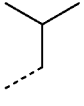 | ND | ND |
| LC-3-035 | 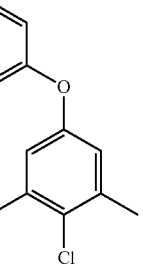 | 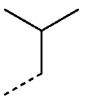 | 0.261 ± 0.558 | ND |

TABLE 6-2-continued

Exemplary functionalized salicylate analogs with their associated Mcl-1 and Bcl-x$_L$ inhibitory activities.

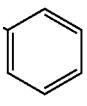

| Compd | R² | R¹ | K$_i$ (μM) Mcl-1 | Bcl-xL |
|---|---|---|---|---|
| 4jc117-1 | 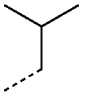 | 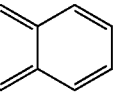 | NA | NA |
| 4jc117-3 | | 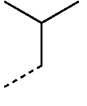 | 60.300 ± 24.434 | ND |
| 4jc117-4 | | 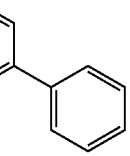 | 7.872 ± 0.263 | ND |
| | | 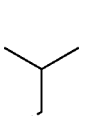 | ND | ND |
| 4jc117-6 | | 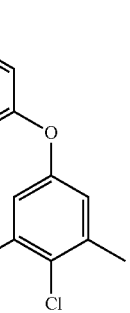 | 0.020 ± 0.012 | 0.05 ± 0.01 |

TABLE 6-3
Exemplary functionalized salicylate analogs with their associated Mcl-1 and Bcl-$x_L$ inhibitory activities
| Compd | R² | R¹ | K$_i$ (μM) Mcl-1 | Bcl-xL |
|---|---|---|---|---|
| 4jc117-2 |  |  | 301.875 ± 31.826 | ND |
| LC-4-099 | 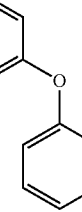 |  | ND | ND |
| LC-4-111 | 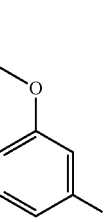 |  | ND | ND |
| LC-4-119 | 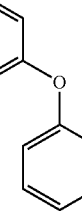 |  | ND | ND |
| LC-4-100 | | 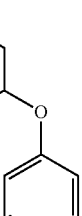 | ND | ND |

TABLE 6-3-continued

Exemplary functionalized salicylate analogs with their associated Mcl-1 and Bcl-x$_L$ inhibitory activities

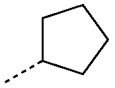

| | | | K$_i$ (µM) | |
| --- | --- | --- | --- | --- |
| Compd | R$^2$ | R$^1$ | Mcl-1 | Bcl-xL |
| LC-4-104 | 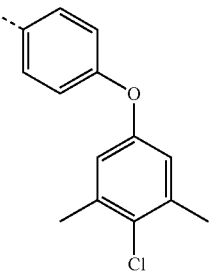 | 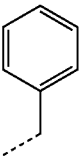 | ND | ND |
| LC-4-118 | 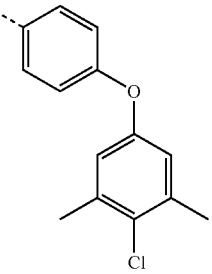 | 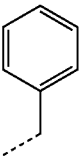 | ND | ND |

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of."

REFERENCES (1) Adams, J. M.; Cory, S. The Bcl-2 Apoptotic Switch in Cancer Development and Therapy. *Oncogene* 2007, 26, 1324-1337.

(2) Youle, R. J.; Strasser, A. The BCL-2 Protein Family: Opposing Activities That Mediate Cell Death. *Nat. Rev. Mol. Cell Biol.* 2008, 9, 47-59.

(3) Wang, S. The Promise of Cancer Therapeutics Targeting the TNF-Related Apoptosis-Inducing Ligand and TRAIL Receptor Pathway. *Oncogene* 2008, 27, 6207-6215.

(4) Oltersdorf, T.; Elmore, S. W.; Shoemaker, A. R.; Armstrong, R. C.; Augeri, D. J.; Belli, B. A.; Bruncko, M.; Deckwerth, T. L.; Dinges, J.; Hajduk, P. J.; Joseph, M. K.; Kitada, S.; Korsmeyer, S. J.; Kunzer, A. R.; Letai, A.; Li, C.; Mitten, M. J.; Nettesheim, D. G.; Ng, S.; Nimmer, P. M.; O'Connor, J. M.; Oleksijew, A.; Petros, A. M.; Reed, J. C.; Shen, W.; Tahir, S. K.; Thompson, C. B.; Tomaselli, K. J.; Wang, B.; Wendt, M. D.; Zhang, H.; Fesik, S. W.; Rosenberg, S. H. An Inhibitor of Bcl-2 Family Proteins Induces Regression of Solid Tumours. *Nature* 2005, 435, 677-681.

(5) Vogler, M.; Dinsdale, D.; Dyer, M. J. S.; Cohen, G. M. Bcl-2 Inhibitors: Small Molecules with a Big Impact on Cancer Therapy. *Cell Death Differ.* 2009, 16, 360-367.

(6) Billard, C. BH3 Mimetics: Status of the Field and New Developments. *Mol. Cancer Ther.* 2013, 12, 1691-1700.

(7) Lessene, G.; Czabotar, P. E.; Colman, P. M. BCL-2 Family Antagonists for Cancer Therapy. *Nat Rev Drug Discov* 2008, 7, 989-1000.

(8) Wilson, W. H.; O'Connor, O. A.; Czuczman, M. S.; LaCasce, A. S.; Gerecitano, J. F.; Leonard, J. P.; Tulpule, A.; Dunleavy, K.; Xiong, H.; Chiu, Y.-L.; Cui, Y.; Busman, T.; Elmore, S. W.; Rosenberg, S. H.; Krivoshik, A. P.; Enschede, S. H.; Humerickhouse, R. A. Navitoclax, a Targeted High-Affinity Inhibitor of BCL-2, in Lymphoid Malignancies: a Phase 1 Dose-Escalation Study of Safety, Pharmacokinetics, Pharmacodynamics, and Antitumour Activity. *Lancet Oncol.* 2010, 11, 1149-1159.

(9) Gandhi, L.; Camidge, D. R.; Ribeiro de Oliveira, M.; Bonomi, P.; Gandara, D.; Khaira, D.; Hann, C. L.; McKeegan, E. M.; Litvinovich, E.; Hemken, P. M.; Dive, C.; Enschede, S. H.; Nolan, C.; Chiu, Y.-L.; Busman, T.; Xiong, H.; Krivoshik, A. P.; Humerickhouse, R.; Shapiro, G. I.; Rudin, C. M. Phase I Study of Navitoclax (ABT-263), a Novel Bcl-2 Family Inhibitor, in Patients with Small-Cell Lung Cancer and Other Solid Tumors. *J. Clin. Oncol.* 2011, 29, 909-916.

(10) Rudin, C. M.; Hann, C. L.; Garon, E. B.; Ribeiro de Oliveira, M.; Bonomi, P. D.; Camidge, D. R.; Chu, Q.; Giaccone, G.; Khaira, D.; Ramalingam, S. S.; Ranson, M. R.; Dive, C.; McKeegan, E. M.; Chyla, B. J.; Dowell, B. L.; Chakravartty, A.; Nolan, C. E.; Rudersdorf, N.; Busman, T. A.; Mabry, M. H.; Krivoshik, A. P.; Humerickhouse, R. A.; Shapiro, G. I.; Gandhi, L. Phase II Study of Single-Agent Navitoclax (ABT-263) and Biomarker Correlates in Patients with Relapsed Small Cell Lung Cancer. *Clin. Cancer Res.* 2012, 18, 3163-3169.

(11) Roberts, A. W.; Seymour, J. F.; Brown, J. R.; Wierda, W. G.; Kipps, T. J.; Khaw, S. L.; Carney, D. A.; He, S. Z.; Huang, D. C. S.; Xiong, H.; Cui, Y.; Busman, T. A.; McKeegan, E. M.; Krivoshik, A. P.; Enschede, S. H.; Humerickhouse, R. Substantial Susceptibility of Chronic Lymphocytic Leukemia to BCL2 Inhibition: Results of a Phase I Study of Navitoclax in Patients with Relapsed or Refractory Disease. *J. Clin. Oncol.* 2012, 30, 488-496.

(12) Warr, M. R.; Shore, G. C. Unique Biology of Mcl-1: Therapeutic Opportunities in Cancer. *Curr. Mol. Med.* 2008, 8, 138-147.

(13) Backus, H. H.; van Riel, J. M.; van Groeningen, C. J.; Vos, W.; Dukers, D. F.; Bloemena, E.; Wouters, D.; Pinedo, H. M.; Peters, G. J. Rb, Mcl-1 and P53 Expression Correlate with Clinical Outcome in Patients with Liver Metastases From Colorectal Cancer. *Ann. Oncol.* 2001, 12, 779-785.

(14) Song, L.; Coppola, D.; Livingston, S.; Cress, W. D.; Haura, E. B. Mcl-1 Regulates Survival and Sensitivity to Diverse Apoptotic Stimuli in Human Non-Small Cell Lung Cancer Cells. *Cancer Biology & Therapy* 2004, 4, 267-276.

(15) Song, L.; Coppola, D.; Livingston, S.; Cress, D.; Haura, E. B. Mcl-1 Regulates Survival and Sensitivity to Diverse Apoptotic Stimuli in Human Non-Small Cell Lung Cancer Cells. *Cancer Biology & Therapy* 2005, 4, 267-276.

(16) Ding, Q.; He, X.; Xia, W.; Hsu, J.-M.; Chen, C.-T.; Li, L.-Y.; Lee, D.-F.; Yang, J.-Y.; Xie, X.; Liu, J.-C.; Hung, M.-C. Myeloid Cell Leukemia-1 Inversely Correlates with Glycogen Synthase Kinase-3beta Activity and Associates with Poor Prognosis in Human Breast Cancer. *Cancer Res.* 2007, 67, 4564-4571.

(17) Y, M.; R, H.; M, W.; JU, L.; T, K.; K, F.; S, T.; S, N.; R, D.; M, K.; Y, S.; M, I. Immunohistochemical Analysis of Bcl-2, Bax, Bcl-X, and Mcl-1 Expression in Pancreatic Cancers. *Oncology* 1998, 56, 73-82.

(18) Zhang, T.; Zhao, C.; Luo, L.; Zhao, H.; Cheng, J.; Xu, F. The Expression of Mcl-1 in Human Cervical Cancer and Its Clinical Significance. *Med. Oncol.* 2012, 29, 1985-1991.

(19) Brotin, E.; Meryet-Figuière, M.; Simonin, K.; Duval, R. E.; Villedieu, M.; Leroy-Dudal, J.; Saison-Behmoaras, E.; Gauduchon, P.; Denoyelle, C.; Poulain, L. Bcl-XL and MCL-1 Constitute Pertinent Targets in Ovarian Carcinoma and Their Concomitant Inhibition Is Sufficient to Induce Apoptosis. *Int. J. Cancer* 2010, 126, 885-895.

(20) Glaser, S. P.; Lee, E. F.; Trounson, E.; Bouillet, P.; Wei, A.; Fairlie, W. D.; Izon, D. J.; Zuber, J.; Rappaport, A. R.; Herold, M. J.; Alexander, W. S.; Lowe, S. W.; Robb, L.; Strasser, A. Anti-Apoptotic Mcl-1 Is Essential for the Development and Sustained Growth of Acute Myeloid Leukemia. *Genes Dev.* 2012, 26, 120-125.

(21) Wenzel, S.-S.; Grau, M.; Mavis, C.; Hailfinger, S.; Wolf, A.; Madle, H.; Deeb, G.; Dörken, B.; Thome, M.; Lenz, P.; Dirnhofer, S.; Hernandez-Ilizaliturri, F. J.; Tzankov, A.; Lenz, G. MCL1 Is Deregulated in Subgroups of Diffuse Large B-Cell Lymphoma. *Leukemia* 2013, 27, 1381-1390.

(22) Konopleva, M.; Contractor, R.; Tsao, T.; Samudio, I.; Ruvolo, P. P.; Kitada, S.; Deng, X.; Zhai, D.; Shi, Y.-X.; Sneed, T.; Verhaegen, M.; Soengas, M.; Ruvolo, V. R.; McQueen, T.; Schober, W. D.; Watt, J. C.; Jiffar, T.; Ling, X.; Marini, F. C.; Harris, D.; Dietrich, M.; Estrov, Z.; McCubrey, J.; May, W. S.; Reed, J. C.; Andreeff, M. Mechanisms of Apoptosis Sensitivity and Resistance to the BH3 Mimetic ABT-737 in Acute Myeloid Leukemia. *Cancer Cell* 2006, 10, 375-388.

(23) van Delft, M. F.; Wei, A. H.; Mason, K. D.; Vandenberg, C. J.; Chen, L.; Czabotar, P. E.; Willis, S. N.; Scott, C. L.; Day, C. L.; Cory, S.; Adams, J. M.; Roberts, A. W.; Huang, D. C. S. The BH3 Mimetic ABT-737 Targets Selective Bcl-2 Proteins and Efficiently Induces Apoptosis via Bak/Bax if Mcl-1 Is Neutralized. *Cancer Cell* 2006, 10, 389-399.

(24) Tahir, S. K.; Yang, X.; Anderson, M. G.; Morgan-Lappe, S. E.; Sarthy, A. V.; Chen, J.; Warner, R. B.; Ng, S.-C.; Fesik, S. W.; Elmore, S. W.; Rosenberg, S. H.; Tse, C. Influence of Bcl-2 Family Members on the Cellular Response of Small-Cell Lung Cancer Cell Lines to ABT-737. *Cancer Res.* 2007, 67, 1176-1183.

(25) Chen, S.; Dai, Y.; Harada, H.; Dent, P.; Grant, S. Mcl-1 Down-Regulation Potentiates ABT-737 Lethality by Cooperatively Inducing Bak Activation and Bax Translocation. *Cancer Res.* 2007, 67, 782-791.

(26) Leverson, J. D.; Zhang, H.; Chen, J.; Tahir, S. K.; Phillips, D. C.; Xue, J.; Nimmer, P.; Jin, S.; Smith, M.; Xiao, Y.; Kovar, P.; Tanaka, A.; Bruncko, M.; Sheppard, G. S.; Wang, L.; Gierke, S.; Kategaya, L.; Anderson, D. J.; Wong, C.; Eastham-Anderson, J.; Ludlam, M. J. C.; Sampath, D.; Fairbrother, W. J.; Wertz, I.; Rosenberg, S. H.; Tse, C.; Elmore, S. W.; Souers, A. J. Potent and Selective Small-Molecule MCL-1 Inhibitors Demonstrate on-Target Cancer Cell Killing Activity as Single Agents and in Combination with ABT-263 (Navitoclax). *Cell Death Dis* 2015, 6, e1590.

(27) Wei, S.-H.; Dong, K.; Lin, F.; Wang, X.; Li, B.; Shen, J.-J.; Zhang, Q.; Wang, R.; Zhang, H.-Z. Inducing Apoptosis and Enhancing Chemosensitivity to Gemcitabine via RNA Interference Targeting Mcl-1 Gene in Pancreatic Carcinoma Cell. *Cancer Chemother. Pharmacol.* 2008, 62, 1055-1064.

(28) Friberg, A.; Vigil, D.; Bin Zhao; Daniels, R. N.; Burke, J. P.; Garcia-Barrantes, P. M.; Camper, D.; Chauder, B. A.; Lee, T.; Olejniczak, E. T.; Fesik, S. W. Discovery of Potent Myeloid Cell Leukemia 1 (Mcl-1) Inhibitors Using Fragment-Based Methods and Structure-Based Design. *J. Med. Chem.* 2012, 56, 15-30.

(29) Cohen, N. A.; Stewart, M. L.; Gavathiotis, E.; Tepper, J. L.; Bruekner, S. R.; Koss, B.; Opferman, J. T.; Walensky, L. D. A Competitive Stapled Peptide Screen Identifies a Selective Small Molecule That Overcomes MCL-1-Dependent Leukemia Cell Survival. *Chem. Biol.* 2012, 19, 1175-1186.

(30) Yap, J. L.; Cao, X.; Vanommeslaeghe, K.; Jung, K.-Y.; Peddaboina, C.; Wilder, P. T.; Nan, A.; MacKerell, A. D.; Smythe, W. R.; Fletcher, S. Relaxation of the Rigid Backbone of an Oligoamide-Foldamer-Based A-Helix Mimetic: Identification of Potent Bcl-xL Inhibitors. *Org. Biomol. Chem.* 2012, 10, 2928-2933.

(31) Cao, X.; Yap, J. L.; Newell-Rogers, M. K.; Peddaboina, C.; Jiang, W.; Papaconstantinou, H. T.; Jupitor, D.; Rai, A.; Jung, K.-Y.; Tubin, R. P.; Yu, W.; Vanommeslaeghe, K.; Wilder, P. T.; MacKerell, A. D.; Fletcher, S.; Smythe, R. W. The Novel BH3 A-Helix Mimetic JY-1-106 Induces Apoptosis in a Subset of Cancer Cells (Lung Cancer, Colon Cancer and Mesothelioma) by Disrupting Bcl-xL and Mcl-1 Protein-Protein Interactions with Bak. *Mol. Cancer* 2013, 12, 42.

(32) Jung, K.-Y.; Vanommeslaeghe, K.; Lanning, M. E.; Yap, J. L.; Gordon, C.; Wilder, P. T.; MacKerell, A. D.; Fletcher, S. Amphipathic A-Helix Mimetics Based on a 1,2-Diphenylacetylene Scaffold. *Org. Lett.* 2013, 15, 3234-3237.

(33) Zhang, Z.; Liu, C.; Li, X.; Song, T.; Wu, Z.; Liang, X.; Zhao, Y.; Shen, X.; Chen, H. Fragment-Based Design, Synthesis, and Biological Evaluation of N-Substituted-5-(4-Isopropylthiophenol)-2-Hydroxynicotinamide Derivatives as Novel Mcl-1 Inhibitors. *Eur J Med Chem* 2013, 60, 410-420.

(34) Zhang, Z.; Song, T.; Li, X.; Wu, Z.; Feng, Y.; Xie, F.; Liu, C.; Qin, J.; Chen, H. Novel Soluble Myeloid Cell Leukemia Sequence 1 (Mcl-1) Inhibitor (E,E)-2-(Benzylaminocarbonyl)-3-Styrylacrylonitrile (4 g) Developed Using a Fragment-Based Approach. *Eur J Med Chem* 2013, 59, 141-149.

(35) Ding, X.; Li, Y.; Lv, L.; Zhou, M.; Han, L.; Zhang, Z.; Ba, Q.; Li, J.; Wang, H.; Liu, H.; Wang, R. De Novo Design, Synthesis and Evaluation of Benzylpiperazine Derivatives as Highly Selective Binders of Mcl-1. *ChemMedChem* 2013, 8, 1986-2014.

(36) Richard, D. J.; Lena, R.; Bannister, T.; Blake, N.; Pierceall, W. E.; Carlson, N. E.; Keller, C. E.; Koenig, M.; He, Y.; Minond, D.; Mishra, J.; Cameron, M.; Spicer, T.; Hodder, P.; Cardone, M. H. Hydroxyquinoline-Derived Compounds and Analoguing of Selective Mcl-1 Inhibitors Using a Functional Biomarker. *Bioorg. Med. Chem.* 2013, 21, 6642-6649.

(37) Petros, A. M.; Swann, S. L.; Song, D.; Swinger, K.; Park, C.; Zhang, H.; Wendt, M. D.; Kunzer, A. R.; Souers, A. J.; Sun, C. Fragment-Based Discovery of Potent Inhibitors of the Anti-Apoptotic MCL-1 Protein. *Bioorganic & Medicinal Chemistry Letters* 2014, 24, 1484-1488.

(38) Abulwerdi, F. A.; Liao, C.; Mady, A. S.; Gavin, J.; Shen, C.; Cierpicki, T.; Stuckey, J. A.; Showalter, H. D. H.; Nikolovska-Coleska, Z. 3-Substituted-N-(4-Hydroxynaphthalen-1-Yl)Arylsulfonamides as a Novel Class of Selective Mcl-1 Inhibitors: Structure-Based Design, Synthesis, SAR, and Biological Evaluation. *J. Med. Chem.* 2014, 57, 4111-4133.

(39) Chen, L.; Lanning, M. E.; Fletcher, S. Small-Molecule Inhibitors of the Mcl-1 Oncoprotein. *Austin J Anal Pharm Chem I*, 1015.

(40) Bruncko, M.; Wang, L.; Sheppard, G. S.; Phillips, D. C.; Tahir, S. K.; Xue, J.; Erickson, S.; Fidanze, S.; Fry, E.; Hasvold, L.; Jenkins, G. J.; Jin, S.; Judge, R. A.; Kovar, P. J.; Madar, D.; Nimmer, P.; Park, C.; Petros, A. M.; Rosenberg, S. H.; Smith, M. L.; Song, X.; Sun, C.; Tao, Z.-F.; Wang, X.; Xiao, Y.; Zhang, H.; Tse, C.; Leverson, J. D.; Elmore, S. W.; Souers, A. J. Structure-Guided Design of a Series of MCL-1 Inhibitors with High Affinity and Selectivity. *J. Med. Chem.* 2015, 58, 2180-2194.

(41) Murayama, R.; Sato, K.; Kawakami, S. Polymerizable Monomer, Polymeric Compound, Charge Control Agent Containing the Polymeric Compound, and Developer Bearing Member and Toner Which Contain the . . . , 2012.

(42) Abulwerdi, F.; Liao, C.; Liu, M.; Azmi, A. S.; Aboukameel, A.; Mady, A. S. A.; Gulappa, T.; Cierpicki, T.; Owens, S.; Zhang, T.; Sun, D.; Stuckey, J. A.; Mohammad, R. M.; Nikolovska-Coleska, Z. A Novel Small-Molecule Inhibitor of Mcl-1 Blocks Pancreatic Cancer Growth in Vitro and in Vivo. *Mol. Cancer Ther.* 2014, 13, 565-575.

(43) Guvench, O.; MacKerell, A. D. Computational Fragment-Based Binding Site Identification by Ligand Competitive Saturation. *PLoS Comput. Biol.* 2009, 5, e1000435.

(44) Raman, E. P.; Yu, W.; Guvench, O.; MacKerell, A. D. Reproducing Crystal Binding Modes of Ligand Functional Groups Using Site-Identification by Ligand Competitive Saturation (SILCS) Simulations. *J Chem Inf Model* 2011, 51, 877-896.

(45) Raman, E. P.; Yu, W.; Lakkaraju, S. K.; MacKerell, A. D. Inclusion of Multiple Fragment Types in the Site Identification by Ligand Competitive Saturation (SILCS) Approach. *J Chem Inf Model* 2013, 53, 3384-3398.

(46) Yu, W.; Lakkaraju, S. K.; Raman, E. P.; MacKerell, A. D. Site-Identification by Ligand Competitive Saturation (SILCS) Assisted Pharmacophore Modeling. *J. Comput. Aided Mol. Des.* 2014, 28, 491-507.

(47) Yu, W.; Lakkaraju, S. K.; Raman, E. P.; Fang, L.; MacKerell, A. D. Pharmacophore Modeling Using Site-Identification by Ligand Competitive Saturation (SILCS) with Multiple Probe Molecules. *J Chem Inf Model* 2015, 55, 407-420.

(48) Zhang, H.; Nimmer, P.; Rosenberg, S. H.; Ng, S.-C.; Joseph, M. Development of a High-Throughput Fluorescence Polarization Assay for Bcl-X(L). *Anal. Biochem.* 2002, 307, 70-75.

(49) Nikolovska-Coleska, Z.; Wang, R.; Fang, X.; Pan, H.; Tomita, Y.; Li, P.; Roller, P. P.; Krajewski, K.; Saito, N. G.; Stuckey, J. A.; Wang, S. Development and Optimization of a Binding Assay for the XIAP BIR3 Domain Using Fluorescence Polarization. *Anal. Biochem.* 2004, 332, 261-273.

(50) Pearlman, D. A.; Charifson, P. S. Are Free Energy Calculations Useful in Practice? a Comparison with Rapid Scoring Functions for the P38 MAP Kinase Protein System. *J. Med. Chem.* 2001, 44, 3417-3423.

(51) Yang, C.-Y.; Wang, S. Analysis of Flexibility and Hotspots in Bcl-xL and Mcl-1 Proteins for the Design of Selective Small-Molecule Inhibitors. *ACS Med Chem Lett* 2012, 3, 308-312.

(52) Word, J. M.; Lovell, S. C.; Richardson, J. S.; Richardson, D. C. Asparagine and Glutamine: Using Hydrogen Atom Contacts in the Choice of Side-Chain Amide Orientation. *J. Mol. Biol.* 1999, 285, 1735-1747.

(53) Van Der Spoel, D.; Lindahl, E.; Hess, B.; Groenhof, G.; Mark, A. E.; Berendsen, H. J. C. GROMACS: Fast, Flexible, and Free. *J Comput Chem* 2005, 26, 1701-1718.

(54) Best, R. B.; Zhu, X.; Shim, J.; Lopes, P. E. M.; Mittal, J.; Feig, M.; MacKerell, A. D. Optimization of the Additive CHARMM All-Atom Protein Force Field Targeting Improved Sampling of the Backbone Φ, Ψ and Side-Chain X(1) and X(2) Dihedral Angles. *J Chem Theory Comput* 2012, 8, 3257-3273.

(55) Vanommeslaeghe, K.; Hatcher, E.; Acharya, C.; Kundu, S.; Zhong, S.; Shim, J.; Darian, E.; Guvench, O.; Lopes, P.; Vorobyov, I.; Mackerell, A. D. CHARMM General Force Field: a Force Field for Drug-Like Molecules Compatible with the CHARMM All-Atom Additive Biological Force Fields. *J Comput Chem* 2010, 31, 671-690.

(56) Yu, W.; He, X.; Vanommeslaeghe, K.; MacKerell, A. D. Extension of the CHARMM General Force Field to Sulfonyl-Containing Compounds and Its Utility in Biomolecular Simulations. *J Comput Chem* 2012, 33, 2451-2468.

(57) Jorgensen, W. L.; Chandrasekhar, J.; Madura, J. D.; Impey, R. W.; Klein, M. L. Comparison of Simple Potential Functions for Simulating Liquid Water. *The Journal of Chemical Physics* 1983, 79, 926-935.

(58) Molecular Operating Environment (MOE), Version 2012.10 (2012). Chemical Computing Group Inc., Montreal, Canada.

(59) Marion, D.; Driscoll, P. C.; Kay, L. E.; Wingfield, P. T.; Bax, A.; Gronenborn, A. M.; Clore, G. M. Overcoming the Overlap Problem in the Assignment of 1H NMR Spectra of Larger Proteins by Use of Three-Dimensional Heteronuclear 1H-15N Hartmann-Hahn-Multiple Quantum Coherence and Nuclear Overhauser-Multiple Quantum Coherence Spectroscopy: Application to Interleukin 1 Beta. *Biochemistry* 1989, 28, 6150-6156.

(60) Bax, A.; Ikura, M. An Efficient 3D NMR Technique for Correlating the Proton and 15N Backbone Amide Resonances with the Alpha-Carbon of the Preceding Residue in Uniformly 15N/13C Enriched Proteins. *J. Biomol. NMR* 1991, 1, 99-104.

(61) Delaglio, F.; Grzesiek, S.; Vuister, G. W.; Zhu, G.; Pfeifer, J.; Bax, A. NMRPipe: a Multidimensional Spectral Processing System Based on UNIX Pipes. *J. Biomol. NMR* 1995, 6, 277-293.

(62) Edison, A. S.; Abildgaard, F.; Westler, W. M.; Mooberry, E. S.; Markley, J. L. Practical Introduction to Theory and Implementation of Multinuclear, Multidimensional Nuclear Magnetic Resonance Experiments. *Meth. Enzymol.* 1994, 239, 3-79.

(63) Spera, S.; Ikura, M.; Bax, A. Measurement of the Exchange Rates of Rapidly Exchanging Amide Protons: Application to the Study of Calmodulin and Its Complex with a Myosin Light Chain Kinase Fragment. *J. Biomol. NMR* 1991, 1, 155-165.

(64) Mori, S.; Abeygunawardana, C.; Johnson, M. O.; van Zijl, P. C. Improved Sensitivity of HSQC Spectra of Exchanging Protons at Short Interscan Delays Using a New Fast HSQC (FHSQC) Detection Scheme That Avoids Water Saturation. *J Magn Reson B* 1995, 108, 94-98.

(65) R. M. Perciavalle and J. T. Opferman, Trends Cell Biol., 2013, 23, 22-9.

(66) L. W. Thomas, C. Lam and S. W. Edwards, FEBS Lett., 2010, 584, 2981-9.

(67) S. Krajewski, M. Krajewska, J. Ehrmann, M. Sikorska, B. Lach, J. Chatten and J. C. Reed, Am. J. Pathol., 1997, 150, 805-14.

(68) M. Krajewska, C. M. Fenoglio-Preiser, S. Krajewski, K. Song, J. S. Macdonald, G. Stemmerman and J. C. Reed, Am. J. Pathol., 1996, 149, 1449-57.

(69) C. Tse, A. R. Shoemaker, J. Adickes, M. G. Anderson, J. Chen, S. Jin, E. F. Johnson, K. C. Marsh, M. J. Mitten, P. Nimmer, L. Roberts, S. K. Tahir, Y. Xiao, X. Yang, H. Zhang, S. Fesik, S. H. Rosenberg and S. W. Elmore, Cancer Res., 2008, 68, 3421-8.

(70) A. J. Souers, J. D. Leverson, E. R. Boghaert, S. L. Ackler, N. D. Catron, J. Chen, B. D. Dayton, H. Ding, S. H. Enschede, W. J. Fairbrother, D. C. S. Huang, S. G. Hymowitz, S. Jin, S. L. Khaw, P. J. Kovar, L. T. Lam, J. Lee, H. L. Maecker, K. C. Marsh, K. D. Mason, M. J. Mitten, P. M. Nimmer, A. Oleksijew, C. H. Park, C.-M. Park, D. C. Phillips, A. W. Roberts, D. Sampath, J. F. Seymour, M. L. Smith, G. M. Sullivan, S. K. Tahir, C. Tse, M. D. Wendt, Y. Xiao, J. C. Xue, H. Zhang, R. A. Humerickhouse, S. H. Rosenberg and S. W. Elmore, Nat. Med., 2013, 19, 202-8.

(71) S. P. Glaser, E. F. Lee, E. Trounson, P. Bouillet, A. Wei, W. D. Fairlie, D. J. Izon, J. Zuber, A. R. Rappaport, M. J. Herold, W. S. Alexander, S. W. Lowe, L. Robb and A. Strasser, Genes Dev., 2012, 26, 120-5.

(72) N. Chetoui, K. Sylla, J.-V. Gagnon-Houde, C. Alcaide-Loridan, D. Charron, R. Al-Daccak and F. Aoudjit, Mol. Cancer Res., 2008, 6, 42-52.

(73) H. Zhang, S. Guttikonda, L. Roberts, T. Uziel, D. Semizarov, S. W. Elmore, J. D. Leverson and L. T. Lam, Oncogene, 2011, 30, 1963-8.

(74) Y. Miyamoto, R. Hosotani, M. Wada, J. U. Lee, T. Koshiba, K. Fujimoto, S. Tsuji, S. Nakajima, R. Doi, M. Kato, Y. Shimada and M. Imamura, Oncology, 1999, 56, 73-82.

(75) M. Krajewska, S. Krajewski, J. I. Epstein, A. Shabaik, J. Sauvageot, K. Song, S. Kitada and J. C. Reed, Am. J. Pathol., 1996, 148, 1567-76.

(76) E. Brotin, M. Meryet-Figuière, K. Simonin, R. E. Duval, M. Villedieu, J. Leroy-Dudal, E. Saison-Behmoaras, P. Gauduchon, C. Denoyelle and L. Poulain, Int. J. Cancer, 2010, 126, 885-95.

(77) M. Konopleva, R. Contractor, T. Tsao, I. Samudio, P. P. Ruvolo, S. Kitada, X. Deng, D. Zhai, Y.-X. Shi, T. Sneed, M. Verhaegen, M. Soengas, V. R. Ruvolo, T. McQueen, W. D. Schober, J. C. Watt, T. Jiffar, X. Ling, F. C. Marini, D. Harris, M. Dietrich, Z. Estrov, J. McCubrey, W. S. May, J. C. Reed and M. Andreeff, Cancer Cell, 2006, 10, 375-88.

(78) M. F. van Delft, A. H. Wei, K. D. Mason, C. J. Vandenberg, L. Chen, P. E. Czabotar, S. N. Willis, C. L. Scott, C. L. Day, S. Cory, J. M. Adams, A. W. Roberts and D. C. S. Huang, Cancer Cell, 2006, 10, 389-99.

(79) J. Belmar and S. W. Fesik, Pharmacol. Ther., 2015, 145, 76-84.

(80) L. Chen, M. E. Lanning and S. Fletcher, Austin J. Anal. Pharm. Chem., 2014, 1, 1015.

(81) M. L. Stewart, E. Fire, A. E. Keating and L. D. Walensky, Nat. Chem. Biol., 2010, 6, 595-601.

(82) E. F. Lee, P. E. Czabotar, B. J. Smith, K. Deshayes, K. Zobel, P. M. Colman and W. D. Fairlie, Cell Death Differ., 2007, 14, 1711-3.

(83) T. Oltersdorf, S. W. Elmore, A. R. Shoemaker, R. C. Armstrong, D. J. Augeri, B. a Belli, M. Bruncko, T. L. Deckwerth, J. Dinges, P. J. Hajduk, M. K. Joseph, S. Kitada, S. J. Korsmeyer, A. R. Kunzer, A. Letai, C. Li, M. J. Mitten, D. G. Nettesheim, S. Ng, P. M. Nimmer, J. M. O'Connor, A. Oleksijew, A. M. Petros, J. C. Reed, W. Shen, S. K. Tahir, C. B. Thompson, K. J. Tomaselli, B. Wang, M. D. Wendt, H. Zhang, S. W. Fesik and S. H. Rosenberg, Nature, 2005, 435, 677-81.

(84) X. Cao, J. L. Yap, M. K. Newell-Rogers, C. Peddaboina, W. Jiang, H. T. Papaconstantinou, D. Jupitor, A. Rai, K.-Y. Jung, R. P. Tubin, W. Yu, K. Vanommeslaeghe, P. T. Wilder, A. D. MacKerell, S. Fletcher and R. W. Smythe, Mol. Cancer, 2013, 12, 42.

(85) C. Gloaguen, A. S. Voisin-Chiret, J. Sopkova-de Oliveira Santos, J. Fogha, F. Gautier, M. De Giorgi, G. Burzicki, S. Perato, C. Pétigny-Lechartier, K. Simonin-Le Jeune, E. Brotin, D. Goux, M. N'Diaye, B. Lambert, M.-H. Louis, L. Ligat, F. Lopez, P. Juin, R. Bureau, S. Rault and L. Poulain, J. Med. Chem., 2015, 58, 1644-68.

(86) M. E. Lanning, P. T. Wilder, H. Bailey, B. Drennen, M. Cavalier, L. Chen, J. L. Yap, M. Raje and S. Fletcher, Org. Biomol. Chem., 2015, 13, 8642-6.

(87) H. Moon, W. S. Lee, M. Oh, H. Lee, J. H. Lee, W. Im and H.-S. Lim, ACS Comb. Sci., 2014, 16, 695-701.

(88) J. L. Yap, X. Cao, K. Vanommeslaeghe, K.-Y. Jung, C. Peddaboina, P. T. Wilder, A. Nan, A. D. MacKerell, W. R. Smythe and S. Fletcher, Org. Biomol. Chem., 2012, 10, 2928.

(89) M. Bruncko, L. Wang, G. S. Sheppard, D. C. Phillips, S. K. Tahir, J. Xue, S. Erickson, S. Fidanze, E. Fry, L. Hasvold, G. J. Jenkins, S. Jin, R. a. Judge, P. J. Kovar, D. Madar, P. Nimmer, C. Park, A. M. Petros, S. H. Rosenberg, M. L. Smith, X. Song, C. Sun, Z.-F. Tao, X. Wang, Y. Xiao, H. Zhang, C. Tse, J. D. Leverson, S. W. Elmore and A. J. Souers, J. Med. Chem., 2015, 58, 2180-2194.

(90) J. P. Burke, Z. Bian, S. Shaw, B. Zhao, C. M. Goodwin, J. Belmar, C. F. Browning, D. Vigil, A. Friberg, D. Camper, O. W. Rossanese, T. Lee, E. T. Olejniczak and S. W. Fesik, J. Med. Chem., 2015, 58, 3794-3805.

(91) A. M. Petros, S. L. Swann, D. Song, K. Swinger, C. Park, H. Zhang, M. D. Wendt, A. R. Kunzer, A. J. Souers and C. Sun, Bioorg. Med. Chem. Lett., 2014, 24, 1484-8.

(92) Y. Tanaka, K. Aikawa and G. Nishida, J. Med. Chem., 2013, 56, 9635-9645.

(93) A. Friberg, D. Vigil, B. Zhao, R. N. Daniels, J. P. Burke, P. M. Garcia-barrantes, D. Camper, B. A. Chauder, T. Lee, E. T. Olejniczak and S. W. Fesik, J. Med. Chem., 2013, 56, 15-30.

(94) F. A. Abulwerdi, C. Liao, A. S. Mady, J. Gavin, C. Shen, T. Cierpicki, J. A. Stuckey, H. D. H. Showalter and Z. Nikolovska-Coleska, J. Med. Chem., 2014, 57, 4111-33.

What is claimed is:
1. A compound comprising formula (II):

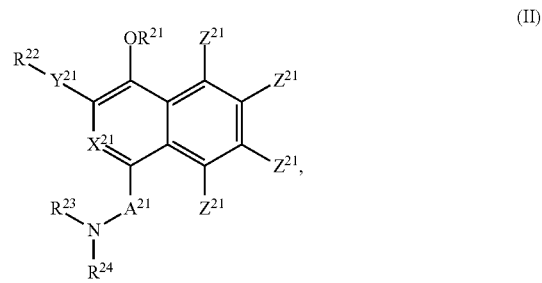

wherein each $R^{21}$ and $R^{22}$ can independently represent a substituent selected from the group consisting of H and optionally substituted alkyl and aryl;
$A^{21}$ is a substituent selected from the group consisting of $S(=O)$, $S(=O)_2$, and $C(=O)$;
$X^{21}$ is CH;
each $Z^{21}$ can independently represent a substituent selected from the group consisting of H, halo, cyano, hydroxy, nitro, and optionally substituted acylsulfonamide, alkyl, alkylaryl, alkylhetaryl, alkylheterocycloalkyl, alkenyl, alkynyl, alkenyl-cycloalkyl, alkynyl-cycloalkyl, carbonyl, carboxaldehyde, carboxyl, cycloalkyl, cycloalkyl-alkenyl, cycloalkyl-heterocycloalkyl, cycloalkyl-heteroaryl, alkoxy, alkoxycarbonyl, acyl, acyloxy, amino, amido, aryl, aralkyl, ester, fluoroalkyl, heteroalkyl, heteroalkenyl, heteroalkynyl, heteroalkylaryl, heteroalkylheteroaryl, heteroalkylheterocycloalkyl, heteroalkylcycloalkyl, heteroaryl, heteroarylalkyl, heterocycloalkyl, hydroxamate, sulfanyl, sulfinyl, sulfonyl, sulfonamidyl, sulfoxyl, and sulfonate;
$Y^{21}$ is a substituent selected from the group consisting of —C(O)O—, —CONR²²—, —CONR²²—SO₂—, —CONR²²O—,

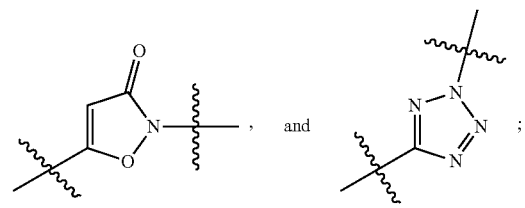 [SMILES: *c1cc(=O)n(*)o1 ; *c1nnn(*)n1]

$R^{23}$ and $R^{24}$ each independently represents a substituent selected from the group consisting of optionally substituted alkyl and aryl; and $R^{23}$ and $R^{24}$ can, taken together, comprise an optionally substituted cycloalkyl or heterocycloalkyl ring;
pharmaceutically acceptable salts, solvates, hydrates, cocrystals, or prodrugs thereof.

2. The compound of claim 1, wherein the compound is 4-(N-(4-(4-chloro-3,5-dimethylphenoxy)phenyl)-N-isobutylsulfamoyl)-1-hydroxy-2-naphthoic acid, and the pharmaceutically acceptable salts, solvates, hydrates, cocrystals, or prodrugs thereof.

3. A method of treating cancer by inhibiting Mcl-1 protein activity in a patient in need of said treatment, the method comprising administering to the patient a therapeutically effective amount of a compound of claim 1, or a pharmaceutically acceptable salt, solvate, hydrate, cocrystal, or prodrug thereof.

4. A method of treating cancer by inhibiting Mcl-1 protein activity in a patient in need of said treatment, the method comprising administering to the patient a therapeutically effective amount of one or more compounds selected from the group consisting of:

- 4-(N-(4-(4-chloro-3,5-dimethylphenoxy)phenyl)-N-isobutylsulfamoyl)-1-hydroxy-2-naphthoic acid,
- 4-(N-benzyl-N-(4-(4-chloro-3,5-dimethylphenoxy)phenyl)sulfamoyl)-1-hydroxy-2-naphthoic acid,
- 1-hydroxy-4-((4-phenylpiperazin-1-yl)sulfonyl)-2-naphthoic acid,
- methyl 4-(N-(4-bromophenyl)-N-isobutylsulfamoyl)-1-methoxy-2-naphthoate,
- methyl 4-(N-(4-bromophenyl)-N-isobutylsulfamoyl)-1-hydroxy-2-naphthoate,
- 4-(N-(4-bromophenyl)-N-isobutylsulfamoyl)-1-methoxy-2-naphthoic acid,
- 1-hydroxy-4-(piperidin-1-ylsulfonyl)-2-naphthoic acid,
- 4-(N,N-dimethylsulfamoyl)-1-hydroxy-2-naphthoic acid,
- 4-((4-benzylpiperazin-1-yl)sulfonyl)-1-hydroxy-2-naphthoic acid,
- 4-(N-(4-bromophenyl)-N-isobutylsulfamoyl)-1-hydroxy-2-naphthoic acid,
- 1-hydroxy-4-(N-isobutyl-N-(4-isopropoxyphenyl)sulfamoyl)-2-naphthoic acid,
- methyl 1-hydroxy-4-(N-isobutyl-N-(4-isopropoxyphenyl)sulfamoyl)-2-naphthoate,
- acetoxymethyl 1-hydroxy-4-(N-isobutyl-N-(4-isopropoxyphenyl)sulfamoyl)-2-naphthoate, and the pharmaceutically acceptable salts, solvates, hydrates, cocrystals, or prodrugs thereof.

5. A method of treating cancer by inhibiting Mcl-1 protein activity in a patient in need of said treatment, the method comprising administering to the patient a therapeutically effective amount of one or more compounds selected from the group consisting of:

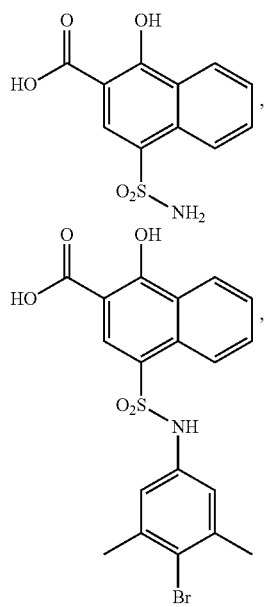

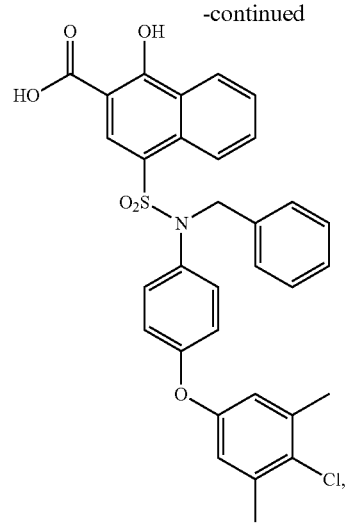

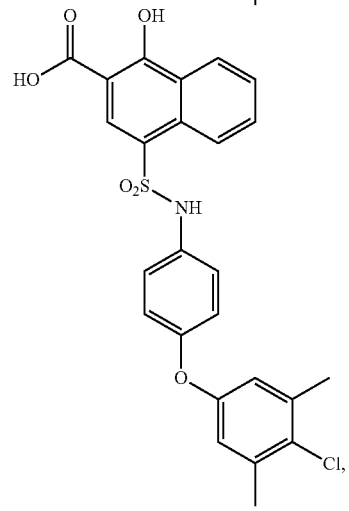

and the pharmaceutically acceptable salts, solvates, hydrates, cocrystals, or prodrugs thereof.

6. The method of claim 3, wherein the cancer is selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

7. The method of claim 5, wherein the cancer is selected from the group consisting of myeloid leukemia, non-small cell lung cancer, pancreatic cancer, prostate cancer, and ovarian cancer.

8. A pharmaceutical composition for treating cancer by inhibiting Mcl-1 protein activity, the pharmaceutical composition comprising one or more compounds according to claim 1, and a pharmaceutically acceptable carrier.

9. The compound of claim 1, wherein the compound is 4-(N-benzyl-N-(4-(4-chloro-3,5-dimethylphenoxy)phenyl)sulfamoyl)-1-hydroxy-2-naphthoic acid, and the pharmaceutically acceptable salts, solvates, hydrates, cocrystals, or prodrugs thereof.

10. The compound of claim 1, wherein the compound is 1-hydroxy-4-((4-phenylpiperazin-1-yl)sulfonyl)-2-naphthoic acid, and the pharmaceutically acceptable salts, solvates, hydrates, cocrystals, or prodrugs thereof.

11. The compound of claim 1, wherein the compound is methyl 4-(N-(4-bromophenyl)-N-isobutylsulfamoyl)-1-methoxy-2-naphthoate, and the pharmaceutically acceptable salts, solvates, hydrates, cocrystals, or prodrugs thereof.

12. The compound of claim 1, wherein the compound is methyl 4-(N-(4-bromophenyl)-N-isobutylsulfamoyl)-1-hydroxy-2-naphthoate, and the pharmaceutically acceptable salts, solvates, hydrates, cocrystals, or prodrugs thereof.

13. The compound of claim 1, wherein the compound is 4-(N-(4-bromophenyl)-N-isobutylsulfamoyl)-1-methoxy-2-naphthoic acid, and the pharmaceutically acceptable salts, solvates, hydrates, cocrystals, or prodrugs thereof.

14. The compound of claim 1, wherein the compound is 1-hydroxy-4-(piperidin-1-ylsulfonyl)-2-naphthoic acid, and the pharmaceutically acceptable salts, solvates, hydrates, cocrystals, or prodrugs thereof.

15. The compound of claim 1, wherein the compound is 4-(N,N-dimethylsulfamoyl)-1-hydroxy-2-naphthoic acid, and the pharmaceutically acceptable salts, solvates, hydrates, cocrystals, or prodrugs thereof.

16. The compound of claim 1, wherein the compound is 4-((4-benzylpiperazin-1-yl)sulfonyl)-1-hydroxy-2-naphthoic acid, and the pharmaceutically acceptable salts, solvates, hydrates, cocrystals, or prodrugs thereof.

17. The compound of claim 1, wherein the compound is 4-(N-(4-bromophenyl)-N-isobutylsulfamoyl)-1-hydroxy-2-naphthoic acid, and the pharmaceutically acceptable salts, solvates, hydrates, cocrystals, or prodrugs thereof.

18. The compound of claim 1, wherein the compound is 1-hydroxy-4-(N-isobutyl-N-(4-isopropoxyphenyl)sulfamoyl)-2-naphthoic acid, and the pharmaceutically acceptable salts, solvates, hydrates, cocrystals, or prodrugs thereof.

19. The compound of claim 1, wherein the compound is methyl 1-hydroxy-4-(N-isobutyl-N-(4-isopropoxyphenyl)sulfamoyl)-2-naphthoate, and the pharmaceutically acceptable salts, solvates, hydrates, cocrystals, or prodrugs thereof.

20. The compound of claim 1, wherein the compound is acetoxymethyl 1-hydroxy-4-(N-isobutyl-N-(4-isopropoxyphenyl)sulfamoyl)-2-naphthoate, and the pharmaceutically acceptable salts, solvates, hydrates, cocrystals, or prodrugs thereof.

* * * * *